US012590311B2

(12) United States Patent
Lieberman et al.

(10) Patent No.: US 12,590,311 B2
(45) Date of Patent: Mar. 31, 2026

(54) METHODS AND COMPOSITIONS FOR THE TREATMENT OF CANCER

(71) Applicant: THE CHILDREN'S MEDICAL CENTER CORPORATION, Boston, MA (US)

(72) Inventors: Judy Lieberman, Brookline, MA (US); Ying Zhang, Boston, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 1135 days.

(21) Appl. No.: 17/619,712

(22) PCT Filed: Jun. 18, 2020

(86) PCT No.: PCT/US2020/038355
§ 371 (c)(1),
(2) Date: Dec. 16, 2021

(87) PCT Pub. No.: WO2020/257401
PCT Pub. Date: Dec. 24, 2020

(65) Prior Publication Data
US 2022/0340906 A1 Oct. 27, 2022

Related U.S. Application Data

(60) Provisional application No. 62/864,726, filed on Jun. 21, 2019.

(51) Int. Cl.
*C12N 15/115* (2010.01)
*A61K 35/00* (2006.01)
*A61K 47/10* (2017.01)
*C12N 15/113* (2010.01)
*C12Q 1/68* (2018.01)

(52) U.S. Cl.
CPC ............ *C12N 15/115* (2013.01); *A61K 35/00* (2013.01); *A61K 47/10* (2013.01); *C12N 15/1138* (2013.01); *C12N 2310/16* (2013.01)

(58) Field of Classification Search
None
See application file for complete search history.

(56) References Cited

U.S. PATENT DOCUMENTS

| | | |
|---|---|---|
| 2005/0147593 A1 | 7/2005 | Kinch |
| 2007/0093653 A1 | 4/2007 | Khvorova et al. |
| 2012/0014875 A1 | 1/2012 | Giangrande et al. |
| 2012/0263740 A1 | 10/2012 | Gilboa et al. |
| 2015/0197755 A1 | 7/2015 | Duan |
| 2017/0275629 A1 | 9/2017 | Lieberman et al. |
| 2018/0105815 A1 | 4/2018 | Liu |
| 2018/0171337 A1 | 6/2018 | O'Neill et al. |
| 2019/0151469 A1 | 5/2019 | Fotin-Mleczek et al. |

FOREIGN PATENT DOCUMENTS

| | | |
|---|---|---|
| CN | 101766817 A | 7/2010 |
| CN | 103977433 A | 8/2014 |
| JP | 2017526367 A | 9/2017 |
| WO | 2010/017319 A2 | 2/2010 |
| WO | 2010/019446 A1 | 2/2010 |
| WO | 2011005566 A2 | 1/2011 |
| WO | 2011/130458 A2 | 10/2011 |
| WO | 2011/142970 A2 | 11/2011 |
| WO | 2012/078637 A2 | 6/2012 |
| WO | 2013/025930 A1 | 2/2013 |
| WO | 2014/019025 A1 | 2/2014 |
| WO | 2014/068408 A2 | 5/2014 |
| WO | 2014/093698 A1 | 6/2014 |
| WO | 2014/126160 A1 | 8/2014 |
| WO | 2016033472 A1 | 3/2016 |
| WO | 2016/127216 A1 | 8/2016 |
| WO | 2018/213791 A1 | 11/2018 |

OTHER PUBLICATIONS

Lian et al., EBioMedicine vol. 42:281-295, Mar. 14, 2019.*
Aliabadi et al., "Effective response of doxorubicin-sensitive and-resistant breast cancer cells to combinational siRNA therapy." Journal of Controlled Release 172(1):219-228 (2013).
Burnett et al., "RNA-based therapeutics: current progress and future prospects." Chemistry & Biology 19(1):60-71 (2012).
Dassie et al., "Systemic administration of optimized aptamer-siRNA chimeras promotes regression of PSMA-expressing tumors." Nature Biotechnology 27(9):839-849 (2009).
Fox et al., "Invasiveness of breast carcinoma cells and transcript profile: Eph receptors and ephrin ligands as molecular markers of potential diagnostic and prognostic application." Biochemical and Biophysical Research Communications 318(4):882-892 (2004).
Gilboa-Geffen et al., "Abstract CN01-02: Targeting basal-like TNBCs and epithelial tumor-initiating cells with aptamer-siRNA chimeras", Molecular Cancer Therapeutics 12(11 Suppl): (2013). (2 pages).
Gilboa-Geffen et al., "Gene knockdown by EpCAM aptamer-siRNA chimeras suppresses epithelial breast cancers and their tumor-initiating cells." Molecular Cancer Therapeutics 14(10):2279-2291 (2015).
Kim et al., "In Vitro Selection of RNA Aptamer and Specific Targeting of ErbB2 in Breast Cancer Cells." Nucleic Acid Therapeutics 21(3):173-178 (2011).

(Continued)

*Primary Examiner* — Sean McGarry
(74) *Attorney, Agent, or Firm* — NIXON PEABODY LLP; David S. Resnick; Nicole D. Kling

(57) ABSTRACT

The technology described herein is directed to improved chimeric molecules for, e.g, the treatment of cancer. As described herein, the inventors have developed novel chimeric aptamer-siRNA molecules (AsiCs) which demonstrate improved efficacy over existing AsiCs and which can successfully synergize in treating cancer. These AsiC's target cancer cell markers to direct therapeutic siRNA molecules specifically to cancer cells, increasing delivery efficacy and therapeutic effectiveness while reducing the potential for side effects.

20 Claims, 74 Drawing Sheets

Specification includes a Sequence Listing.

(56)                    References Cited

OTHER PUBLICATIONS

Machine translation of CN 101766817 A.

McNamara et al., "Cell type-specific delivery of siRNAs with aptamer-siRNA chimeras." Nature Biotechnology 24(8):1005-1015 (2006).

McNamara et al., "Multivalent 4-1BB binding aptamers costimulate CD8+ T cells and inhibit tumor growth in mice." The Journal of Clinical Investigation 118(1):376-386 (2008).

Neff et al., "An aptamer-siRNA chimera suppresses HIV-1 viral loads and protects from helper CD4+ T cell decline in humanized mice." Science Translational Medicine 3(66ra6):1-27 (2011).

Pastor et al. "Targeting 4-1BB costimulation to disseminated tumor lesions with bi-specific oligonucleotide aptamers." Molecular Therapy 19(10):1878-1886 (2011).

Pastor et al., "Induction of tumour immunity by targeted inhibition of nonsense-mediated mRNA decay." Nature 465(7295):227-230 (2010).

Petrocca et al., "A genome-wide siRNA screen identifies proteasome addiction as a vulnerability of basal-like triple-negative breast cancer cells." Cancer Cell 24(2):182-196 (2013).

Rockey et al., "Rational Truncation of an RNA Aptamer to Prostate-Specific Membrane Antigen Using Computational Structural Modeling." Nucleic Acid Therapeutics 21(5):299-314 (2011).

Shigdar et al., "RNA aptamer against a cancer stem cell marker epithelial cell adhesion molecule." Cancer Science 102(5):991-998 (2011).

Subramanian et al., "EpCAM aptamer-siRNA chimera targets and regress epithelial cancer." PloS One 10(7):e0132407 (2015).

Thiel et al., "Delivery of chemo-sensitizing siRNAs to HER2+-breast cancer cells using RNA aptamers." Nucleic Acids Research 40(13):6319-6337 (2012).

Wheeler et al., "Durable knockdown and protection from HIV transmission in humanized mice treated with gel-formulated CD4 aptamer-siRNA chimeras." Molecular Therapy 21(7):1378-1389 (2013).

Wheeler et al., "Inhibition of HIV transmission in human cervicovaginal explants and humanized mice using CD4 aptamer-siRNA chimeras." The Journal of Clinical Investigation 121(6):2401-2412 (2011).

Yang et al., "Wnt modulates MCL1 to control cell survival in triple negative breast cancer." BMC Cancer 14(124):1-13 (2014).

Zhang et al., "Synergistic effect of the γ-secretase inhibitor PF-03084014 and docetaxel in breast cancer models." Stem Cells Translational Medicine 2(3):233-242 (2013).

Zhou et al., "Aptamer-targeted cell-specific RNA interference." Silence 1(4):1-10 (2010).

Zhou et al., "Cell-specific aptamer-mediated targeted drug delivery." Oligonucleotides 21(1):1-10 (2011).

Zhou et al., "Cell-type-specific, aptamer-functionalized agents for targeted disease therapy." Molecular Therapy—Nucleic Acids 3(6):e169 (2014).

Zhou et al., "Novel dual inhibitory function aptamer-siRNA delivery system for HIV-1 therapy." Molecular Therapy 16(8):1481-1489 (2008).

Zhou et al., "Selection, characterization and application of new RNA HIV gp 120 aptamers for facile delivery of Dicer substrate siRNAs into HIV infected cells." Nucleic Acids Research 37(9):3094-3109 (2009).

Lai et al. "PARP1-siRNA suppresses human prostate cancer cell growth and progression." Oncol Rep 39(4):1901-1909 (2018).

Maire et al. "Polo-like kinase 1: a potential therapeutic option in combination with conventional chemotherapy for the management of patients with triple-negative breast cancer." Cancer Research 73(2): 813-823 (2013).

Takai et al. "Polo-like kinases (Plks) and cancer." Oncogene 24(2):287-291 (2005).

Wang et al. "Intravenous Delivery of siRNA Targeting CD47 Effectively Inhibits Melanoma Tumor Growth and Lung Metastasis." Mol Ther 21(10):1919-1929 (2013).

Subramanian et al., "Targeting cancer cells using LNA-modified aptamer-siRNA chimeras." nucleic acid therapeutics 25.6: 317-322 (2015).

Wang et al., "EpCAM aptamer-mediated survivin silencing sensitized cancer stem cells to doxorubicin in a breast cancer model." Theranostics 5.12: 1456 (2015).

* cited by examiner

| Tumor type | High/medium EpCAM, % |
|---|---|
| Colorectal | 100 |
| Ovarian | 100 |
| Thyroid | 100 |
| Lung | 92 |
| Prostate | 90 |
| Endometrial | 83 |
| Carcinoid | 75 |
| Stomach | 72 |
| Pancreatic | 66 |
| Breast | 45 |
| Cervical | 45 |
| Liver | 42 |
| Skin carcinoma | 33 |
| Testis | 27 |
| Head and Neck | 25 |
| Urothelial | 9 |
| Lymphoma | 0 |
| Melanoma | 0 |
| Renal | 0 |
| Glioma | 0 |

EpCAM IHC (n = 216)

FIG. 1

Luminescent imaging 5, 10, 15 d 24 h

Implant cells sc

Treat MB468-Luc cells ex vivo

EpCAM aptamer

UPF2 AsiC

■ EpCAM aptamer

□ UPF2 AsiC

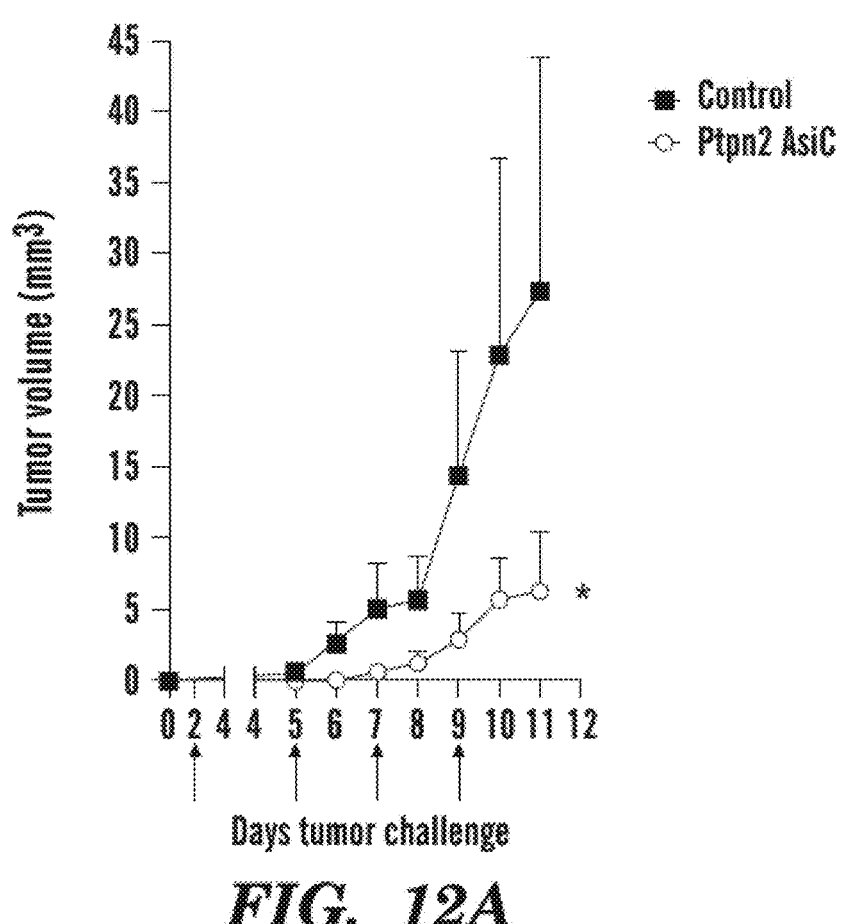
*FIG. 12A*
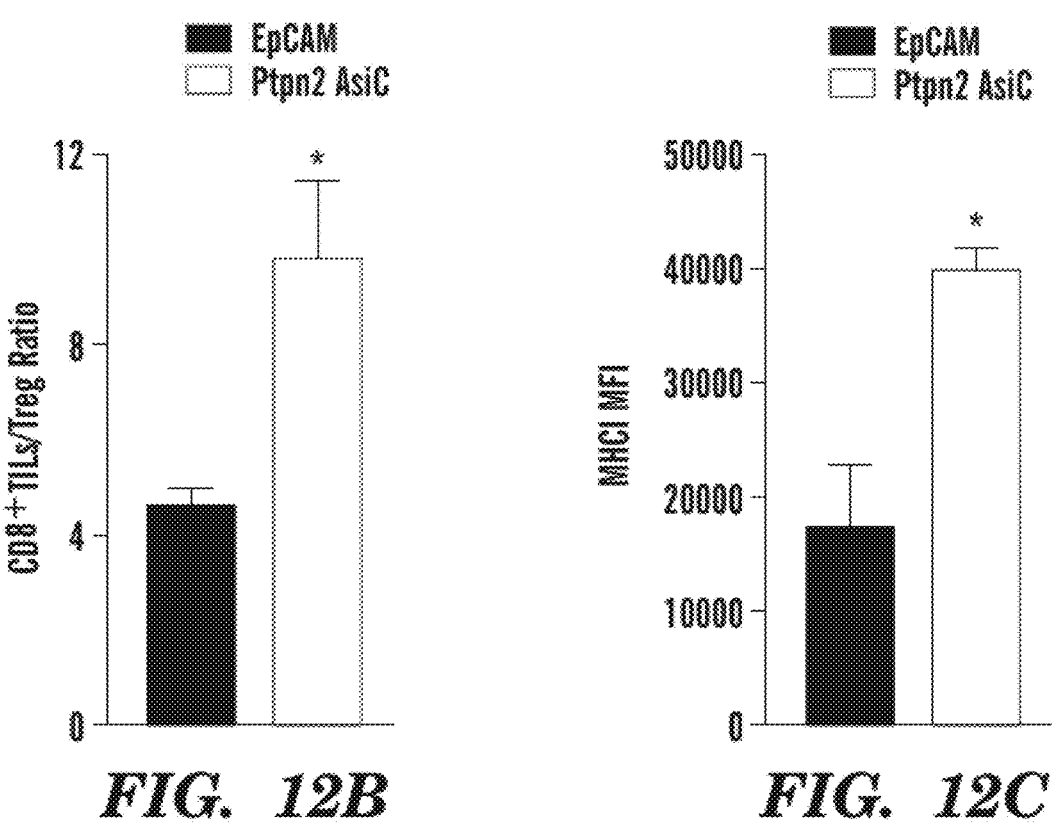
*FIG. 12B* *FIG. 12C*

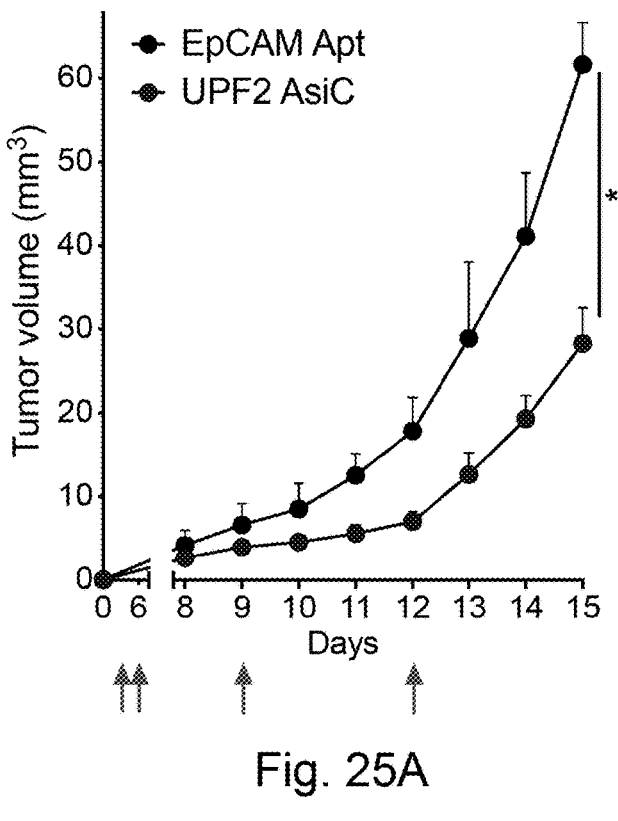
Fig. 25A
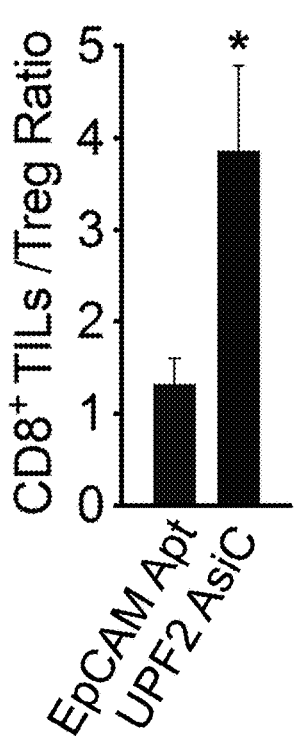
Fig. 25B
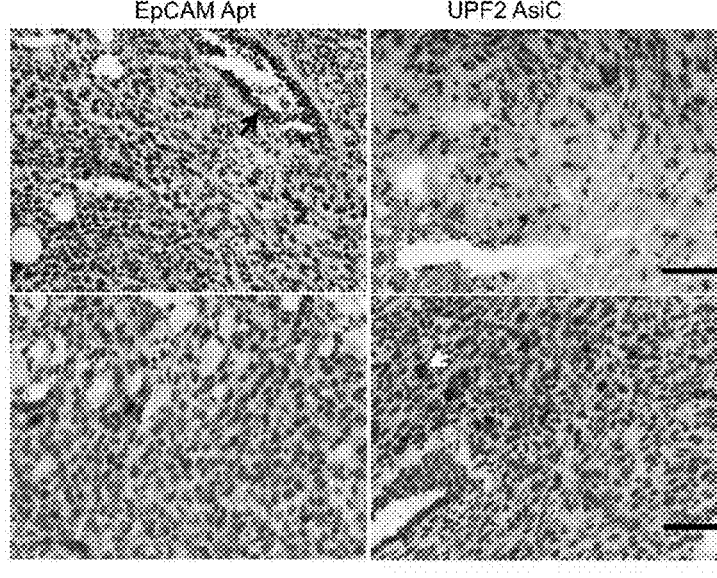
Fig. 25C
Fig. 25D

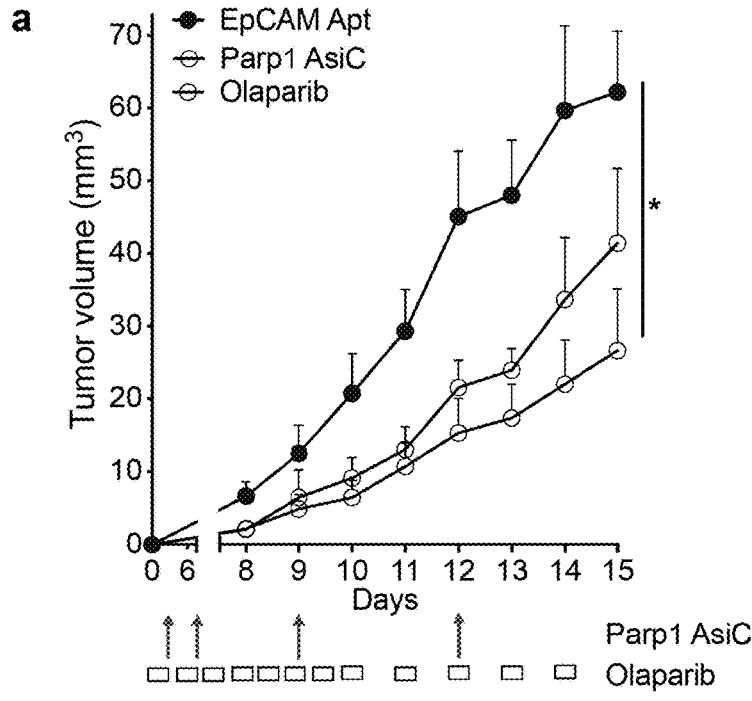
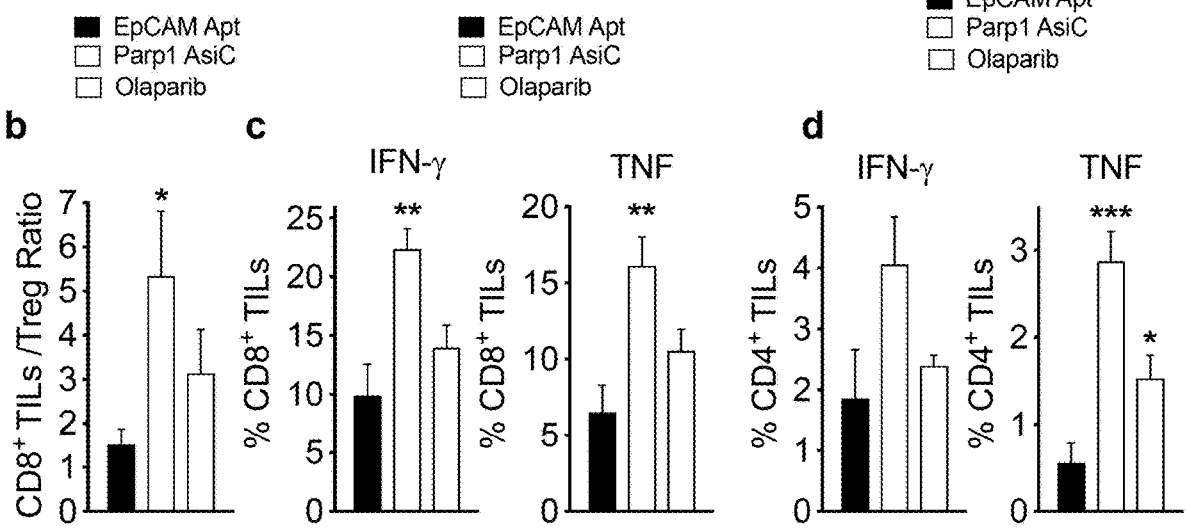
Figs. 26A-26D

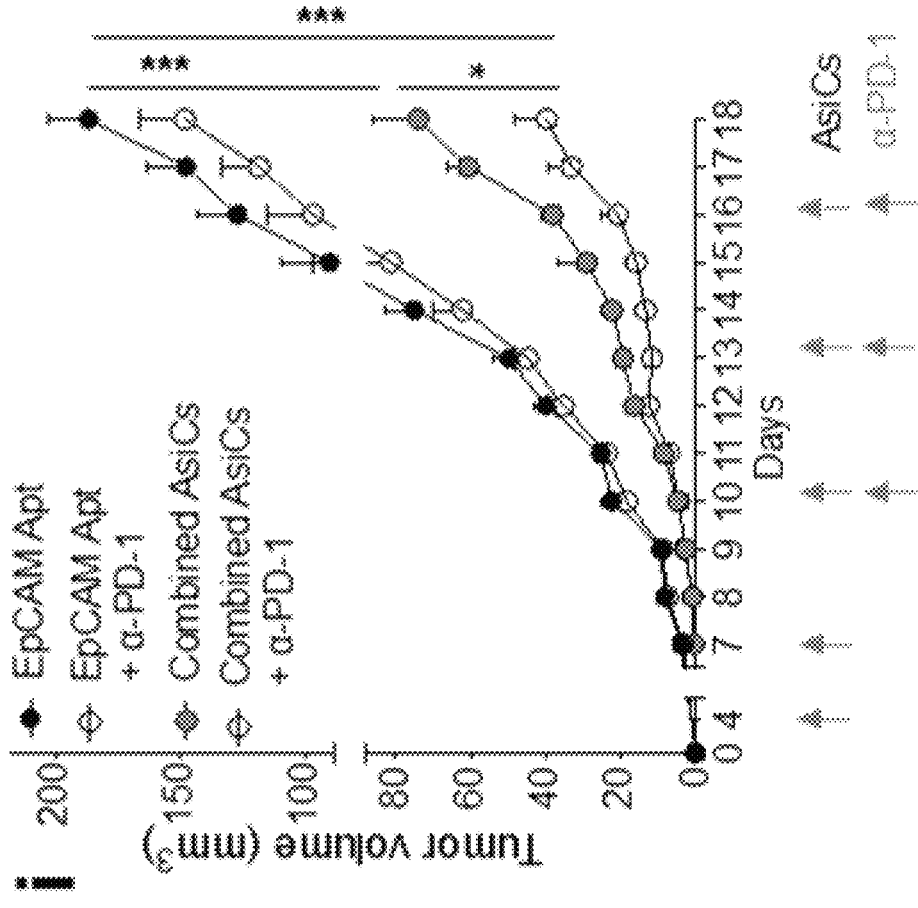
Figs. 28H-28I
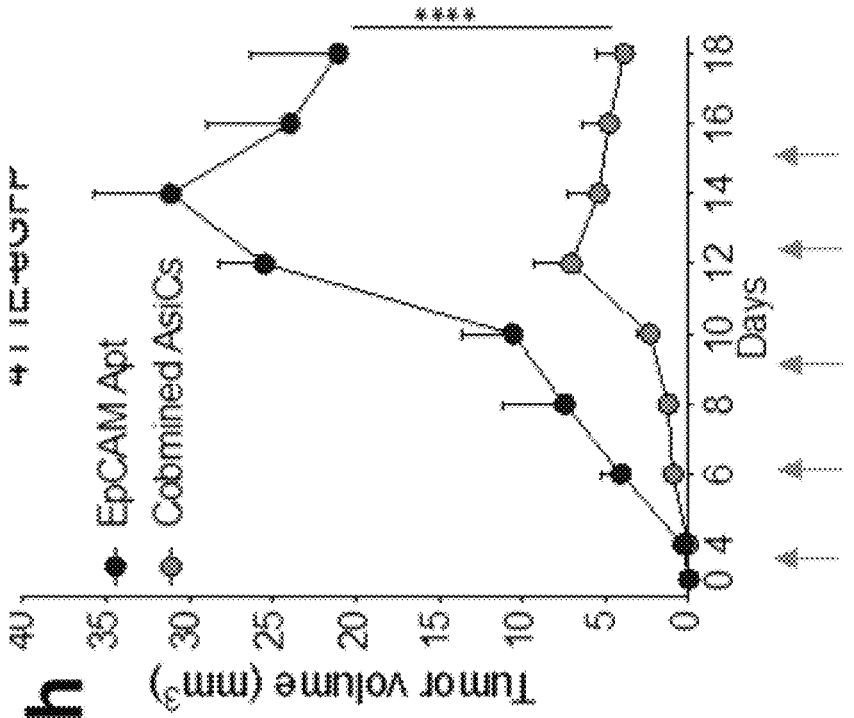

c

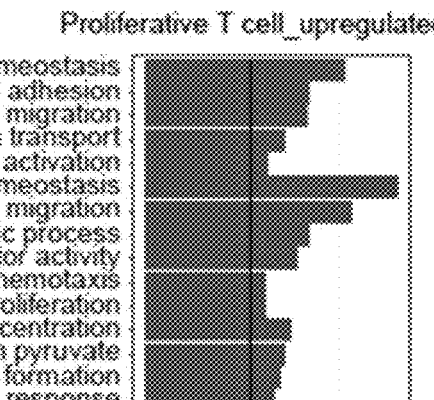

Proliferative T cell_upregulated cellular calcium ion homeostasis
leukocyte cell-cell adhesion
leukocyte migration
calcium ion transport
T cell activation
mitochondrial calcium ion homeostasis
T cell migration
pyruvate metabolic process
positive regulation of NF-kappaB transcription factor activity
leukocyte chemotaxis
T cell proliferation
positive regulation of mitochondrial calcium ion concentration
acetyl-CoA biosynthetic process from pyruvate
immunological synapse formation
leukocyte migration involved in inflammatory response
T cell chemotaxis
positive regulation of antigen receptor-mediated signaling pathway d

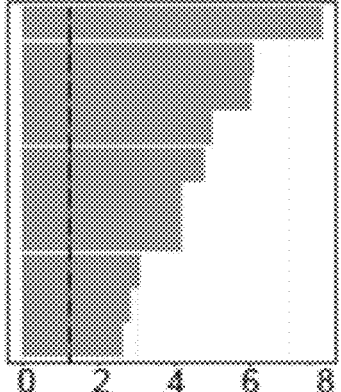

Mono/Macro (1) _upregulated positive regulation of leukocyte migration
calcium ion homeostasis
positive regulation of response to external stimulus
regulation of endocytosis
macrophage migration
regulation of cell-cell adhesion
regulation of cytokine secretion
regulation of immune effector process
receptor-mediated endocytosis
cell-cell recognition

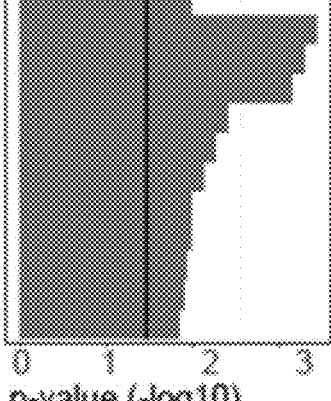

Mono/Macro (2) _upregulated positive regulation of toll-like receptor signaling pathway
positive regulation of chemokine production
macrophage activation
myeloid cell activation involved in immune response
myeloid leukocyte activation
macrophage activation involved in immune response
cell activation involved in immune response
regulation of immune response to tumor cell
positive regulation of interferon-alpha production
positive regulation of interleukin-1 beta secretion
interferon-alpha production
positive regulation of interferon-beta production p-value (-log10)

Figs. 29C-29D

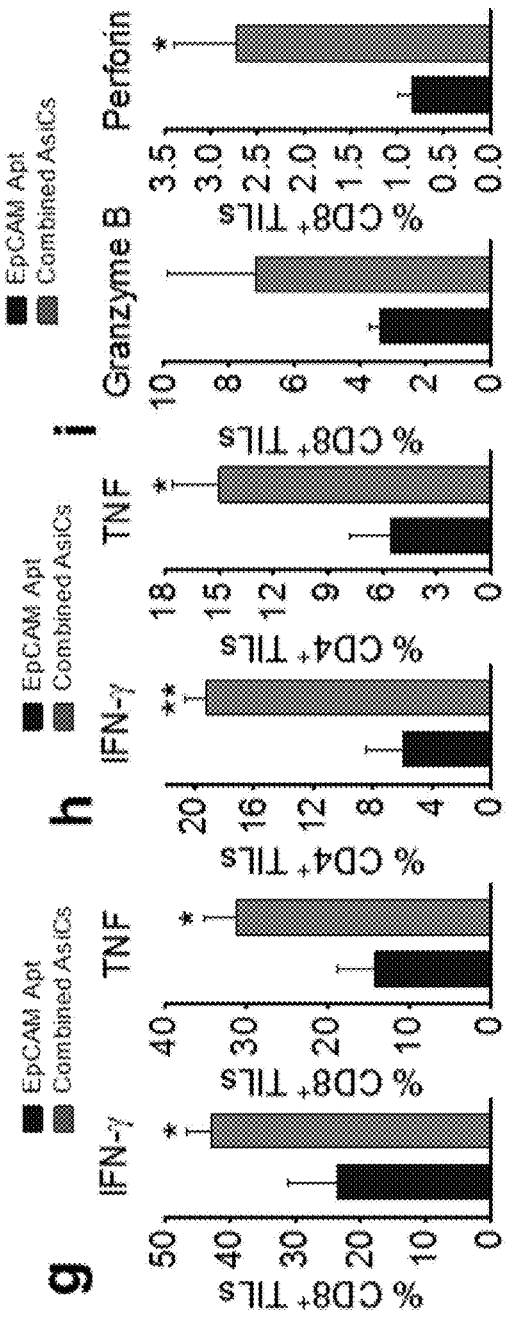
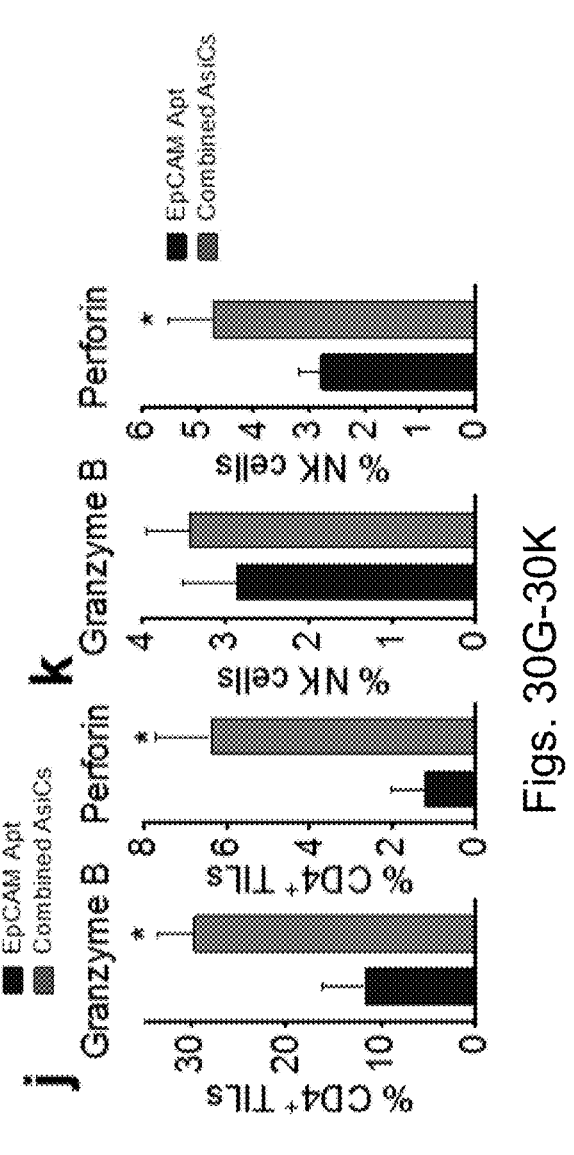
Figs. 30G-30K

EpCAM AsiC

SEQUENCE LISTING

<160> NUMBER OF SEQ ID NOS: 202

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggucuagaga guugcgaau                                                     19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gcauguaccu uguguagaa                                                     19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cguuauguuu gguggaaga                                                     19

-continued

```
<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
caucagaguc agugcuaua                                                    19

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcuuuuguc ccagccaucu u                                                 21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guggaaauuu aaaggaagau u                                                 21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aaguauacgu aaaguggaau u                                                 21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
auacaaccuc cuaggaauau u                                                 21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugacuuuagu agugcaaaau u                                                 21

<210> SEQ ID NO 10
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cuaugagacc cuuacgugau uguua                                            25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcacaugcau cuucuguaug gacaa                                            25

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaaaacaggu auuggauau                                                   19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guucuuagcg cacaucuug                                                   19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccaauaggcu uaauccugu                                                   19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgaguacag ugcgaguca                                                   19

<210> SEQ ID NO 16
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
acggugaucg guagcaacaa a                                                21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgagaaauc ucuuaccuca a                                                21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggacagagcc agaggccaau u                                                21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggaagaagcc ccagauauau u                                                21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggauuaagaa gaaaggauuu u                                                21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gagccuggau uaagaagaau u                                                21

<210> SEQ ID NO 22
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 22
caaaguuucu uacggcauau u                                              21

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gucugguacg acuggagua                                                 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
ccugccacac tcaagaucu                                                 19

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gaugggcuuc gagccuggau uaaga                                          25

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
caucaagucc ugagugguau u                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ccaccaauuc caagagagau u                                              21

<210> SEQ ID NO 28
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
cacaacaacu aaugagauuu u                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
auuccaagag agaggagaau u                                              21

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ccuacuggca uuugcugaac gcauu                                          25

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ggaaugugcu gcuggcuuuu u                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ggaaugugcu gcuggcuuuu u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ggaaugugcu gcuggcuuuu u                                              21

<210> SEQ ID NO 34
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaaggacac aaagccaauu u                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gacgauguga aaucguugut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ccuuuguggc uaaacacuut t                                              21

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaaattcttt cacttcatt                                                 19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cagaauaggu cuagaagaau u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
```

-continued

```
gaauaggucu agaagaagau u                                                          21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gaauaggucu agaagaagau u                                                          21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uggagaaaga aucgguuaau u                                                          21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggagauucua guauacagau u                                                          21

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
guacaggacu uuccucuaa                                                             19

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaugaauggu ggagaguuau u                                                          21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccuuagaguu ccugagaaau u                                                          21
```

```
<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gcagaaaggu gguugacaau u                                                21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gcaaacuacu ggaggaaauu u                                                21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
guguaugugc gccaaaguat t                                                21

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ccaggacacg aggaaacug                                                   19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aaaucucggu gcacuagga                                                   19

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
```

```
ccaagaccau cugcugucau u                                          21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
acaaugguga ccgcuacgau u                                          21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
agaaaugauu cgagaagaau u                                          21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
aagagaagcu uaaggaaauu u                                          21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
agacugggau ggagaauuau u                                          21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
aaagagaagc uuaaggaaau u                                          21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
```
gagaagaugu ccauggaaau u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ggaucaagaa gaaugaauau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
augaagaucu ggaggugaau u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
caaccaaagu cgaauaugau u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaccaguggu ucgagagaca g                                              21

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aagggcggcu uugccaagug cuu                                            23

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgcggcacac acttctatct ttgcggaact cctgcggctc                          40

<210> SEQ ID NO 64
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
acguaucccu uuucgcgu                                                              18

<210> SEQ ID NO 65
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgcggaagcg tgctgggcca acagagggac aaacggggga agatttgacg tcgacgacac       60
ataacccaga ggtcgat                                                        77

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gcgacugguu acccggucgu                                                     20

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcgacugguu acccggucg                                                      19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gcgacugguu acccggucg                                                      19

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 69
gcguuauguu ugguggaagt t                                          21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
cuuccaccaa acauaacgct t                                          21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
gcguuauguu ugguggaagt t                                          21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
cuuccaccaa acauaacgct t                                          21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
cggcaaaccu ggagaguauu u                                          21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uggaagaaga uaagagaaau u                                          21

-continued

```
<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
gaucauagcu cuagcagaat t                                                21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
uucugcuaga gcuaugauct t                                                21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
gaucauagcu cuagcagaat t                                                21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
uucugcuaga gcuaugauct t                                                21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gagaaaagcc cgugaagaau u                                                21

<210> SEQ ID NO 80
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gcgcaaagca ccgaagaaau u                                                21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ccaaaggaau uccgagaaat t                                                21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
uuucucggaa uuccuuuggt t                                                21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
ccaaaggaau uccgagaaat t                                                21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
uuucucggaa uuccuuuggt t                                                21

<210> SEQ ID NO 85
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 85
ccaaaggaau uccgagaaau u                                                21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gggcaagcac agugucaaau u                                                21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
ggugauugug gcugaauuut t                                                21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
aaauucagcc acaaucacct t                                                21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
ggugauugug gcugaauuut t                                                21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 90
aaauucagcc acaaucacct t                                                21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cugcauugug ugacagcaau u                                                21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ccaacacugc uuacgcuuau u                                                21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
agacguaagc aguguugaat t                                                21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
uucaacacug cuuacgucut t                                                21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
agacguaagc aguguugaat t                                                                21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
uucaacacug cuuacgucut t                                                                21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ggaaaaggaa gaugagcaau u                                                                21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
aaacgaaggc gauguuaaat t                                                                21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
uuuaacaucg ccuucguuut t                                                                21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
aaacgaaggc gauguuaaat t                                                                21

```
<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
uuuaacaucg ccuucguuut t                                                     21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aggaagagga cgaccuauau u                                                     21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
gagaauaggu ucagaagaut t                                                     21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
aucuucugaa ccuauucuct t                                                     21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
gagaauaggu ucagaagaut t                                                     21

<210> SEQ ID NO 106
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
aucuucugaa ccuauucuct t                                                21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gagugauggu ugagaaguau u                                                21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gaaauggugu uuaaggaaau u                                                21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
uuucaguguu agucauggct t                                                21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
gccaugacua acacugaaat t                                                21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
    oligonucleotide
<220> FEATURE:
<223> OTHER INFORMATION: Description of Combined DNA/RNA Molecule:
      Synthetic oligonucleotide

<400> SEQUENCE: 111
uuucaguguu agucauggct t                                                      21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
gccaugacua acacugaaat t                                                      21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
cucagcaucu gucaguggat t                                                      21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
uccacugaca gaugcugagt t                                                      21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
cucagcaucu gucaguggat t                                                      21

<210> SEQ ID NO 116
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
uccacugaca gaugcugagt t                                                        21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
gaacuugaau ccagcgaaat t                                                        21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
uuucgcugga uucaaguuct t                                                        21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
gaacuugaau ccagcgaaat t                                                        21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
uuucgcugga uucaaguuct t                                                        21

<210> SEQ ID NO 121
<211> LENGTH: 21
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 121
agacugggau ggagaguuau u                                                21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
agaaaugauc cgagaagaau u                                                21

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
ugaagaagau cacccuccuu att                                              23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
uaaggagggu gaucuucuuc att                                              23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
ugaagaagau cacccuccuu att                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 126
uaaggagggu gaucuucuuc att                                                        23

<210> SEQ ID NO 127
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gcgacugguu acccggucgu uugcguuaug uuuggguggaa gtt                                 43

<210> SEQ ID NO 128
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
gcgacugguu acccggucgu uugaucauag cucuagcaga att                                  43

<210> SEQ ID NO 129
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
gcgacugguu acccggucgu uuccaaagga auuccgagaa att                                  43

<210> SEQ ID NO 130
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
gcgacugguu acccggucgu uuggugauug uggcugaauu utt                                  43

<210> SEQ ID NO 131
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 131
gcgacugguu acccggucgu uuagacguaa gcaguguuga att                          43

<210> SEQ ID NO 132
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
gcgacugguu acccggucgu uuaaacgaag gcgauguuaa att                          43

<210> SEQ ID NO 133
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
gcgacugguu acccggucgu uugagaauag guucagaaga utt                          43

<210> SEQ ID NO 134
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
gcgacugguu acccggucgu uuuuucagug uuagucaugg ctt                          43

<210> SEQ ID NO 135
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gcgacugguu acccggucgu uucucagcau cugucagugg att                          43

<210> SEQ ID NO 136
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 136
gcgacugguu acccggucgu uugaacuuga auccagcgaa att                              43

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gcgacugguu acccggucgu uuugaagaag aucacccucc uuatt                           45

<210> SEQ ID NO 138
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Leu Glu Ala Leu Ala Glu Ala Leu Glu Ala Leu Ala Glu Ala
1               5                   10                  15

<210> SEQ ID NO 141
<211> LENGTH: 16
<212> TYPE: PRT
<213> ORGANISM: Unknown
<220> FEATURE:
<223> OTHER INFORMATION: Description of Unknown: RFGF peptide

<400> SEQUENCE: 141

Ala Ala Val Ala Leu Leu Pro Ala Val Leu Leu Ala Leu Leu Ala Pro
1               5                   10                  15

<210> SEQ ID NO 142
<211> LENGTH: 11
<212> TYPE: PRT
<213> ORGANISM: Unknown
<220> FEATURE:
<223> OTHER INFORMATION: Description of Unknown: RFGF analogue
      peptide

<400> SEQUENCE: 142

Ala Ala Leu Leu Pro Val Leu Leu Ala Ala Pro
1               5                   10

<210> SEQ ID NO 143
<211> LENGTH: 13
<212> TYPE: PRT
<213> ORGANISM: Human immunodeficiency virus

<400> SEQUENCE: 143

Gly Arg Lys Lys Arg Arg Gln Arg Arg Arg Pro Pro Gln
1               5                   10

<210> SEQ ID NO 144
<211> LENGTH: 16
<212> TYPE: PRT
<213> ORGANISM: Drosophila sp.

<400> SEQUENCE: 144

Arg Gln Ile Lys Ile Trp Phe Gln Asn Arg Arg Met Lys Trp Lys Lys
1               5                   10                  15

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gtgacctgtt ttggaccgga                                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tctccgcatc gtgtacttcc                                                    20

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

```
accgtactcg tcaattccaa ggg                                            23

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tgccgccatt attacgacaa gc                                             22

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gaucauagcu cuagcagaa                                                 19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gagaaaagcc cgugaagaa                                                 19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcgcaaagca ccgaagaaa                                                 19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uauccuaccu caagaaguu                                                 19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
```

-continued

```
ccaaaggaau uccgagaaa                                                    19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gggcaagcac agugucaaa                                                    19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ccaacacugc uuacgcuua                                                    19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ggugauugug gcugaauuu                                                    19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cugcauugug ugacagcaa                                                    19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aaacgaaggc gauguuaaa                                                    19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ccgaaaggcg gcugcauaa                                                    19
```

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
aggaagagga cgaccuaua                                                     19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
agacguaagc aguguugaa                                                     19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ggaaaaggaa gaugagcaa                                                     19

<210> SEQ ID NO 163
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
gcgacugguu acccggucgu uugcguuaug uuugguggaa gtt                          43

<210> SEQ ID NO 164
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
gcgacugguu acccggucgu uugaucauag cucuagcaga att                          43

<210> SEQ ID NO 165
<211> LENGTH: 43
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 165
gcgacugguu acccggucgu uuccaaagga auuccgagaa att                        43

<210> SEQ ID NO 166
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
gcgacugguu acccggucgu uuaaacgaag gcgauguuaa att                        43

<210> SEQ ID NO 167
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
gcgacugguu acccggucgu uuggugauug uggcugaauu utt                        43

<210> SEQ ID NO 168
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
gcgacugguu acccggucgu uuagacguaa gcaguguuga att                        43

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tgttgcagtc tcttgcacag c                                                21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 170
ggatcaacgt ctcctcccac c                                              21

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ccatcgacgt caactacgag                                                20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gtgcgtggta gcatgagtgt                                                20

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aggagaaaag cccgtgaag                                                 19

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tggcaatggt gaaagaggtc                                                20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ttgtaaggac gaaacgggac                                                20

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
```
tctaggtcct gtacgtggaa g                                                                21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gggtgattgt ggctgaattt g                                                                21

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gctgtcggta ttccagtctt ac                                                               22

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ctcattgtag tgtccacggt c                                                                21

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acgatcagag ggttcaacac                                                                  20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ccactcacgg caaattcaac                                                                  20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182

-continued ctccacgaca tactcagcac                                              20

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
caagaacagg gatctaggtg ag                                           22

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
agaggctgta aacccatgaa g                                            21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aatcccatca ccatcttcca g                                            21

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
aaatgagccc cagccttc                                                18

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
agaccccgga cctgcactg                                               19

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ttcggatgcc atcaccgttc                                              20

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agaccccgga cctgcactg                                                        19

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
acccacgagc ttagacacgc                                                       20

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gccaaactga tgaatgtgga cc                                                    22

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agcagaacga ctggatcagg                                                       20

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tctgacgacc ccctgacact c                                                     21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
atgcctgata cccggacgat g                                                     21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cagatccaca gcgatatcca g                                                    21

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
agagacaacg gcacactttg                                                     20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tggccttgtc gctgtcttgc                                                     20

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tttctccttc tctgctcctg tcc                                                 23

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ggagtatgag atgcagtgta gc                                                  22

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
caaggtctgt gaggaagagg                                                     20

-continued

```
<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
agatcgaggt catgattgca g                                                    21

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
acaatcagcc accatccag                                                       19
```

METHODS AND COMPOSITIONS FOR THE TREATMENT OF CANCER

CROSS-REFERENCE TO RELATED APPLICATIONS

This application is a 35 U.S.C. § 371 National Phase Entry Application of International Application No. PCT/US2020/038355 filed Jun. 18, 2020, which designates the U.S. and claims benefit under 35 U.S.C. § 119(e) of U.S. Provisional Application No. 62/864,726 filed Jun. 21, 2019, the contents of which are incorporated herein by reference in their entireties.

GOVERNMENT SUPPORT

This invention was made with government support under Grant Nos. CA184718 awarded by the National Institutes of Health, and under Grant no. W81XWH-19-1-0039, awarded by the U.S. Department of the Army. The government has certain rights in the invention.

SEQUENCE LISTING

The instant application contains a Sequence Listing which has been submitted electronically in ASCII format and is hereby incorporated by reference in its entirety. Said ASCII copy, created on Jun. 18, 2020, is named 701039-095310WOPT_SL.txt and is 53,904 bytes in size.

TECHNICAL FIELD

The technology described herein relates to chimeric molecules comprising an EpCAM binding-molecule and an inhibitory nucleic acid and methods of using such compositions for the treatment of cancer, e.g. epithelial cancer.

BACKGROUND

RNA interference (RNAi) has been explored for therapeutic use in reducing gene expression in the liver. However, the liver is unique in being easy to transfect with RNAi molecules. Delivery of small RNAs and resulting gene knockdown in other tissues continues to be inefficient and ultimately ineffective. In particular, the delivery roadblock is a major obstacle to harnessing RNAi to treat cancer.

SUMMARY

As described herein, the inventors have developed novel chimeric aptamer-siRNA molecules (AsiCs) which demonstrate improved efficacy over existing AsiCs and which can successfully synergize in treating cancer. These AsiC's target cancer cell markers to direct therapeutic siRNA molecules specifically to cancer cells, increasing delivery efficacy and therapeutic effectiveness while reducing the potential for side effects.

In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; APE1; PD-L1; MCL1; PTPN2; SMG1; TREX1; CMAS; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; APE1; PD-L1; MCL1; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; MCL1; and CD47.

In some embodiments of any of the aspects, the molecule is ari aptamer-siRNA chimera (AsiC). In some embodiments of any of the aspects, the inhibitory nucleic acid specifically binds to a gene product of the selected gene.

In some embodiments of any of the aspects, the EpCam-binding aptamer domain comprises the sequence of any of SEQ ID NOs: 63-68. In some embodiments of any of the aspects, the inhibitory nucleic acid domain comprises a sequence selected from SEQ ID NOs: 1-62 and 69-126, or the reverse complement thereof.

In some embodiments of any of the aspects, the chimeric molecule comprises a first and at least one further inhibitory nucleic acid domain. In some embodiments of any of the aspects, the first and at least one further inhibitory nucleic acid domains comprise different sequences but each inhibit the expression of the same gene. In some embodiments of any of the aspects, the first and at least one further inhibitory nucleic acid domains each inhibit the expression of a different gene. In some embodiments of any of the aspects, the at least a second inhibitory nucleic acid domain inhibits the expression of a gene selected from the group consisting of: PLK1 and MCL1.

In some embodiments of any of the aspects, the molecule comprises the sequence of one of SEQ ID NOs: 127-137. In some embodiments of any of the aspects, the 3' end of the chimeric molecule comprises dTdT. In some embodiments of any of the aspects, the chimeric molecule comprises at least one 2'-F pyrimidine. In some embodiments of any of the aspects, the chimeric molecule further comprises a chemotherapeutic agent.

In one aspect of any of the embodiments, described herein is a pharmaceutical composition, kit, or combination comprising a chimeric molecule described herein and optionally a pharmaceutically acceptable carrier. In some embodiments of any of the aspects, the composition, kit, or combination of comprises at least two chimeric molecules, wherein the chimeric molecules have different aptamer domains or inhibitory nucleic acid domains. In some embodiments of any of the aspects, the different inhibitory nucleic acid domains recognize different targets. In some embodiments of any of the aspects, the different inhibitory nucleic acid domains have different sequences and recognize the same target.

In one aspect of any of the embodiments, described herein is a pharmaceutical composition, kit, or combination comprising:
a. a first chimeric molecule as described herein;
b. a second chimeric molecule comprising:
    i. a chimeric molecule as described herein, wherein the inhibitory nucleic acid domain of the second chimeric molecule inhibits the expression of a different gene than the first chimeric molecule; or
    ii. a chimeric molecule comprising an EpCAM-binding aptamer domain and an inhibitory nucleic acid domain which inhibits the expression of a gene selected from the group consisting of:
        PLK1 and MCL1; and
c. optionally a pharmaceutically acceptable carrier
In one aspect of any of the embodiments, described herein is a method of treating cancer in a subject in need thereof, the method comprising administering a chimeric molecule, composition, kit, or combination as described herein to the subject. In some embodiments of any of the aspects, the cancer is an epithelial cancer, breast cancer, colon cancer, or triple-negative breast cancer. In some embodiments of any of the aspects, the administration is subcutaneous. In some embodiments of any of the aspects, the subject is further administered an additional cancer treatment. In some embodiments of any of the aspects, the cancer treatment is paclitaxel.

BRIEF DESCRIPTION OF THE DRAWINGS

FIG. 1 demonstrates that EpCAM is highly expressed in epithelial cancers.

FIG. 9A demonstrates tumor suppression, FIG. 9B demonstrates an increase in CD8+ TILs, FIG. 9C demonstrates reduced inhibitory receptors on CD8+ TILs, (first series is EpCAM aptamer, second series is UPF2 AsiC), FIG. 9D demonstrates more degranulation and tumor killing by CD8+ TILs, and FIG. 9E demonstrates more cytokine production by CD8+ TILs.

FIGS. 12A-12E demonstrate that knocking down PTPNT2 enhances anti-tumor immunity. FIG. 12A demonstrates tumor suppression, FIG. 12B demonstrates an increase in CD8+ TILs, FIG. 12C demonstrates increased tumor antigen presentation, FIG. 12D demonstrates more cytokine production by CD8+ TILs, and FIG. 12E demonstrates more cytokine production by CD4+ TILs.

FIG. 15A depicts increases in CD8+ Tcells and a reduction in suppressive Tregs in the tumor. FIG. 15B demonstrates increased activity of the T cells in the tumor. In both FIGS. 15A and 15B, the series are, in order, EpCAM aptamer and CD47 AsiC.

FIG. 18A depicts UPF2+CD47, FIG. 18B depicts UPF2+CD47+MCL1, FIG. 18C depicts UPF2+CD47+MCL1+PLK1, FIG. 18D depicts UPF2+CD47+MCL1+PLK1+PARP1+APE1+PD-L1. FIG. 18E depicts the effect on CD8+ TILs of PARP1-AsiC, PARP1+PD-L1 AsiCs, and mixed AsiCs (UPF2+CD47+MCL1+PLK1+PARP1+APE1+PD-L1 AsiCs). The series in FIG. 18E are, in order, control, PARP1 AsiC, PARP1+PD-L1 AsiCs, and mixed AsiCs.

FIGS. 25A-25G demonstrate tumor inhibition and immune modulation capacity of UPF2 AsiC. FIG. 25A Comparison of tumor growth kinetics in mice challenged with 4T1E tumors and treated with either EpCAM Apt or UPF2 AsiC (5 mg/kg, every $3^{rd}$ day, as indicated by red arrows).

FIG. 25B, Ratio of $CD8^+$ TILs over tumor-infiltrating $CD4^+Foxp3^+$ Tregs in each group of tumors. a-b, n=5 mice/group. FIG. 25C, H&E staining (upper) and IHC staining for $CD8^+$ TILs (lower) using orthotopically implanted 4T1E tumors from mice treated with either EPCAM Apt or UPF2 AsiC. Black arrow indicates mammary gland. Tailless arrow indicates necrotic area. White arrow indicates $CD8^+$ TILs. Two mice per group were used for imaging with similar results. Scale bars: 100 mM. FIG. 25D, Comparison of $CD8^+$ TIL counts per selected area. For each group, 6 fields/section were selected for counting. Two tumors/group were examined with similar results. FIG. 25E, Percentages of $CD8^+$ TIL producing IFN-g and TNF induced by PMA ad ionomycin. FIG. 25F, Degranulation of $CD8^+$ TILs measured by their CD107a/CD107b surface expression, and the cytotoxic molecules granzyme B and perforin expression after 6 hours of co-incubation with 4T1E tumor cells that had been knocked down of UPF2 by UPF2 siRNA. Representative flow image of $CD8^+$ TIL degranulation were also shown (right). (FIG. 25G) Target $^{51}$Cr-labeled, UPF2 siRNA treated-4T1E tumor cell lysis by $CD8^+$ TILs enriched from either EpCAM Apt or UPF2 AsiC treated 4T1E tumors. Effector:Target ratio is 5:1. FIGS. 25E-25F, n=5 samples/group. FIG. 26G, n=3 samples/group, for each sample $CD8^+$ TILs were pooled from two mice. Data show mean+s.e.m and are representative of at least two experiments. For all figures: *p≤0.05, p≤0.01, *p≤0.001, ****p≤0.0001.

FIGS. 26A-26D depict tumor inhibition and immune modulation capacity comparison between PARP1 AsiC and PARP1 inhibitor Olaparib. FIG. 26A, Comparison of tumor growth in mice bearing 4T1E tumors and treated with EpCAM Apt, PARP1 AsiC (5 mg/kg, every 3rd day) or Olaparib (50 mg/kg, daily). FIG. 26B, Comparison of the ratios of $CD8^+$ TILs over tumor-infiltrating CD4+ Tregs in each group of tumors. FIG. 26C, Percentage of $CD8^+$ TILs producing cytokines IFN-g and TNF induced by PMA and ionomycin. FIG. 26D, Percentage of CD4+ TILs producing cytokines IFN-g and TNF induced by PMA and ionomycin. n=4 mice/group. Data shown are mean+s.e.m.

FIG. 27A, Comparison of tumor growth in mice bearing 4T1E tumors and treated with either EpCAM Apt or CD47 AsiC. Arrows indicate each treatment. FIG. 27B, Ratio of CD8+ TILs over tumor-infiltrating CD4+ Tregs in each group of tumors. FIGS. 27C-27D, Percentage of CD8+ TILs (FIG. 27C) and CD4+ TILs (FIG. 27D) producing IFN-g and TNF induced by PMA and ionomycin.

FIG. 27E, Cytotoxic granules granzyme B and perforin production by CD8+ TILs. FIG. 27F, Ratio of M1-like TAMs over M2-like TAMs in mice treated with either EpCAM Apt or CD47 AsiC. FIG. 27G, Percentages of CD11c+ DEC205+ DCs over CD45+ cells in each group of tumors. FIG. 27H, MFI levels of CD40, CD86, and MHCII on CD11c+ DEC205+ DCs. FIGS. 27A-27H, n=5 mice/group. FIGS. 27I, Percentages of eGFP+ TAMs from 4T1E-eGFP tumors that phagocytosed tumor cells. n=5 mice/group. FIG. 27J, The phagocytosis of 4T1E-eGFP tumor cells treated with control or CD47 siRNA by TAMs in vitro. n=3 samples/ group. FIG. 27K, Comparison of tumor growth in 4T1E tumor-bearing mice treated with EpCAM Apt or CD47 AsiC and injected with isotype control Ab or were depleted of CD8+ T cells, CD4+ T cells or macrophages. FIG. 27L, CD8+ TILs isolated from tumors of mice treated with EpCAM Apt, CD47 AsiC or CD47 AsiC with Mac depletion were stimulated with 4T1E tumor cells for 6 hours. The cytokine production (left) and degranulation of CD8+ TILs were compared. Series are, from left to right, EpCAM Apt, CD47 AsiC, and CD47 AsiC+Mac depl. FIGS. 27K-27L, n=5 samples/group. FIG. 27M, Comparison of 4T1E tumor growth in mice treated with either EpCAM Apt, CD47 AsiC, or anti-CD47 antibody (Ab). n=5 mice/group. a-m, Data shown are mean+s.e.m and are representative of at least two experiments.

FIGS. 28A-28I depict the synergistic antitumor effect of the immune-modulating EpCAM-AsiCs and EpCAM-AsiCs combined with anti-PD-1. FIG. 28A, Comparison of tumor growth in mice bearing 4T1E tumors and treated with EpCAM aptamer or eGFP AsiC as control, UPF2 AsiC, CD47 AsiC, MCL1 AsiC, Parp1 AsiC, or the combination of four immune-modulating EpCAM-AsiCs targeting UPF2, CD47, MCL1 and Parp1. Arrows indicate days that mice received AsiC subcutaneously. FIG. 28B, Individual tumor growth curves in mice treated with either EpCAM aptamer or the combination of the four EpCAM-AsiCs. FIG. 28C, Comparison of the numbers of CD8+ TILs per mg of tumor between mice treated with EpCAM Apt or combined AsiCs. FIG. 28D, Ratio of CD8+ TILs to tumor-infiltrating CD4+ Foxp3+ Tregs in each group of tumors. FIG. 28E, Percentage of CD8+ TILs producing IFN-g and TNF induced by PMA and ionomycin. Right: representative flow plots. FIG. 28F, Percentage of CD4+ TILs producing IFN-g and TNF induced by PMA and ionomycin. FIG. 28G, Cytotoxic granules granzyme B and perforin production by CD8+ TILs. FIGS. 28A-28G, n=4 mice/group. FIG. 28H, Comparison of tumor growth in mice bearing 4T1E-eGFP tumors and treated with EpCAM aptamer or the combination of the four immune-modulating EpCAM-AsiCs. n=5 mice/group. FIG. 28I, Comparison of tumor growth in mice bearing 4T1E tumors and treated with EpCAM aptamer or the combined AsiCs together with isotype control or anti-PD-1

Ab. n=4 mice/group. FIGS. 28A, 28H 28I Arrows indicate the time for each treatment. Data shown are mean+s.e.m.

FIGS. 29A-29F depict the impact of the immune-modulating EpCAM-AsiCs on tumor-infiltrating immune cells analyzed by single-cell RNA-seq. Enriched CD45+ cells from mice bearing orthotopic 4T1E tumor-bearing mice treated with either EpCAM aptamer or the EpCAM-AsiCs cocktail (n=2 mice/group) were pooled for single cell-RNA sequencing. FIG. 29A, The immune cells from combining all four samples were projected onto the Uniform manifold approximation and projection (UMAP) plot. Each dot represents a cell that were colored by inferred cluster identity. Cont: contaminated cells. FIG. 29B, Heatmap showing the Z-score-normalized expression of differentially expressed genes (DEGs) as canonical and cell-type markers across different clusters. Each lane represents a biological sample. FIGS. 29C-29D, Gene ontology (GO) enrichment for DEGs upregulated in the EpCAM-AsiCs cocktail-treated group for proliferative T cells (FIG. 29C) and monocytes/macrophages (FIG. 29D). Dashed lines indicate p-value=0.05. FIGS. 29E-29F, Heatmap showing expression of genes known to be involved in T cell activation, effector function and memory formation as well as exhaustion in T cell clusters (FIG. 29E), or genes involved in defining monocyte/ macrophages phenotype and functions in monocyte/macrophage clusters (FIG. 29F), averaged per cluster and Z score standardized across clusters.

FIGS. 30A-30K depict the antitumor efficacy of combined immune-modulating EpCAM-AsiCs in ErbB2ΔEx16 transgenic mice. FIG. 30A, Experimental scheme of tumor induction and treatment in ErbB2ΔEx16 transgenic mice. FIG. 30B, Left: quantitative comparison of EpCAM expression on GFP+4T1E-eGFP tumor cells and GFP+ ErbB2ΔEx16 transgenic tumor cells. Right: representative histograms of EpCAM expression on GFP+ tumor cells. FIG. 30C, Comparison of the percentage of CD8+ TILs (left) and CD4+ TILs (right) over live cells in 4T1E-eGFP tumors and ErbB2ΔEx16 transgenic tumors. FIGS. 30B-30C, 4T1E-eGFP, n=5 mice/group, ErbB2ΔEx16, n=7 mice/ group. FIG. 30D, Comparison of tumor growth in doxycycline-fed ErbB2ΔEx16 transgenic mice and treated with EpCAM aptamer or the combination of the four immune-modulating EpCAM-AsiCs.

FIG. 30E, Left: histogram shows the comparison of EpCAM expression on tumor cells from mice treated with EpCAM aptamer or the combined EpCAM-AsiCs. Right: quantitative comparison of EpCAM expression on the two groups of tumor cells. FIG. 30F, In vivo TAM phagocytosis as measured by percentage of GFP+ TAMs in each group of ErbB2ΔEx16 transgenic mice. FIGS. 30G-30H, Percentage of CD8+ TILs (FIG. 30G) and CD4+ TILs (FIG. 30H) producing IFN-g and TNF induced by PMA and ionomycin. FIGS. 30I-30K, Cytotoxic granules granzyme B and perforin production by CD8+ TILs (FIG. 30I), CD4+ TILs (FIG. 30J) and NK cells (FIG. 30K) in each group of tumors. FIGS. 30D-30K, n=6 mice/group. FIGS. 30B-30K, Data shown are mean+s.e.m.

FIG. 31A, Representative luminescent images of the mice lung areas at different time points after tail-vein injection of 4T1E-Luc tumor cells. Upper lanes: EpCAM aptamer treated group. Lower lanes: combined EpCAM-AsiCs treated group. FIG. 31B, Total luminescent photon flux of lung metastases in each treatment group at different time points after tumor cell implantation. Data show mean+/−s.e.m. FIG. 31C, Percentage of CD8+ TILs producing IFN-g and TNF induced by PMA and ionomycin. FIG. 31D, Percentage of CD8+ TILs producing IFN-g and TNF induced by PMA and ionomycin. FIGS. 31A-31D, EpCAM aptamer, n=5 mice/group, Combined AsiCs, n=6 mice/group. FIGS. 31C-31D, Data show mean+ s.e.m.

FIG. 32A, EpCAM protein expression on mouse (upper) and human (lower) BC cells. Mouse L929 cell line is used as negative control. Numbers on each graph indicate EpCAM MFI values. FIG. 32B, Fitting curve analysis to measure the binding/internalization affinity of Cy3-labeled EpCAM aptamer by different mouse (left) and human (right) BC cell lines. The binding/internalization affinity values (Kd) for each cell line is shown in the tables. Each data point is collected from sample pooled from three replicated wells. Each experiment was repeated at least twice with similar results.

FIG. 33A, Comparison of UPF2 mRNA levels in MDA-MB-231 cells transfected with different concentrations of human-specific or mouse and human cross-reactive (CR) UPF2 siRNAs. FIG. 33B, UPF2 gene knockdown efficiency of 100 nM UPF2 CR siRNA in different mouse and human BC cell lines. FIGS. 33C-33G, Comparison of CD47 (FIG. 33C), PARP1 (FIG. 33D), APE1 (FIG. 33E), MCL1 (FIG. 33F) and PD-L1 (FIG. 33G mRNA levels in 4T1E cells transfected with different concentrations of mouse-specific and/or mouse and human CR siRNAs. Arrow in each graph indicates the selected siRNA for EpCAM AsiC design. Data represent mean+sem performed in duplicate (FIGS. 33A, 33C-33G, n=2/condition) or triplicate (FIG. 33B, n=3).

FIGS. 34A-34l depict EpCAM AsiCs knockdown gene expression in EpCAM+4T1E cells in vitro and in vivo. FIG. 34A, Gene knockdown efficiency of 100 nM siRNAs targeting each genes in 4T1E tumor cells (n=3/group). Controls were negative control siRNA-treated cells. FIG. 34B, Design of CD47 AsiC. The EpCAM aptamer folding structure is predicted by the mfold web server. FIG. 34B discloses SEQ ID NOS 128 and 78, respectively, in order of appearance. FIG. 34C, Gene knockdown efficiency of 4 mM EpCAM-AsiCs targeting each gene in 4T1E tumor cells (n=3/group). Controls were EpCAM aptamer (Apt)-treated cells. Mock: medium control. FIG. 34D, Comparison of UPF2 mRNA levels in EpCAM+4T1E tumor cells and EpCAM-CD45− cells isolated from 4T1E tumors treated with EpCAM aptamer, eGFP AsiC or UPF2 AsiC. FIG. 34E, Comparison of % UPF2+ cells in EpCAM+4T1E tumor cells from mice treated with EpCAM aptamer, eGFP AsiC or UPF2 AsiC. Right: representative flow image. FIG. 34F, Ratios of mRNA over pre-mRNA for well-established NMD substrates in EpCAM+ tumor cells from mice treated with UPF2 AsiC normalized to those from mice treated with EpCAM aptamer. FIGS. 34D-34F, n=3 mice/group. FIGS. 34G-34l, Comparison of CD47 mRNA (FIG. 34GF), PARP1 mRNA (FIG. 34H) and MCL1 mRNA levels (FIG. 34l) in EpCAM+4T1E tumor cells and EpCAM-CD45− cells isolated from 4T1E tumors treated with EpCAM aptamer, CD47 AsiC, PARP1 AsiC, or MCL1 AsiC. n=3 mice/group. Data are mean+s.e.m. and represents at least two independent experiments.

FIG. 35A, Viability of 4T1E tumor cells treated with negative control siRNA, or with siRNAs to knockdown UPF2, CD47, PARP1, APEX1, PD-L1 or MCL1 for 72 hours. Cell viability was assessed by CellTiter-Glo. n=5 samples/group. FIGS. 35B-35C, Viability of 4T1E tumor cells treated with medium (mock), 4 mM EpCAM aptamer, or 4 mM EpCAM AsiCs targeting UPF2 or CD47 for 72 hours (FIG. 35B) and the rates of cell proliferation over three days (FIG. 35C). n=4/group. Data shown are mean+s.e.m.

FIG. 36A, Mice bearing 8-day-old 4T1E tumors were treated with either EpCAM Apt or UPF2 AsiC (5 mg/kg, every 3rd day, as indica mice challenged by arrows). Tumor growth kinetics are shown. FIG. 36B, Percentages of CD8$^+$ TIL producing IFN-g and TNF induced by PMA ad ionomycin. EpCAM Apt group, n=7, UPF2 AsiC group, n=8. Data show mean+ s.e.m.

FIG. 37A Left: Different mRNA isoforms (including NMD insensitive and NMD sensitive transcripts) for DNAJC2 gene (upper) and LAT2 gene (lower). Right: Comparison of the isoform fractions (IF) between negative siRNA (light grey) and UPF2 siRNA (black) treated cells. FIG. 37B, Left: Two mRNA isoforms (one protein coding transcript and one NMD sensitive transcript) for CENPH gene. Right: Comparison of the isoform fractions (IF) between negative siRNA (light grey) and UPF2 siRNA (black) treated cells. FIGS. 37A-37B, For left side graphs, Longer black bars indicate protein-coding exons; shorter black bars indicate non-coding exons; lines in between represent introns.

FIG. 38A, Comparison of tumor growth in mice bearing 4T1E tumors and treated with EpCAM Apt or APE1 AsiC. FIG. 38B, Expression of PD-L1 on EpCAM+4T1E tumor cells from mice bearing two-week-old 4T1E tumors. Cells were gated on live+CD45-EpCAM+ cells. FIG. 38C, Comparison of 4T1E tumor growth in mice treated with EpCAM Apt or PD-L1 AsiC. FIGS. 38A and 38C, n=5 mice/group. Arrows indicate each treatment. Data show mean+s.e.m.

FIG. 39A, Mononuclear, singlet and live tumor-infiltrating immune cells were first gated on CD45+ cells while gating out CD3+/CD19+/TCRb+/Ter119+ cells. The remaining CD45+ myeloid cells were gated for Gr-1hiCD11b+ PMN-MDSCs, Gr-1intCD11b+MO-MDSCs and Gr-1-CD11b+ cells. The Gr-1-CD11b+ cells were then gated for F4/80+ TAMs and for for CD206-MHCII+M1-like TAMs and CD206+MHCII+M2-like TAMs. FIG. 39B, Comparison of M1 to M2 TAM ratios in EpCAM aptamer or CD47 AsiC treated 4T1E tumors. Cells were gated on CD45+CD11b+F4/80+MCHII+ TAMs. Numbers indicate percentages of each subset over TAMs.

FIG. 39C, Phagocytosis of negative siRNA or CD47 siRNA treated 4T1E-eGFP tumor cells by TAMs in vitro. Numbers indicate percentages GFP+ TAMs.

FIG. 40B, Representative flow plots of CD4+ and CD8+ T cells in peripheral blood of mice treated with isotype control Ab or anti-CD8 and/or anti-CD4 Abs. FIG. 40C, Effect of TAM depletion in mice treated with isotype control or anti-CSF1R Ab (0.3 mg/treatment). Data shown are percentage of CD11b+F4/80+MHCII+ TAMs over CD45+ tumor-infiltrating immune cells. n=5 mice/group. Data shown are mean+ s.e.m.

FIGS. 41A-41B, Percentage of CD8+ TILs (FIG. 41A) and CD4+ TILs (FIG. 41B) producing IFN-g and TNF induced by PMA and ionomycin cells in mice treated with either EpCAM Apt, CD47 AsiC, or anti-CD47 Ab. FIG. 41C, Percentages of PMN-MDSCs and MO-MDSCs over live cells. Right: representative flow plots of these two cell subsets in the three groups of mice. a-c, n=5 mice/group. Data shown are mean+s.e.m.

FIG. 42A, Viability of 4T1E tumor cells treated with 4 mM of EpCAM aptamer or EpCAM AsiC targeting MCL1 for 48-96 hours. n=3 samples/group. FIG. 42B, Comparison of tumor growth in mice bearing 4T1E tumors and treated with either EpCAM Apt or MCL1 AsiC. Arrows indicate each treatment. FIG. 42C, Ratio of CD8+ TILs to tumor-infiltrating CD4+Foxp3+ Tregs in each group of tumors. FIGS. 42D-42E, Percentage of CD8+ TILs (FIG. 42Dd) and CD4+ TILs (FIG. 42E) producing IFN-g and TNF induced by PMA and ionomycin. FIG. 42F, Cytotoxic molecules granzyme B and perforin production by CD8+ TILs. FIGS. 42B-42F, n=5 mice/group. FIGS. 42A-42F, Data shown are mean+s.e.m. and representative of two experiments.

FIG. 43A, Numbers of CD8+ TILs per mg of tumor in 4T1E-eGFP tumor-bearing mice treated with EpCAM aptamer or the combination of four EpCAM-AsiCs targeting UPF2, CD47, MCL1 and Parp1. FIG. 43B, Ratio of CD8+ TILs over tumor-infiltrating CD4+Foxp3+ Tregs in each group of tumors. c-d, Percentage of CD8+ TILs (FIG. 43C) and CD4+ TILs (FIG. 43D) producing IFN-g and TNF induced by PMA and ionomycin. FIGS. 43E-43F, Cytotoxic granules granzyme B and perforin production by CD8$^+$ TILs (FIG. 43E) and CD4$^+$ TILs (FIG. 43F). FIG. 43G, The mean fluorescence intensity (MFI) of EpCAM expression on eGFP+ tumor cells from each group of tumors. FIGS. 43A-43G, n=5 mice/group. Data shown are mean+s.e.m.

FIG. 44A, The MFI levels of co-inhibitors PD-1, CTLA-4, 2B4, TIM-3 and LAG-3 expression on CD44+CD8+ TILs in mice bearing 4T1E tumors and treated with EpCAM aptamer or the combined AsiCs together with isotype or anti-PD-1 antibodies. FIG. 44B, Numbers of CD8+ TILs per mg of tumor in each group of mice. FIG. 44C, Numbers of NK cells per mg of tumor. FIGS. 44D-44E, Percentage of CD8+ TILs (FIG. 44D) and CD4+ TILs (FIG. 44E) producing IFN-g and TNF induced by PMA and ionomycin. FIGS. 44A-44E, n=4 mice/group. Data shown are mean+s.e.m.

DETAILED DESCRIPTION

Figure 2:
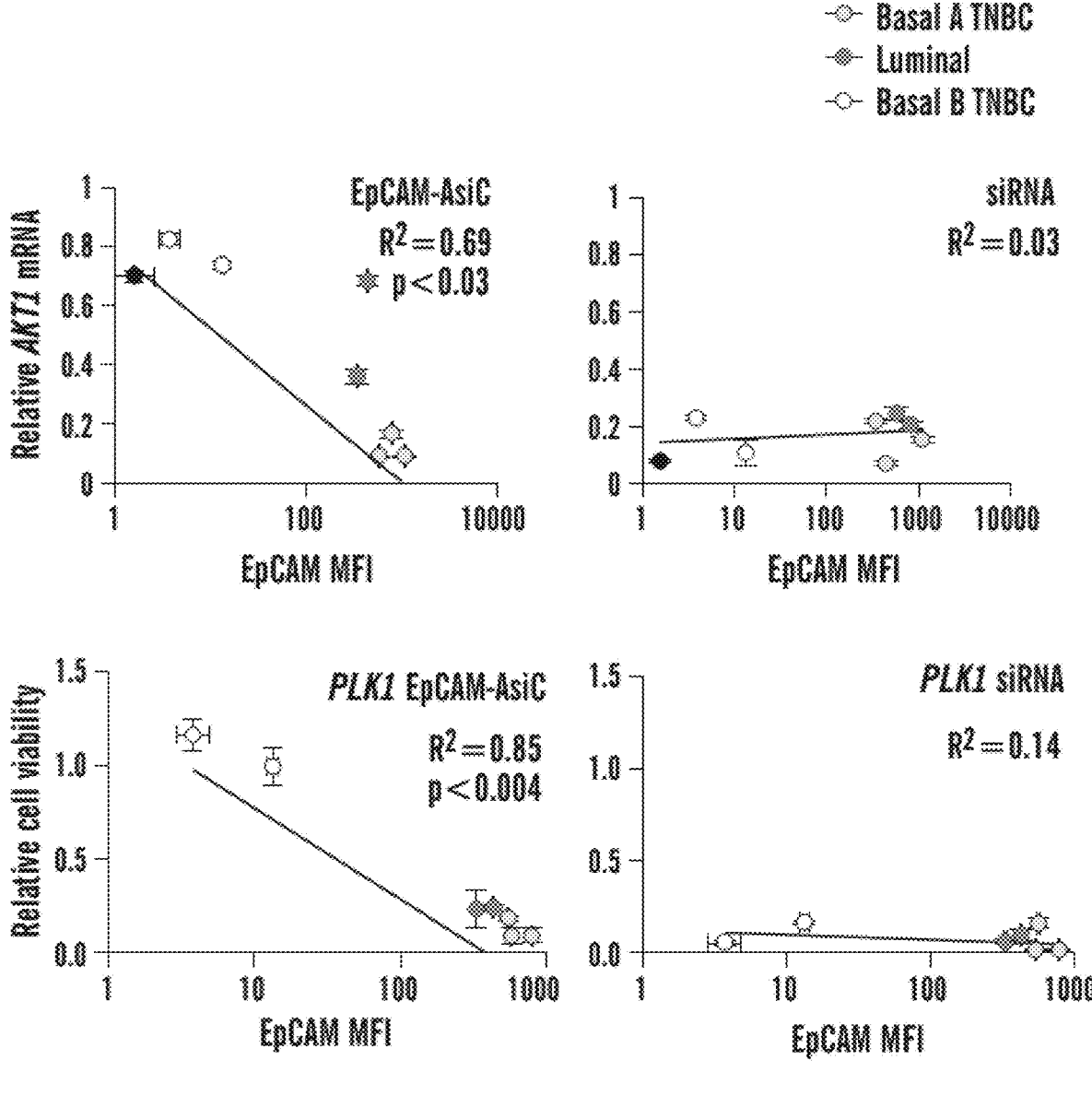
FIG. 2 depicts graphs of gene knockdown in the indicated cell types using the indicated AsiC's.

Targeting therapeutic molecules to diseased cells can improve the effectiveness of a treatment and reduce side effects. The technology described herein relates to chimeric molecules which bind to EpCAM, a common marker of epithelial cancer cells, and inhibitory nucleic acids designed to target certain genes which the inventors have demonstrated are essential to cancer cell growth and survival. The specific chimeric molecules described herein are demonstrated to have surprisingly improved efficacy over earlier generations of such chimeras and furthermore, are able to synergize when used in combination. Accordingly, described herein are improved compositions and methods for the treatment of cancer, e.g., epithelial cancer.

In one aspect of any of the embodiments, described herein is a chimeric molecule comprising an EpCAM-binding aptamer domain and at least one inhibitory nucleic acid domain which inhibits the expression of a gene selected from the group consisting of UPF2; PARP1; APE1; PD-L1; PTPN2; MCL1; SMG1; TREX1; CMAS; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; APE1; PD-L1; MCL1; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; MCL1; and CD47.

As used herein "chimeric molecule" refers to a molecule, e.g., a nucleic acid molecule which comprises two or more distinct regions, each made up of at least one monomer unit, i.e., a nucleotide in the case of a AsiC compound. Chimeras are not naturally-occurring molecules and are by definition engineered. The regions can be distinct in function or structure.

The EpCAM-binding aptamer domain binds specifically to EpCAM, thereby targeting the chimeric molecule to cells expressing EpCAM, e.g., cancer cells. This reduces both the therapeutic dose size and the opportunity for off-target effects. As used herein the term, "aptamer" refers to single-stranded nucleic acids that are capable of binding to cells and target molecules (e.g., polypeptides). Nucleic acid aptamers include RNA, DNA, and/or synthetic nucleic acid analogs (e.g., PNA) capable of specifically binding target molecules. The generation and therapeutic use of aptamers are well established in the art. See, e.g., U.S. Pat. No. 5,475,096.

As used herein, "EpCAM" or "epithelial cell adhesion molecule" refers to a transmembrane glycoprotein mediating Ca2+-independent homotypic cell-cell adhesion in epithelial cells. Sequences for EpCAM are known for a variety of species, e.g., human EpCAM (see, e.g., NCBI Gene ID: 4072; protein sequence: NCBI Ref Seq: NP 002345.2).

By way of non-limiting example, exemplary EpCAM-binding aptamers are provided herein. In some embodiments of any of the aspects, the EpCAM aptamer can comprise or consist of, or consist essentially of a sequence of SEQ ID NO: 67 or 68. This aptamer has the particular advantage that it works with similar potency against human and mouse EpCAM, which permits testing it in vivo in immune competent mice, to determine whether it is immune stimulating.

11

TABLE 1

Exemplary EpCAM aptamer sequences.
[f] indicates 2' fluro-pyrimidine
modification;

| EPCAM-AsiC sequence | SEQ ID NO: |
|---|---|
| G[fC]GA[fC][fU]GG[fU][fU]A[fC][fC][fC]GG[fU][fC]G | 67 |
| GCGACUGGUUACCCGGUCG | 68 |

Figure 45:
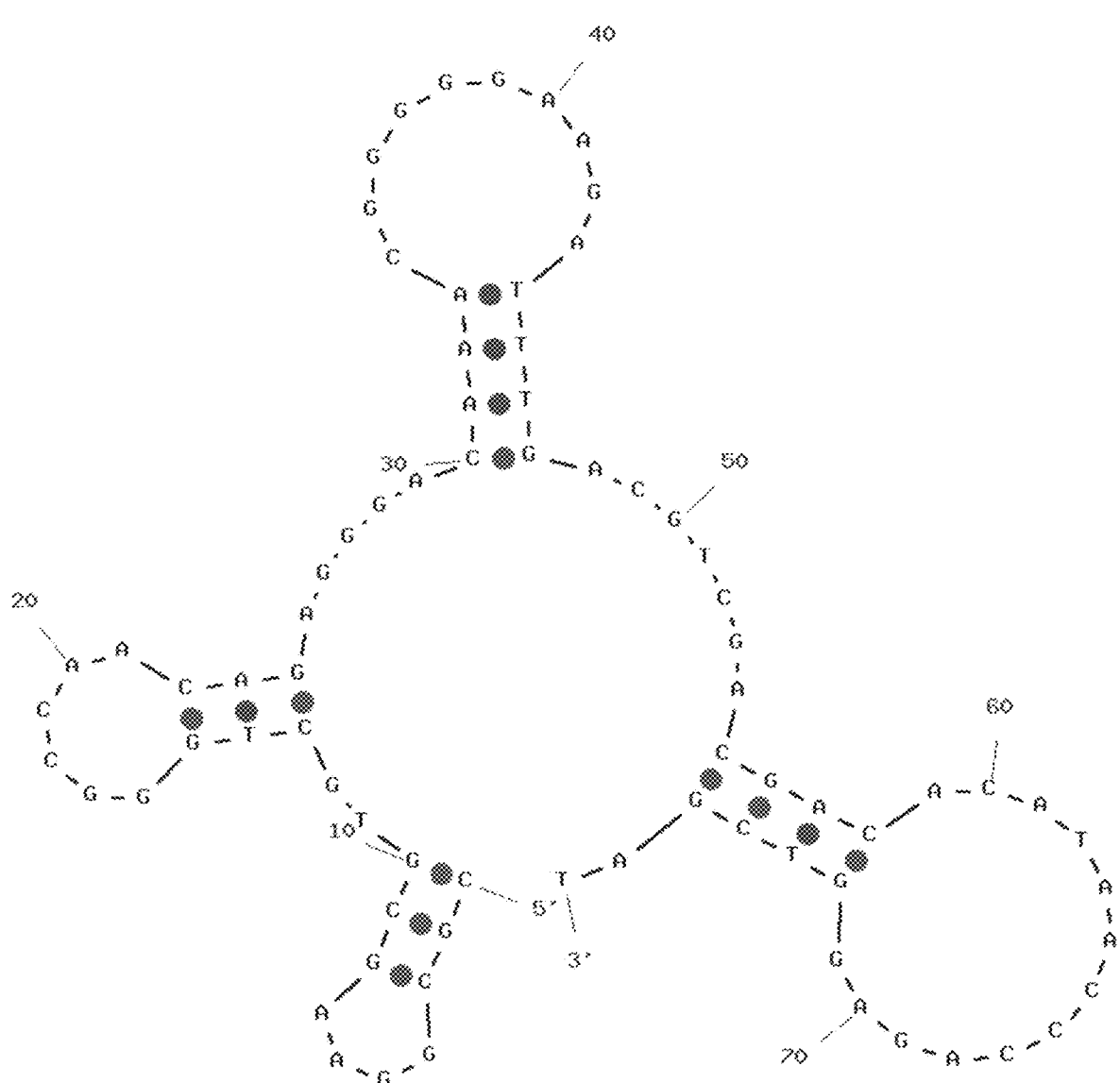
FIG. 45 depicts SEQ ID NO: 65.

Additional EpCAM aptamers are known in the art. For example: TGCGGCACACACTTCTATCTTTGCG-GAACTCCTGCGGCTC (ssDNA based EpCAM aptamer; SEQ ID NO: 63), ACGUAUCCCUUUUCGCGU (18 nt RNA EpCAM aptamer; SEQ ID NO: 64), and the aptamer depicted in FIG. 45 are known EpCAM aptamers.

Figure 46:
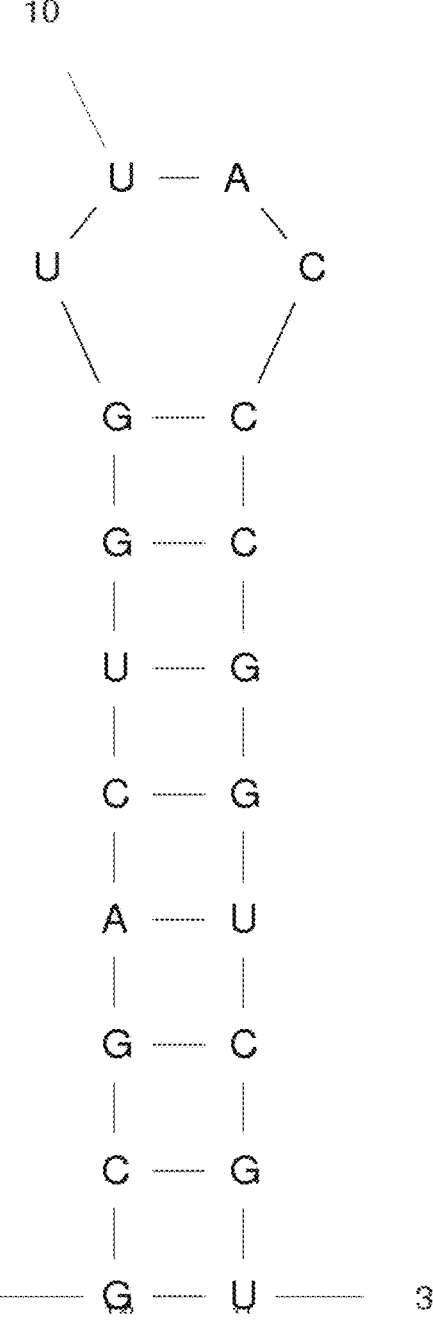
FIG. 46 depicts SEQ ID NO: 66.

A further exemplary EpCAM aptamer is depicted in FIG. 46 and available commercially from Aptagen (see, e.g., Kim et al. Identification of DNA Aptamers toward Epithelial Cell Adhesion Molecule via Cell-SELEX. Molecules and Cells, 2014, 37(10), 742-746 ISSN: 0219-1032; which is incorporated by reference herein in its entirety).

In some embodiments of any of the aspects, the EpCAM aptamer can comprise or consist of, or consist essentially of a sequence of any of SEQ ID NOs: 63-68.

In some embodiments of any of the aspects, the EpCAM aptamer can comprise or consist of, or consist essentially of a sequence having at least 80%, at least 85%, at least 90%, at least 95%, at least 98% or greater sequence identity to a sequence of any of SEQ ID NOs: 63-68. In some embodiments of any of the aspects, the EpCAM aptamer can comprise or consist of, or consist essentially of a sequence having at least 80%, at least 85%, at least 90%, at least 95%, at least 98% or greater sequence identity to a sequence of any of SEQ ID NOs: 63-68 and which retains wild-type EpCAM-binding activity.

As noted above, the chimeric molecules further comprise an inhibitory nucleic acid domain. As used herein, "inhibitory nucleic acid domain" refers to a domain comprising an inhibitory nucleic acid. As used herein, "inhibitory nucleic acid" refers to a nucleic acid molecule which can inhibit the expression of a target, e.g., double-stranded RNAs (dsRNAs), siRNAs, miRNA, antisense oligonucleotides and the like. The use of inhibitory nucleic acids (iNAs) permits the targeted degradation of mRNA transcripts, resulting in decreased expression and/or activity of the target or changes in mRNA processing (e.g., splicing changes).

The inhibitory nucleic acid domain comprises one inhibitory nucleic acid, but a chimeric molecule as described herein can comprise multiple inhibitory nucleic acid domains, e.g., repeats of a single inhibitory nucleic acid domain, or a collection of multiple different inhibitory nucleic acid domains.

In some embodiments of any of the aspects, the inhibitory nucleic acid can be a siRNA. In some embodiments of any of the aspects, a composition as described herein can comprise an EpCAM-binding domain comprising an aptamer and an inhibitory nucleic acid domain comprising an siRNA, e.g. the composition can comprise an aptamer-siRNA chimera (AsiC).

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript.

As used herein, the term "inhibitory oligonucleotide," "inhibitory nucleic acid," or "iNA" refers to an agent that contains an oligonucleotide, e.g. a DNA or RNA molecule which mediates the targeted cleavage of an RNA transcript. In some embodiments of any of the aspects, an inhibitory oligonucleotide as described herein effects inhibition of the expression and/or activity of a target gene. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid and modulate its function. In some embodiments of any of the aspects, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

In some embodiments of any of the aspects, an iNA as described herein effects inhibition of the expression and/or activity of a target, e.g. one or more of the genes described herein. In some embodiments of any of the aspects, contacting a cell with the inhibitor (e.g. an iNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iNA. In some embodiments of any of the aspects, administering an inhibitor (e.g. an iNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iNA.

In some embodiments of any of the aspects, the iNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 22 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art.

In some embodiments of any of the aspects, the nucleic acid of an iNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specified examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3-5' linkages, 2'-5' linked analogs of these, and those) having inverted polarity wherein the adjacent pairs of nucleoside units are linked 3'-5' to 5'-3' or 2-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N (CH3)-O—CH2- [known as a methylene (methylimino) or MMI backbone], —CH2-O—N(CH3)-CH2-, —CH2-N (CH3)-N(CH3)-CH2- and —N(CH3)-CH2-CH2- [wherein the native phosphodiester backbone is represented as —O—P—O—CH2-].

In other RNA mimetics suitable or contemplated for use in iNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

The RNA of an iRNA can also be modified to include one more unlocked nucleic acids (UNA). UNAs are acyclic derivatives of RNA lacking the C2'-C3' bond of the ribose ring. See, e.g., Langkjaer et al. Bioorganic & Medicinal Chemistry 2009 17:5420-5. An UNA at the 5' end of a RNA molecule can improve iRNA targeting, see e.g., Snead et al. Molecular Therapy Nucleic Acids 2013 2:E103. In some embodiments, the 5' position of the chimeric molecule and/or the inhibitory nucleic acid is a UNA.

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2)·nOCH3, O(CH2) nNH2, O(CH2) nCH3, O(CH2)nONH2, and O(CH2)nON [(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloal-kyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the phar-macodynamic properties of an iRNA, and other substituents having similar properties. In some embodiments of any of the aspects, the modification includes a 2' methoxyethoxy (2'-O—CH2CH2OCH3, also known as 2'-O-(2-methoxy-ethyl) or 2'-MOE) (Martin et al., Helv. Chim. Acta, 1995, 78:486-504) i.e., an alkoxy-alkoxy group. Another exem-plary modification is 2'-dimethylaminooxyethoxy, i.e., a O(CH2)2ON(CH3)2 group, also known as 2'-DMAOE, as described in examples herein below, and 2'-dimethylamino-ethoxyethoxy (also known in the art as 2'-O-dimethylami-noethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and gua-nine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-ami-noadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hy-droxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deaz-aguanine and 7-daazaadenine and 3-deazaguanine and 3-deazaadenine. Certain of these nucleobases are particu-larly useful for increasing the binding affinity of the inhibi-tory nucleic acids featured in the invention. These include 5-substituted pyrimidines, 6-azapyrimidines and N-2, N-6 and 0-6 substituted purines, including 2-aminopropylad-enine, 5-propynyluracil and 5-propynylcytosine. 5-methyl-eytosine substitutions have been shown to increase nucleic acid duplex stability by 0.6-1.2° C. (Sanghvi, Y. S., Crooke, S. T. and Lebleu, B., Eds., dsRNA Research and Applica-tions, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid fea-tured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Mano-haran et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholes-terol (Oberhauser et al., Nucl. Acids Res., 1992, 20:533-538), an aliphatic chain, e.g., dodecandiol or undecyl resi-dues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospho-lipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

A double-stranded inhibitory nucleic acid as described herein can further include one or more single-stranded nucleotide overhangs. The double-stranded inhibitory nucleic acid can be synthesized by standard methods known in the art as further discussed below, e.g., by use of an automated DNA synthesizer, such as are commercially available from, for example, Biosearch, Applied Biosys-tems, Inc. In some embodiments of any of the aspects, the antisense strand of a double-stranded inhibitory nucleic acid has a 1-10 nucleotide overhang at the 3' end and/or the 5' end. In some embodiments of any of the aspects, the sense strand of a double-stranded inhibitory nucleic acid has a 1-10 nucleotide overhang at the 3' end and/or the 5' end. In some embodiments of any of the aspects, at least one end of a double-stranded inhibitory nucleic acid has a single-stranded nucleotide overhang of 1 to 4, generally 1 or 2 nucleotides. Double-stranded inhibitory nucleic acids hav-ing at least one nucleotide overhang have unexpectedly superior inhibitory properties relative to their blunt-ended counterparts. In some embodiments of any of the aspects, one or more of the nucleotides in the overhang is replaced with a nucleoside thiophosphate.

As used herein, the term "nucleotide overhang" refers to at least one unpaired nucleotide that protrudes from the duplex structure of an inhibitory nucleic acid, e.g., a dsRNA. For example, when a 3'-end of one strand of a double-stranded inhibitory nucleic acid extends beyond the 5'-end of the other strand, or vice versa, there is a nucleotide over-hang. A double-stranded inhibitory nucleic acid can com-prise an overhang of at least one nucleotide; alternatively the overhang can comprise at least two nucleotides, at least three nucleotides, at least four nucleotides, at least five nucleo-tides or more. A nucleotide overhang can comprise or consist of a nucleotide/nucleoside analog, including a deoxynucle-otide/nucleoside. The overhang(s) may be on the sense strand, the antisense strand or any combination thereof. Furthermore, the nucleotide(s) of an overhang can be present on the 5' end, 3' end or both ends of either an antisense or sense strand of a double-stranded inhibitory nucleic acid.

The terms "blunt" or "blunt ended" as used herein in reference to a double-stranded inhibitory nucleic acid mean that there are no unpaired nucleotides or nucleotide analogs at a given terminal end of a dsRNA, i.e., no nucleotide overhang. One or both ends of a double-stranded inhibitory nucleic acid can be blunt. Where both ends of a double-stranded inhibitory nucleic acid are blunt, the double-stranded inhibitory nucleic acid is said to be blunt ended. To be clear, a "blunt ended" double-stranded inhibitory nucleic acid is a double-stranded inhibitory nucleic acid that is blunt at both ends, i.e., no nucleotide overhang at either end of the molecule. Most often such a molecule will be double-stranded over its entire length.

In this aspect, one of the two strands is complementary to the other of the two strands, with one of the strands being substantially complementary to a sequence of the target gene precursor or mature miRNA. As such, in this aspect, a double-stranded inhibitory nucleic acid will include two oligonucleotides, where one oligonucleotide is described as the sense strand and the second oligonucleotide is described as the corresponding antisense strand of the sense strand. As described elsewhere herein and as known in the art, the complementary sequences of a double-stranded inhibitory nucleic acid can also be contained as self-complementary regions of a single nucleic acid molecule, as opposed to being on separate oligonucleotides. In some embodiments, only a portion the molecule, e.g., the inhibitory nucleic acid domain is a double-stranded molecule.

The skilled person is well aware that inhibitory nucleic acid having a duplex structure of between 20 and 23, but specifically 21, base pairs have been hailed as particularly effective in inducing antisense-mediated inhibition (Elbashir et al., EMBO 2001, 20:6877-6888). However, others have found that shorter or longer inhibitory nucleic acids can be effective as well.

Further, it is contemplated that for any sequence identified, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of inhibitory nucleic acids based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An inhibitory nucleic acid as described herein can contain one or more mismatches to the target sequence. In some embodiments of any of the aspects, an inhibitory nucleic acid as described herein contains no more than 3 mismatches. If the antisense strand of the inhibitory nucleic acid contains mismatches to a target sequence, it is preferable that the area of mismatch not be located in the center of the region of complementarity. If the antisense strand of the inhibitory nucleic acid contains mismatches to the target sequence, it is preferable that the mismatch be restricted to be within the last 5 nucleotides from either the 5' or 3' end of the region of complementarity. For example, for a 23 nucleotide inhibitory nucleic acid agent strand which is complementary to a region of the target gene or a precursor thereof, the strand generally does not contain any mismatch within the central 13 nucleotides. The methods described herein or methods known in the art can be used to determine whether an inhibitory nucleic acid containing a mismatch to a target sequence is effective in inhibiting the expression of the target gene. Consideration of the efficacy of inhibitory nucleic acids with mismatches in inhibiting expression of the target gene is important, especially if the particular region of complementarity in the target gene is known to have polymorphic sequence variation within the population.

In some embodiments of any of the aspects, a ligand alters the distribution, targeting or lifetime of an inhibitory nucleic acid agent into which it is incorporated. In some embodiments of any of the aspects, a ligand provides an enhanced affinity for a selected target, e.g, molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as an hepatopcyte or a macrophage, among others. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP Ligands can be proteins, e.g., glycoproteins, or peptides, e.g., molecules having a specific affinity for a co-ligand, or antibodies e.g., an antibody, that binds to a specified cell type such as a hepatocyte or macrophage. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g, a drug, which can increase the uptake of the inhibitory nucleic acid agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments of any of the aspects, a ligand attached to an inhibitory nucleic acid as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

For macromolecular drugs and hydrophilic drug molecules, which cannot easily cross bilayer membranes, entrapment in endosomal/lysosomal compartments of the cell is thought to be the biggest hurdle for effective delivery to their site of action. A number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. Chem. Biol. 11, 713-723.). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. Polymers Adv. Technol. 13, 992-999; Kakudo, Chaki, T., S. et al. (2004). Transferrin-Modified Liposomes Equipped with a pH-Sensitive Fusogenic Peptide: An Artificial Viral-like Delivery System. Biochemistry 436, 5618-5628; Yessine, M. A. and Leroux, J. C. (2004). Membrane-destabilizing polyanions: interaction with lipid bilayers and endosomal escape of biomacromolecules. Adv. Drug Deliv. Rev. 56, 999-1021; Oliveira, S., van Rooy, I. et al. (2007). Fusogenic peptides enhance endosomal escape improving inhibitory nucleic acid-induced silencing of oncogenes. Int. J. Pharm. 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs is described in Biochim. Biophys. Acta 1559, 56-68).

The chimeric molecules described herein can be conjugated or bound to macromolecules to extend their half-life. Suitable macromolecules include cholesterol, PEG, a liposome, or Fc.

In certain embodiments, the endosomolytic components can be polyanionic peptides or peptidomimetics which show pH-dependent membrane activity and/or fusogenicity. A peptidomimetic can be a small protein-like chain designed to mimic a peptide. A peptidomimetic can arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Exemplary endosomolytic components include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component can contain a chemical group (e.g., an amino acid) which will undergo a change in charge or protonation in response to a change in pH. The endosomolytic component may be linear or branched. Exemplary primary sequences of endosomolytic components include H2N-(AALEALAEALEALAEALEA-LAEAAAAGGC)-CO2H (SEQ ID NO: 138); H2N-(AA-LAEALAEALAEALAEALAEALAAAAGGC)-CO2H (SEQ ID NO: 139); and H2N-(ALEALAEALEALAEA)-CONH2 (SEQ ID NO: 140).

In certain embodiments, more than one endosomolytic component can be incorporated into the inhibitory nucleic acid agent of the invention. In some embodiments of any of the aspects, this will entail incorporating more than one of the same endosomolytic component into the inhibitory nucleic acid agent. In other embodiments, this will entail incorporating two or more different endosomolytic components into inhibitory nucleic acid agent.

These endosomolytic components can mediate endosomal escape by, for example, changing conformation at endosomal pH. In certain embodiments, the endosomolytic components can exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH~7.4). "Fusogenic activity," as used herein, is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

Suitable endosomolytic components can be tested and identified by a skilled artisan. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an inhibitory nucleic acid agent described herein is constructed using one or more test or putative fusogenic agents. The inhibitory nucleic acid agent can be labeled for easy visualization. The ability of the endosomolytic component to promote endosomal escape, once the inhibitory nucleic acid agent is taken up by the cell, can be evaluated, e.g., by preparation of an endosome preparation, or by microscopy techniques, which enable visualization of the labeled inhibitory nucleic acid agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition. A two-step assay can also be performed, wherein a first assay evaluates the ability of a test compound alone to respond to changes in pH, and a second assay evaluates the ability of a modular composition that includes the test compound to respond to changes in pH.

In some embodiments of the aspects described herein, a ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

In another aspect, the ligand is a cell-permeation agent, preferably a helical cell-permeation agent. Preferably, such agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides suitable for use with the present invention can be a natural peptide, e.g., tat or antennopedia peptide, a synthetic peptide, or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to inhibitory nucleic acid agents can affect pharmacokinetic distribution of the inhibitory nucleic acid, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 141). An RFGF analogue (e.g., amino acid sequence AALLPVL-LAAP (SEQ ID NO: 142)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 143)) and the *Drosophila* Antennapedia protein (RQIKIWFQNRRMKWKK (SEQ ID NO: 144)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In some embodiments of any of the aspects, the inhibitory nucleic acid oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and poly-saccharides such as starches, glycogen, cellulose and poly-saccharide gums. Specific monosaccharides include C5 and above (preferably C5-C8) sugars; di- and trisaccharides include sugars having two or three monosaccharide units (preferably C5-C8). In some embodiments of any of the aspects, the carbohydrate conjugate further comprises other ligand such as, but not limited to, PK modulator, endoso-molytic ligand, and cell permeation peptide.

In some embodiments of any of the aspects, the inhibitory nucleic acid domain specifically binds to a gene product of one of the genes recited herein (e.g., UPF2; PARP1; APE1; PD-L1; PTPN2; SMG1; TREX1; CMAS; CD47; PLK1; and/or MCL-1). One of ordinary skill in the art is aware of how to design and produce inhibitory nucleic acids that inhibit one or more of the genes described herein. Exem-plary, non-limiting examples of inhibitory nucleic acid domain sequences are provided below herein.

In some embodiments of any of the aspects, the inhibitory nucleic acid domain inhibits the expression of a gene selected from the group consisting of UPF2; PARP1; APE1; PD-L1; PTPN2; SMG1; MCL1; TREX1; CMAS; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; APE1; PD-L1; MCL1; and CD47. In one aspect of any of the embodiments, described herein is a chimeric molecule comprising an EpCAM-binding aptamer domain and at least one inhibitory nucleic acid domain which inhibits the expression of a gene selected from the group consisting of: UPF2; PARP1; MCL1; and CD47.

As used herein, "UPF2", or "regulator of nonsense tran-scripts 2" refers to a gene encoding a protein that is part of the exon junction complex, which regulates mRNA surveil-lance. Sequences for UPF2 are known in the art for a number of species, e.g., human UPF2 (NCBI Gene ID: 26019) mRNA (NCBI Ref Seq: NM_015542.4 and NM_0805992.2).

As used herein, "PARP1", or "Poly [ADP-ribose]poly-merase 1" refers to a gene encoding a poly ADP-ribosylase that targets nuclear proteins on single strands of DNA. Sequences for PARP1 are known in the art for a number of species, e.g., human PARP1 (NCBI Gene ID: 142) mRNA (NCBI Ref Seq: NM_001618.4).

As used herein, "APE1", "APEX1", or "Apurinic/apy-rimidinic (AP) endonuclease 1" refers to a gene encoding an endonuclease involved in base excision repair. Sequences for APE1 are known in the art for a number of species, e.g., human APE1 (NCBI Gene ID: 328) mRNA (NCBI Ref Seq: NM_001244249.2, NM 001641.4, NM_080648.3, and NM_080649.3).

As used herein, "PD-L1" or "Programmed Death Ligand 1" refers to a gene encoding a transmembrane protein that modulates immune activity. Sequences for PD-L1 are known in the art for a number of species, e.g., human PD-L1

(NCBI Gene ID: 29126) mRNA (NCBI Ref Seq: NM_001267706.1, NM_001314029.2, and NM_014143.4).

As used herein, "PTPN2" or "Tyrosine-protein phos-phatase non-receptor type 2" refers to a gene encoding a tyrosine phosphatase which acts on EGFR and Shc. Sequences for PTPN2 are known in the art for a number of species, e.g., human PTPN2 (NCBI Gene ID: 5771) mRNA (NCBI Ref Seq: NM_001207013.1, NM_001308287.1, NM 002828.4, NM_080422.2, and NM_080423.2).

As used herein, "SMG1" or "Serine/threonine-protein kinase 1" refers to a gene encoding a phosphatidylinositol 3-kinase-related kinase protein family member that partici-pates in the nonsense-mediated mRNA decay (NMD) path-way. Sequences for PTPN2 are known in the art for a number of species, e.g., human SMG1 (NCBI Gene ID: 23049) mRNA (NCBI Ref Seq: NM_015092.4).

As used herein, "TREX1" or "Three prime repair exonu-clease 1" refers to a gene encoding a 5'-3' exonuclease that forms part of the SET complex. Sequences for TREX1 are known in the art for a number of species, e.g., human TREX1 (NCBI Gene ID: 11277) mRNA (NCBI Ref Seq: NM_007248.5 and NM_033629.6).

As used herein, "CMAS" or "cytidine monophosphate N-acetylneuraminic acid synthetas" refers to a gene encod-ing an enzyme that converts N-acetylneuraminic acid (Neu-NAc) to cytidine 5'-monophosphate N-acetylneuraminic acid (CMP-NeuNAc). This process is important in the formation of sialylated glycoprotein and glycolipids. This modification plays a role in cell-cell communications and immune responses. Sequences for CMAS are known in the art for a number of species, e.g., human CMAS (NCBI Gene ID: 55907) mRNA (NCBI Ref Seq: NM_018686.6).

As used herein, "CD47" refers to a gene encoding a membrane protein, which is involved in the increase in intracellular calcium concentration that occurs upon cell adhesion to extracellular matrix. The encoded protein is also a receptor for the C-terminal cell binding domain of throm-bospondin, and it may play a role in membrane transport and signal transduction. Sequences for CD47 are known in the art for a number of species, e.g., human CD47 (NCBI Gene ID: 961) mRNA (NCBI Ref Seq: NM_001777.3 and NM_198793.2).

The inhibitory nucleic acid domains of the chimeric molecules described herein can comprise one or more siRNA sequences. Exemplary siRNA sequences are pro-vided in Tables 2 and 3 below as well as in Tables 5 and 6.

In some embodiments of any of the aspects, the inhibitory nucleic acid domain comprises, consists of, or consists essentially of a sequence selected from SEQ ID NOs: 1-62, 69-126, and 149-162. In some embodiments of any of the aspects, the inhibitory nucleic acid domain comprises, con-sists of, or consists essentially of a sequence having at least 80%, at least 85%, at least 90%, at least 95%, at least 98% or greater sequence identity to a sequence selected from SEQ ID NOs: 1-62, 69-126, and 149-162. In some embodi-ments of any of the aspects, the inhibitory nucleic acid domain comprises, consists of, or consists essentially of a sequence having at least 80%, at least 85%, at least 90%, at least 95%, at least 98% or greater sequence identity to a sequence selected from SEQ ID NOs: 1-62, 69-126, and 149-162 and which retains the wild-type activity of the reference sequence (e.g., ability to specifically bind the target gene product and/or inhibit expression of the target gene).

In some embodiments of any of the aspects, the inhibitory nucleic acid domain comprises, consists of, or consists essentially of a sequence selected from SEQ ID NOs: 1-30, 38-56, 63-97, and 103-122. In some embodiments of any of the aspects, the inhibitory nucleic acid domain comprises, consists of, or consists essentially of a sequence having at least 80%, at least 85%, at least 90%, at least 95%, at least 98% or greater sequence identity to a sequence selected from SEQ ID NOs: 1-30, 38-56, 63-97, and 103-122. In some embodiments of any of the aspects, the inhibitory nucleic acid domain-comprises, consists of, or consists essentially of a sequence having at least 80%, at least 85%, at least 90%, at least 95%, at least 98% or greater sequence identity to a sequence selected from SEQ ID NOs: 1-30, 38-56, 63-97, and 103-122 and which retains the wild-type activity of the reference sequence (e.g., ability to specifically bind the target gene product and/or inhibit expression of the target gene).

In some embodiments of any of the aspects, the inhibitory nucleic acid domain comprises, consists of, or consists essentially of a sequence selected from SEQ ID NOs: 1-25, 38-56, 63-92, and 103-122. In some embodiments of any of the aspects, the inhibitory nucleic acid domain comprises, consists of, or consists essentially of a sequence having at least 80%, at least 85%, at least 90%, at least 95%, at least 98% or greater sequence identity to a sequence selected from SEQ ID NOs: 1-25, 38-56, 63-92, and 103-122. In some embodiments of any of the aspects, the inhibitory nucleic acid domain comprises, consists of, or consists essentially of a sequence having at least 80%, at least 85%, at least 90%, at least 95%, at least 98% or greater sequence identity to a sequence selected from SEQ ID NOs: 1-25, 38-56, 63-92, and 103-122 and which retains the wild-type activity of the reference sequence (e.g., ability to specifically bind the target gene product and/or inhibit expression of the target gene).

TABLE 2

Exemplary siRNA sequences

| SEQ ID NO | Target | Exemplary siRNA sequence |
|---|---|---|
| 1 | UPF2 | 5' GGUCUAGAGAGUUGCGAAU 3' |
| 2 | | 5' GCAUGUACCUUGUGUAGAA 3' |
| 3 | | 5' CGUUAUGUUUGGUGGAAGA 3' |
| 4 | | 5' CAUCAGAGUCAGUGCUAUA 3' |
| 5 | | 5' GGCUUUUGUCCCAGCCAUCUU 3' |
| 6 | CD47 | 5' GUGGAAAUUUAAAGGAAGAUU 3' |
| 7 | | 5' AAGUAUACGUAAAGUGGAAUU 3' |
| 8 | | 5' AUACAACCUCCUAGGAAUAUU 3' |
| 9 | | 5' UGACUUUAGUAGUGCAAAAUU 3' |
| 10 | | 5'-CUAUGAGACCCUUACGUGAUUGUUA-3' |
| 11 | | 5'-GCACAUGCAUCUUCUGUAUGGACAA-3' |
| 12 | PARP1 | 5' GAAAACAGGUAUUGGAUAU 3' |
| 13 | | 5' GUUCUUAGCGCACAUCUUG 3' |
| 14 | | 5' CCAAUAGGCUUAAUCCUGU 3' |
| 15 | | 5' CCGAGUACAGUGCGAGUCA 3' |

Exemplary siRNA sequences

| SEQ ID NO | Target | Exemplary siRNA sequence |
|---|---|---|
| 16 | | 5' ACGGUGAUCGGUAGCAACAAA 3' |
| 17 | | 5' CCGAGAAAUCUCUUACCUCAA 3' |
| 18 | APE1 | 5' GGACAGAGCCAGAGGCCAAUU 3' |
| 19 | | 5' GGAAGAAGCCCCAGAUAUAUU 3' |
| 20 | | 5' GGAUUAAGAAGAAAGGAUUUU 3' |
| 21 | | 5' GAGCCUGGAUUAAGAAGAAUU 3' |
| 22 | | 5' CAAAGUUUCUUACGGCAUAUU 3' |
| 23 | | 5' GUCUGGUACGACUGGAGU A-3' |
| 24 | | 5' CCUGCCACACTCAAGAUCU-3' |
| 25 | | 5' GAUGGGCUUCGAGCCUGGAUUAAGA 3' |
| 26 | PD-L1 | 5' CAUCAAGUCCUGAGUGGUAUU 3' |
| 27 | | 5' CCACCAAUUCCAAGAGAGAUU 3' |
| 28 | | 5' CACAACAACUAAUGAGAUUUU 3' |
| 29 | | 5' AUUCCAAGAGAGAGGAGAAUU 3' |
| 30 | | 5' CCUACUGGCAUUUGCUGAACGCAUU 3' |
| 31 | MCL1 | 5' GGAAUGUGCUGCUGGCUUUUU 3' |
| 32 | | 5' GGAAUGUGCUGCUGGCUUUUU 3' |
| 33 | | 5' GGAAUGUGCUGCUGGCUUUUU 3' |
| 34 | | 5' CCAAGGACACAAAGCCAAUUU 3' |
| 35 | | 5' GACGAUGUGAAAUCGUUGUTT 3' |
| 36 | | 5' CCUUUGUGGCUAAACACUUTT 3' |
| 37 | | 5' GAAATTCTTTCACTTCATT 3' |
| 38 | PTPN2 | 5' CAGAAUAGGUCUAGAAGAAUU 3' |
| 39 | | 5' GAAUAGGUCUAGAAGAAGAUU 3' |
| 40 | | 5' GAAUAGGUCUAGAAGAAGAUU 3' |
| 41 | | 5' UGGAGAAAGAAUCGGUUAAUU 3' |
| 42 | | 5-GGAGAUUCUAGUAUACAGAUU-3' |
| 43 | | 5-GUACAGGACUUUCCUCUAA-3' |
| 44 | SMG1 | 5' GAUGAAUGGUGGAGAGUUAUU 3' |
| 45 | | 5' CCUUAGAGUUCCUGAGAAAUU 3' |
| 46 | | 5' GCAGAAAGGUGGUUGACAAUU 3' |
| 47 | | 5' GCAAACUACUGGAGGAAAUUU 3' |
| 48 | | 5' GUGUAUGUGCGCCAAAGUATT 3' |
| 49 | | 5'-CCAGGACACGAGGAAACUG-3' |
| 50 | | 5'-AAAUCUCGGUGCACUAGGA-3' |
| 51 | TREX1 | 5' CCAAGACCAUCUGCUGUCAUU 3' |
| 52 | | 5' ACAAUGGUGACCGCUACGAUU 3' |

TABLE 2-continued

Exemplary siRNA sequences

| SEQ ID NO | Target | Exemplary siRNA sequence |
|---|---|---|
| 53 | CMAS | 5' AGAAAUGAUUCGAGAAGAAUU 3' |
| 54 | | 5' AAGAGAAGCUUAAGGAAAUUU 3' |
| 55 | | 5' AGACUGGGAUGGAGAAUUAUU 3' |
| 56 | | 5' AAAGAGAAGCUUAAGGAAAUU 3' |
| 57 | PLK1 | 5' GAGAAGAUGUCCAUGGAAAUU 3' |
| 58 | | 5' GGAUCAAGAAGAAUGAAUAUU 3' |
| 59 | | 5' AUGAAGAUCUGGAGGUGAAUU 3' |
| 60 | | 5' CAACCAAAGUCGAAUAUGAU.U 3' |

TABLE 2-continued

Exemplary siRNA sequences

| SEQ ID NO | Target | Exemplary siRNA sequence |
|---|---|---|
| 61 | | 5' AACCAGUGGUUCGAGAGACAG 3' |
| 62 | | 5' AAGGGCGGCUUUGCCAAGUGCUU 3' |

In Table 3, pairs of sense and antisense sequences are provided. Due to the function of an siRNA, it is contemplated herein that either the sense or antisense sequence can be incorporated into the chimeric molecule, e.g., in the same continuous nucleic acid strand as the aptamer. Accordingly, in some embodiments of any of the aspects, any chimeric molecule described herein can comprise one of the inhibitory nucleic acid sequences provided herein or the reverse complement thereof.

TABLE 3

Exemplary inhibitory nucleic acid domains. [f] indicates 2' fluro-pyrimidine modification; {Phos(H).} indicates 5' phosphate; d indicates 2' deoxy base. Where antisense sequences are provided, they are the antisense with respect to the immediately proceeding sense sequence.

| | sequence | SEQ ID NO: |
|---|---|---|
| UPF2 | | |
| Sense | G[fC]G[fU][fU]A[fU]G[fU][fU][fU]GG[fU]GGAAG[dT][dT] | 69 |
| Antisense | {Phos(H).} CUUCCACCAAACAUAACGC [dT][dT] | 70 |
| Sense | GCGUUAUGUUUGGUGGAAGTT | 71 |
| Antisense | CUUCCACCAAACAUAACGCTT | 72 |
| Alternative siRNA sequence (sense) | 5' CGGCAAACCUGGAGAGUAUUU 3' | 73 |
| Alternative siRNA sequence (antisense) | 5' UGGAAGAAGAUAAGAGAAAUU 3' | 74 |
| CD47 | | |
| Sense | GA[fU][fC]A[fU]AG[fC][fU][fC][fU]AG[fC]AGAA[dT][dT] | 75 |
| Antisense | {Phos(H).} UUCUGCUAGAGCUAUGAUC [dT][dT] | 76 |
| Sense | GAUCAUAGCUCUAGCAGAATT | 77 |
| Antisense | UUCUGCUAGAGCUAUGAUCTT | 78 |
| Alternative siRNA sequence (sense) | 5' GAGAAAAGCCCGUGAAGAAUU 3' | 79 |
| Alternative siRNA sequence (antisense) | 5' GCGCAAAGCACCGAAGAAAUU 3' | 80 |
| PARP1 | | |
| Sense | [fC][fC]AAAGGAA[fU][fU][fC][fC]GAGAAA [dT][dT] | 81 |
| Antisense | {Phos(H).} UUUCUCGGAAUUCCUUUGG [dT][dT] | 82 |
| Sense | CCAAAGGAAUUCCGAGAAATT | 83 |
| Antisense | UUUCUCGGAAUUCCUUUGGTT | 84 |

TABLE 3-continued

Exemplary inhibitory nucleic acid domains. [f] indicates
2' fluro-pyrimidine modification; {Phos(H).} indicates
5' phosphate; d indicates 2' deoxy base. Where antisense
sequences are provided, they are the antisense with respect
to the immediately proceeding sense sequence.

| | sequence | SEQ ID NO: |
|---|---|---|
| Alternative siRNA sequence (sense) | 5' CCAAAGGAAUUCCGAGAAAUU 3' | 85 |
| Alternative siRNA sequence (antisense) | 5' GGGCAAGCACAGUGUCAAAUU 3' | 86 |
| APE1 | | |
| Sense | GG[fU]GA[fU][fU]G[fU]GG[fC][fU]GAA[fU][fU][fU][dT][dT] | 87 |
| Antisense | {Phos(H).} AAAUUCAGCCACAAUCACC [dT][dT] | 88 |
| Sense | GGUGAUUGUGGCUGAAUUUTT | 89 |
| Antisense | AAAUUCAGCCACAAUCACCTT | 90 |
| Alternative siRNA sequence (sense) | 5' CUGCAUUGUGUGACAGCAAUU 3' | 91 |
| Alternative siRNA sequence (antisense) | 5' CCAACACUGCUUACGCUUAUU 3' | 92 |
| PD-L1 | | |
| Sense | AGA[fC]G[fU]AAG[fC]Ag[fU]G[U][fU]GAA [dT][dT] | 93 |
| Antisense | {Phos(H).} UUCAACACUGCUUACGUCU[dT][dT] | 94 |
| Sense | AGACGUAAGCAGUGUUGAATT | 95 |
| Antisense | UUCAACACUGCUUACGUCUTT | 96 |
| Alternative siRNA sequence (sense) | 5' GGAAAAGGAAGAUGAGCAAUU 3' | 97 |
| MCL1 | | |
| Sense | AAA[fC]GAAGG[fC]GA[fU]G[fU][fU]AAA [dT][dT] | 98 |
| Antisense | {Phos(H).}UUUAACAUCGCCUUCGUUU [dT][dT] | 99 |
| Sense | AAACGAAGGCGAUGUUAAATT | 100 |
| Antisense | UUUAACAUCGCCUUCGUUUTT | 101 |
| Alternative siRNA sequence (sense) | 5' AGGAAGAGGACGACCUAUAUU 3' | 102 |
| PTPN2 | | |
| Sense | GAGAA[fU]AGG[fU][fU][fC]AGAAGA[fU] [dT][dT] | 103 |
| Antisense | {Phos(H).} AUCUUCUGAACCUAUUCUC [dT][dT] | 104 |
| Sense | GAGAAUAGGUUCAGAAGAUTT | 105 |
| Antisense | AUCUUCUGAACCUAUUCUCTT | 106 |
| Alternative siRNA sequence (sense) | 5' GAGUGAUGGUUGAGAAGUAUU 3' | 107 |
| Alternative siRNA sequence (antisense) | 5' GAAAUGGUGUUUAAGGAAAUU 3' | 108 |
| SMG1 | | |
| Sense | F[U][fU][fU][fC]AG[fU]G[fU][fU]AG[fU][fC]A[fU]GG[fC][dT][dT] | 109 |

TABLE 3-continued

Exemplary inhibitory nucleic acid domains. [f] indicates
2' fluro-pyrimidine modification; {Phos(H).} indicates
5' phosphate; d indicates 2' deoxy base. Where antisense
sequences are provided, they are the antisense with respect
to the immediately proceeding sense sequence.

| | sequence | SEQ ID NO: |
|---|---|---|
| Antisense | {Phos(H).} GCCAUGACUAACACUGAAA [dT][dT] | 110 |
| Sense | UUUCAGUGUUAGUCAUGGCTT | 111 |
| Antisense | GCCAUGACUAACACUGAAATT | 112 |
| TREX1 | | |
| Sense | [fC][fU][fG]AG[fC]A[fU][fC][fU]G[fU][fC]AG [fU]GGA[dT][dT] | 113 |
| Antisense | {Phos(H).} UCCACUGACAGAUGCUGAG [dT][dT] | 114 |
| Sense | CUCAGCAUCUGUCAGUGGATT | 115 |
| Antisense | UCCACUGACAGAUGCUGAGTT | 116 |
| CMAS | | |
| Sense | GAA[fC][fU][fU]GAA[fU][fC][fC]AG[fC]GAAA [dT][dT] | 117 |
| Antisense | {Phos(H).} UUUCGCUGGAUUCAAGUUC [dT][dT] | 118 |
| Sense | GAACUUGAAUCCAGCGAAATT | 119 |
| Antisense | UUUCGCUGGAUUCAAGUUCTT | 120 |
| Alternative siRNA sequence (sense) | 5' AGACUGGGAUGGAGAGUUAUU 3' | 121 |
| Alternative siRNA sequence (antisense) | 5' AGAAAUGAUCCGAGAAGAAUU 3' | 122 |
| PLK1 | | |
| Sense | [fU]GAAGAAGA[fU][fC]A[fC][fC][fC][fU] [fC][fC][fU][fU]A [dT][dT] | 123 |
| Antisense | {Phos(H).} UAAGGAGGGUGAUCUUCUUCA [dT][dT] | 124 |
| Sense | UGAAGAAGAUCACCCUCCUUATT | 125 |
| Antisense | UAAGGAGGGUGAUCUUCUUCATT | 126 |

A chimeric molecule described herein can comprise more than one inhibitory nucleic acid domain, e.g., in series or flanking the aptamer. Such a structure permits the chimeric molecule to inhibit the expression of multiple genes, to provide an increased dose of inhibitory nucleic acid domains, and/or to provide multiple different inhibitory nucleic acid domains to target the same gene thereby permitting greater inhibition.

In some embodiments of any of the aspects, wherein the chimeric molecule comprises a first and at least one further inhibitory nucleic acid domain, e.g., a second and optionally a third, fourth, fifth, or more inhibitory nucleic acid domains.

In some embodiments of any of the aspects, the first and at least one further inhibitory nucleic acid domains comprise identical sequences. In some embodiments of any of the aspects, the first and at least one further inhibitory nucleic acid domains comprise different sequences but each inhibit the expression of the same gene. In some embodiments of any of the aspects, the first and at least one further inhibitory nucleic acid domains comprise different sequences and each inhibit the expression of a different gene. Any of the foregoing combinations of inhibitory nucleic acid domains can be reflect any of the possible pairwise combinations when three or more inhibitory nucleic acid domains are used. For example, in a chimeric molecule with three inhibitory nucleic acid domains where the first and second domains comprise identical sequences, the third domain can comprise i) an identical sequence, ii) a different sequence which inhibits the expression of the same gene, or iii) a different sequence which inhibits the expression of a different gene.

In some embodiments of any of the aspects, the at least a second inhibitory nucleic acid domain inhibits the expression of a gene selected from the group consisting of PLK1 and MCL1.

As used herein, "PLK1" or "polo like kinase 1" refers to a gene encoding a Ser/Thr protein kinase belonging to the CDC5/Polo subfamily. It is highly expressed during mitosis. Sequences for PLK1 are known in the art for a number of species, e.g., human PLK1 (NCBI Gene ID: 5347) mRNA (NCBI Ref Seq: NM_005030.6).

As used herein, "MCL1" or "myeloid leukemia cell differentiation protein 1" refers to a gene encoding a member of the Bcl-2 family which regulates apoptosis. Sequences for MCL1 are known in the art for a number of species, e.g., human MCL1 (NCBI Gene ID: 4170) mRNA (NCBI Ref Seq: NM_001197320.1 and NM 021960.5).

In some embodiments of any of the aspects, described herein is a first chimeric molecule comprising an inhibitory nucleic acid domain that inhibits the expression of a gene selected from UPF2; PARP1; APE1; PD-L1; MCL1; PTPN2; SMG1; TREX1; CMAS; and CD47; and a second chimeric molecule comprising an inhibitory nucleic acid domain that inhibits the expression of a second and different gene selected from UPF2; PARP1; APE1; PD-L1; MCL1; PTPN2; SMG1; TREX1; CMAS; and CD47. In some embodiments of any of the aspects, described herein is a first chimeric molecule comprising an inhibitory nucleic acid domain that inhibits the expression of a gene selected from UPF2; PARP1; APE1; PD-L1; MCL1; and CD47; and a second chimeric molecule comprising an inhibitory nucleic acid domain that inhibits the expression of a second and different gene selected from UPF2; PARP1; APE1; PD-L1; MCL1; and CD47. In some embodiments of any of the aspects, described herein is a first chimeric molecule comprising an inhibitory nucleic acid domain that inhibits the expression of a gene selected from UPF2; PARP1; and CD47; and a second chimeric molecule comprising an inhibitory nucleic acid domain that inhibits the expression of a second and different gene selected from UPF2; PARP1; APE1; PD-L1; and CD47.

In some embodiments of any of the aspects, described herein are at least four chimeric molecules, collectively comprising inhibitory nucleic acid domains that inhibit the expression of each of UPF2; PARP1; and CD47. In some embodiments of any of the aspects, described herein are at least six chimeric molecules, collectively comprising inhibitory nucleic acid domains that inhibit the expression of each of UPF2; PARP1; MCL1; PD-L1; and CD47.

In some embodiments of any of the aspects, the chimeric molecule described herein can comprise one or more linkers, e.g., between the EpCAM-binding domain and the inhibitory nucleic acid or between one or both of those domains and a further ligand or moiety. The linkers can be cleavable or non-cleavable.

The term "linker" or "linking group" means a moiety (e.g., an organic moiety) that connects two parts of a compound. In some embodiments of any of the aspects, a linker can be a polypeptide or a nucleic acid that functions to attach two domains or moieties. In some embodiments of any of the aspects, the linker connects a 5' EpCAM-binding domain to at least one 3' inhibitory nucleic acid domain. In some embodiments of any of the aspects, the linker connects a 3' EpCAM-binding domain to at least one 5' inhibitory nucleic acid domain.

A linker can comprise, for example, 1 to 1000 nucleotides or more. In some embodiments of any of the aspects, the linker comprises 1-100, 10-100, 100-900, 200-800, 300-700, 500-1000, or 700-1000 nucleotides. In some embodiments of any of the aspects, a linker can be 1-10 nucleotides in length, e.g., 1-5 nucleotides or 3 nucleotides in length The length of the linker can be optimized for one or more desired properties (e.g., separation of the domains, prevention of self-hybridization, etc).

In some embodiments of any of the aspects, linkers can comprise a direct bond or an atom such as carbon, oxygen, or sulfur, a unit such as NR8, C(O), C(O)NH, SO, SO2, SO2NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO2, N(R8), C(O), substituted or unsubstituted aryl, substituted or unsubstituted heteroaryl, substituted or unsubstituted heterocyclic; where R8 is hydrogen, acyl, aliphatic or substituted aliphatic. In some embodiments of any of the aspects, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In some embodiments of any of the aspects, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. Further examples of cleavable linking groups include but are not limited to, redox-cleavable linking groups (e.g. a disulphide linking group (—S—S—)), phosphate-based cleavable linkage groups, ester-based cleavable linking groups, and peptide-based cleavable linking groups. Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In some embodiments of any of the aspects, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

It is not necessary for all positions in a given compound to be uniformly modified, and in fact more than one of the aforementioned modifications can be incorporated in a single compound or even at a single nucleoside within an inhibitory nucleic acid.

In some embodiments of any of the aspects, the chimeric molecules described herein can comprise at least one region wherein the nucleic acid is modified so as to confer upon the inhibitory nucleic acid increased resistance to nuclease degradation, increased cellular uptake, and/or increased binding affinity for the target nucleic acid. An additional region of the inhibitory nucleic acid may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibitory nucleic acid inhibition of gene expression. Consequently, comparable results can often be obtained with shorter inhibitory nucleic acids when chimeric inhibitory nucleic acids are used, compared to, e.g., phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the nucleic acid of an inhibitory nucleic acid can be modified by a non-ligand group. A number of non-ligand molecules have been conjugated to inhibitory nucleic acids in order to enhance the activity, cellular distribution or cellular uptake of the inhibitory nucleic acid, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such nucleic acid conjugates have been listed above. Typical conjugation protocols involve the synthesis of a nucleic acid bearing an aminolinker at one or more positions of the sequence. The amino group is then reacted with the molecule being conjugated using appropriate coupling or activating reagents. The conjugation reaction may be performed either with the nucleic acid still bound to the solid support or following cleavage of the nucleic acid, in solution phase. Purification of the nucleic acid conjugate by HPLC typically affords the pure conjugate.

In some embodiments of any of the aspects, a chimeric molecule can further comprise a second strand, e.g. a nucleic acid strand which can hybridize with at least part of an inhibitory nucleic acid domain. Exemplary second or complementary (antisense) strands are provided elsewhere herein.

In some embodiments of any of the aspects, a chimeric molecule can further comprise a domain which is complementary to at least a portion of an inhibitory nucleic acid domain, e.g. a nucleic acid sequence which can hybridize with at least part of the inhibitory nucleic acid domain. Exemplary sequences are those are provided elsewhere herein as second or complementary (antisense) strands.

In some embodiments of any of the aspects, the chimeric molecule described herein can comprise, consist of, or consist essentially of a sequence of one of SEQ ID NOs: 127-137 and 163-168. In some embodiments of any of the aspects, the chimeric molecule described herein can comprise, consist of, or consist essentially of a sequence having at least 80%, at least 85%, at least 90%, at least 95%, at least 98%, or greater sequence identity to the sequence of one of SEQ ID NOs: 127-137 and 163-168. In some embodiments of any of the aspects, the chimeric molecule described herein can comprise, consist of, or consist essentially of a sequence having at least 80%, at least 85%, at least 90%, at least 95%, at least 98%, or greater sequence identity to the sequence of one of SEQ ID NOs: 127-137 and 163-168 and which retains the wild-type activity of the reference sequence (e.g. binding ability or cancer inhibition activity).

In some embodiments of any of the aspects, the chimeric molecule described herein can comprise, consist of, or consist essentially of a sequence of one of SEQ ID NOs: 127-137 and 163-168 hybridized with an antisense sequence as indicated in Table 4, 5, or 6. In some embodiments of any of the aspects, the chimeric molecule described herein can comprise, consist of, or consist essentially of a sequence having at least 80%, at least 85%, at least 90%, at least 95%, at least 98%, or greater sequence identity to the sequence of one of SEQ ID NOs: 127-137 and 163-168, hybridized with an antisense sequence having at least 80%, at least 85%, at least 90%, at least 95%, at least 98%, or greater sequence identity to the antisense sequence as indicated in Table 4, 5, or 6. In some embodiments of any of the aspects, the chimeric molecule described herein can comprise, consist of, or consist essentially of a sequence having at least 80%, at least 85%, at least 90%, at least 95%, at least 98%, or greater sequence identity to the sequence of one of SEQ ID NOs: 127-137 and 163-168 which is hybridized with an antisense sequence having at least 80%, at least 85%, at least 90%, at least 95%, at least 98%, or greater sequence identity to the antisense sequence as indicated in Table 4, 5, or 6 and which retains the wild-type activity of the reference sequence (e.g. binding ability or cancer inhibition activity).

TABLE 4

Exemplary AsiCs.

| EPCAM-AsiC sequence | | SEQ ID NO: |
|---|---|---|
| UPF2 | | |
| Sense | G[fC]GA[fC][fU]GG[fU][fU]A[fC][fC][fC]GG[fU][fC]G[fU][fU][fU]G[fC]G[fU][fU]A[fU]G[fU][fU][fU]GG[fU]GGAAG[dT][dT] | 127 |
| Antisense | {Phos(H).} CUUCCACCAAACAUAACGC [dT][dT] | 70 |
| CD47 | | |
| Sense | G[fC]GA[fC][fU]GG[fU][fU]A[fC][fC][fC]GG[fU][fC]G[fU][fU][fU]GA[fU][fC]A[fU]AG[fC][fU][fC][fU]AG[fC]AGAA[dT][dT] | 128 |
| Antisense | {Phos(H).} UUCUGCUAGAGCUAUGAUC [dT][dT] | 76 |
| PARP1 | | |
| Sense | G[fC]GA[fC][fU]GG[fU][fU]A[fC][fC][fC]GG[fU][fC]G[fU][fU][fU][fC][fC]AAAGGAA[fU][fU][fC][fC]GA GAAA [dT][dT] | 129 |
| Antisense | {Phos(H).} UUUCUCGGAAUUCCUUUGG [dT][dT] | 82 |
| APE1 | | |
| Sense | G[fC]GA[fC][fU]GG[fU][fU]A[fC][fC][fC]GG[fU][fC]G[fU][fU][fU]GG[fU]GA[fU][fU]G[fU]GG[fC][fU]GAA[fU][fU][fU][dT][dT] | 130 |
| Antisense | {Phos(H).} AAAUUCAGCCACAAUCACC [dT][dT] | 88 |
| PD-L1 | | |
| Sense | G[fC]GA[fC][fU]GG[fU][fU]A[fC][fC][fC]GG[fU][fC]G[fU][fU][fU]AGA[fC]G[fU]AAG[fC]AG[fU]G[fU][fU]GAA [dT][dT] | 131 |
| Antisense | {Phos(H).} UUCAACACUGCUUACGUCU[dT][dT] | 94 |
| MCL1 | | |
| Sense | G[fC]GA[fC][fU]GG[fU][fU]A[fC][fC][fC]GG[fU][fC]G[fU][fU][fU]AAA[fC]GAAGG[fC]GA[fU]G[fU][fU]AAA [dT][dT] | 132 |
| Antisense | {Phos(H).} UUUAACAUCGCCUUCGUUU [dT][dT] | 99 |
| PTPN2 | | |
| Sense | G[fC]GA[fC][fU]GG[fU][fU]A[fC][fC][fC]GG[fU][fC]G[fU][fU][fU]GAGAA[fU]AGG[fU][fU][fC]AGAAGA[fU] [dT][dT] | 133 |
| Antisense | {Phos(H).} AUCUUCUGAACCUAUUCUC [dT][dT] | 104 |
| SMG1 | | |
| Sense | G[fC]GA[fC][fU]GG[fU][fU]A[fC][fC][fC]GG[fU][fC]G[fU][fU][fU][fU][fU][fU][fC]AG[fU]G[fU][fU]AG[fU][fC]A[fU]GG[fC][dT][dT] | 134 |
| Antisense | {Phos(H).} GCCAUGACUAACACUGAAA [dT][dT] | 110 |

TABLE 4-continued

Exemplary AsiCs.

| | EPCAM-AsiC sequence | SEQ ID NO: |
|---|---|---|
| TREX1 | | |
| Sense | G[fC]GA[fC][fU]GG[fU][fU]A[fC][fC][fC]GG[fU][fC]G[*fU*][*fU*][*fU*] [fC][fU][fC]AG[fC]A[fU][fC][fU]G[fU][fC]AG[fU]GGA[dT][dT] | 135 |
| Antisense | {Phos(H).} UCCACUGACAGAUGCUGAG [dT][dT] | 114 |
| CMAS | | |
| Sense | G[fC]GA[fC][fU]GG[fU][fU]A[fC][fC][fC]GG[fU][fC]G[*fU*][*fU*][*fU*] GAA[fC][fU][fU]GAA[fU][fC][fC]AG[fC]GAAA[dT][dT] | 136 |
| Antisense | {Phos(H).} UUUCGCUGGAUUCAAGUUC [dT][dT] | 118 |
| PLK1 | | |
| Sense | G[fC]GA[fC][fU]GG[fU][fU]A[fC][fC][fC]GG[fU][fC]G[*fU*][*fU*][*fU*] [fU]GAAGAAGA[fU][fC]A[fC][fC][fC][fU][fC][fC][fU][fU]A [dT][dT] | 137 |
| Antisense | {Phos(H).} UAAGGAGGGUGAUCUUCUUCA [dT][dT] | 124 |

Note:
Bold portion shows EpCAM aptamer sequence;
italics portion (UUU) is the linker region,
normal text region is the siRNA region
[f] indicates 2' fluro-pyrimidine modification;
{Phos(H).} indicates 5' phosphate;
d indicates 2' deoxy base In some embodiments of any of the aspects, a chimeric molecule described herein can further comprise a chemotherapeutic agent, e.g., conjugated to the chimeric molecule. Exemplary, non-limiting chemotherapeutic agents include paclitaxel and other chemotherapeutics described herein.

In one aspect of any of the embodiments, described herein is a pharmaceutical composition, kit, or combination comprising at least one chimeric molecule as described herein and, optionally, a pharmaceutically acceptable carrier. Compositions, kits, or combinations can comprise multiple sequence-distinct chimeric molecules or a population of a single chimeric molecule.

In some embodiments of any of the aspects, the composition, kit, or combination comprises at least two chimeric molecules, wherein the chimeric molecules have different aptamer domains or inhibitory nucleic acid domains. In some embodiments of any of the aspects, the different inhibitory nucleic acid domains recognize different targets. In some embodiments of any of the aspects, the different inhibitory nucleic acid domains have different sequences and recognize the same target.

In one aspect of any of the embodiments, described herein is a pharmaceutical composition, kit, or combination comprising: i) a first chimeric molecule as described herein comprising at least one inhibitory nucleic acid domain that inhibits the expression of a gene selected from UPF2; PARP1; APE1; MCL1; PD-L1; PTPN2; SMG1; TREX1; CMAS; and CD47; and ii) a second chimeric molecule comprising: a chimeric molecule as described herein, wherein the at least one inhibitory nucleic acid domain of the second chimeric molecule inhibits the expression of a different gene than the first chimeric molecule and/or inhibits the expression of a gene selected from the group consisting of PLK1 and MCL1.

A kit is an assemblage of materials or components, including at least one of the chimeric molecules described herein. The exact nature of the components configured in the kit depends on its intended purpose. In some embodiments of any of the aspects, the kit is configured particularly for human subjects. In further embodiments, the kit is configured for veterinary applications, treating subjects such as, but not limited to, farm animals, domestic animals, and laboratory animals.

In some embodiments of any of the aspects, a kit includes instructions for use. "Instructions for use" typically include a tangible expression describing the technique to be employed in using the components of the kit to affect a desired outcome in a subject. Still in accordance with the present invention, "instructions for use" may include a tangible expression describing the preparation of a chimeric molecule and/or at least one method parameter, such as dosage requirements and administration instructions, and the like, typically for an intended purpose. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of a chimeric molecule described herein. The packaging material generally has an external label which indicates the contents and/or purpose of the kit and/or its components.

In a combination of multiple chimeric molecules, the different chimeric molecules can be provided in a mixture or single formulation. Alternatively, the different chimeric molecules can be provided in separate formulations that are packaged or provided as a set or kit.

In some embodiments of any of the aspects, the technology described herein relates to a pharmaceutical composition comprising at least one chimeric molecule as described herein, and optionally a pharmaceutically acceptable carrier. In some embodiments of any of the aspects, the active ingredients of the pharmaceutical composition comprise at least one chimeric molecule as described herein. In some embodiments of any of the aspects, the active ingredients of the pharmaceutical composition consist essentially of at least one chimeric molecule as described herein. In some embodiments of any of the aspects, the active ingredients of the pharmaceutical composition consist of at least one chimeric molecule as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C$_2$-C$_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. at least one chimeric molecule as described herein.

In some embodiments of any of the aspects, the pharmaceutical composition comprising at least one chimeric molecule as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of at least one chimeric molecule as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of the active ingredient as disclosed herein can also be incorporated into the parenteral dosage forms of the disclosure, including conventional and controlled-release parenteral dosage forms.

Pharmaceutical compositions comprising at least one chimeric molecule can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the at least one chimeric molecule can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the chimeric molecule(s) described herein are provided in a kit or combination with, or provided in a composition further comprising, or are administered with an immune checkpoint inhibitor, e.g., an immune checkpoint inhibitor antibody reagent.

Immune checkpoint inhibitors inhibit one or more immune checkpoint proteins. The immune system has multiple inhibitory pathways that are critical for maintaining self-tolerance and modulating immune responses. For example, in T-cells, the amplitude and quality of response is initiated through antigen recognition by the T-cell receptor and is regulated by immune checkpoint proteins that balance co-stimulatory and inhibitory signals. In some embodiments of any of the aspects, a subject or patient is treated with at least one inhibitor of an immune checkpoint protein. As used herein, "immune checkpoint protein" refers to a protein which, when active, exhibits an inhibitory effect on immune activity, e.g., T cell activity. Exemplary immune checkpoint proteins can include PD-1 (e.g., NCBI Gene ID: 5133); PD-L1 (e.g., NCBI Gene ID: 29126); PD-L2 (e.g., NCBI Gene ID: 80380); TIM-3 (e.g., NCBI Gene ID: 84868); CTLA4 (e.g., NCBI Gene ID: 1493); TIGIT (e.g., NCBI Gene ID: 201633); KIR (e.g., NCBI Gene ID: 3811); LAG3 (e.g., NCBI Gene ID: 3902); DD1-α (e.g., NCBI Gene ID: 64115); A2AR (e.g., NCBI Gene ID: 135); B7-H3 (e.g., NCBI Gene ID: 80381); B7-H4 (e.g., NCBI Gene ID: 79679); BTLA (e.g., NCBI Gene ID: 151888); IDO (e.g., NCBI Gene ID: 3620); TDO (e.g., NCBI Gene ID: 6999); HVEM (e.g., NCBI Gene ID: 8764); GAL9 (e.g., NCBI Gene ID: 3965); 2B4 (belongs to the CD2 family of molecules and is expressed on all NK, γδ, and memory CD8+ (cp) T cells) (e.g., NCBI Gene ID: 51744); CD160 (also referred to as BY55) (e.g., NCBI Gene ID: 11126); and various B-7 family ligands. B7 family ligands include, but are not limited to, B7-1, B7-2, B7-DC, B7-H1, B7-H2, B7-H3, B7-H4, B7-H5, B7-H6 and B7-H7.

Non-limiting examples of immune checkpoint inhibitors (with checkpoint targets and manufacturers noted in parantheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CellDex); MEDI-6769 (Ox40; MedImmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); IMP321, a soluble Ig fusion protein (Brignone et al., 2007, J. Immunol. 179:4202-4211); the anti-B7-H3 antibody MGA271 (Loo et al., 2012, Clin. Cancer Res. July 15 (18) 3834); TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94); anti-CTLA-4 antibodies described in U.S. Pat. Nos. 5,811,097; 5,811,097; 5,855, 887; 6,051,227; 6,207,157; 6,682,736; 6,984,720; and 7,605,238; tremelimumab, (ticilimumab, CP-675,206); ipilimumab (also known as 10D1, MDX-D010); PD-1 and PD-L1 blockers described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; nivolumab (MDX 1106, BMS 936558, ONO 4538); lambrolizumab (MK-3475 or SCH 900475); CT-011; AMP-224; and BMS-936559 (MDX-1105-01). The foregoing references are incorporated by reference herein in their entireties.

In some embodiments of any of the aspects, the immune checkpoint protein is PD-1 or PD-L1. In some embodiments of any of the aspects, the immune checkpoint protein is PD-1.

In some embodiments of any of the aspects, the immune checkpoint inhibitor is pembrolizumab (PD-1; Merck); nivolumab (PD-1; Bristol Meyers Squibb); atezolizumab (PD-L1; Genentech); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); or a PD-1 and PD-L1 blocker described in U.S. Pat. Nos. 7,488,802; 7,943,743; 8,008, 449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments of any of the aspects, the immune checkpoint inhibitor is pembrolizumab (PD-1; Merck);

nivolumab (PD-1; Bristol Meyers Squibb); pidilizumab (PD-1; Medivation); AUNP12 (PD-1; Aurigene); or a PD-1 blocker described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof, including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994; which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998'EMBO J. 17: 3512-3520; each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies, being extremely thermostable, stable to extreme pH and to proteolytic digestion, and poorly antigenic. See U.S. patent application 20040161738 published Aug. 19, 2004; which is incorporated by reference herein in its entirety. These features combined with the low antigenicity to humans indicate great therapeutic potential.

In some embodiments of any of the aspects, the methods described herein relate to treating a subject having or diagnosed as having cancer with a composition as described herein. Subjects having cancer can be identified by a physician using current methods of diagnosing cancer. Symptoms and/or complications of cancer which characterize these conditions and aid in diagnosis are well known in the art and include but are not limited to, for example, in the case of breast cancer a lump or mass in the breast tissue, swelling of all or part of a breast, skin irritation, dimpling of the breast, pain in the breast or nipple, nipple retraction, redness, scaliness, or irritation of the breast or nipple, and nipple discharge. Tests that may aid in a diagnosis of, e.g. breast cancer include, but are not limited to, mammograms, x-rays, MRI, ultrasound, ductogram, a biopsy, and ductal lavage. A family history of cancer or exposure to risk factors for cancer (e.g. smoke, radiation, pollutants, BRCA1 mutation, etc.)

In some embodiments of any of the aspects, the chimeric molecules described herein provide a therapeutic effect via immune therapy, e.g., as opposed merely to direct killing of tumor cells. As described herein, certain chimeric molecules that directly kill the tumor also induce immune responses in the tumor and combinations of cytotoxic and immune-modulating AsiCs improve tumor suppression.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In some embodiments of any of the aspects, the cancer is an epithelial cancer. In some embodiments of any of the aspects, the cancer is breast cancer, colon cancer, or triple-negative breast cancer. In some embodiments of any of the aspects, the cancer is a HER2+ cancer. In some embodiments of any of the aspects, the cancer is not BRCA1 deficient, e.g., the patient does not have a BRCA1 mutation or oncomutation.

The compositions and methods described herein can be administered to a subject having or diagnosed as having cancer. In some embodiments of any of the aspects, the methods described herein comprise administering an effective amount of compositions described herein to a subject in order to alleviate a symptom of a cancer. As used herein, "alleviating a symptom" of a cancer is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic. In some embodiments of any of the aspects, the administration is subcutaneous.

The term "effective amount" as used herein refers to the amount of at least one chimeric molecule needed to alleviate at least one or more symptom of the disease or disorder, and relates to a sufficient amount of pharmacological composition to provide the desired effect. The term "therapeutically effective amount" therefore refers to an amount of at least one chimeric molecule that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor growth, among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments of any of the aspects, the at least one chimeric molecule described herein is administered as a monotherapy, e.g., another treatment for the cancer is not administered to the subject.

In some embodiments of any of the aspects, the methods described herein can further comprise administering a second agent and/or treatment to the subject, e.g. as part of a combinatorial therapy. In some embodiments of any of the aspects, the second agent is paclitaxel. In some embodiments of any of the aspects, described herein, the second agent is a taxane (e.g. docetaxel or paclitaxel).

Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate;

hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising at least one chimeric molecule as described herein can be administered to a patient once. In certain embodiments, an effective dose of a composition comprising at least one chimeric molecule can be administered to a patient repeatedly. For systemic administration, subjects can be administered a therapeutic amount of a composition comprising at least one chimeric molecule, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size or growth rate by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the at least one chimeric molecule. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising at least one chimeric molecule can be administered over a period of time, such as over a 5 minute, 10 minute, 15 minute, 20 minute, or 25 minute period.

The dosage ranges for the administration of at least one chimeric molecule, according to the methods described herein depend upon, for example, the form of the at least one chimeric molecule, its potency, and the extent to which symptoms, markers, or indicators of a condition described herein are desired to be reduced, for example the percentage reduction desired for tumor size or growth rate. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of the at least one chimeric molecule in, e.g. the treatment of a condition described herein, or to induce a response as described herein (e.g. reduction in tumor size and/or growth rate) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. cancer cell survival. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. the targeted gene in cancer cells.

In vitro and animal model assays are provided herein which allow the assessment of a given dose of the at least one chimeric molecule. By way of non-limiting example, the effects of a dose of the at least one chimeric molecule can be assessed by cancer cell expression analysis or survival rates. The efficacy of a given dosage combination can also be assessed in an animal model, e.g. a mouse model of cancer.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In some embodiments of any of the aspects, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments of any of the aspects, the expression of a biomarker(s), target(s), or gene/polypeptide described herein is/are tissue-specific. In some embodiments of any of the aspects, the expression of a biomarker(s), target(s), or gene/polypeptide described herein is/are global. In some embodiments of any of the aspects, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer"

sequences, as well as intervening sequences (introns) between individual coding segments (exons).

"Marker" in the context of the present invention refers to an expression product, e.g., nucleic acid or polypeptide which is differentially present in a sample taken from subjects having having cancer, as compared to a comparable sample taken from control subjects (e.g., a healthy subject). The term "biomarker" is used interchangeably with the term "marker."

In some embodiments of any of the aspects, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean 11%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A chimeric molecule comprising an EpCAM-binding aptamer domain and at least one inhibitory nucleic acid domain which inhibits the expression of a gene selected from the group consisting of:
UPF2; PARP1; APE1; PD-L1; PTPN2; SMG1; TREX1; CMAS; and CD47.

2. The molecule of paragraph 1, wherein the molecule is an aptamer-siRNA chimera (AsiC).

3. The molecule of any of paragraphs 1-2, wherein the inhibitory nucleic acid specifically binds to a gene product of the selected gene.

4. The molecule of any of paragraphs 1-3, wherein the EpCam-binding aptamer domain comprises the sequence of any of SEQ ID NOs: 63-68.

5. The molecule of any of paragraphs 1-4, wherein the inhibitory nucleic acid domain comprises a sequence selected from SEQ ID NOs: 1-62 and 69-126, or the reverse complement thereof.

6. The molecule of any of paragraphs 1-5, wherein the chimeric molecule comprises a first and at least one further inhibitory nucleic acid domain.

7. The molecule of paragraph 6, wherein the first and at least one further inhibitory nucleic acid domains comprise different sequences but each inhibit the expression of the same gene.

8. The molecule of paragraph 6, wherein the first and at least one further inhibitory nucleic acid domains each inhibit the expression of a different gene.

9. The molecule of paragraph 8, wherein the at least a second inhibitory nucleic acid domain inhibits the expression of a gene selected from the group consisting of:
PLK1 and MCL1.

10. The molecule of any of paragraphs 1-9, comprising the sequence of one of SEQ ID NOs: 127-137.

11. The molecule of any of paragraphs 1-10, wherein the 3' end of the chimeric molecule comprises dTdT.

12. The molecule of any of paragraphs 1-11, wherein the chimeric molecule comprises at least one 2'-F pyrimidine.

13. The molecule of any of paragraphs 1-12, wherein the chimeric molecule further comprises a chemotherapeutic agent.

14. A pharmaceutical composition, kit, or combination comprising the chimeric molecule of any of paragraphs 1-13 and optionally a pharmaceutically acceptable carrier.

15. The composition, kit, or combination of paragraph 14, comprising at least two chimeric molecules, wherein the chimeric molecules have different aptamer domains or inhibitory nucleic acid domains.

16. The composition, kit, or combination of paragraph 15, wherein the different inhibitory nucleic acid domains recognize different targets.

17. The composition, kit, or combination of paragraph 15, wherein the different inhibitory nucleic acid domains have different sequences and recognize the same target.

18. A pharmaceutical composition, kit, or combination comprising:
a. a first chimeric molecule of any of paragraphs 1-13;
b. a second chimeric molecule comprising:
i. a chimeric molecule of any of paragraph 1-13, wherein the inhibitory nucleic acid domain of the second chimeric molecule inhibits the expression of a different gene than the first chimeric molecule; or
ii. a chimeric molecule comprising an EpCAM-binding aptamer domain and an inhibitory nucleic acid domain which inhibits the expression of a gene selected from the group consisting of:
PLK1 and MCL1; and
c. optionally a pharmaceutically acceptable carrier 19. A method of treating cancer in a subject in need thereof, the method comprising administering a chimeric molecule, composition, kit, or combination of any of paragraphs 1-18 to the subject.

20. The method of paragraph 19, wherein the cancer is an epithelial cancer, breast cancer, colon cancer, or triple-negative breast cancer.

21. The method of any of paragraphs 19-20, wherein the administration is subcutaneous.

22. The method of any of paragraphs 19-21, wherein the subject is further administered an additional cancer treatment.

23. The method of paragraph 22, wherein the cancer treatment is paclitaxel.

24. A chimeric molecule, composition, or kit of any of paragraphs 1-18, for use in a method of treating cancer in a subject in need thereof, the method comprising administering the chimeric molecule, to the subject.

25. The chimeric molecule, composition, or kit of paragraph 24, wherein the cancer is an epithelial cancer, breast cancer, colon cancer, or triple-negative breast cancer.

26. The chimeric molecule, composition, or kit of any of paragraphs 24-25, wherein the administration is subcutaneous.

27. The chimeric molecule, composition, or kit of any of paragraphs 24-26, wherein the subject is further administered an additional cancer treatment.

28. The kit of any of paragraphs 24-26, further comprising an additional cancer treatment in the same or a separate formulation as the chimeric molecule.

29. The chimeric molecule, composition, or kit of any of paragraphs 27-28, wherein the cancer treatment is paclitaxel.

Some embodiments of the technology described herein can be defined according to any of the following numbered paragraphs:

1. A chimeric molecule comprising an EpCAM-binding aptamer domain and at least one inhibitory nucleic acid domain which inhibits the expression of a gene selected from the group consisting of:
UPF2; PARP1; APE1; PD-L1; MCL1; PTPN2; SMG1; TREX1; CMAS; and CD47.

2. The molecule of paragraph 1, wherein the gene is selected from the group consisting of:
UPF2; PARP1; APE1; PD-L1; MCL1; and CD47.

3. The molecule of paragraph 1, wherein the gene is selected from the group consisting of:
UPF2; PD-L1; MCL1; and CD47.

4. The molecule of any of the preceding paragraphs, wherein the molecule is an aptamer-siRNA chimera (AsiC).

5. The molecule of any of the preceding paragraphs, wherein the inhibitory nucleic acid specifically binds to a gene product of the selected gene.

6. The molecule of any of the preceding paragraphs, wherein the EpCam-binding aptamer domain comprises the sequence of any of SEQ ID NOs: 63-68.

7. The molecule of any of the preceding paragraphs, wherein the inhibitory nucleic acid domain comprises a sequence selected from SEQ ID NOs: 1-62, 69-126, and 149-162, or the reverse complement thereof.

8. The molecule of any of the preceding paragraphs, wherein the chimeric molecule comprises a first and at least one further inhibitory nucleic acid domain.

9. The molecule of paragraph 8, wherein the first and at least one further inhibitory nucleic acid domains comprise different sequences but each inhibit the expression of the same gene.

10. The molecule of paragraph 8, wherein the first and at least one further inhibitory nucleic acid domains each inhibit the expression of a different gene.

11. The molecule of paragraph 10, wherein the at least a second inhibitory nucleic acid domain inhibits the expression of a gene selected from the group consisting of:
   PLK1 and MCL1.

12. The molecule of any of the preceding paragraphs, comprising the sequence of one of SEQ ID NOs: 127-137 or 163-168.

13. The molecule of any of the preceding paragraphs, wherein the molecule is a single-stranded nucleic acid.

14. The molecule of any of paragraphs 1-12, wherein the molecule comprises a double-stranded portion.

15. The molecule of paragraph 14, wherein the double-stranded portion comprises two separate nucleic acids hybridized to each other or comprises a single nucleic acid in which two portions of the single nucleic acid are hybridized to each other (e.g., a hairpin structure).

16. The molecule of any of the preceding paragraphs, wherein the 3' end of the chimeric molecule comprises dTdT.

17. The molecule of any of the preceding paragraphs, wherein the chimeric molecule comprises at least one 2'-F pyrimidine.

18. The molecule of any of the preceding paragraphs, wherein the chimeric molecule comprises one or more of a 2' sugar modification, a phosphothiorate backbone modification, and a 5' unlocked nucleic acid modification.

19. The molecule of any of the preceding paragraphs, wherein the chimeric molecule is conjugated or bound to a cholesterol, a PEG, or a liposome.

20. The molecule of any of the preceding paragraphs, wherein the chimeric molecule further comprises a chemotherapeutic agent.

21. A pharmaceutical composition, kit, or combination comprising the chimeric molecule of any of paragraphs 1-20 and optionally a pharmaceutically acceptable carrier.

22. The composition, kit, or combination of paragraph 21, comprising at least two different chimeric molecules of any of paragraphs 1-20, wherein the chimeric molecules have different aptamer domains or inhibitory nucleic acid domains.

23. The composition, kit, or combination of paragraph 21, wherein the different inhibitory nucleic acid domains recognize different targets.

24. The composition, kit, or combination of paragraph 21, wherein the different inhibitory nucleic acid domains have different sequences and recognize the same target.

25. The composition, kit, or combination of any of paragraphs 21-24, wherein a first chimeric molecule of paragraphs 1-20 comprises an inhibitory nucleic acid domain that inhibits the expression of a gene selected from:
   UPF2; PARP1; APE1; PD-L1; MCL1; PTPN2; SMG1; TREX1; CMAS; and CD47; and
   a second chimeric molecule of paragraphs 1-20 comprises an inhibitory nucleic acid domain that inhibits the expression of a second and different gene selected from:
   UPF2; PARP1; APE1; PD-L1; MCL1; PTPN2; SMG1; TREX1; CMAS; and CD47.

26. The composition, kit, or combination of any of paragraphs 21-25, wherein a first chimeric molecule of paragraphs 1-20 comprises an inhibitory nucleic acid domain that inhibits the expression of a gene selected from:
   UPF2; PARP1; APE1; PD-L1; MCL1; and CD47; and
   a second chimeric molecule of paragraphs 1-20 comprises an inhibitory nucleic acid domain that inhibits the expression of a second and different gene selected from:
   UPF2; PARP1; APE1; PD-L1; MCL1; and CD47.

27. The composition, kit, or combination of any of paragraphs 21-26, comprising at least six different chimeric molecules of paragraphs 1-20, collectively comprise inhibitory nucleic acid domains that inhibit the expression of each of UPF2; PARP1; APE1; PD-L1; MCL1; and CD47.

28. The composition, kit, or combination of any of paragraphs 21-27, wherein a first chimeric molecule of paragraphs 1-20 comprises an inhibitory nucleic acid domain that inhibits the expression of a gene selected from:
   UPF2; PD-L1; MCL1; and CD47; and
   a second chimeric molecule of paragraphs 1-20 comprises an inhibitory nucleic acid domain that inhibits the expression of a second and different gene selected from:
   UPF2; PD-L1; MCL1; and CD47.

29. The composition, kit, or combination of any of paragraphs 21-28, comprising at least four different chimeric molecules of paragraphs 1-20, collectively comprise inhibitory nucleic acid domains that inhibit the expression of each of UPF2; PD-L1; MCL1; and CD47.

30. A pharmaceutical composition, kit, or combination comprising:
   a. a first chimeric molecule of any of paragraphs 1-20;
   b. a second chimeric molecule comprising:
      i. a chimeric molecule of any of paragraph 1-20, wherein the inhibitory nucleic acid domain of the second chimeric molecule inhibits the expression of a different gene than the first chimeric molecule; or
      ii. a chimeric molecule comprising an EpCAM-binding aptamer domain and an inhibitory nucleic acid domain which inhibits the expression of a gene selected from the group consisting of:
         PLK1 and MCL1; and
   c. optionally a pharmaceutically acceptable carrier 31. The composition, kit, or combination of any of paragraphs 21-30, further comprising an immune checkpoint inhibitor.

32. The composition, kit, or combination of paragraph 31, wherein the immune checkpoint protein is PD-1 or PD-L1.

33. The composition, kit, or combination of paragraph 32, wherein the immune checkpoint protein is PD-1.

34. The composition, kit, or combination of paragraph 33, wherein the immune checkpoint inhibitor is pembrolizumab; nivolumab; pidilizumab; or AUNP12.

35. A method of treating cancer in a subject in need thereof, the method comprising administering a chimeric molecule, composition, kit, or combination of any of paragraphs 1-34 to the subject.

36. The method of paragraph 35, wherein the cancer is an epithelial cancer, breast cancer, or colon cancer.

37. The method of paragraph 36, wherein the breast cancer is a HER2+ or triple-negative breast cancer (TNBC).

38. The method of paragraph 36, wherein the breast cancer is not BRCA1 deficient.

39. The method of any of paragraphs 35-38, wherein the administration is subcutaneous.

40. The method of any of paragraphs 35-39, wherein the subject is further administered an additional cancer treatment.

41. The method of paragraph 40, wherein the cancer treatment is paclitaxel.

42. A chimeric molecule, composition, or kit of any of paragraphs 1-34, for use in a method of treating cancer in a subject in need thereof, the method comprising administering the chimeric molecule, to the subject.

43. The chimeric molecule, composition, or kit of paragraph 42, wherein the cancer is an epithelial cancer, breast cancer, or colon cancer.

44. The chimeric molecule, composition, or kit of paragraph 43, wherein the breast cancer is a HER2+ or triple-negative breast cancer (TNBC).

45. The chimeric molecule, composition, or kit of paragraph 44, wherein the breast cancer is not BRCA1 deficient.

46. The chimeric molecule, composition, or kit of any of paragraphs 42-46, wherein the administration is subcutaneous.

47. The chimeric molecule, composition, or kit of any of paragraphs 42-46, wherein the subject is further administered an additional cancer treatment.

48. The kit of any of paragraphs 42-47, further comprising an additional cancer treatment in the same or a separate formulation as the chimeric molecule.

49. The chimeric molecule, composition, or kit of any of paragraphs 42-48, wherein the cancer treatment is paclitaxel.

EXAMPLES

Example 1: Enhancing Immunotherapy Triple-Negative and HER+2 Breast Cancer Using EpCAM Aptamer-siRNA Mediated Gene Knockdown Described herein are conjugates of an EpCAM aptamer and a siRNA, the conjugate is two RNA molecules. The ends are complementary and bind to each other. Once the conjugate enters a cell the enzyme Dicer destroys the double stranded RNA freeing the siRNA to knockout its complementary mRNA—effectively shutting down the targeted gene. Triple negative and HER2 breast cancers are not well treated with present technology, a need which is addressed by the compositions described herein.

Triple-negative (TNBC) and HER2+ breast cancers (BCs) are especially aggressive tumors with the worst prognosis.

They are prone to relapse and metastasize post chemo- or targeted therapy. Immunotherapy, which has achieved significant therapeutic benefits in some cancers, provides a promising, but unproven, alternative approach for treating poor prognosis BCs. BCs have relatively low nonsynonymous mutation rates, which make many of them poorly immunogenic. Novel strategies to increase BC cell immunogenicity and improve tumor-antigen specific T cell responses will be critical to enhance the efficacy of BC immune therapy.

Described herein are methods of increasing the immunogenicity of breast tumors by taking advantage of the unique strength of EpCAM aptamer carried small interfering RNAs (AsiCs). EpCAM-AsiCs can specifically knockdown any gene product, including intracellular and undruggable targets, selectively in EpCAM+ BC tumor cells. Immune-modulating EpCAM-AsiCs target genes involved in different functional process of the cancer-immunity cycle, which makes aggressive BCs visible to T cells, improves T cell tumor recruitment and functions and therefore enhances antitumor immune responses.

These AsiCs administered subcutaneously (sc) are selectively taken up by cells at distant sites in the body bearing the receptor recognized by the aptamer. Inside cells, AsiCs are cleaved by the RNA interference nuclease Dicer to liberate an active siRNA that causes efficient gene knockdown. EpCAM is a tumor-specific antigen expressed at several logs higher levels on all epithelial cancers relative to normal epithelia, including 97% of BCs, and their 'cancer stem cells'. Described herein are high affinity EpCAM-AsiCs, using an EpCAM aptamer that binds with low nanomolar affinity to both mouse and human EpCAM. These EpCAM-AsiCs accumulate selectively in EpCAM+ BCs, but not normal tissue. To be clinically useful, EpCAM-AsiCs need to be taken up by distant tumors. sc injected EpCAM-AsiC concentrate in distant EpCAM+ but not EpCAM– TNBC xenografts in mice and persisted there for at least 4 days.

The use of EpCAM-AsiCs for BC immune modulation was explored by knocking down genes controlling different functional processes. 1) Nonsense-mediated mRNA decay (NMD) is an evolutionarily conserved surveillance mechanism that detects and degrades mRNAs that contain premature termination codons (PTCs), which can arise from different gene mutations and frame-shifts. These mRNAs, if translated, produce truncated proteins with aberrant functions. UPF2 is a key enzyme in NMD. Knocking down UPF2 in EpCAM+ BC cells will cause them to express and present neoantigens that T cells recognize. As described herein, UPF2 EpCAM-AsiC can boost antitumor T cell responses.

2) PARP1 is involved in the detection of DNA damage, DNA repair, and the maintenance of genomic stability. PARP1 inhibition leads to chromosomal abnormalities and may contribute to overall genome instability. The major function of APE1 is to repair the abasic sites in base excision repair (BER). In addition, APE1 functions as a reduction-oxidation regulator, which plays a critical role in tumor cell survival. Knocking down DNA repair enzymes PARP1 and APE1 in tumor cells according to the method described herein can produce more DNA strand break related mutations, therefore introducing tumor-specific neoantigens to the immune system. In addition, inhibiting the redox activity of APE1 can directly suppress tumor growth. It is demonstrated herein that both Parp1-AsiC and APE1-AsiC significantly suppress tumor progression and enhance the function of CD8+ tumor-infiltrating lymphocytes (TILs). PARP1-AsiC also outperforms the FDA-approved drug Olaparib to further inhibit 4T1E (4T1 cell line with high EpCAM expression) breast tumor growth.

3) Tumor cells evade immune surveillance by up-regulating CD47, which binds to signal-regulatory protein (SIRP)a on macrophages and dendritic cells (DCs), inhibiting phagocytosis and antigen cross-presentation. Animal studies show that anti-CD47 therapy enhances antitumor immunity, suppresses tumor outgrowth and synergizes with chemo- and radiotherapy, by promoting the cross-presentation of TAs to T cells. It is demonstrated herein that CD47-AsiC enhances the CD8+TIL/Regulatory T cells (Treg) ratio, reduces co-inhibitor expression and improves the functions of CM+ TILs, and suppresses 4T1E tumor growth. Tumor-associated macrophages (TAMs) from CD47-AsiC treated tumors show improved phagocytic capacity. It is further demonstrated that CD47-AsiC outperforms the anti-CD47 antibody in suppressing 4T1E tumor growth.

4) The present data show that EpCAM-AsiCs targeting essential genes that BC cells rely on for survival, PLK1 and MCL1, directly kill tumor cells. PLK1 is a serine threonine kinase essential for mitosis and maintaining DNA integrity. MCL1 works by sequestering the apoptotic effector Bak and other pro-apoptotic proteins and is a critical survival factor in TNBC. Both PLK1 and MCL1 are overexpressed in BC cells. The increased tumor cell death induced by PLK1 or MCL1 knockdown can promote both tumor cell death and tumor antigen cross-presentation to CD8+ T cells, thereby improving antitumor T cell responses. The present data show that PLK1 and MCL1 EpCAM-AsiCs slow tumor growth and enhance the number and functions of CD8+ TILs.

Finally, it is demonstrated that UPF2, CD47, PARP1, PLK1 and MCL1 AsiCs work in synergy to further delay tumor growth, and even lead to tumor regression, compared to single AsiC treatment. The combination therapy significantly increased the amount of CD8+ TILs, reduced the Tregs and myeloid-derived suppressor cells (MDSCs) in the tumor, and improved the functions of both CD4+ and CD8+ TILs.

As far as we know, AsiCs do not induce immune responses like antibodies. By modulating the tumor rather than systemically activating T cells, we can avoid the worrisome autoimmune side effects that occur when multiple checkpoint inhibitors are combined. Cytotoxic siRNAs that target tumor-dependency genes can be readily combined with immune modulating siRNAs. EpCAM is highly expressed by all epithelial cancers and their stem cells. Therefore, the approach described herein to treat breast cancer can be applied to other poorly treated solid tumors and any epithelial cancer—namely lung, colon, pancreatic, prostate, bladder, stomach, head and neck, esophageal, cholangiocarcinoma.

Immune-modulating EpCAM-AsiCs have great potential to revitalize immune responses and to treat less immunogenic BC. Importantly, the EpCAM-AsiCs conjugates possess high affinity and tumor selectivity, which reduces toxicity compared to checkpoint blockade antibodies. Moreover, these drugs are small molecules that diffuse into poorly vascularized tumors. The present data indicate that these novel EpCAM-AsiCs, with their small size and high selectivity, have great potential to improve therapeutic efficacy and reduce toxicity for BC patients compared to current checkpoint inhibitor drugs.

Example 2

AsiCs solve the delivery problem beyond the liver and provide exquisitely specific drug uptake and knockdown only in targeted cell. Subcutaneous administration results in penetration of all tissues, like a small molecule, and AsiC's are stable for days in serum. AsiC's provide durable knockdown with same favorable pharmacodynamics as other siRNA-based drugs with no apparent toxicity or immunogenicity. Chemical synthesis is with existing available manufacturing and the same chemistry can be used to link more than 1 siRNA, miRNA, mRNA, toxin or chemotherapy drug to make multifunctional drugs.

Figure 3:
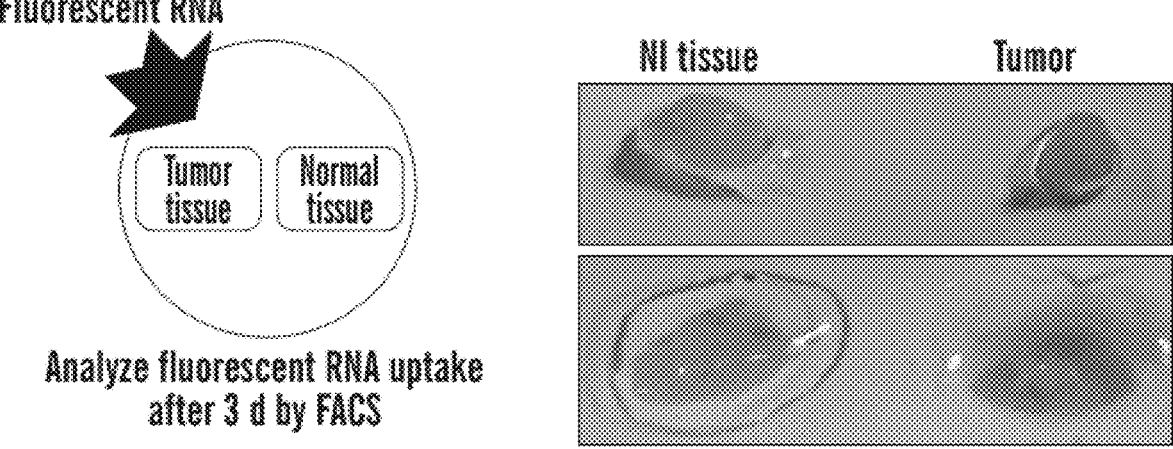
FIG. 3 demonstrates that human TNBC tumors take up Cy3-EpCAM-AsiC at a greater rate than normal breast tissue.
Figure 3:
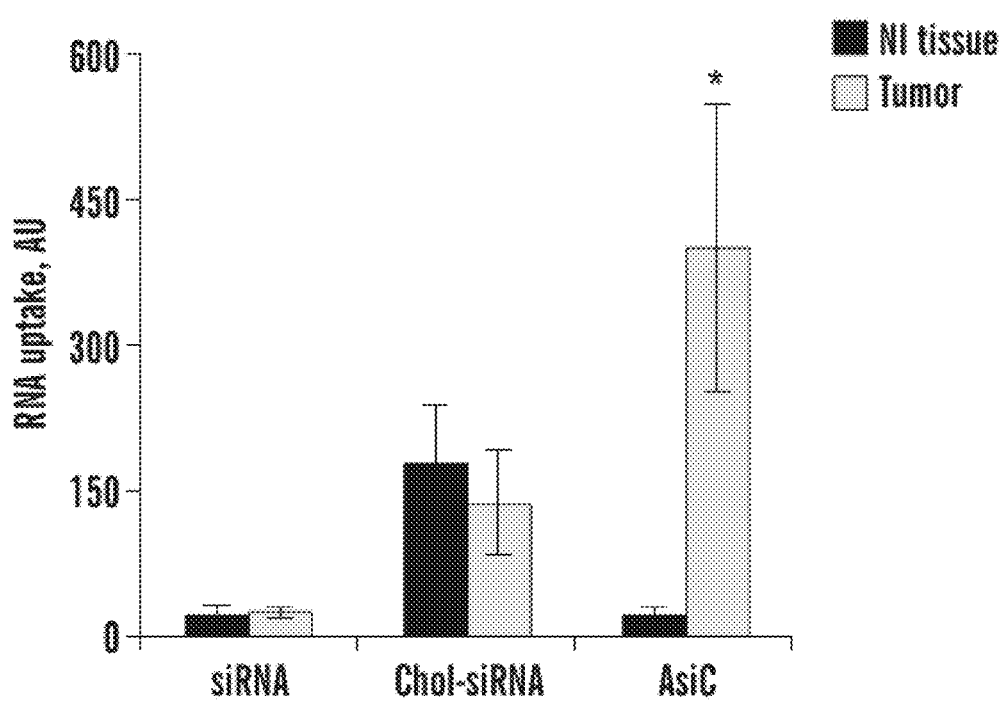
Figure 4:
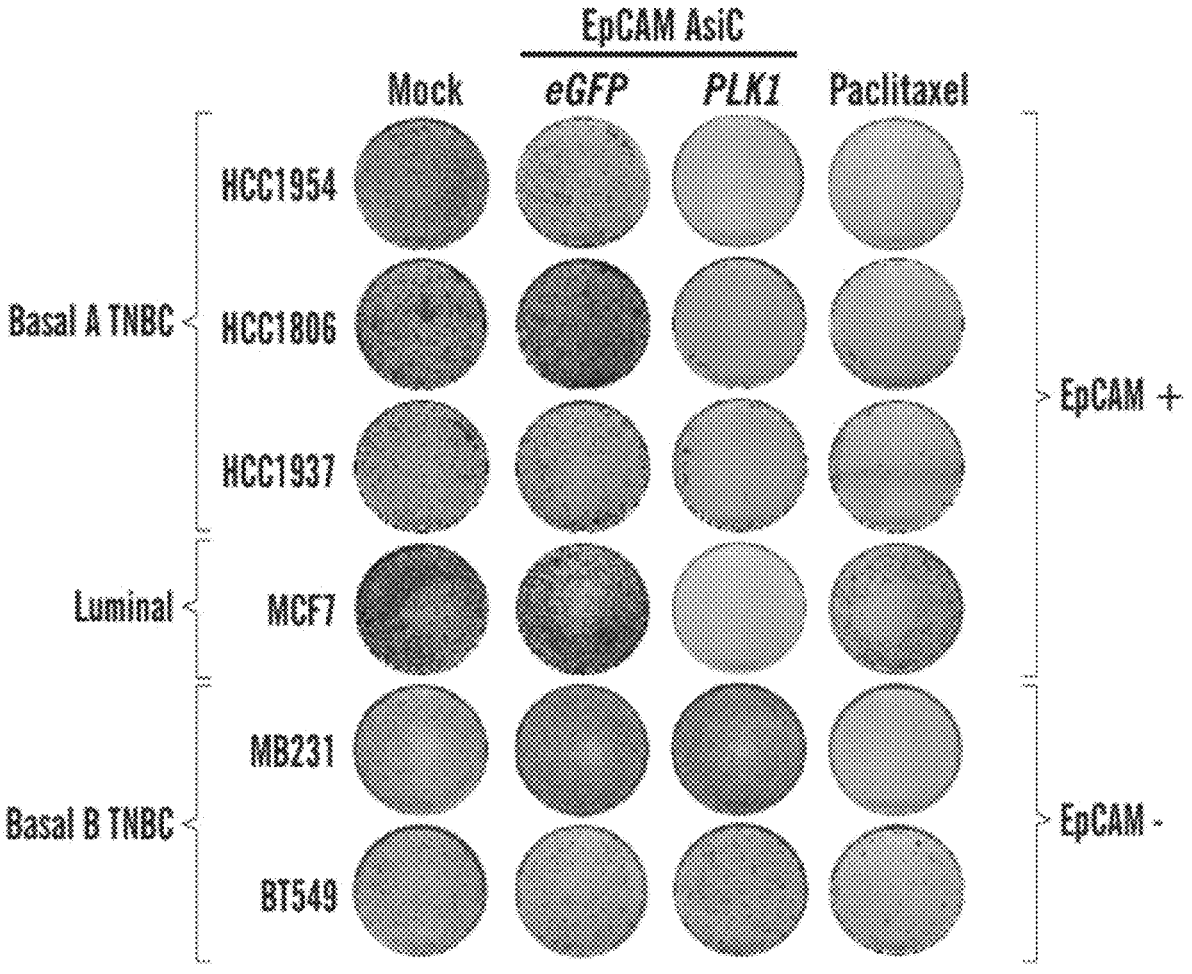
FIG. 4 demonstrates that EpCAM-AsiCs inhibit in vitro cancer stem cell assays of EpCAM+ breast cancer cell lines. The first-third rows are Basal A TNBCs, the fourth row is luminal, and the fifth-sixth rows are Basal B TNBCs.
Figure 5:
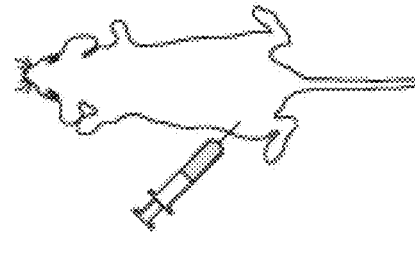
FIG. 5 demonstrates that ex vivo treatment of EpCAM+ TNBC cells prevents tumor initiation.
Figure 5:
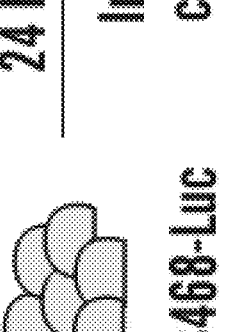
Figure 5:
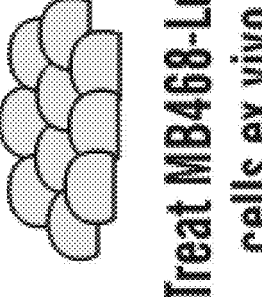
Figure 5:
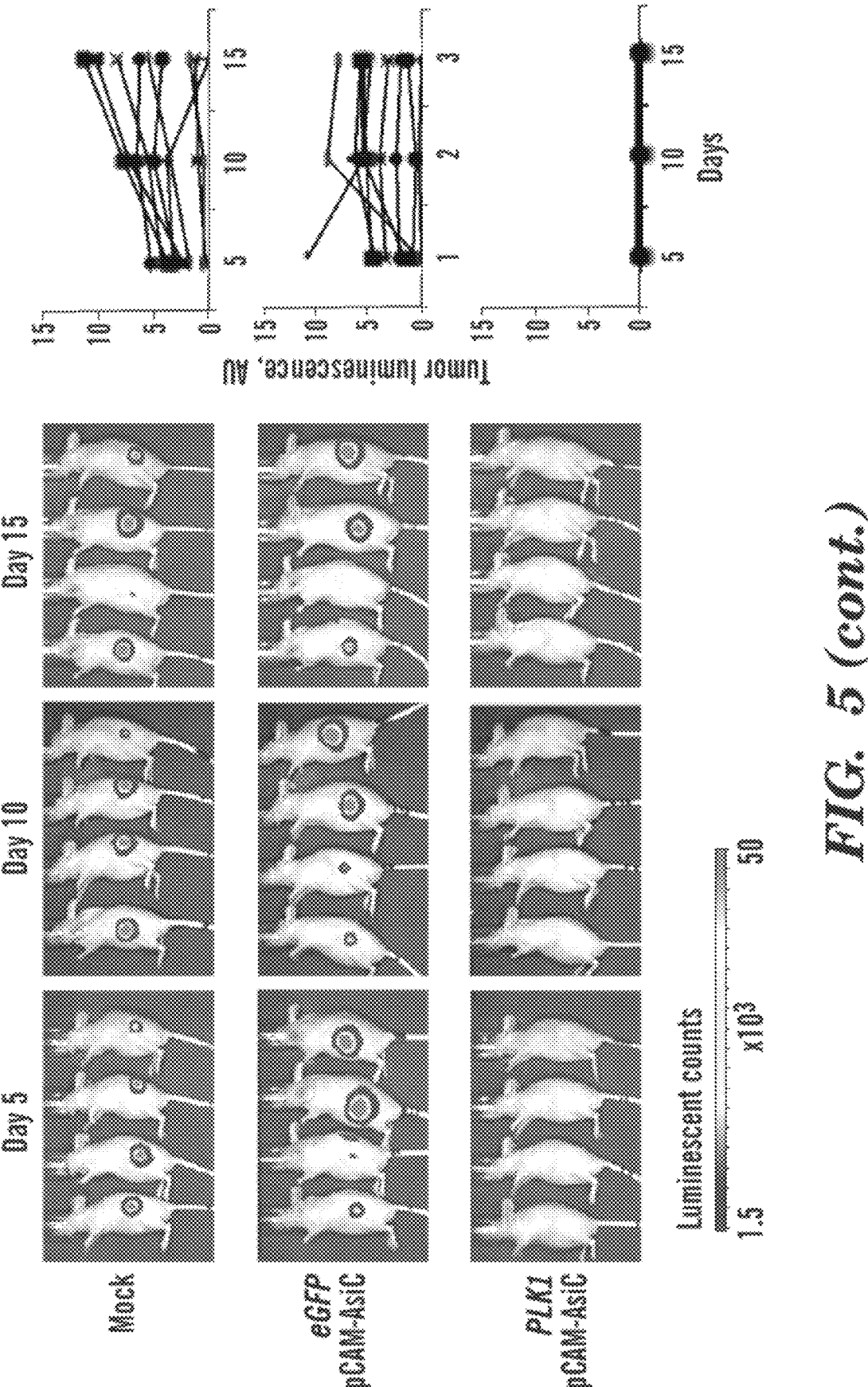
Figure 6:
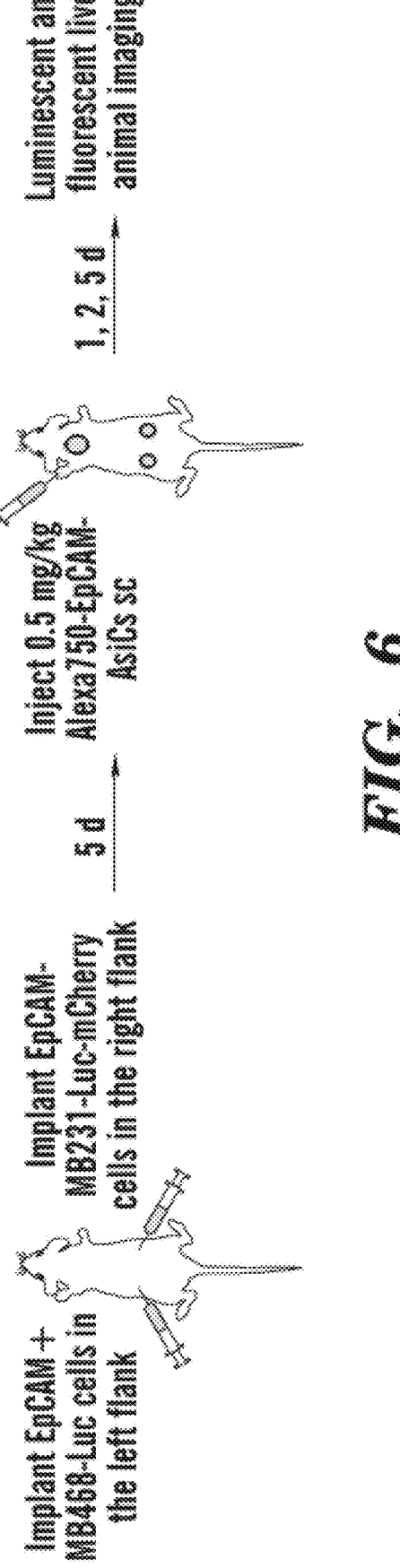
FIG. 6 demonstrates selective uptake of Alexa750-EpCAM-AsiCs into EpCAM+ tumors.
Figure 6:
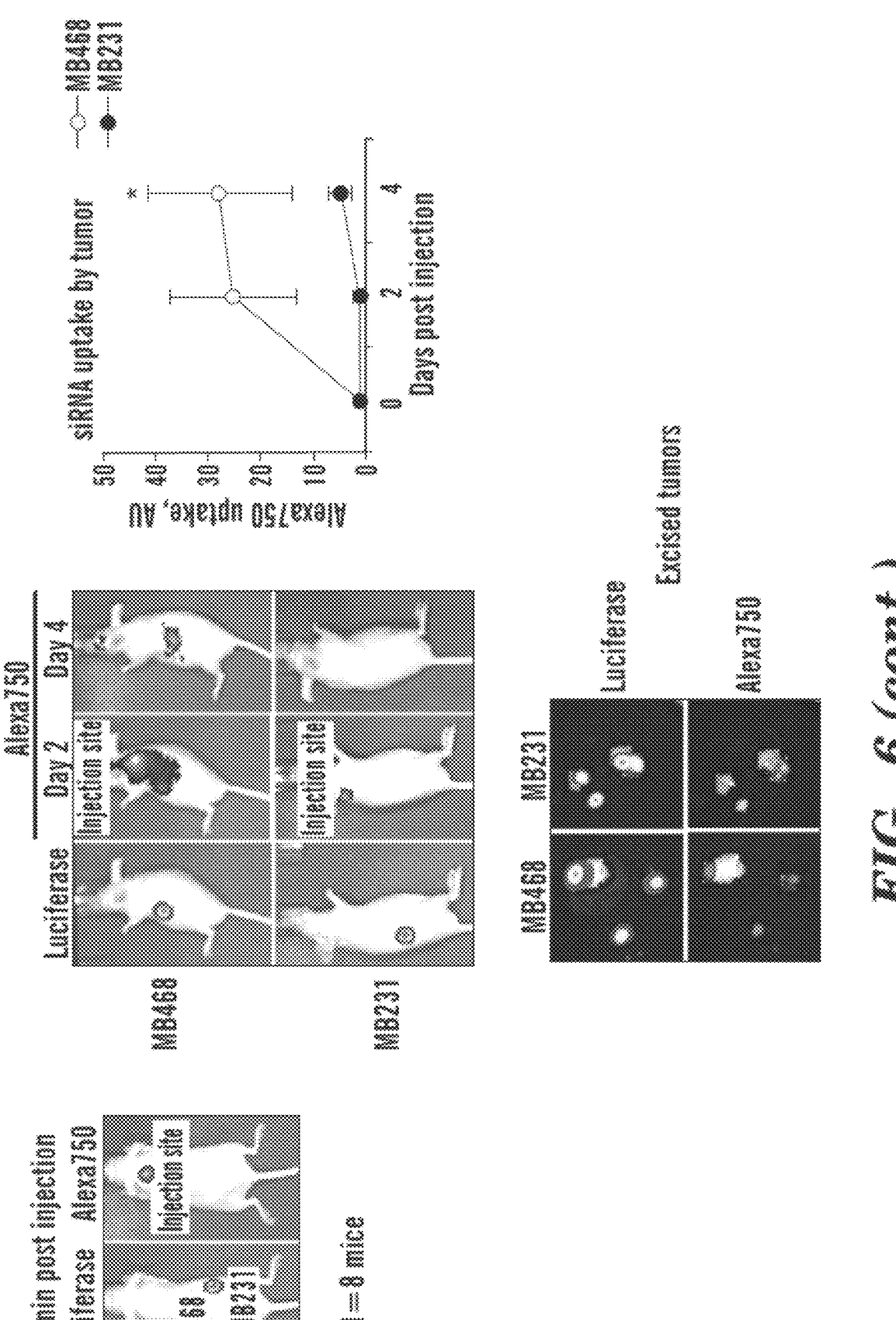
Figure 7:
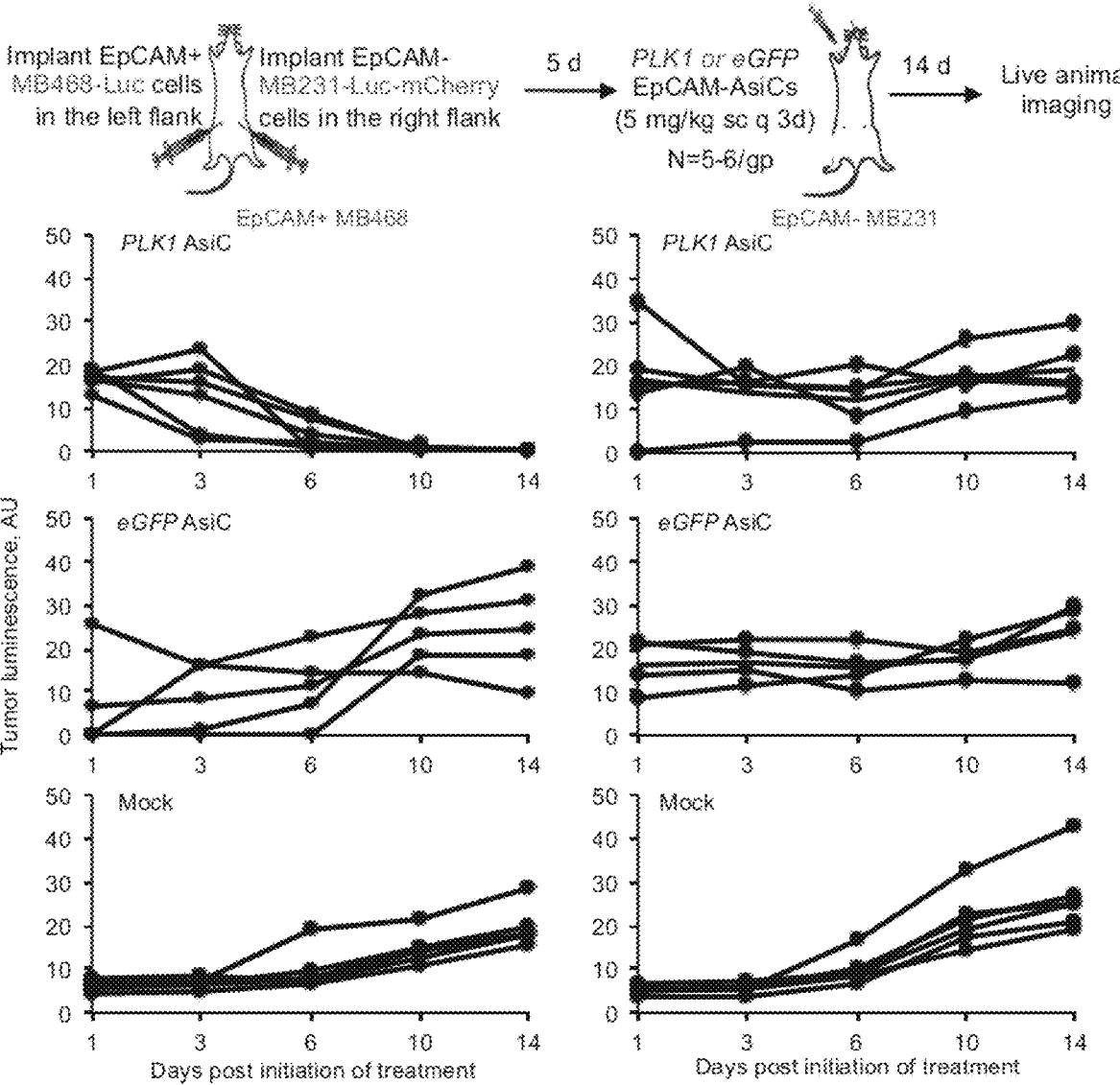
FIG. 7 demonstrates that EpCAM-AsiCs targeting PLK1 inhibit EpCAM+ TNBC tumor growth.

The AsiC's described herein comprise aptamers specific for EpCAM, which is highly expressed in epithelial cancers (FIG. 1). The knock-down effect achieved by EpCAM-AsiC provides an antitumor effect that correlates with EpCAM expression (FIG. 2) and TNBC cells take up EpCAM-AsiC's at a greater rate than normal breast tissue (FIG. 3). Alexa750-EpCAM-AsiCs are uptaken selectively into EpCAM+ tumors (FIG. 6). EpCAM-AsiCs inhibit in vitro cancer stem cell assays of EpCAM+ breast cancer cell lines (FIG. 4). Ex vivo treatment of EpCAM+ TNBC cells prevents tumor initiation (FIG. 5). EpCAM-AsiCs targeting PLK1 inhibit EpCAM+ TNBC tumor growth (FIG. 7).

EpCAM-AsiCs knockdown genes in epithelial breast cancer cells and the tumor-initiating cells within them, sparing normal epithelial cells. Subcutaneously injected EpCAM-AsiCs localize to distant tumors. PLK1 EpCAM-AsiCs suppress tumor growth in vitro and in vivo and eliminate tumor-initiating cells. AsiCs do not trigger innate immunity. Most common epithelial tumors are EpCAM+(colon, lung, prostate, pancreas). Similar results are obtained in HCT116 colon cancer xenografts.

Figure 8:
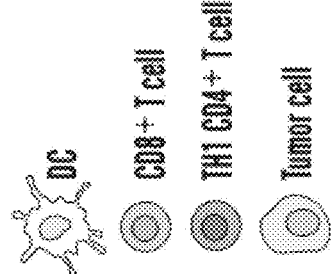
FIG. 8 depicts a diagram for anti-tumor immunity. Taken in part from Sahin and Tureci Science, 2018.
Figure 9A:
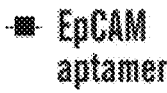
FIGS. 9A-9E demonstrate that knocking down an RNA quality control pathway enhances anti-tumor immunity.
Figure 9A:
Figure 9A:
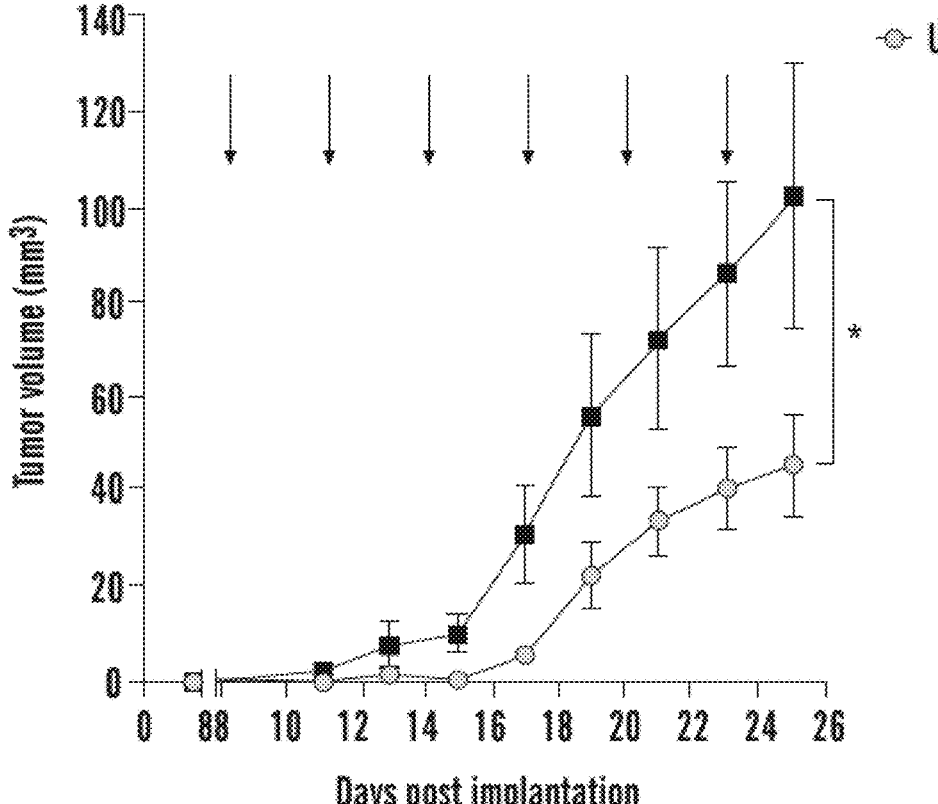
Figure 9B:
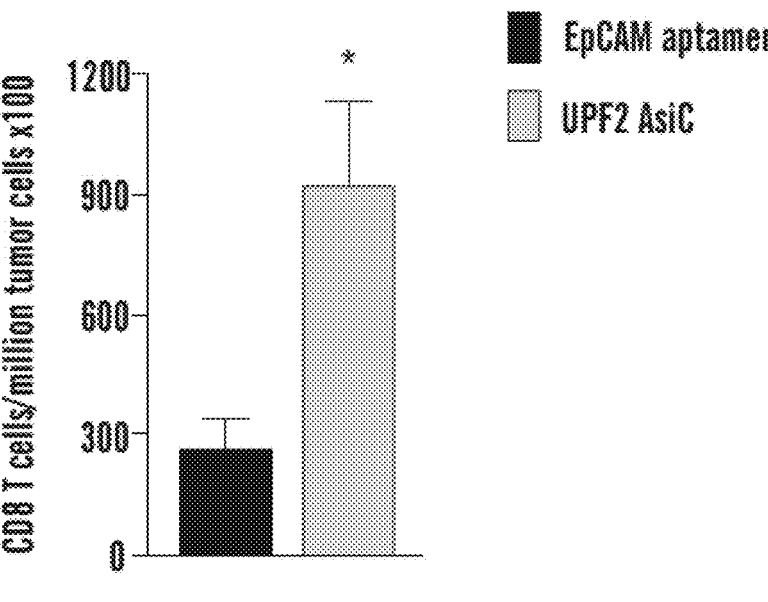
Figure 9C:
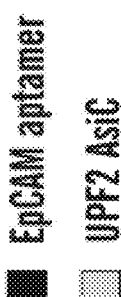
Figure 9C:
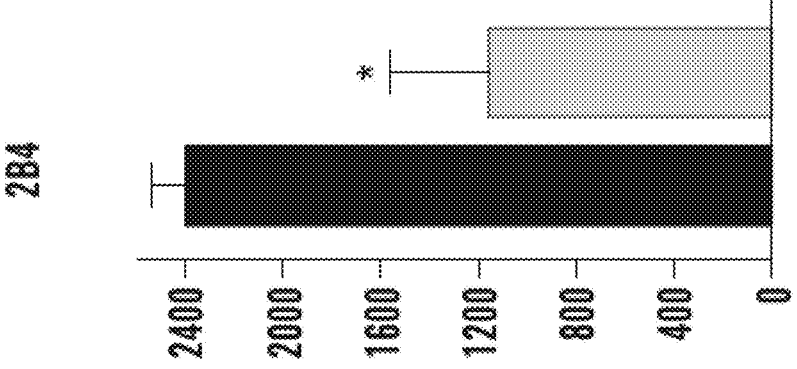
Figure 9C:
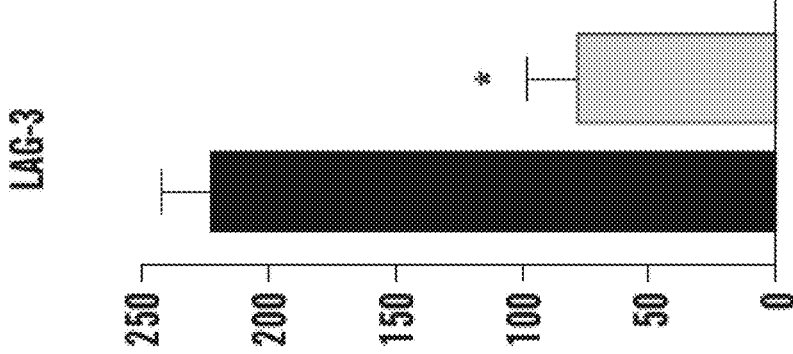
Figure 9C:
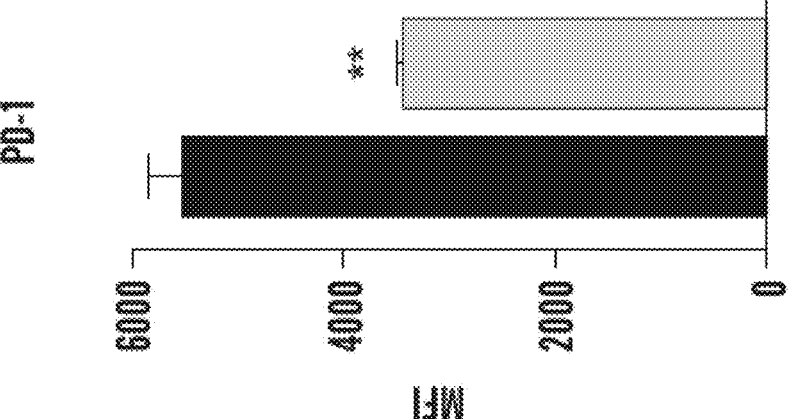
Figure 9D:
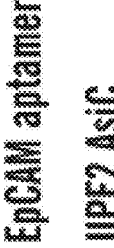
Figure 9D:
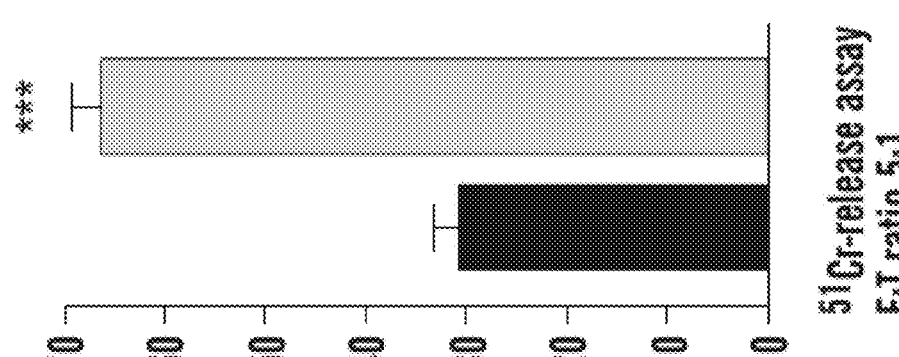
Figure 9D:
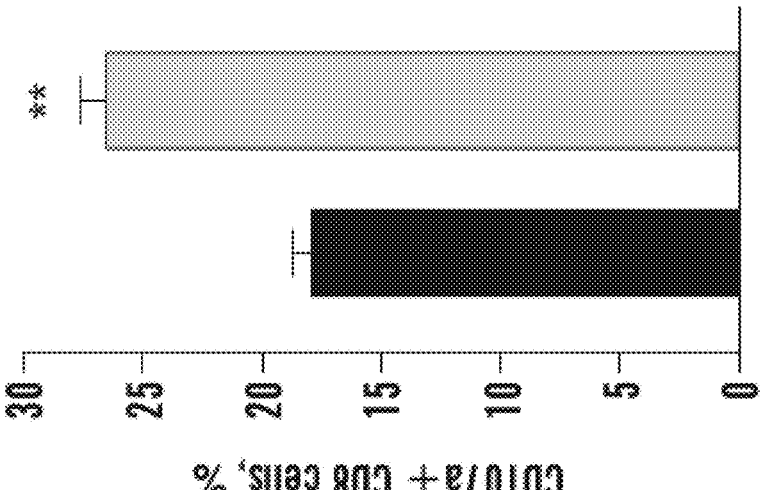
Figure 9E:
Figure 10:
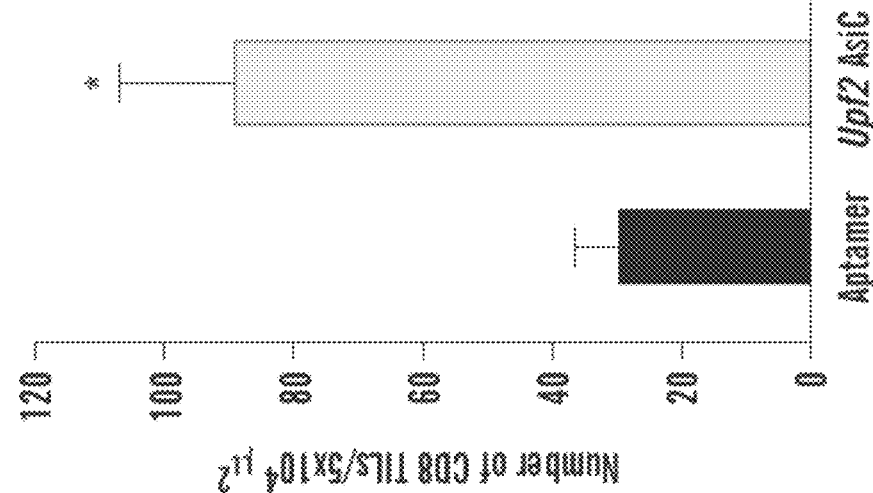
FIG. 10 depicts a graph demonstrating increased CD8 TILs in Upf2 EpCAM-AsiC treated 4T1 tumors.
Figure 10:
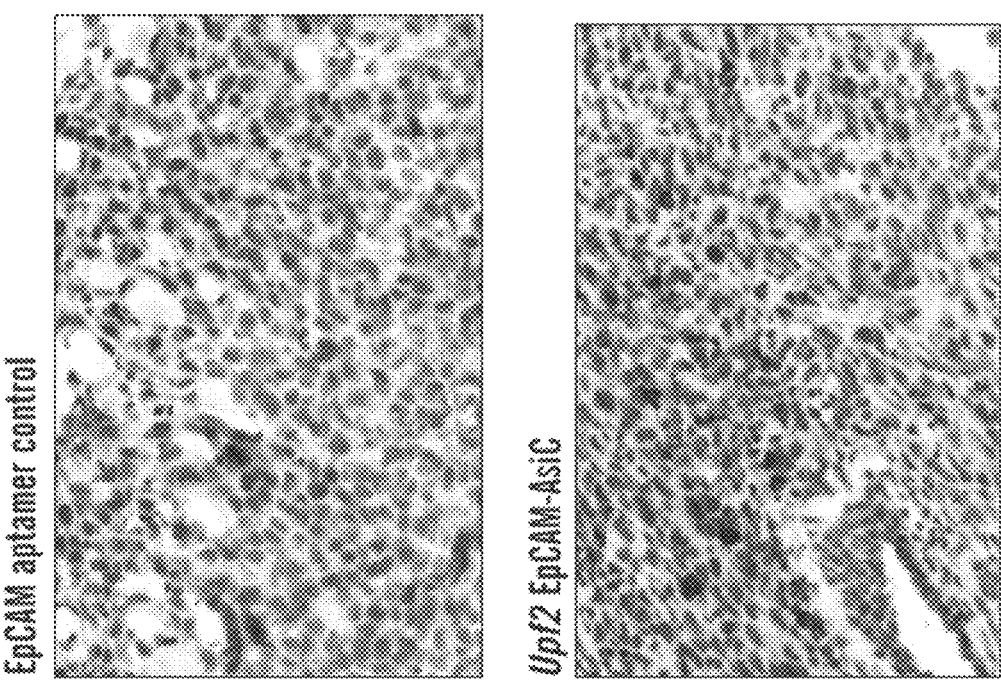

Certain AsiC's described herein seek to manipulate anti-tumor immunity (FIG. 8). Knocking down the UPF2 to inhibit the RNA quality control pathway enhances anti-tumor immunity (FIG. 9A-9E). A similar effect was seen in 4T1 tumors, which had increased levels of CD8+ TILs after UPF2 EpCAM-AsiC treatment (FIG. 10).

Figure 11:
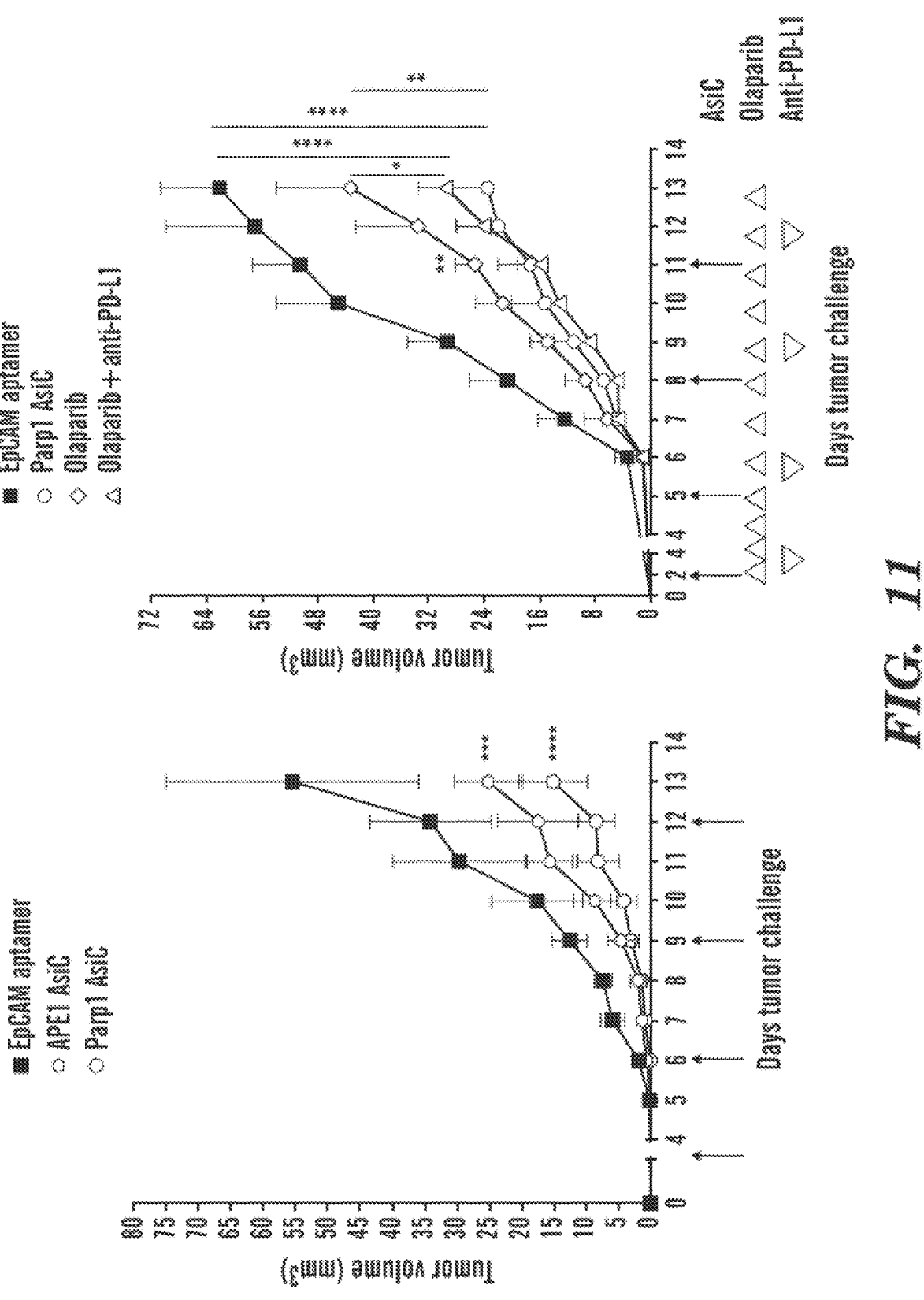
FIG. 11 demonstrates that disrupting DNA Repair by knocking down PARP1 and APE1 improves tumor immunity.
Figure 11:
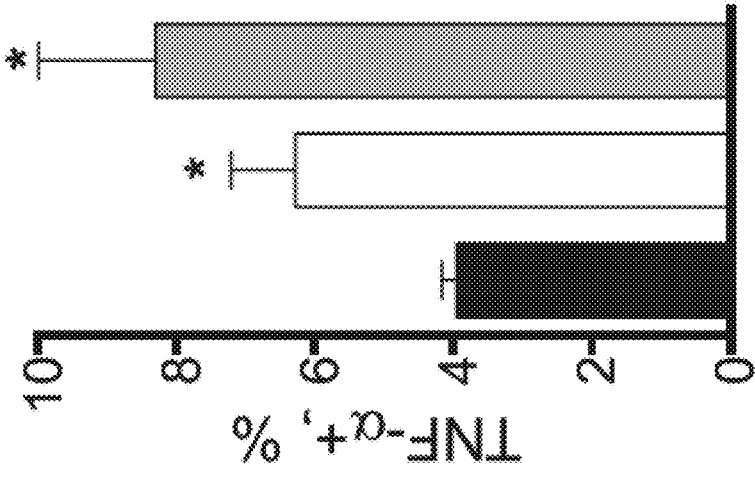
Figure 11:
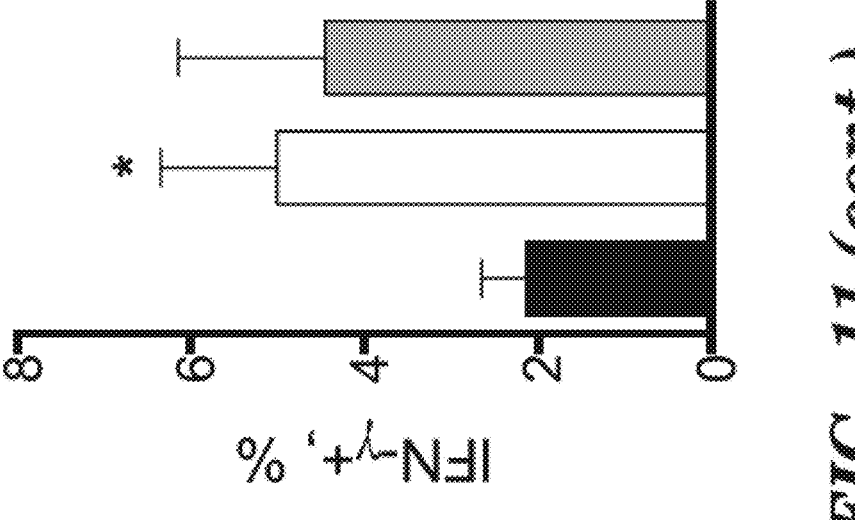
Figure 11:
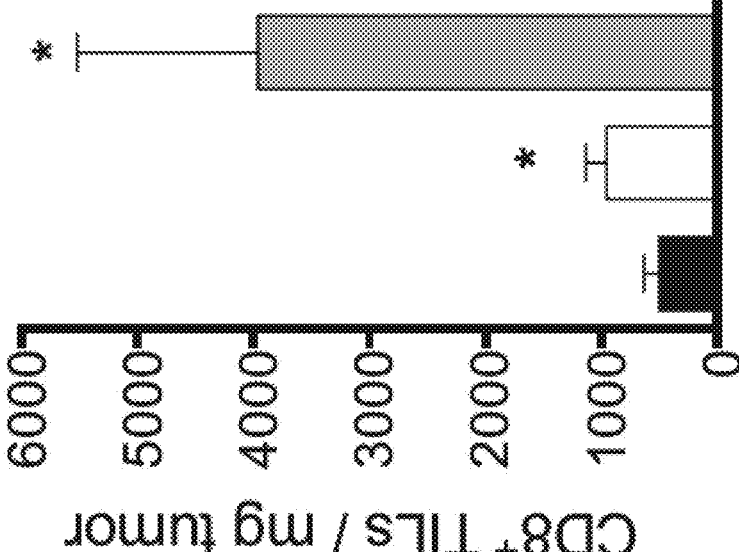

Disrupting DNA Repair by knocking down PARP1 and APE1 improves tumor immunity (FIG. 11). PARP1-AsiC works better than the PARP1 inhibitor drug olaparib (an approved drug for a small subset of breast cancers) and as well as olaparib+checkpoint inhibitor (anti-PDL1). Treatment with PARP1-AsiC results in increased CD8+ TILs and more cytokine production by those cells.

Figure 12D:
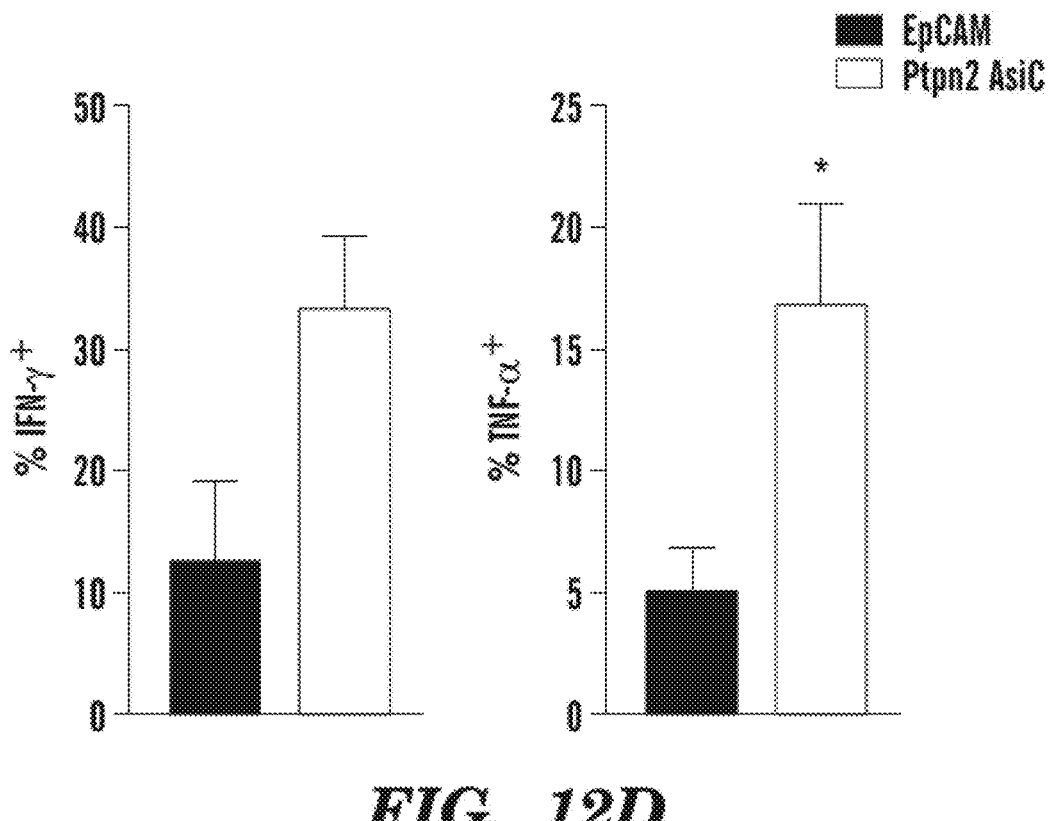
Figure 12E:
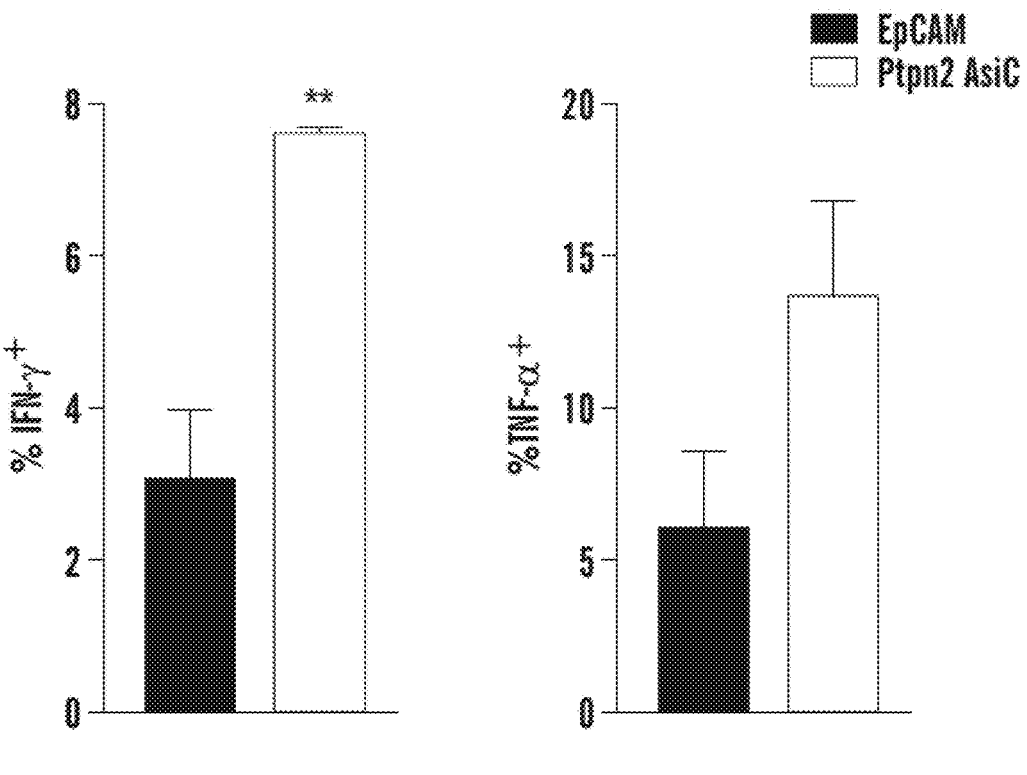

Targeting a phosphatase PTPNT2 enhances interferon signaling by the tumor (FIG. 12). PNPT2 suppresses interferon signaling and loss of PNPT2 improves tumor antigen presentation and T cell responsiveness to the tumor. Treatment with PTPNT2-AsiC suppressed tumor growth, induced CD8+ TILS, increased tumor antigen presentation, and increased the function of CD8+ and CD4+ TILs (FIGS. 12A-12E).

Figure 13:
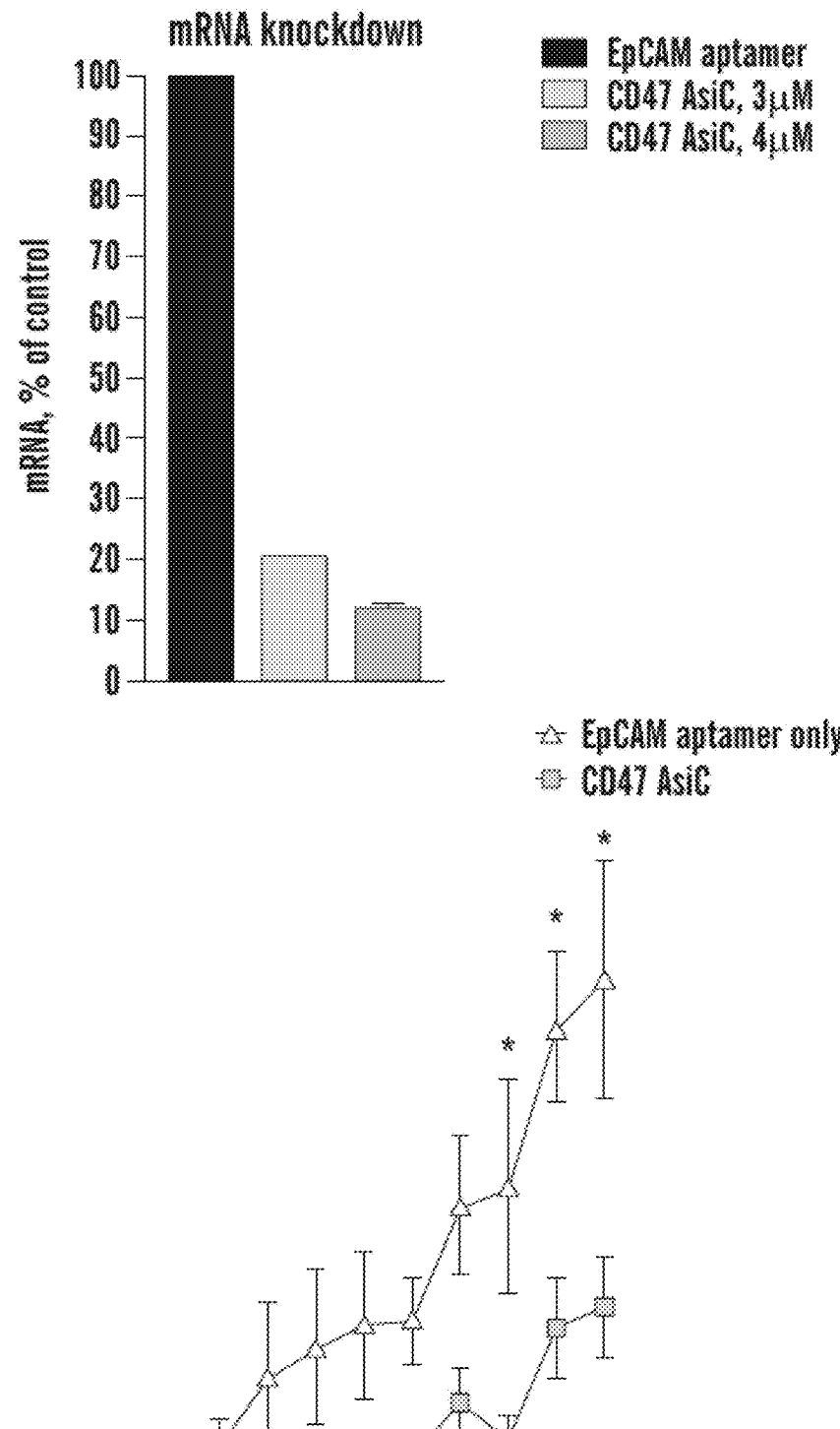
FIG. 13 demonstrates that knock-down of CD47 by AsiC inhibits tumor growth. The series in the bar graph are, in order, EpCAM aptamer, CD47 AsiC at 3 μM, and CD47 AsiC at 4 μM.
Figure 14:
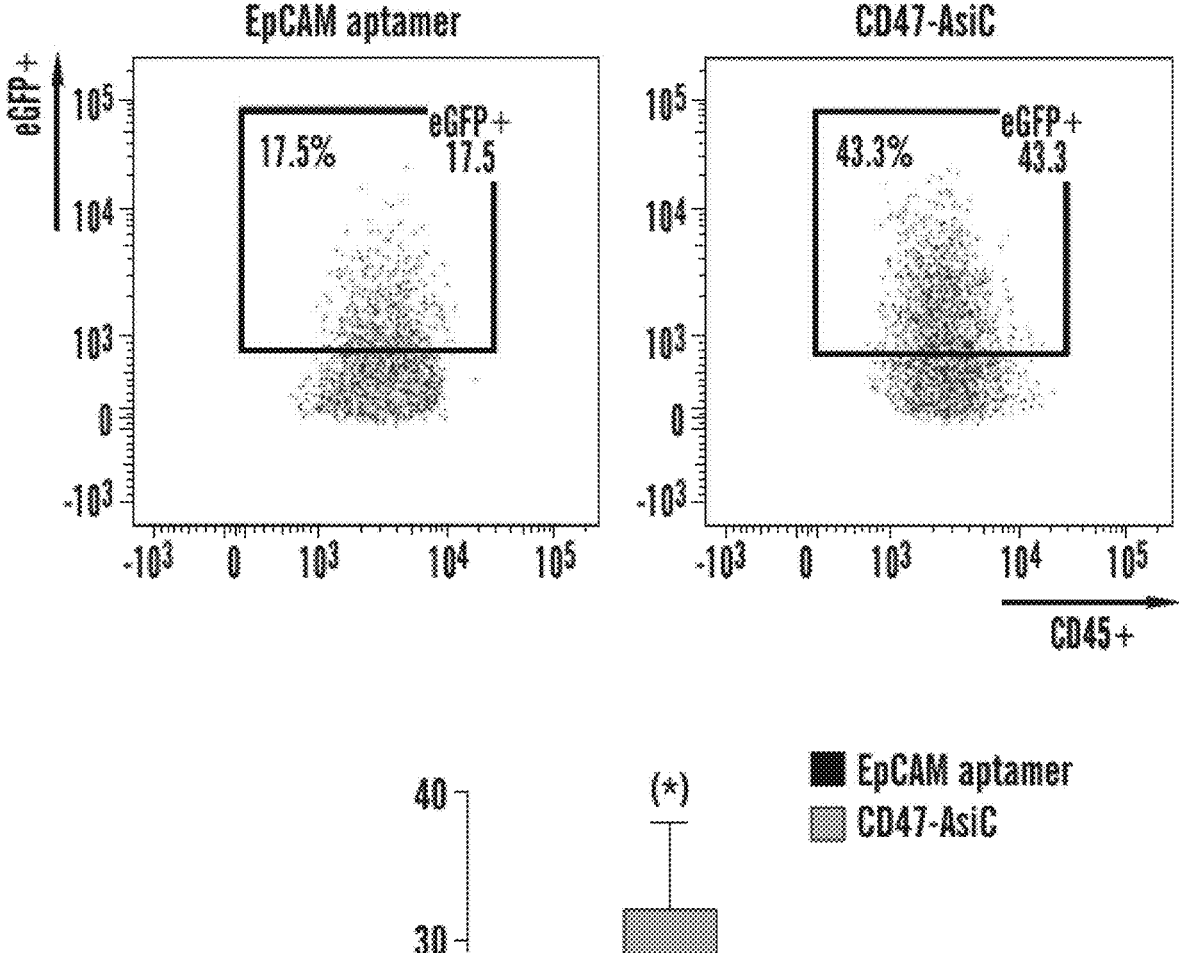
FIG. 14 depicts graphs demonstrating that CD47-AsiCs increases TAM in vivo phagocytosis of 4TE-eGFP tumors.
Figures 15A, 15B:
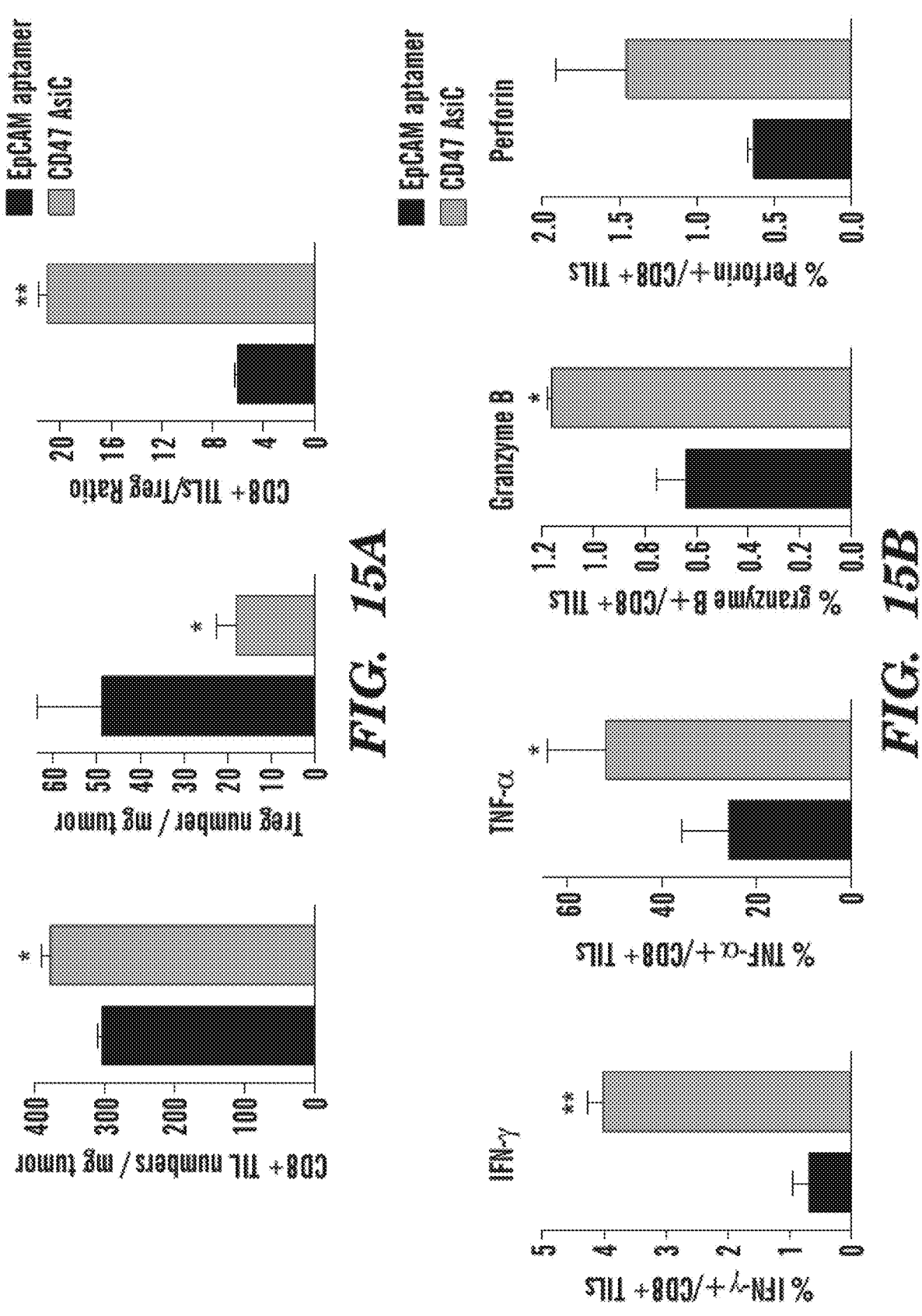
FIGS. 15A-15B demonstrates that CD47 knockdown induces an anti-tumor response.
Figure 16:
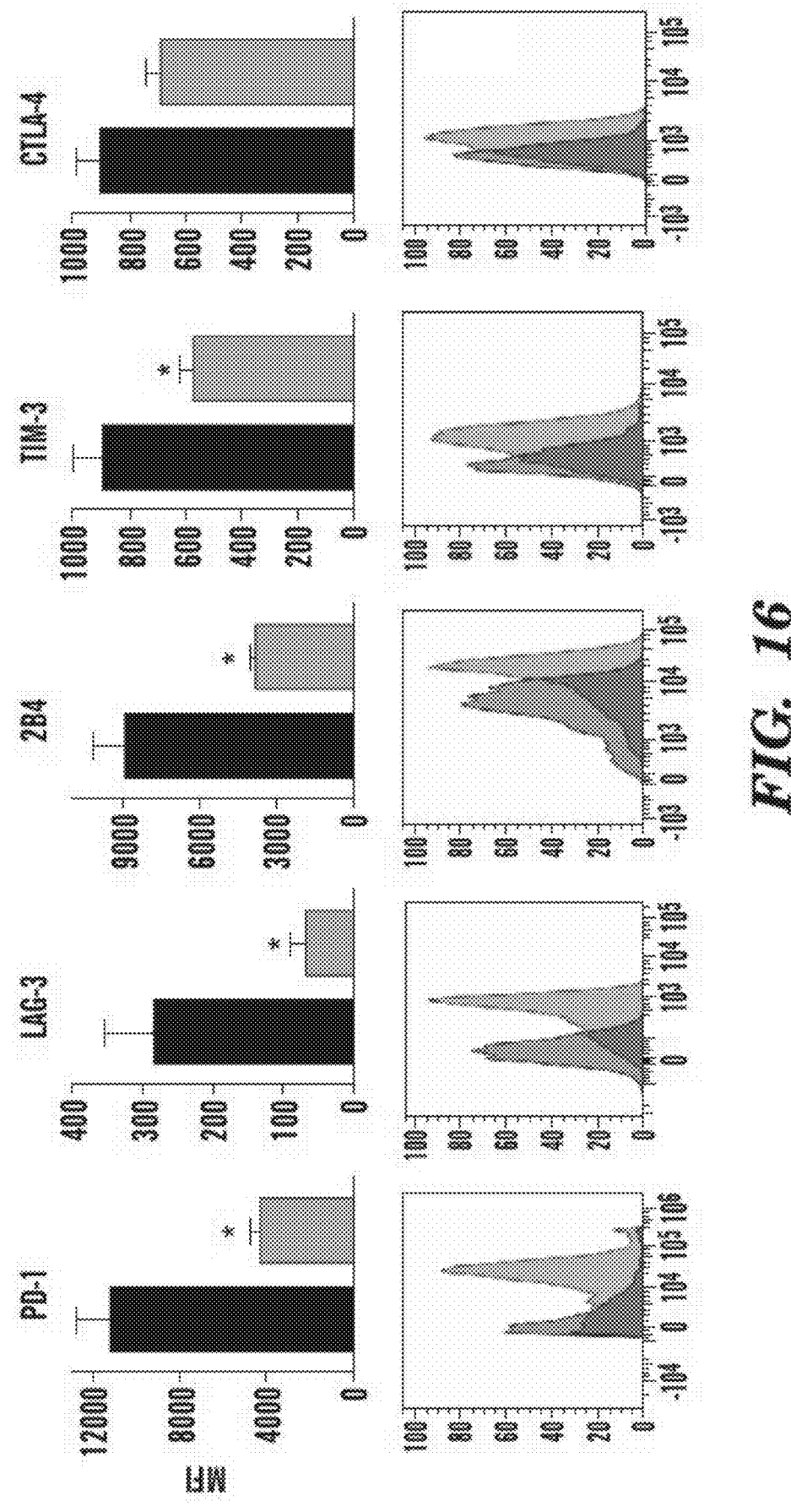
FIG. 16 demonstrates that CD47-AsiC treatment causes TILs to express fewer inhibitory receptors. In the bar graphs, the series are, in order, EpCAM aptamer and CD47 AsiC. In the pie chart, the series begin with the blunt end of the arrow and are, in order, 5, 4, 3, 2, and 1 inhibitory receptors.
Figure 16:
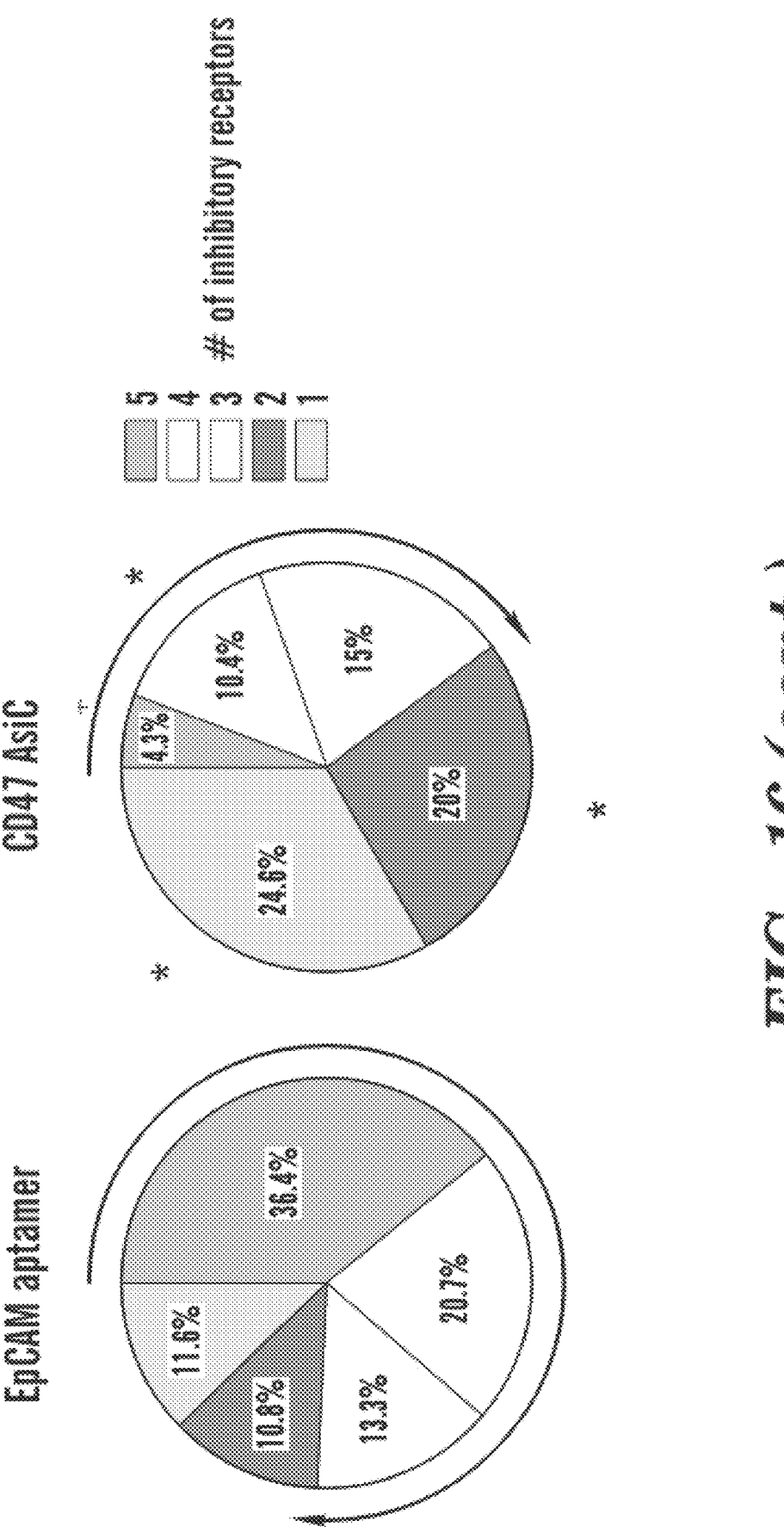
Figure 17:
FIG. 17 demonstrates that CD47-AsiC controls tumor better than anti-CD47 antibody (in phase II clinical trials).
Figure 18A:
FIGS. 18A-18E depicts the synergistic effects of combining AsiCs.
Figure 18B:
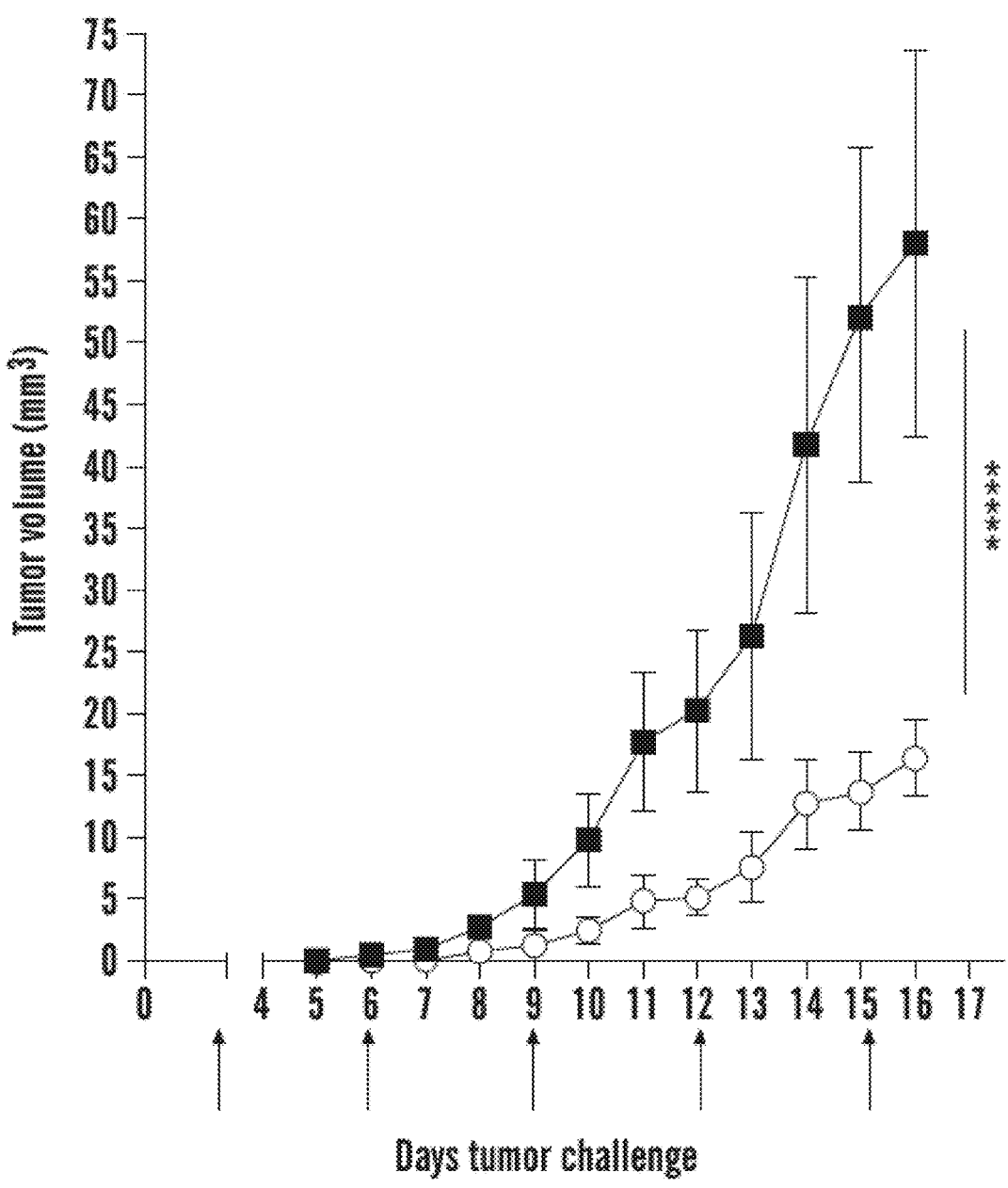
Figure 18C:
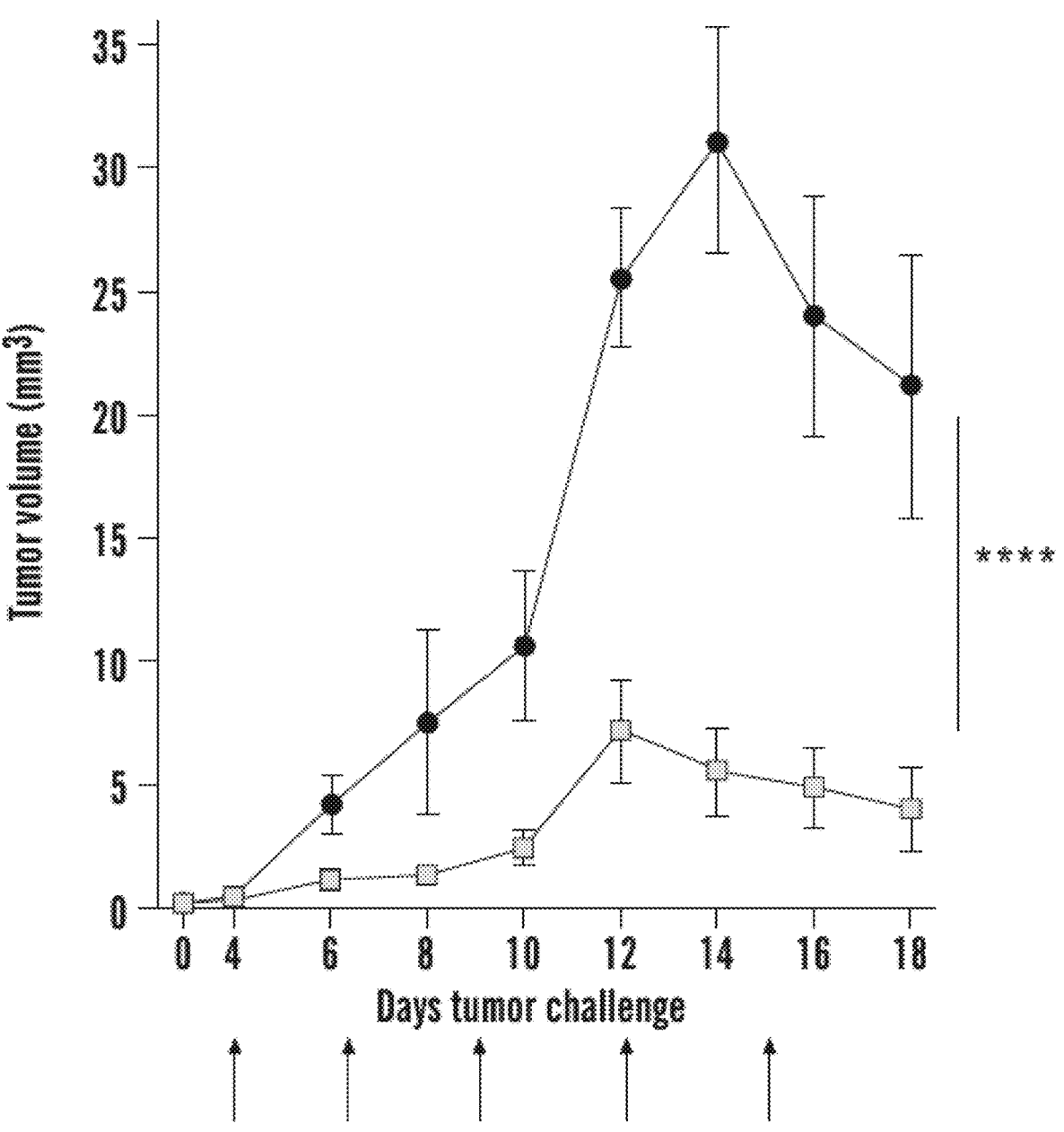
Figure 18D:
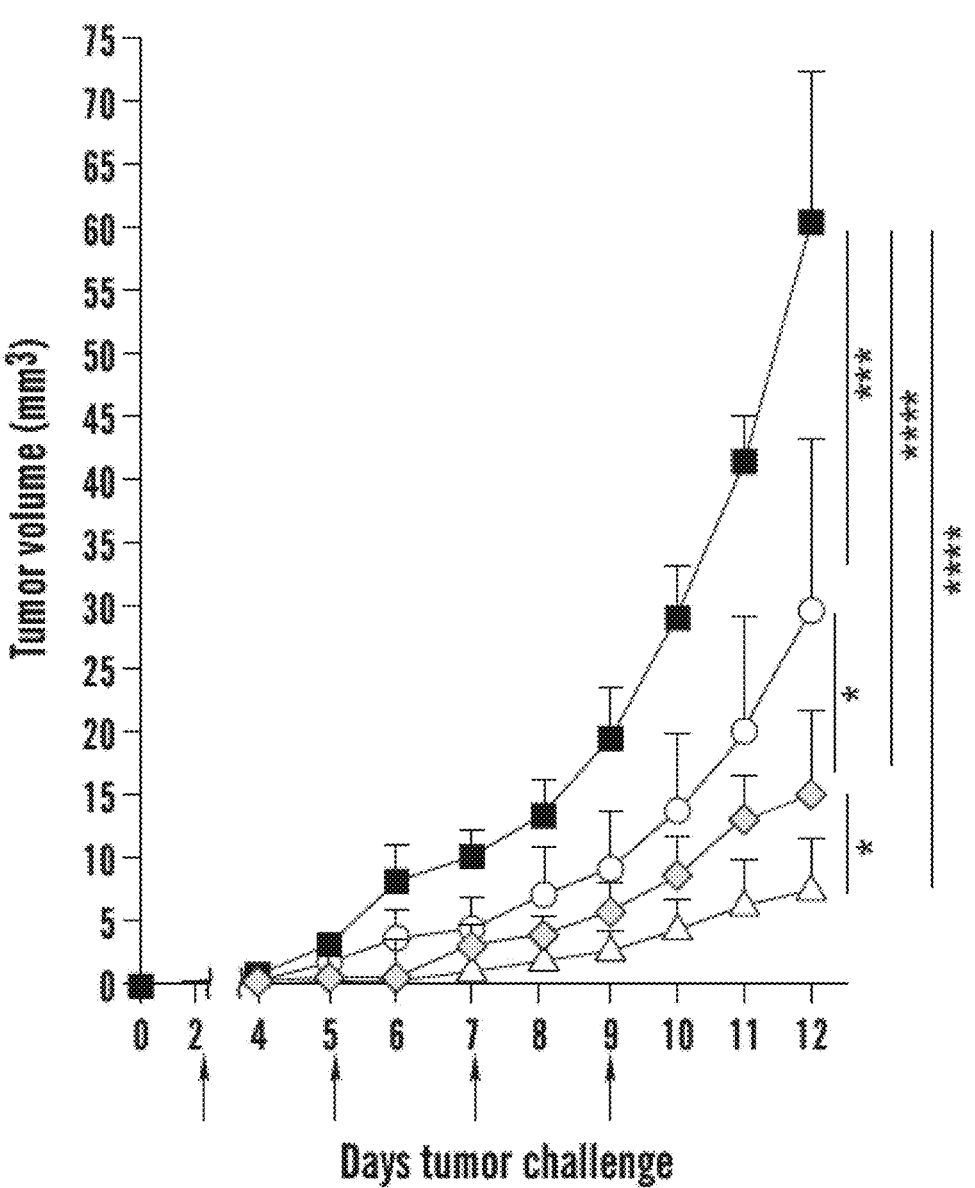
Figure 18D:
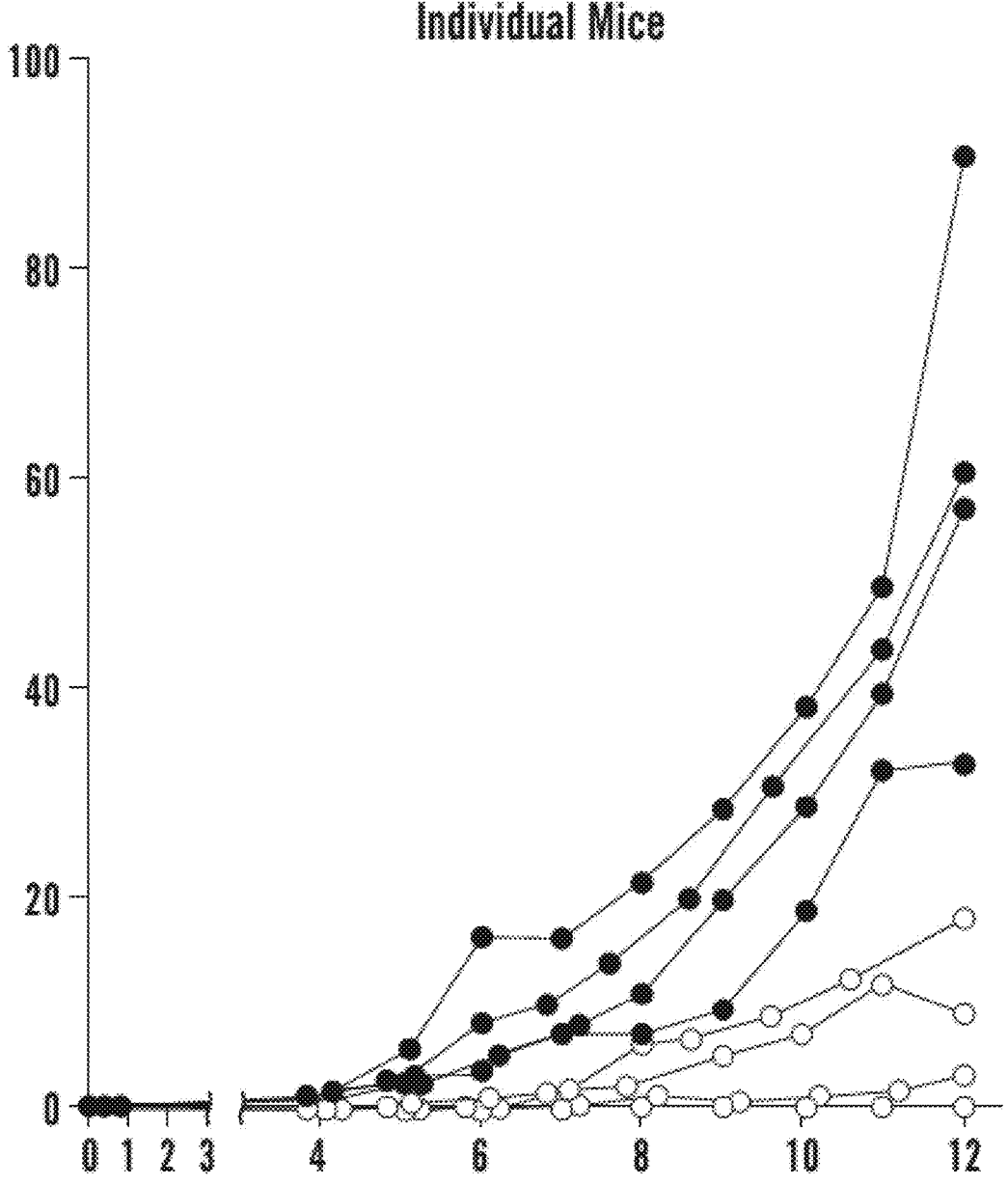
Figure 18E:
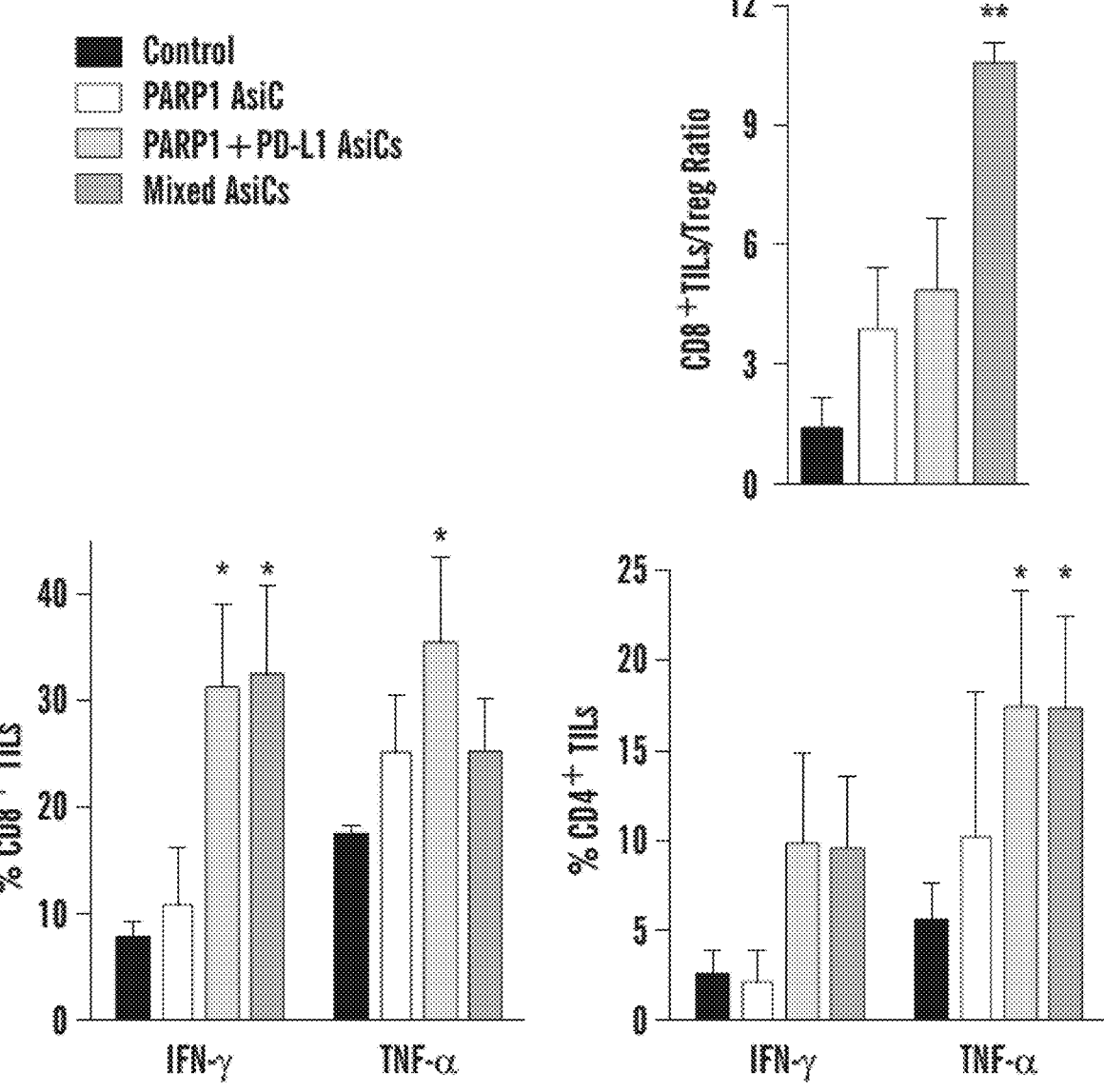

AsiC-mediated CD47 inhibition also reduces tumor growth (FIG. 13). CD47-AsiCs increases TAM in vivo phagocytosis of 4TE-eGFP tumors (FIG. 14) and induce an anti-tumor response (FIGS. 15A-15B). Additionally, TILs express fewer inhibitory receptors after CD47-AsiC treatment (FIG. 16). CD47-AsiC provides more effective treatment than anti-CD47 antibodies in phase II clinical trials (FIG. 17).

Figure 22:
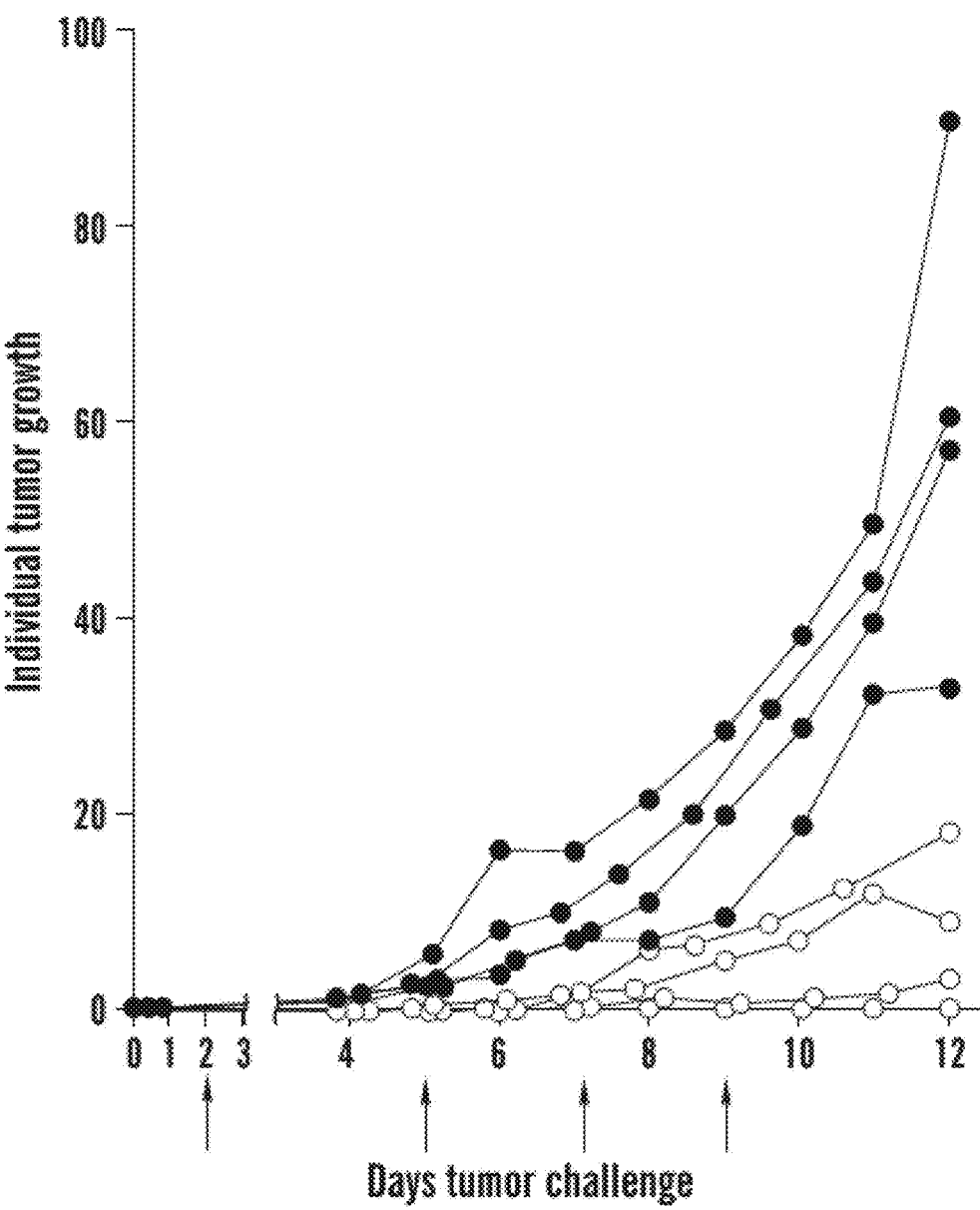
FIG. 22 depicts a combination of seven EpCAM-AsiC's to treat mice with 4T1E tumor.
Figure 23:
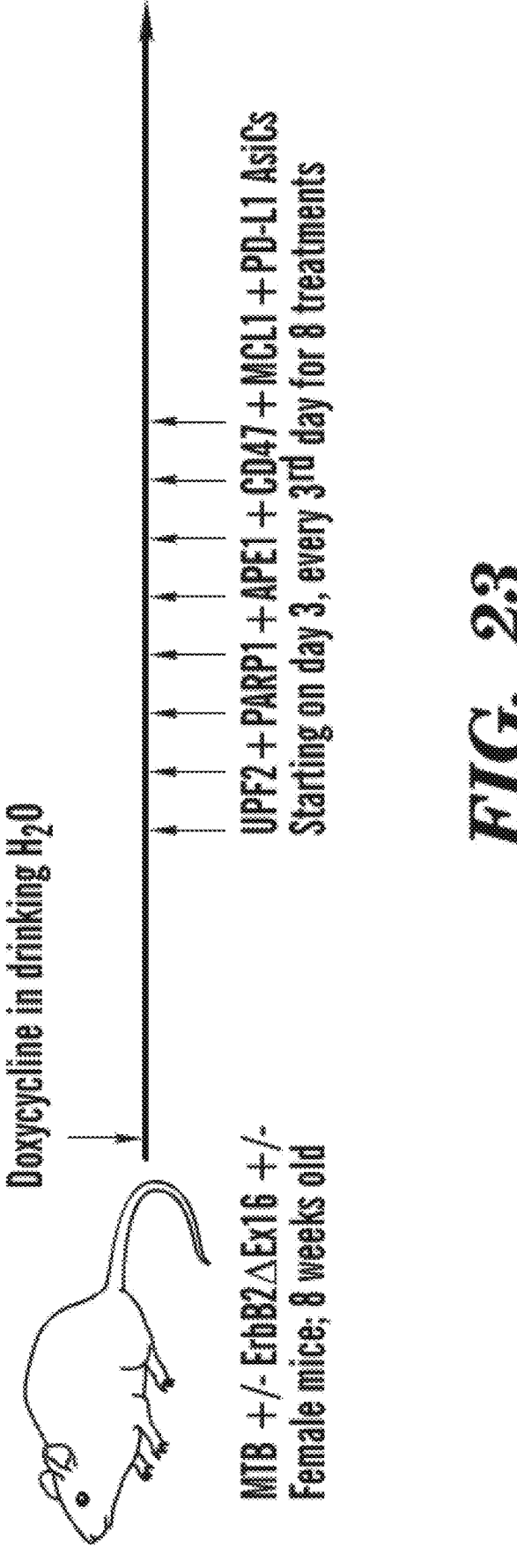
FIGS. 23 and 24 depict the treatment of ErbB2ΔEx16+ mice with combination AsiCs.
Figure 23:
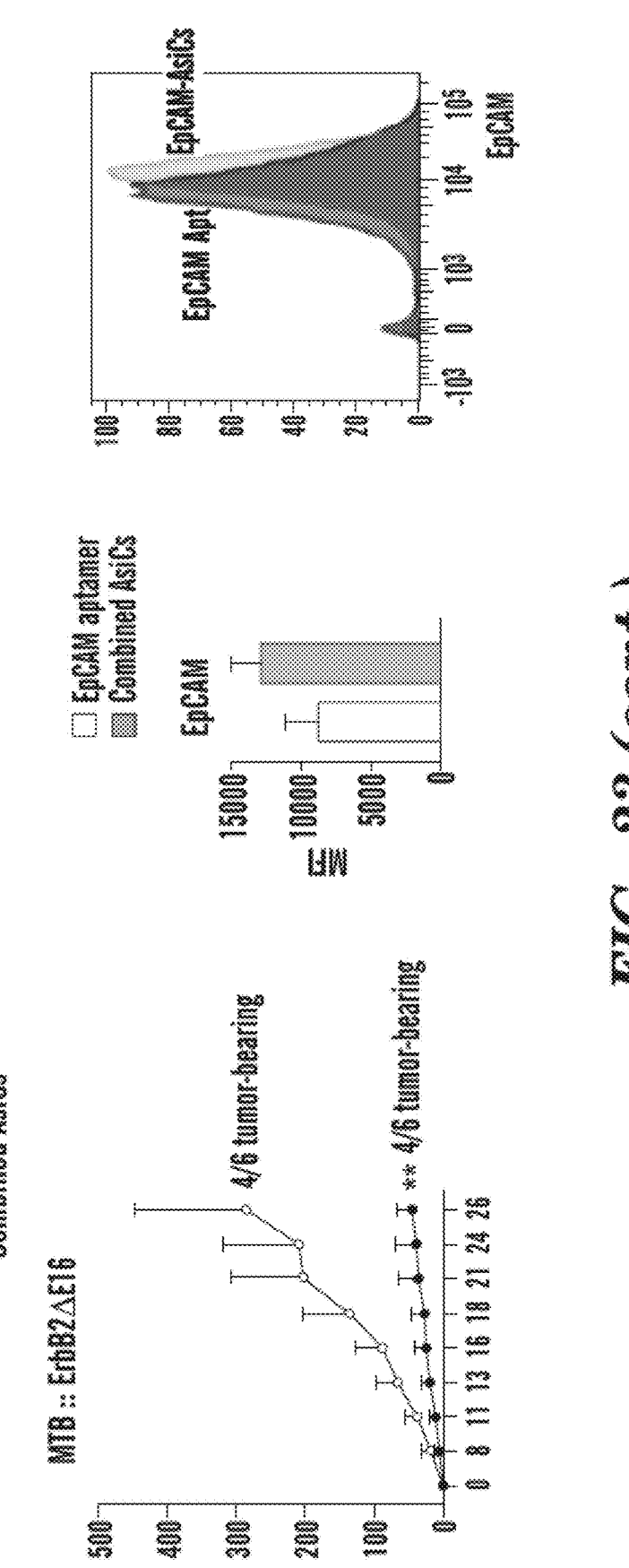
Figure 24:
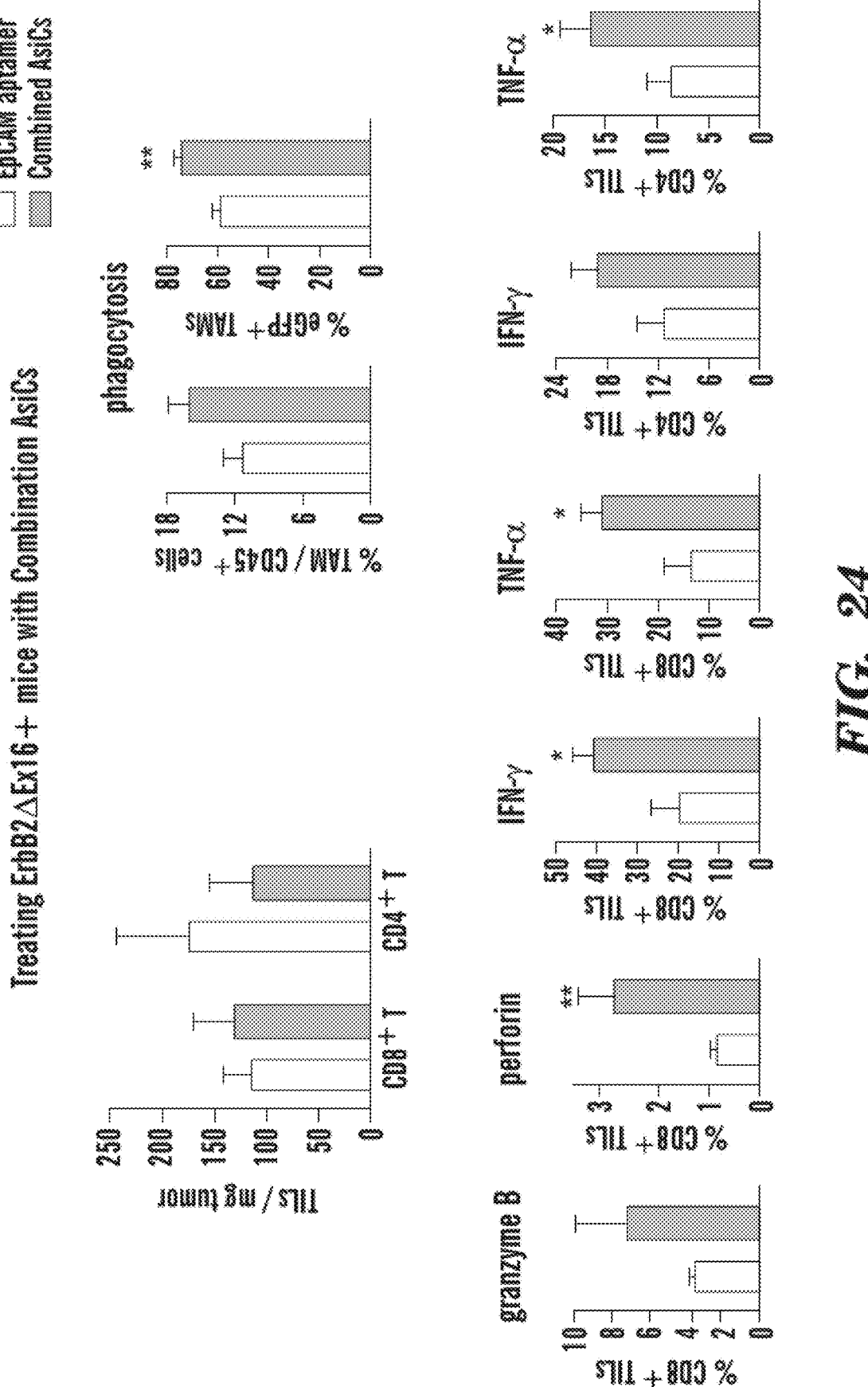

When combined, AsiC's display unexpected synergy (FIGS. 18A-18E, 21). This synergy is also evident in the treatment of mice with 4T1E tumors (FIG. 22) and ErbB2ΔEx16+ mice (FIGS. 23 and 24).

Figure 19:
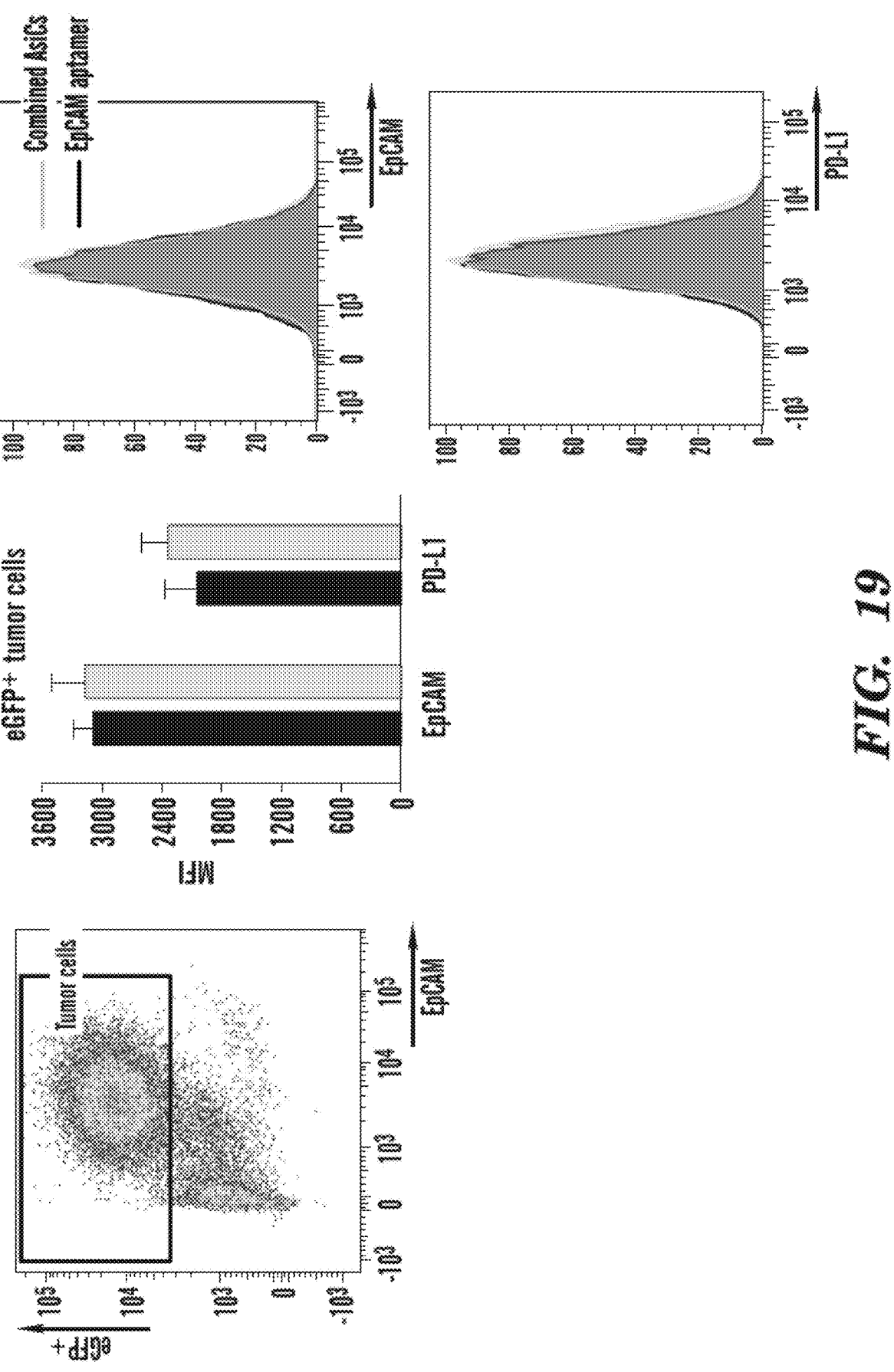
FIG. 19 demonstrates that treated tumor cells don't down-regulate EpCAM. Mice were treated with a cocktail of CD47, UPF2, PLK1 and MCL1 AsiCs.
Figure 20:
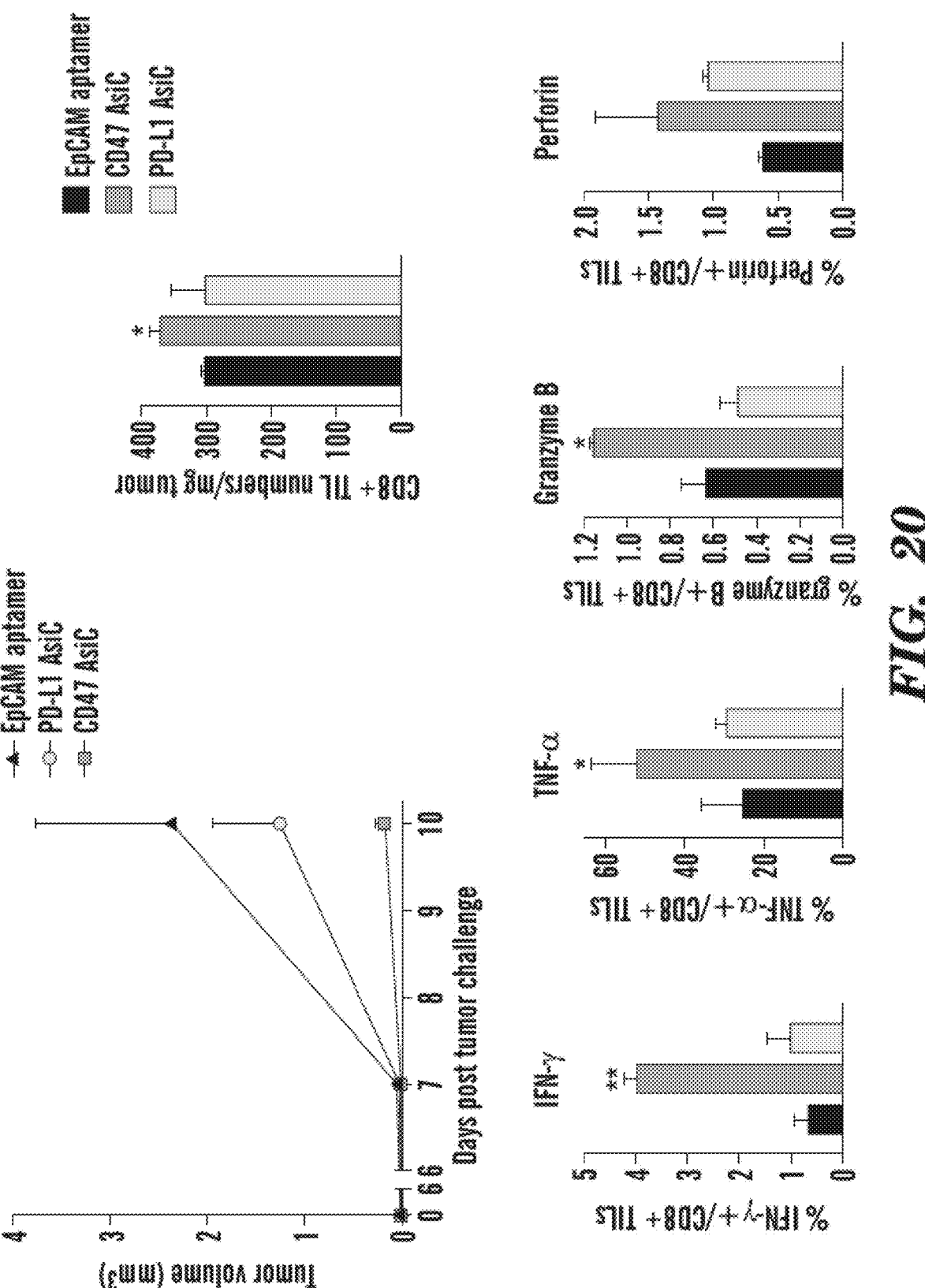
FIG. 20 compares the results for a PD-L1 and CD47 AsiC. The series in the bar graphs are, in order, EpCAM aptamer, CD47 AsiC, and PD-L1 AsiC.
Figure 21:
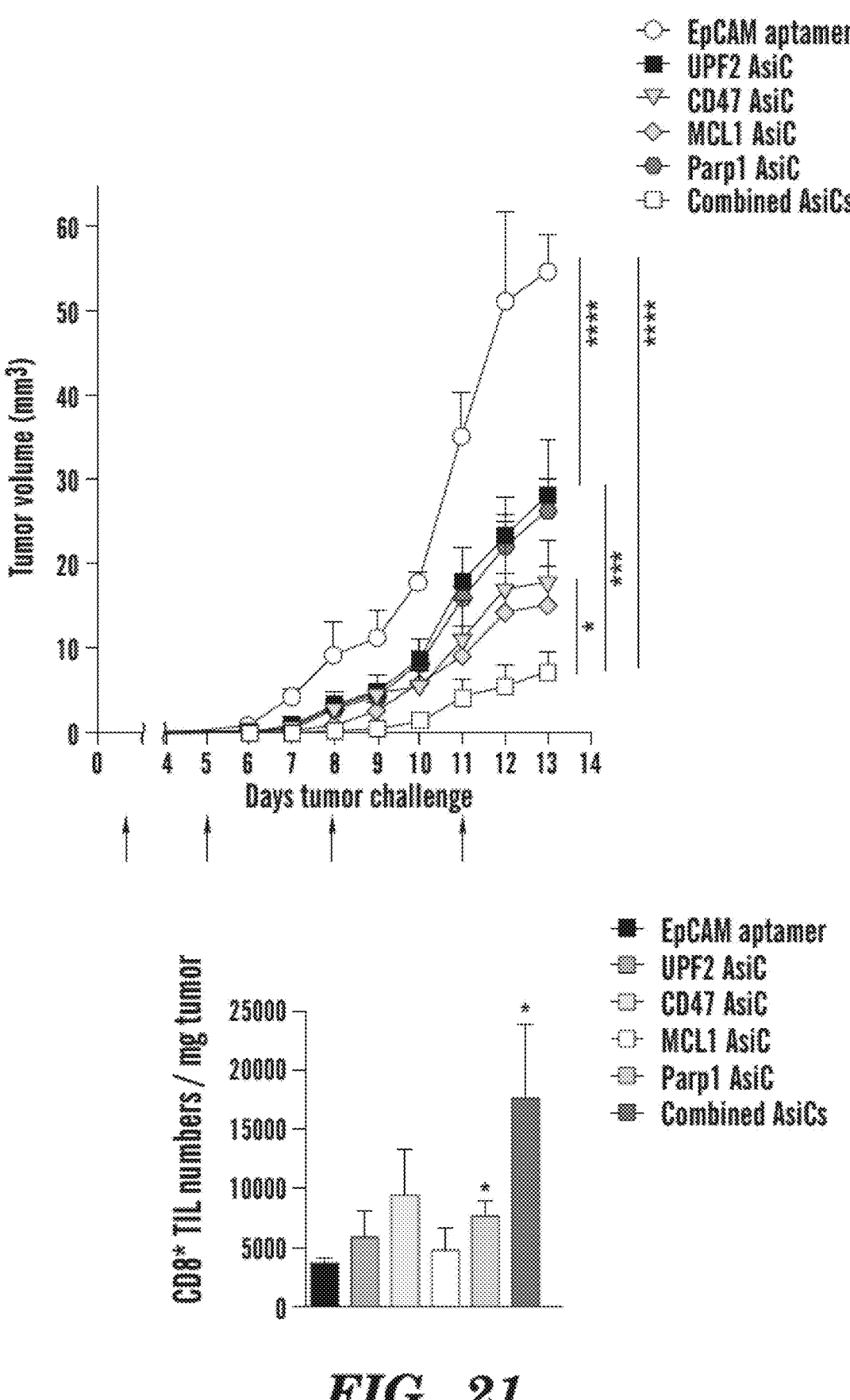
FIG. 21 depicts a comparison of single EpCAM-AsiCs versus a combination of AsiCs.
Figure 21:
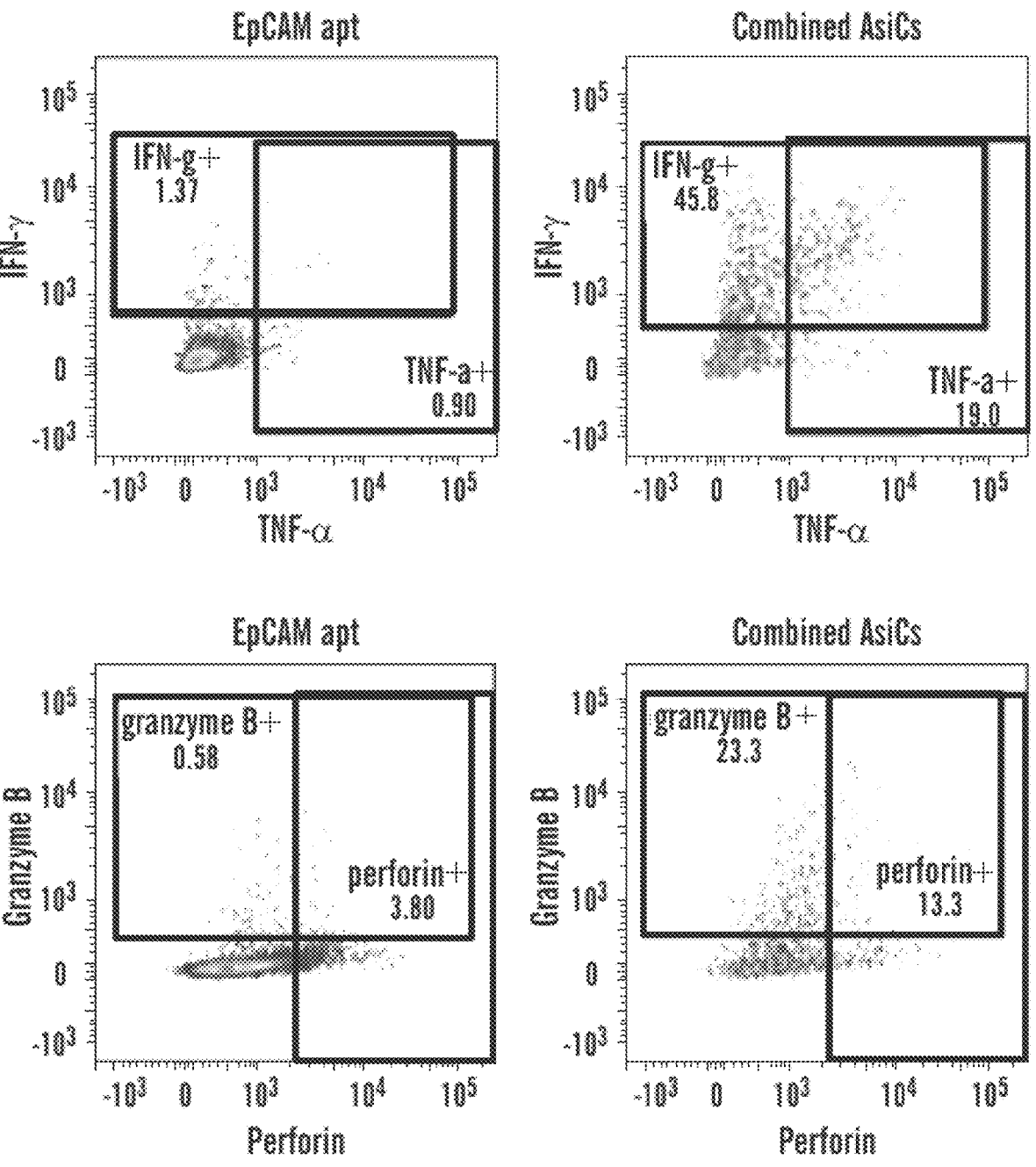

Because only the tumor is targeted, AsiC therapy is both effective and well tolerated. Additionally, the target choice can be customized to patient's tumor. AsiC therapy shows no obvious signs of drug resistance (e.g., no suppression of EpCAM (FIG. 19)) and can be used to treat the common solid tumors for which existing therapy is inadequate.

EpCAM-AsiCs are a flexible platform for selectively knocking down gene expression only in the tumor, including in the most aggressive subset of cancer stem cells. It is possible to use gene knockdown to directly kill the tumor (PLK1, MCL1). These AsiCs also enhance immune responses (data not shown). It is possible to knockdown genes in the tumor to go beyond checkpoint blockade—to modulate multiple pathways to induce immune recognition, activate dysfunctional immune cells and reduce immuno-suppressive cells that interfere with protection. Cocktails of AsiCs are easy to assemble and can synergize to improve tumor control. As shown herein, AsiCs worked better than blocking antibodies or inhibitor drugs.

Example 3: Immunotherapy for Breast Cancer by EpCAM Aptamer-Targeted Gene Knockdown in the Tumor Introduction Triple-negative breast cancer (TNBC) and HER2+ breast cancers (BCs) are the most aggressive BCs with the worst prognosis[1,2]. There is no targeted therapy for TNBCs, and a large fraction of patients relapse and develop metastases after chemotherapy[3]. Although HER2-targeted therapies have radically improved HER2+BC treatment, more than 20% of patients develop recurrent disease within 5 years[4,5]. Thus, novel strategies that could improve the therapeutic efficacies for aggressive BCs are urgently needed. Cancer immunotherapy has exhibited significant and durable responses in patients with multiple types of cancers[6]. Responsive cancers have high somatic mutation rates (i.e., about 100/Mb for melanoma and non-small cell lung cancer), which are believed to contribute to their immunoge-nicit[7]. BCs have previously been viewed as immunologi-cally quiescent, which is associated with their low nonsynonymous mutational burden (about 1/Mb) and their susceptibility to immunotherapy has not been well studied in the clinic[7-9]. However, abundant evidence suggests that the BC tumor microenvironment (TME) is under immune sur-veillance and immunotherapy has shown efficacy in some BCs. Gene expression profiling of BCs indicates that expres-sion of lymphocyte-related genes in the tumor, or genes linked to the activation of type I interferons (IFN-I) are associated with better prognosis[10-11]. Importantly, both TNBC and HER 2+ BC possess higher mutation load, with greater number of patients possessing a robust tumor immune infiltrate compared to other BC subtypes[12,13]. Increased levels of tumor-infiltrating lymphocytes (TILs) are associated with better overall survival (OS) and disease-free survival (DFS) in TNBC and HER2+ BC, with each 10% increase in TIL numbers being linked with a 15-25% decrease in risk of relapse and death[14-16]. Moreover, the long-term effectiveness of some conventional chemotherapy drugs, targeted therapy and radiotherapy depends on their ability to trigger antitumor T cells[11]. These findings high-light the opportunity to develop potent immunotherapeutic approaches to improve the treatment outcome for patients with aggressive BCs.

The use of immune checkpoint inhibitors, e.g. anti-PD-1/PD-L1 antibodies, represents one of the most promising immunotherapeutic approaches for treating aggressive BCs. Anti-PD-L1 antibody atezolizumab combined with chemo-therapeutic drug nab-paclitaxel has been approved for patients with metastatic TNBC in 2019. However, the thera-peutic benefit is limited to a minority of patients[13]. Respon-siveness to checkpoint inhibitors correlates with tumor genomic stability, tumor neoantigen expression and immune recognition[17-22]. Many BCs do not respond to checkpoint blockade, largely due to their low mutation rates that make breast tumor cells not well recognized by the immune system. In addition, checkpoint inhibitors nonspecifically activate T cells systemically and could cause autoimmune side effects[23]. To optimize the efficacy of immunotherapeu-tics for BC treatment, there are a number of challenges in the cancer-immunity cycle that has to be overcome to elicit effective antitumor immunity[24,25]. For instance, tumor cells need to express neoantigens that can be released and taken up/presented by antigen presenting cells (APCs) to prime and active tumor antigen (TA)-specific T cells. The activated T cells also need to infiltrate into the TME and efficiently kill target tumor cells that present the TA.

To achieve this goal, the inventors took advantage of the unique strength of the EpCAM aptamer carried small inter-fering RNAs (siRNAs). The EpCAM aptamer-siRNA chi-meras (AsiCs) can specifically knockdown any gene prod-uct, including intracellular and undruggable targets, selectively in EpCAM+ breast tumor cells, to make aggres-sive BCs visible to T cells and therefore enhance antitumor immune responses. As a tumor-associated antigen, EpCAM is expressed at several logs higher levels on all epithelial cancers relative to normal epithelia, including 97% of BCs and their 'cancer stem cells'[31-34]. EpCAM exhibits onco-genic potential as its expression is associated with enhanced tumor progression, bone metastasis as well as poor progno-sis[32], which may make it hard for tumor cells to develop drug resistance by downregulating EpCAM. The high affin-ity EpCAM aptamer described herein can bind with low nanomolar affinity to both mouse and human EpCAM. To be clinically useful, EpCAM-AsiCs need to be taken up by distant tumors. The inventors have found that subcutane-ously (s.c.) injected EpCAM-AsiC targeting PLK1, a serine-threonine kinase essential for BC cell survival, could con-centrate selectively in distant EpCAM+ but not EpCAM− TNBC xenografts or normal tissues in mice and persisted there for at least four days[26]. In these mice all EpCAM+ tumors completely regressed, while EpCAM+ tumors in mice treated with control AsiC and all EpCAM− tumors continued to grow. Furthermore, the EpCAM-AsiCs did not induce measurable toxicity in treated mice and did not stimulate an innate immune response[26]. These experiments demonstrated the promise of developing EpCAM-AsiCs as an immune-modulating therapy against BC.

Here, to enhance BC cell immunogenicity, the inventors used the EpCAM-AsiCs platform to knock down genes participating in different functional processes of the cancer-immunity cycle in EpCAM+ BC cells, with the goals of making aggressive BCs visible to the immune system and improving antitumor immunity. These targets include: (1) the regulator of nonsense transcripts 2 (UPF2) functioning in the nonsense-mediated mRNA decay (NMD) pathway and the DNA repair enzymes Poly(ADP-Ribose) Polymerase 1 (PARP1) and Apurinic/Apyrimidinic Endodeoxyribonuclease 1 (APEX1), to elicit tumor neoantigen expression; (2) the 'don't eat me' signal CD47 to promote the phagocytosis of cancer cells and their antigen presentation by dendritic cells (DCs) and macrophages; (3) the myeloid cell leukemia 1 (MCL1), which is a critical survival factor in TNBC[35-37], to directly kill tumor cells in order to facilitate TA cross-presentation to activate CD8[+] T cells, thereby improving antitumor T cell responses; and (4) the programmed death-ligand 1 (PD-L1) to improve the function of tumor-infiltrating PD-1[+] T cells. As demonstrated herein, these EpCAM-AsiCs can knockdown target gene expression in EpCAM+ breast tumor cells with high efficiency and selectivity both in vitro and in vivo. Using a mouse orthotopic TNBC model, it is demonstrated that each of the four EpCAM-AsiCs targeting UPF2, PARP1, CD47, and MCL1 markedly suppress breast tumor growth. PARP1 and CD47 AsiCs outperformed FDA-approved PARP1 inhibitor Olaparib and anti-CD47 antibody that has entered multiple clinical trials in inhibiting tumor growth, respectively. These immune-modulating EpCAM-AsiCs also strongly boosted antitumor immunity by enhancing the ratio of CD8[+] tumor-infiltrating lymphocytes (TILs) to CD4[+] regulatory T cells (Tregs) and increasing the functions of CD8[+] and CD4[+] TILs.

Mechanistically, UPF2 knockdown reduced the NMD pathway activity in EpCAM+ tumor cells and promoted the generation of splice variant mRNAs that may encode neoantigens. CD47 knockdown facilitated the phagocytosis of tumor cells by tumor-associated macrophages (TAMs), increased the ratio of tumor-suppressive M1 TAM to tumor-promoting M2 TAMs, and also enhanced the numbers and maturation of tumor-infiltrating DCs, all of which could promote antigen presentation to activate T cells. MCL1 knockdown directly reduced tumor cell viability, which may increase the release of TAs to stimulate TA-specific T cells. Furthermore, the four EpCAM-AsiCs worked in synergy and led to a more significant reduction in tumor growth compared to singe AsiC treatment, and also strongly inhibited lung metastatic BC growth. Single-cell RNA sequencing (scRNA-seq) study indicated that the combined AsiCs simultaneously improved the antitumor potential of both monocytes/macrophages and TILs. The combined AsiCs further synergized with anti-PD-1 and resulted in a more pronounced tumor inhibition. Finally, we showed that a cocktail of EpCAM-AsiCs targeting the six genes UPF2, PARP1, APEX1, CD47, MCL1, and PD-L1 simultaneously suppressed tumor growth in a transgenic mouse model of highly aggressive HER2+BC, indicating the potential of utilizing the immune-modulating EpCAM-AsiCs as a potent immunotherapeutic approach to combat aggressive BC.

Results

Figure 32A:
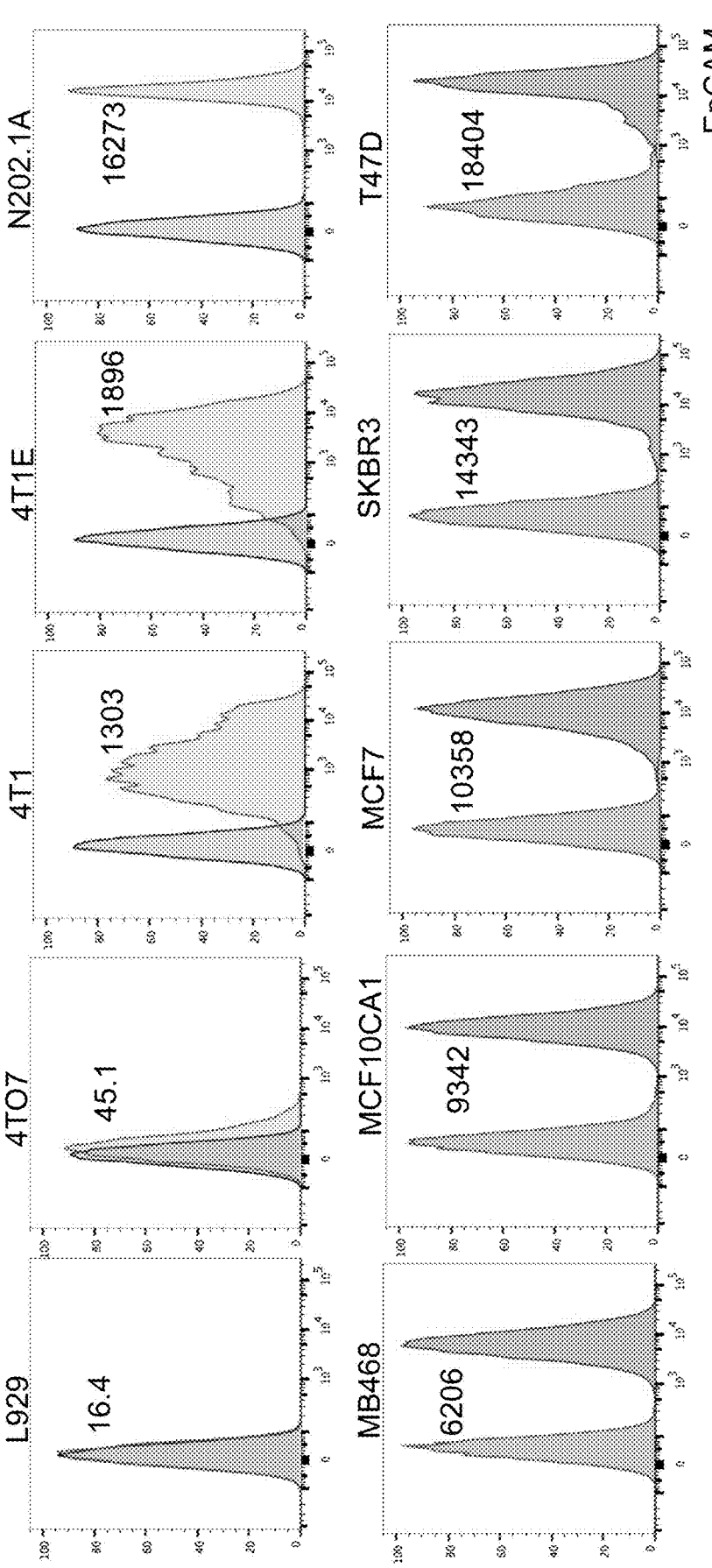
FIGS. 32A-32B demonstrate EpCAM expression and EpCAM aptamer uptake efficiency by mouse and human BC cells.
Figure 32B:
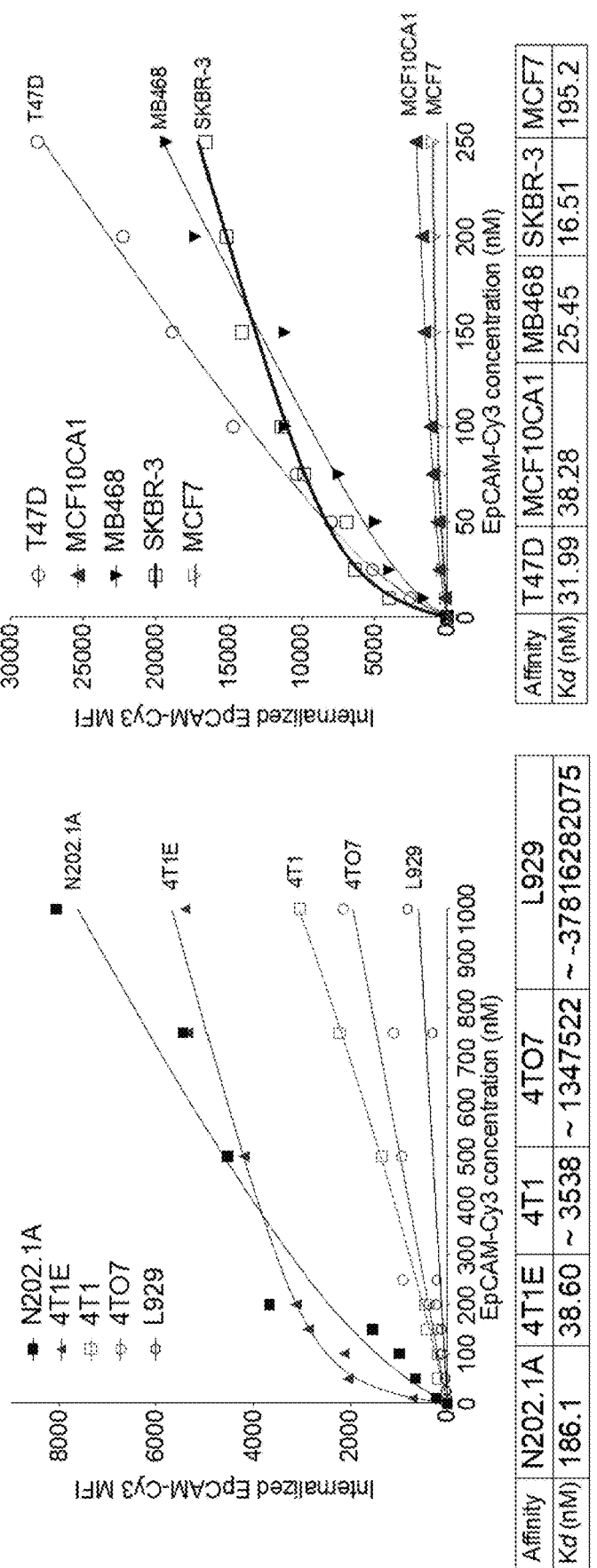

EpCAM Aptamer-siRNAs Selectively Cause Gene Knockdown in EpCAM+ Mouse BC Cell Lines To investigate the use of EpCAM aptamers for cell-specific gene knockdown for BC immunotherapy, the inventors first verified that fluorescently labeled EpCAM aptamer was taken up by mouse EpCAM+ BC cell lines (4T1, 4T1E, N202.1A), but not EpCAM− mouse cell lines (L929, P815, B16-F10) (data not shown). It was hypothesized that knocking down genes in mouse BC cell lines that might increase expression of tumor neoantigens (Upf2, Parp1, Apex), cause tumor cell death (Mcl1), enhance phagocytosis of tumor cells (Cd47), or suppress checkpoint inhibition (Cd274, the gene encoding for PD-L1) could enhance anti-tumor immunity. To test this hypothesis, the inventors designed EpCAM aptamer-siRNA chimeras (AsiC) to knockdown each of these genes using siRNAs that each caused ~90% knockdown in 4T1E TNBC transfected using 100 nM siRNA (FIG. 32A). Transfection of all of these siRNAs had no effect on cell viability or proliferation, except for the Mcl1 siRNA (FIG. 32B).

To construct EpCAM-AsiCs, the inventors linked the sense (passenger or inactive) strand of each selected siRNA to the 3' end of the 19 nt EpCAM aptamer via a U-U-U linker (FIG. 25A, Table 5). This RNA strand was chemically synthesized with 2'-fluoropyrimidine substitutions and a 3'-dTdT overhang to enhance resistance to RNases and then annealed to the antisense (guide or active) strand of each siRNA, which was also modified with fluoropyrimidines and a 3'-dTdT overhang. This configuration is stable for >36 hr in serum in vitro, did not induce innate immune IFN or inflammatory cytokine responses and was cleaved in cells by Dicer to release an active siRNA from the aptamer EpCAM-AsiCs designed to knockdown Upf2, Parp1, Apex, Cd47, Mcl1 or Cd274 knocked down target gene expression in EpCAM+4T1E tumor cells in vitro by 50-90% when measured 72 hr later. As expected, EpCAM-AsiCs did not affect target gene expression in EpCAM-L929 (not shown). Subcutaneous injection of 125 μg (5 mg/kg) AsiCs in the scruff of the neck in mice knocked down gene expression by 50-70% in 4T1E tumors implanted orthotopically in the 4th mammary gland measured 72 hr post injection. Knockdown was specific since injection of the EpCAM aptamer on its own or an EpCAM-AsiC directed against eGFP did not knockdown endogenous genes. Moreover, knockdown did not occur in EpCAM-CD45− cells within the tumor.

EpCAM-AsiCs Targeting UPF2 or PARP1 Inhibit Tumor Growth and Enhance Antitumor T Cell Immunity Knocking down Upf2, which encodes a protein that binds to prematurely terminated mRNAs that arise from a variety of genetic mutations and triggers nonsense-mediated decay, has been postulated to induce tumor cell expression of neoantigens to promote tumor recognition by T cells. To verify that in vivo treatment of mice bearing 4T1E orthotopic tumors with EpCAM-AsiC, which reduced tumor UPF2 mRNA and protein, decreased NMD activity in tumor cells, the inventors compared the ratio of fully spliced mRNA to its precursor pre-mRNA for four known NMD-targeted transcripts (Gadd45α, Gadd45β, Cdkn1a, Nat9). An increase in this ratio indicates diminished NMD activity[39,40]. The mRNA/pre-mRNA ratio for all four genes was significantly higher in the tumors of UPF2 EpCAM-AsiC treated mice than in control mice treated with just the aptamer, indicating impaired NMD activity.

Figure 25E:
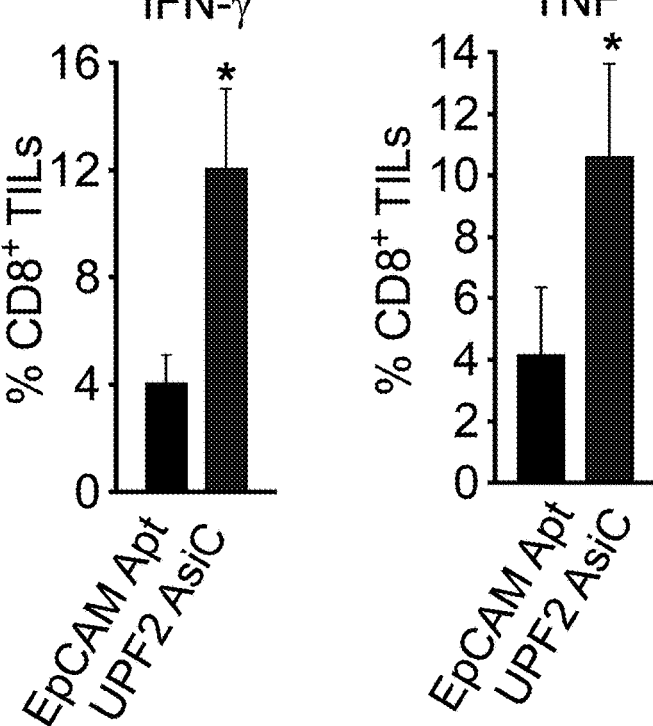
Figure 25G:
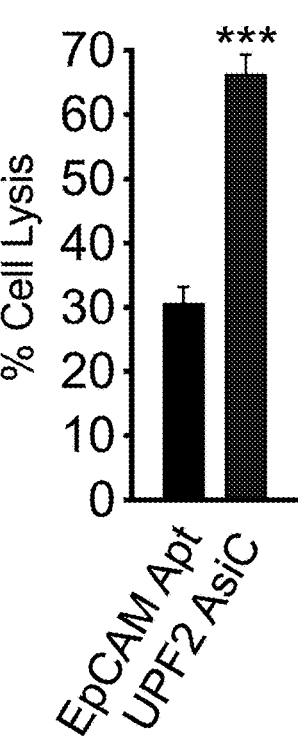
Figure 25F:
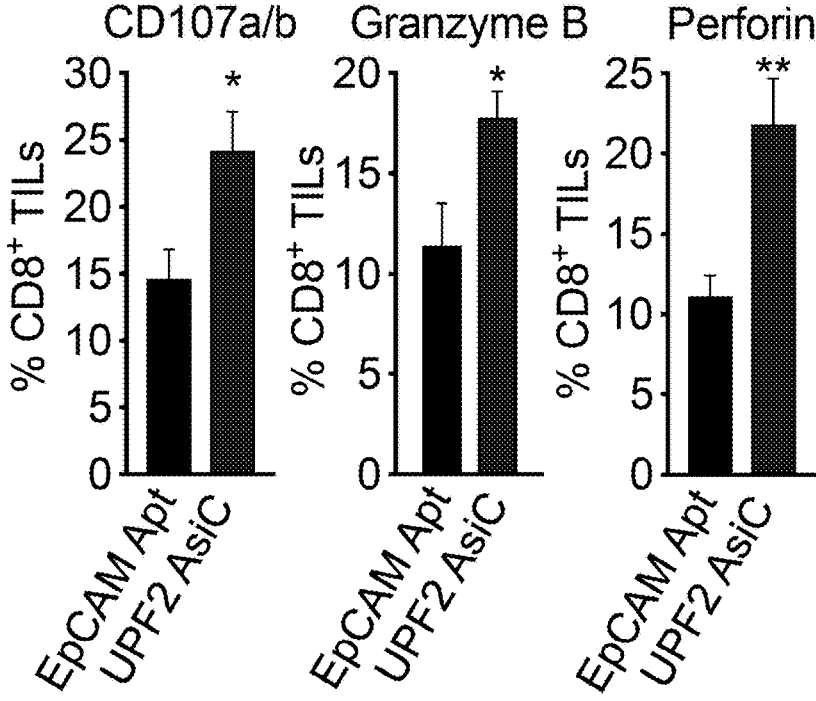
Figure 25F:
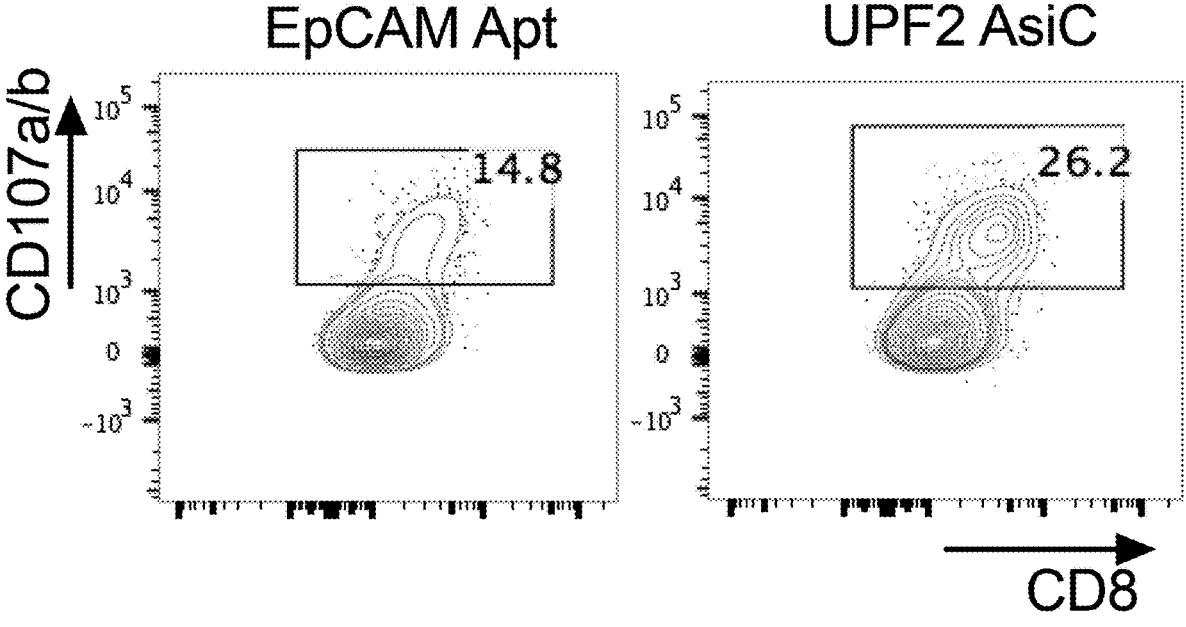

To determine whether EpCAM-AsiCs targeting Upf2 have anti-tumor activity, mice bearing palpable orthotopic 4T1E tumors were treated with 5 mg/kg of EpCAM aptamer or UPF2 EpCAM-AsiC s.c. every three days. 4T1E tumor growth was significantly inhibited in mice treated with UPF2 EpCAM-AsiCs (FIG. 25B). The effect of tumor-targeted Upf2 on tumor-infiltrating lymphocytes (TIL) was assessed by immunohistochemistry (IHC) and flow cytometry analysis of single cell suspensions of tumors harvested on day 16 after 3 AsiC or aptamer injections. UPF2 EpCAM-AsiCs strongly increased the density of CD8[+] TIL measured by IHC by 3-fold (FIG. 25C). The ratio of CD8[+] to CD4[+]Foxp3[+] $T_{reg}$, a parameter strongly associated with antitumor immunity and response to immunotherapy for aggressive BC[43,44], also increased 3-fold in UPF2 AsiC treated tumors by flow cytometry (FIG. 25D). CD8[+] TIL from UPF2 AsiC-treated tumors also produced more IFN-γ and TNF-α after ex vivo stimulation with phorbol 12-myristate 13-acetate (PMA) and ionomycin (FIG. 25E). After co-incubation with UPF2 siRNA-treated 4T1E ex vivo for 6 hours, these CD8$^+$ TIL also degranulated more as measured by CD107a/b surface expression (FIG. 25F) and stained more for the cytotoxic effector molecules, granzyme B and perforin (FIG. 25G). Indeed, CD8$^+$ TIL from UPF2 AsiC-treated tumors compared to aptamer-treated tumors were twice as effective at killing Upf2-knocked down 4T1E cells. Thus, UPF2 EpCAM-AsiCs significantly enhanced antitumor CD8$^+$ T cell immunity and delayed 4T1E tumor growth.

UPF2 Knockdown Induces Novel mRNA Transcripts

To investigate whether UPF2 knockdown in BC generates novel mRNA isoforms, the inventors performed bulk RNA sequencing (RNA-seq) using an EpCAM$^{hi}$ MDA-MB-231 human BC cell line transfected with either noncoding control or UPF2 siRNA for 72 hours. The inventors identified 222 examples of differential exon usage (DEU) events within 281 genes (data not shown). For example, UPF2 knockdown significantly reduced usage of exon 8 in RINL mRNA (transcript ID ENSG00000187994) (log 2 fold change −15.2, adjusted p-value=0.03) and significantly enhanced usage of exon 6 (log 2 fold change of 14.5, adjusted p-value=0.02) in ATP11B mRNA transcript (ENSG00000058063), which was almost not detected in control cells. These DEU events could lead to the expression of novel polypeptides and novel T cell epitopes. The number and diversity of DEUs suggest that UPF2 knockdown could have caused novel alternative splicing.

Figures 33A, 33B, 33C:
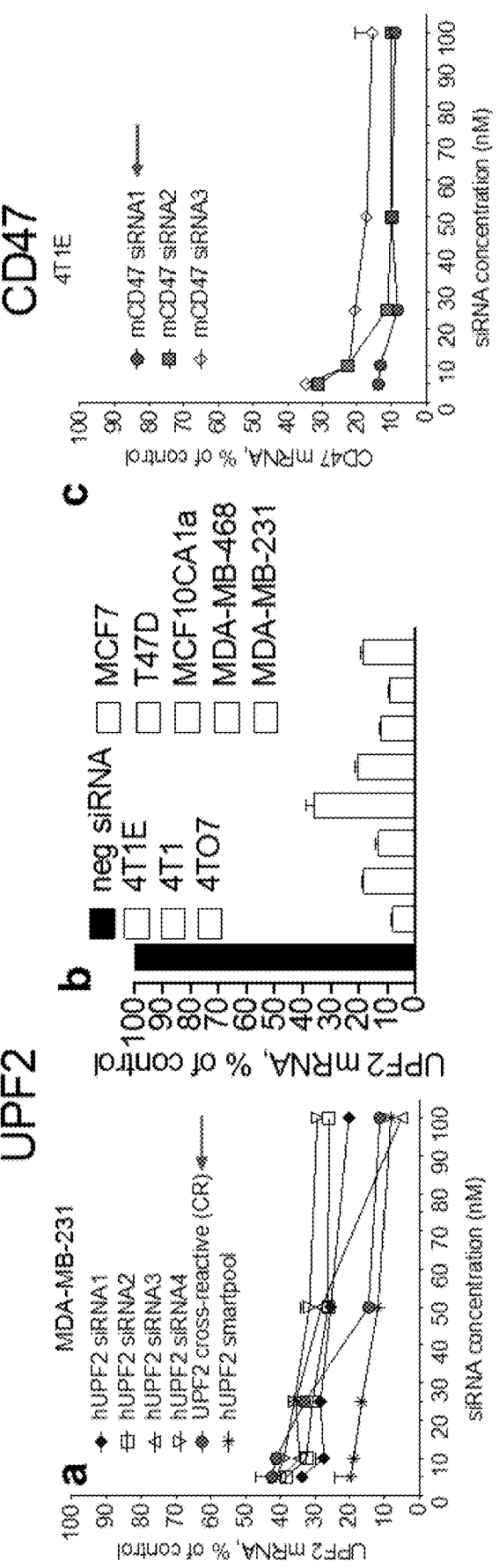
FIGS. 33A-33G depict the titration of siRNAs in BC cells.
Figures 33D, 33E, 33F, 33G:
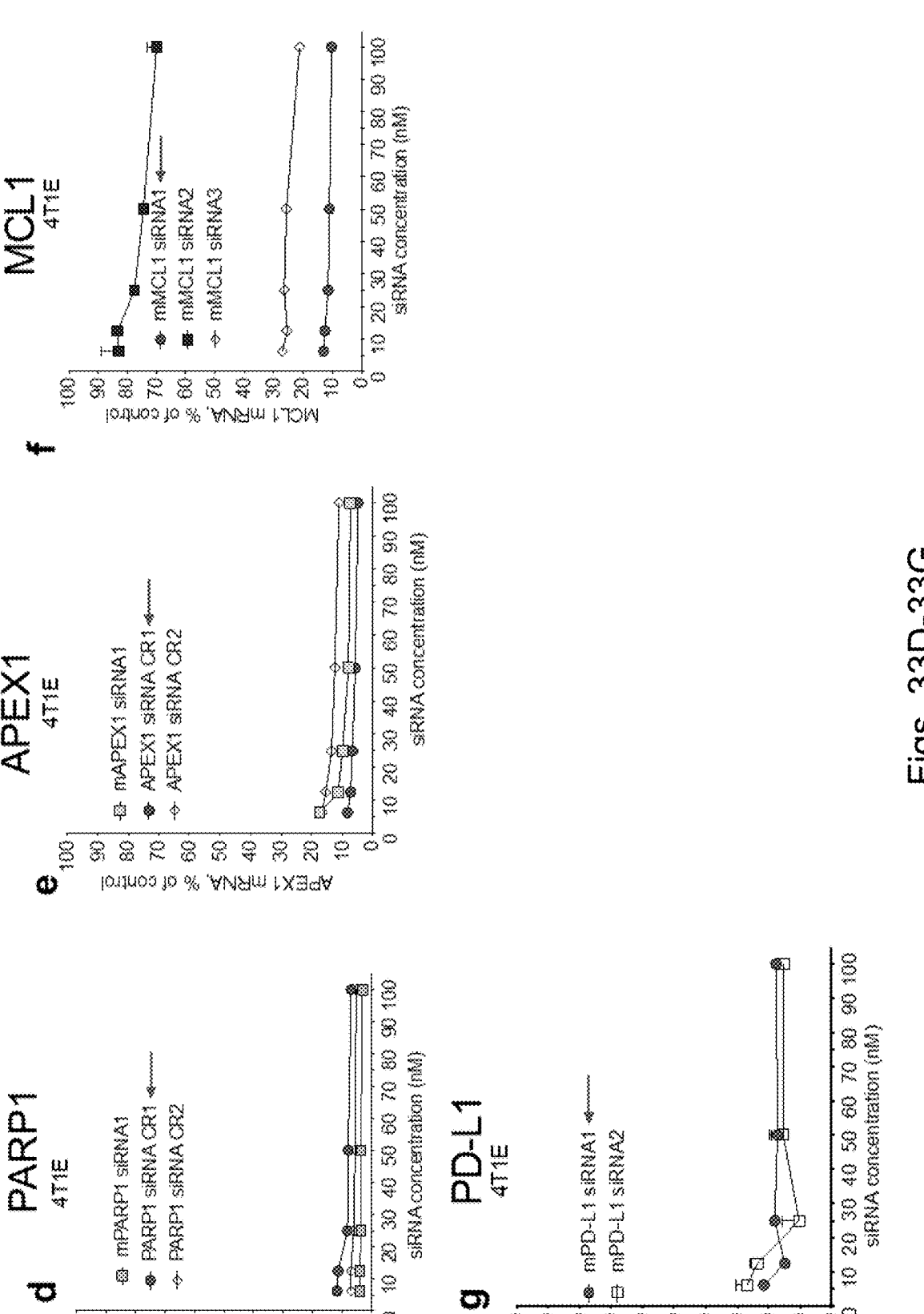

To test this, UPF2 knockdown-mediated transcriptional diversity was deconvoluted to identify and estimate the abundance of transcript isoforms. 42 genes with potential differential isoform usage (DIU) were identified (data not shown). These included seven genes identified as having DEU (CENPH, PFKFB4, UCN2, SNHG8, CDKAL1, TRIM4, TMEM242). These DIU events included examples of novel mRNA isoforms that may encode new polypeptides, e.g. in DNAJC2 and TMPRSS5 LAT2 (FIG. 33A). In addition, a some genes with DIU, such as CENPH, SNRPA1, and EBPL, increased the abundance of mRNA isoforms known to be sensitive to NMD. For instance, UPF2 knockdown increased a CENPH isoform that shows exon-skipping event is predicted to have premature termination codons that make it sensitive to NMD (FIG. 33B). Collectively, this data indicates that reducing NMD activity by UPF2 knockdown induces expression of tumor neoantigens.

Knocking Down Parp1 Reduces Tumor Growth and Enhances Anti-Tumor Immunity

The inventors hypothesized that inhibiting DNA repair in the tumor might be another way to induce tumor neoantigen expression. PARP1 is a critical DNA damage repair protein that senses single-stranded and double-stranded DNA breaks and recruits and activates the DNA repair machinery at the site of the break[45]. Knocking down PARP1 in tumor cells could potentially lead to more DNA break-related mutations, thereby introducing tumor-specific neoantigens that could be recognized by T cells. To test whether Parp1 knockdown activates antitumor immunity, mice bearing palpable orthotopic 4T1E tumors were treated with the EpCAM aptamer, PARP1 EpCAM-AsiC or the FDA-approved PARP1 inhibitor, Olaparib. The PARP1 AsiC more effectively inhibited 4T1E tumor growth than Olaparib, which showed a trend towards inhibition that did not reach not significance (FIG. 26A). The PARP1 AsiC also had a more pronounced effect on antitumor properties of TIL than Olaparib. It induced a potent and significant increase in the CD8$^+$/CD4$^+$ T$_{reg}$ in the tumor (FIG. 26B), activation stimulated production of IFNγ and TNFα by CD8+ TIL (FIG. 26C) and increased TNFα production by CD4+ TIL (FIG. 26D) compared to control aptamer-treated tumors. Olaraprib had a more subtle effect on antitumor immunity that did not reach significance except for an increase in TNFα production by CD4+ TIL. Why Parp1 knockdown has a more potent effect than PARP1 enzymatic inhibition is not clear, but removing PARP1 protein would interfere with the recognition and assembly of repair proteins at sites of DNA damage, whereas inhibiting PARP1's PARylation activity would only act more downstream to inhibit repair. As a consequence, unrepaired DNA damage and genomic instability after Parp1 knockdown might be more extensive than after inhibiting PARP1 enzymatic activity.

Knocking Down Apex1 Effects Tumor Growth

APEX1 is a key endonuclease in base excision repair (BER), which repairs the most common DNA damage in cells, the formation of abasic sites by oxidative DNA damage[47-48]. Apex1 genetic deficiency leads to early embryonic lethality (E4-6.5) and cell lines deficient in Apex1 do not grow. Of note, tumors do not mutate this essential gene. The inventors therefore investigated Apex1 knockdown since it might be directly cytotoxic and also induce mutations that could activate T cell immunity. Perhaps because it is such as essential gene, in vivo Apex1 knockdown by EpCAM-AsiCs was only 50%, less effective than for other EpCAM-AsiCs. When administered in the same dose and schedule as other EpCAM-AsiCs, tumor targeted Apex1 knockdown reduced 4T1E tumor growth, but the difference compared to mice treated with just the aptamer did not reach significance (FIG. 26E).

CD47 EpCAM-AsiC Promotes EpCAM$^+$ BC Cell Phagocytosis by Macrophages and Enhances Antitumor T Cell Immunity Tumor cells change expression of many genes to avoid immune elimination, a process called tumor editing. One strategy is tumor upregulation of the surface glycoprotein CD47, which binds to signal-regulatory protein SIRPα on macrophages and DCs and acts as a potent "don't eat me" signal to inhibit phagocytosis and antigen cross-presentation[49]. To evaluate the antitumor effect of Cd47 knockdown, orthotopic 4T1E tumor-bearing mice were treated with EpCAM aptamer or CD47 EpCAM-AsiC. CD47 EpCAM-AsiC inhibited tumor growth (FIG. 27A) and promoted antitumor immunity, as indicated by an increased CD8$^+$/CD4$^+$ T$_{reg}$ TIL ratio (FIG. 27B), and increased functional capacity of CD8$^+$ and CD4$^+$ TIL to produce IFN-γ (FIGS. 27C-27D) and of CD8$^+$ TIL expression of GzmB (FIG. 27E), compared to mice treated with EpCAM aptamer.

Figures 27A, 27B, 27C, 27D, 27E, 27F, 27G, 27H, 27I, 27J:
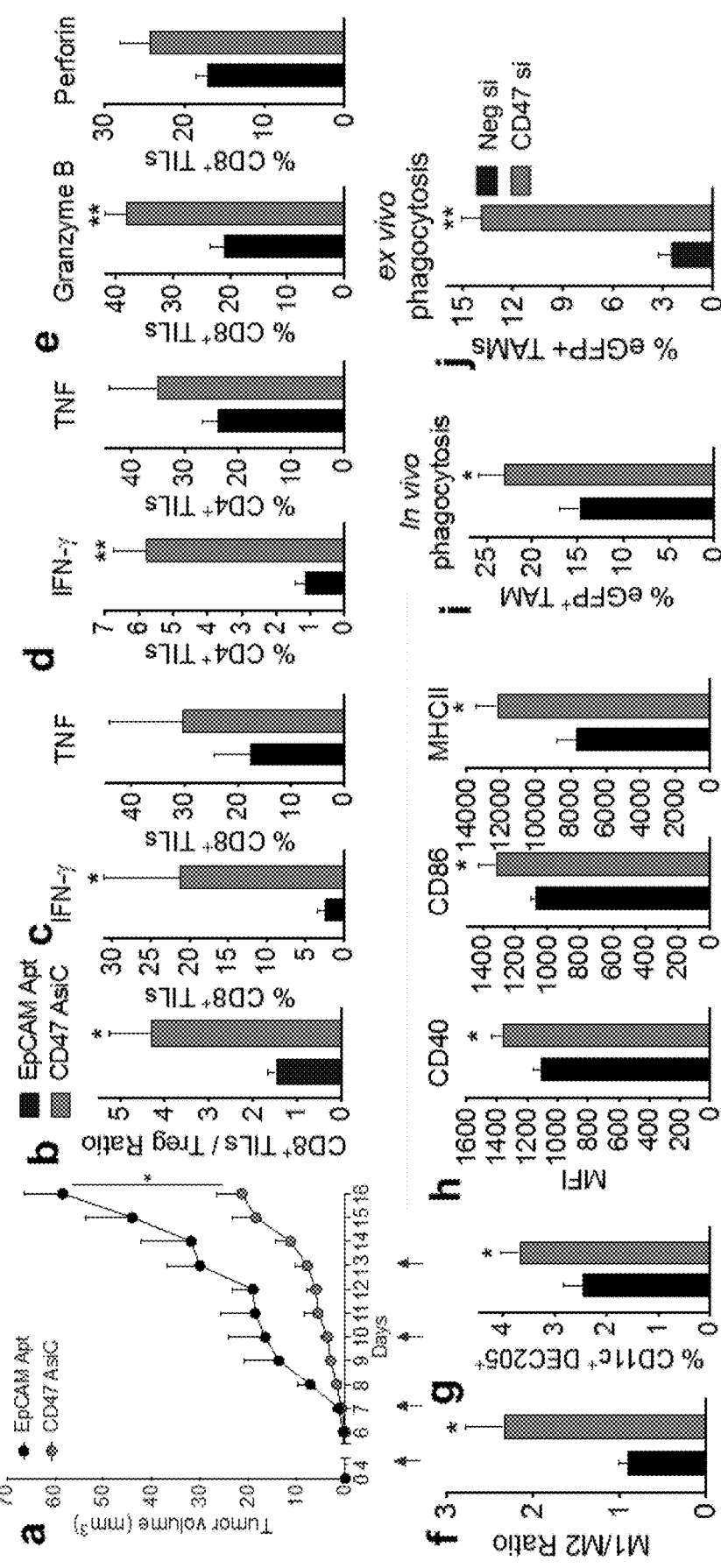
FIGS. 27A-27M demonstrate tumor inhibition and immune modulation capacity of CD47 AsiC.
Figures 34A, 34B, 34C:
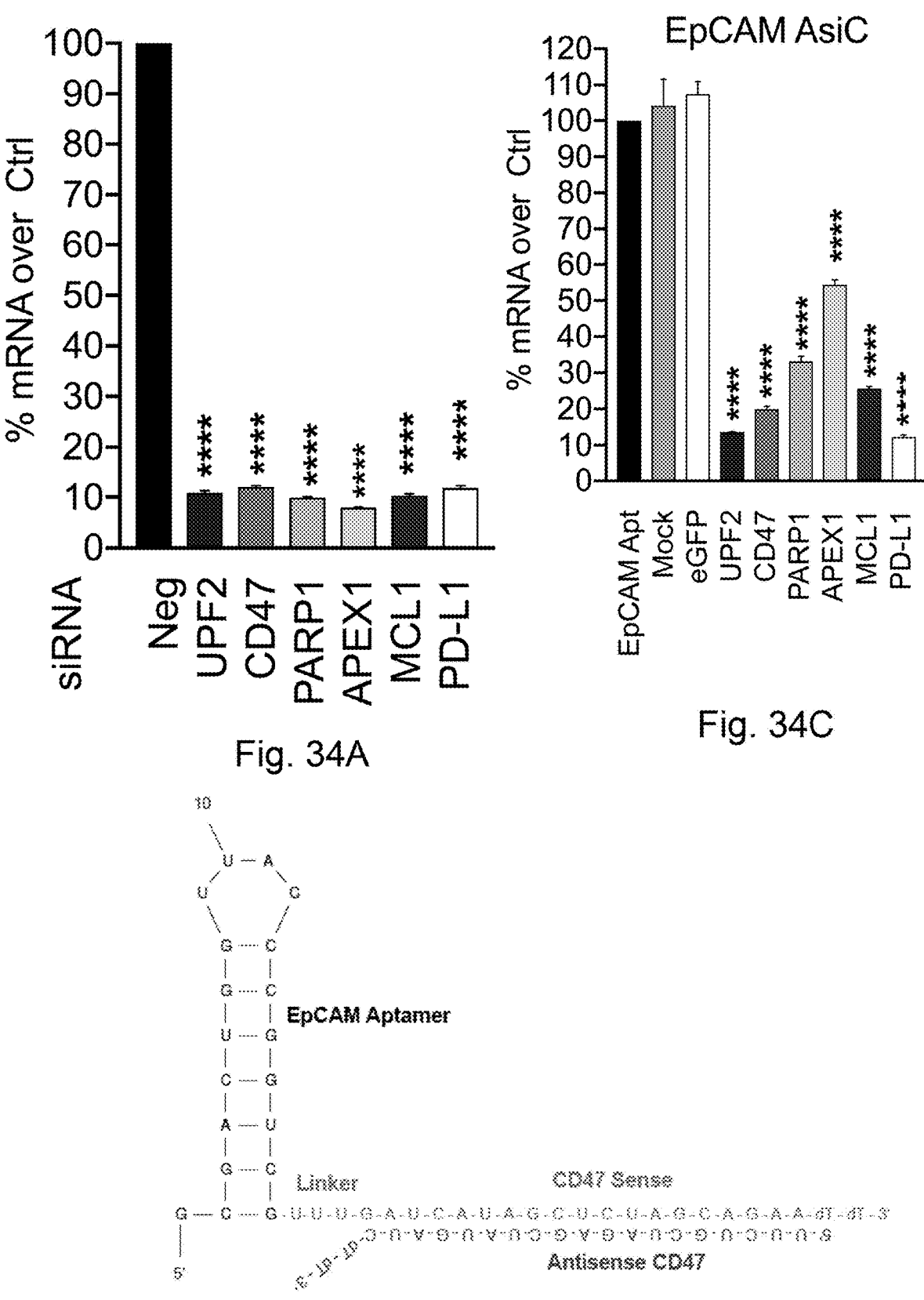
Figures 34D, 34E, 34F:
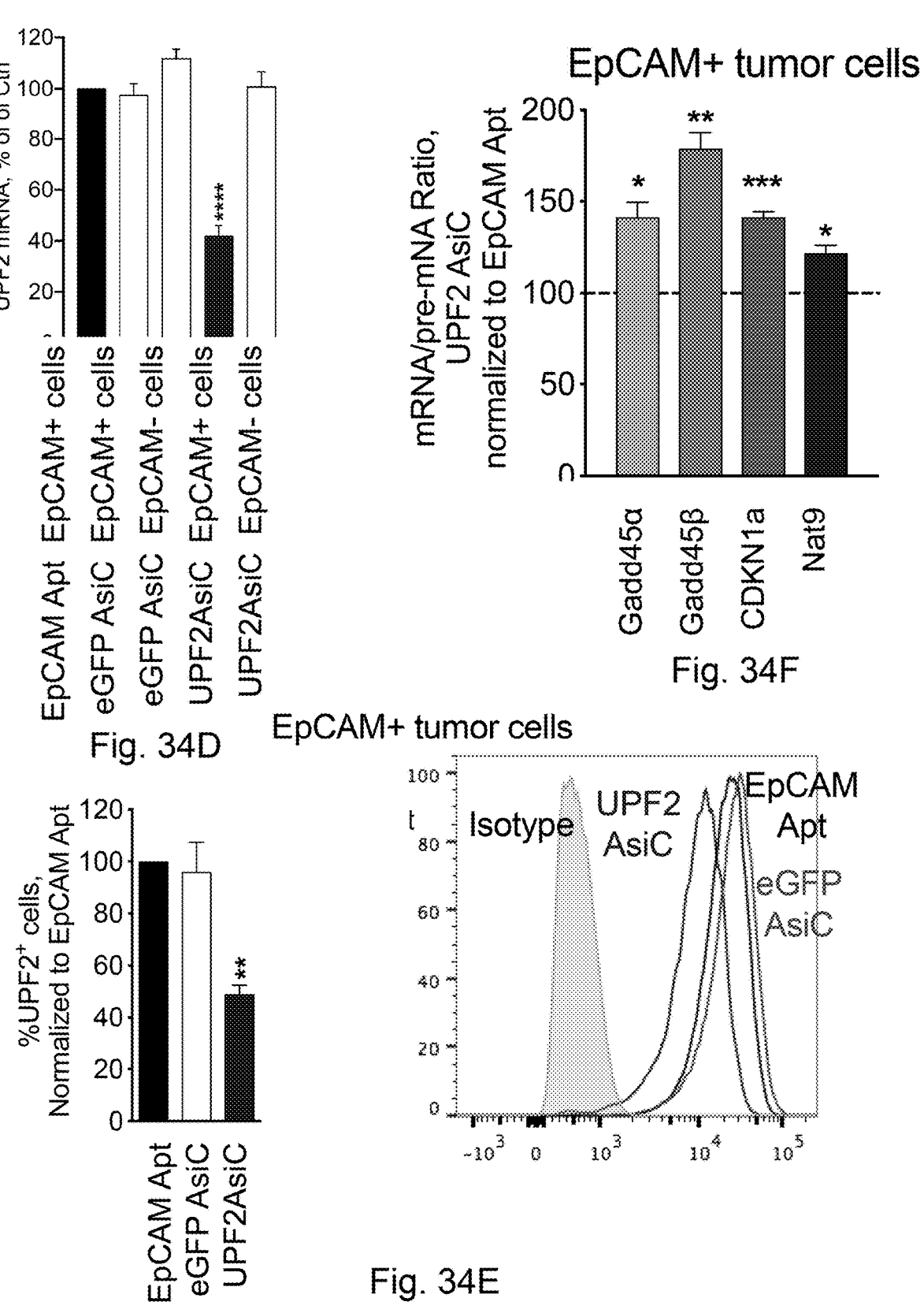
Figures 34G, 34H, 34I:
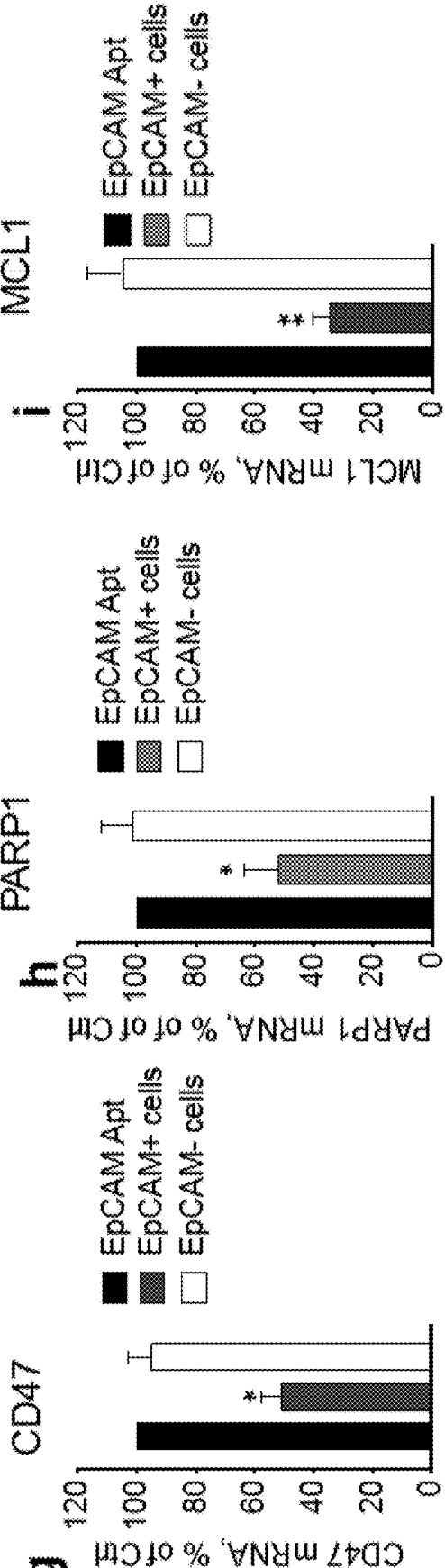

Next, the inventors analyzed the impact of Cd47 knockdown in the tumor on tumor-associated macrophages (TAM) and dendritic cells (DC). In response to tumor environmental cues, TAM can polarize into either pro-inflammatory, classically activated M1-like macrophages with antitumor properties or anti-inflammatory, alternatively activated M2-like macrophages that are immunosuppressive and correlate with tumor progression, metastasis, and poor prognosiss[52-54] Although CD47 EpCAM-AsiCs did not significantly change the numbers of TAM (not shown), the ratio of M1/M2 TAM significantly increased in CD47 EpCAM-AsiC treated tumors (FIG. 27F, FIG. 34B). In addition, the percentage of CD11c$^+$DC205$^+$ DC the CD45+ hematopoietic cells in the tumor was significantly higher after CD47 EpCAM-AsiC treatment compared to aptamer treatment (FIG. 27G). DCs in Cd47 EpCAM-AsiC treated tumors expressed more costimulatory CD80 and CD86 and surface MHC-II, suggesting they were more effective APCs (FIG. 27H). To determine whether TAM phagocytosis of tumor cells increased in vivo after aptamer or CD47 EpCAM-AsiC treatment, the inventors substituted 4T1E tumors with 4T1E tumors stably expressing eGFP (4T1E-eGFP) and examined TAM GFP fluorescence. Significantly more TAM were GFP+ in CD47 EpCAM-AsiC treated tumors, indicating increased in vivo phagocytosis (FIG. 27I). To confirm that enhanced TAM phagocytosis was due to reduced CD47 expression on tumor cells, the inventors cocultured TAM from CD47 EpCAM-AsiC-treated tumors with 4T1E-eGFP that were treated with nontargeting or Cd47 siRNA. TAM phagocytosis of CD47 knocked down 4T1E-eGFP was 4-fold greater than in control tumors (FIG. 27J).

Figures 27K, 27L, 27M:
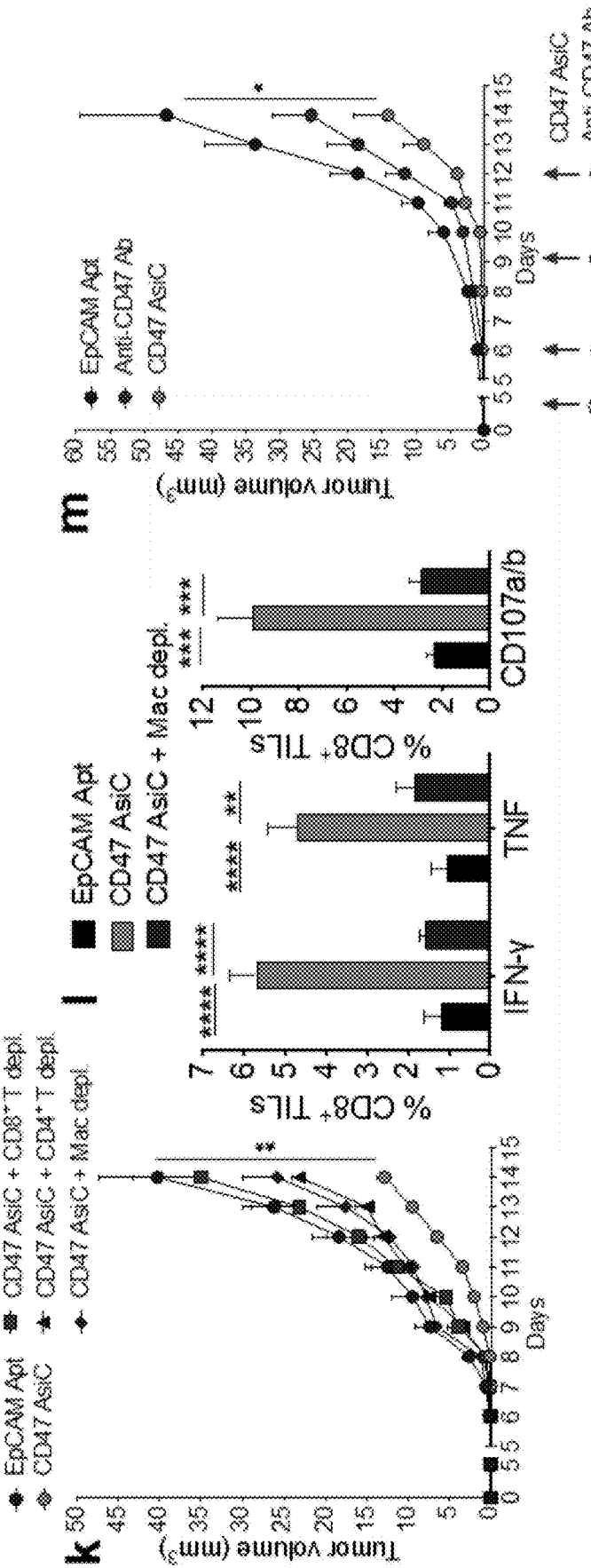
Figures 35A, 35B, 35C:
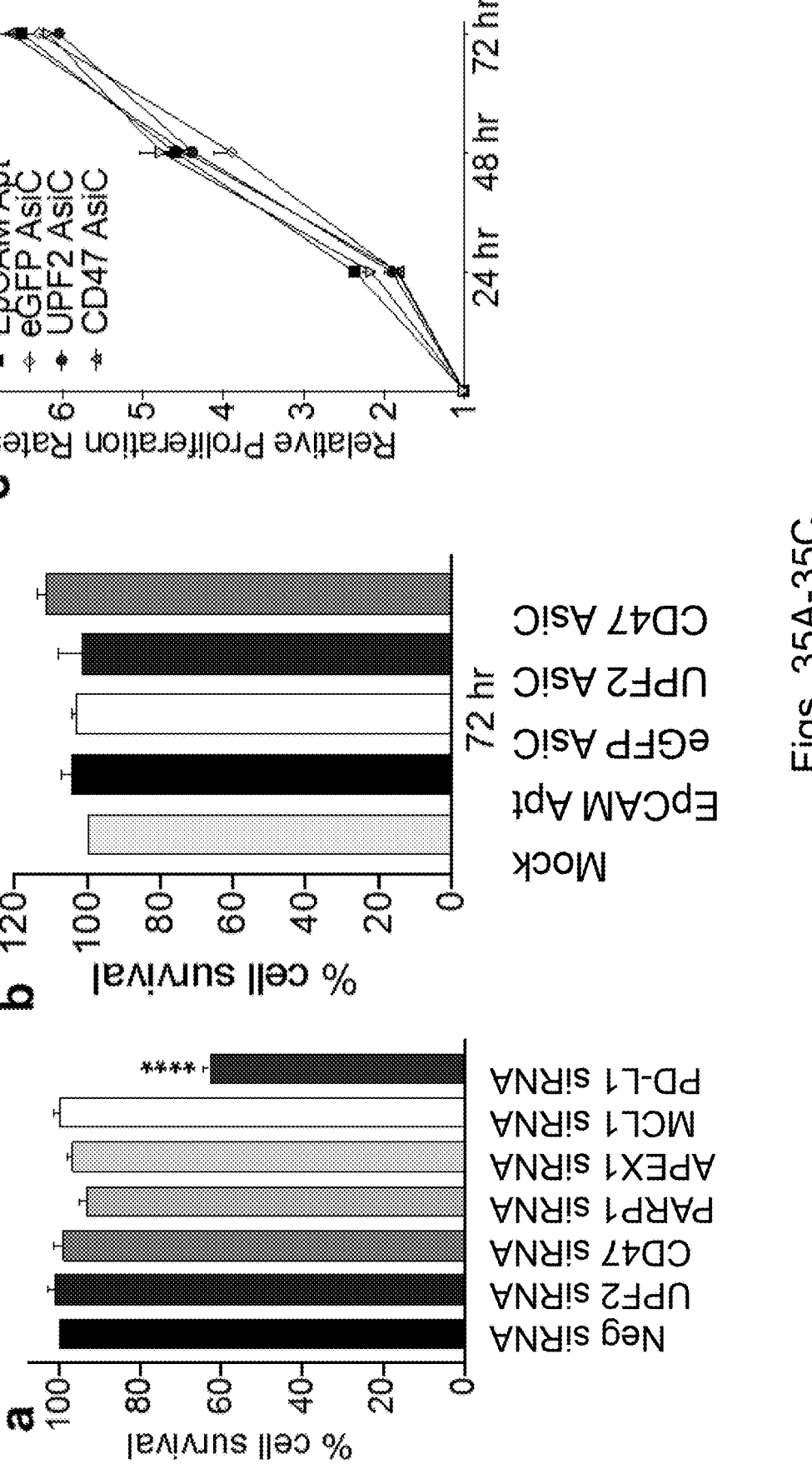
FIGS. 35A-35C depict the effect of siRNA gene knockdown and EpCAM-AsiCs on BC cell viability.

To determine whether the tumor suppressive effect of CD47 EpCAM-AsiCs was mediated by TIL and/or TAM, the inventors depleted CD8+ or CD4+ T cells or macrophages in orthotopic 4T1E tumor-bearing mice before treatment with CD47 EpCAM-AsiCs using antibodies to CD4, CD8 or CSF1R, respectively (FIGS. 35A-35C). Depletion of CD8+ T cells completely abrogated the antitumor effect of CD47 EpCAM-AsiCs, but CD4+ T cell or macrophage depletion had less of an effect (FIG. 27K). However, macrophage depletion was less complete than T cell depletion since about 30% of TAM persisted after depletion. The increased functionality of CD8+ TIL from CD47 EpCAM-AsiC treated tumors, assessed by IFN-$\gamma$ and TNF-$\alpha$ production and degranulation in response to incubation with 4T1E, was reduced to background levels in mice depleted of macrophages, indicating the importance of TAM in promoting CD8+ TIL anti-tumor immunity in CD47 AsiC-treated tumors (FIG. 27L).

To compare the effectiveness of blocking antibodies and knockdown with AsiCs, the inventors evaluated the antitumor effect between CD47 AsiC and anti-CD47 antibody. Although both treatments reduced tumor volumes, especially at later time points, only CD47 AsiC treatment significantly inhibited tumor growth (FIG. 27M). CD8+ TIL from CD47 EpCAM-AsiC and anti-CD47 treated mice both produced more IFN-7 after PMA and ionomycin stimulation than those in control tumors, but only CD47 AsiC significantly increased stimulated TNF-$\alpha$ production of CD4+ TIL. In addition, CD47 EpCAM-AsiC, but not anti-CD47, significantly reduced the numbers of tumor-infiltrating immunosuppressive polymorphonuclear myeloid-derived suppressor cells (PMN-MDSCs) and mononuclear (MO)-MDSCs compared to control tumors. Thus, CD47 EpCAM-AsiCs were more effective than anti-CD47 at controlling tumor growth and inducing anti-tumor immunity.

CD274 (PD-L1) EpCAM-AsiCs have a Modest Effect on Tumor Growth

Figures 36A, 36B:
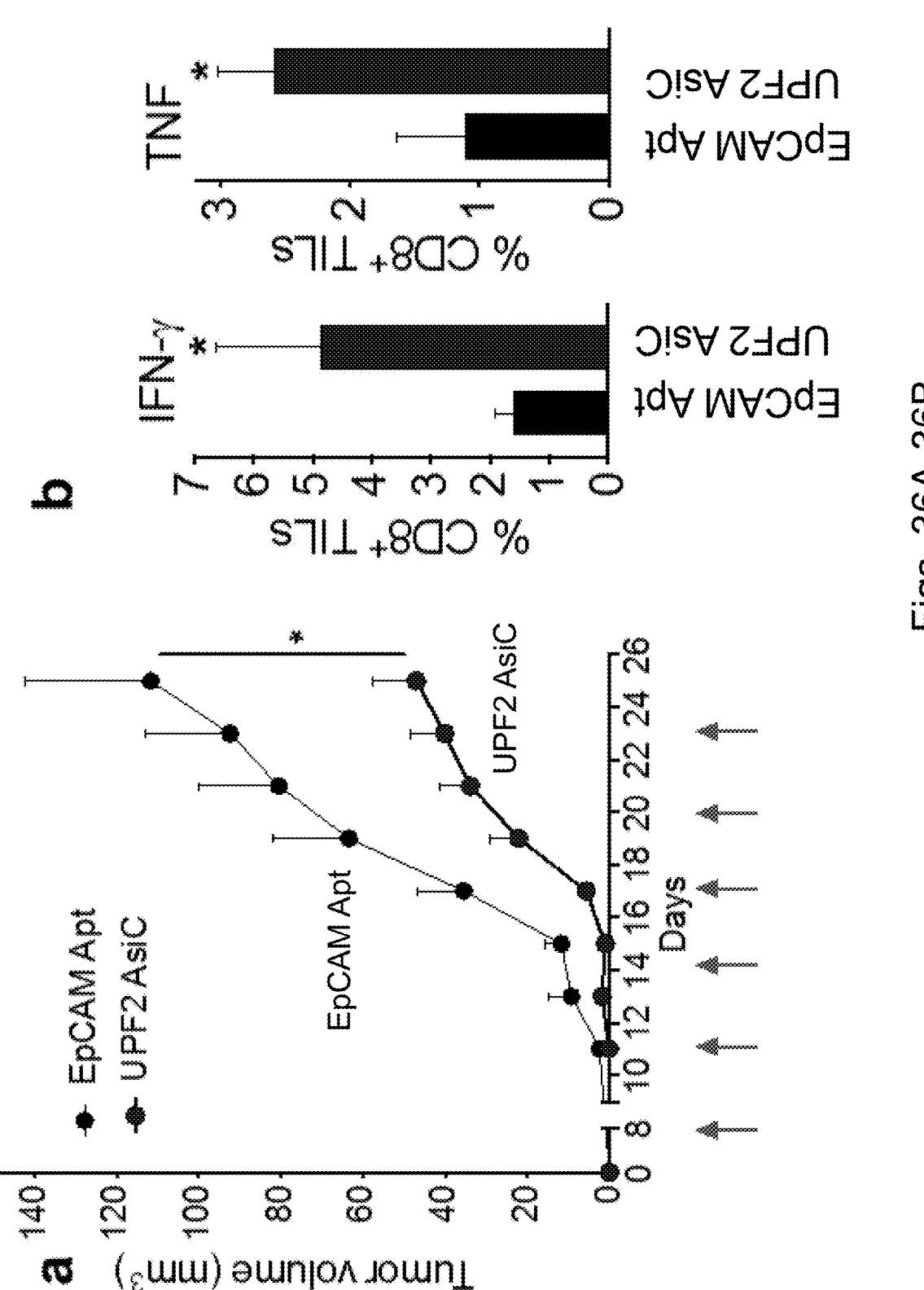
FIGS. 36A-36B demonstrate the longer-term tumor inhibition and immune modulation capacity of UPF2 AsiC.

Checkpoint inhibition induces protective immunity with dramatic and durable responses in some cancers. Although breast cancers are not generally that sensitive to checkpoint inhibitors, last year anti-PD-L1 administered with protein-bound paclitaxel was shown to improve survival for a few months in the subset of TNBC patients whose tumors express PD-L1 and was the first checkpoint inhibition therapy approved by the FDA for that subset of patients. 4T1E strongly and uniformly express PD-L1 (FIG. 36A). The inventors therefore assessed the antitumor activity of CD274 EpCAM AsiC targeting PD-L1. CD274 EpCAM-AsiC inhibited tumor growth, but the effect was not statistically significant (FIG. 36B), indicating that combining CD274 EpCAM-AsiCs with other therapies might be necessary to improve antitumor immunity.

MCL1 EpCAM-AsiCs Induce Anti-Tumor Immunity

Figures 37A, 37B:
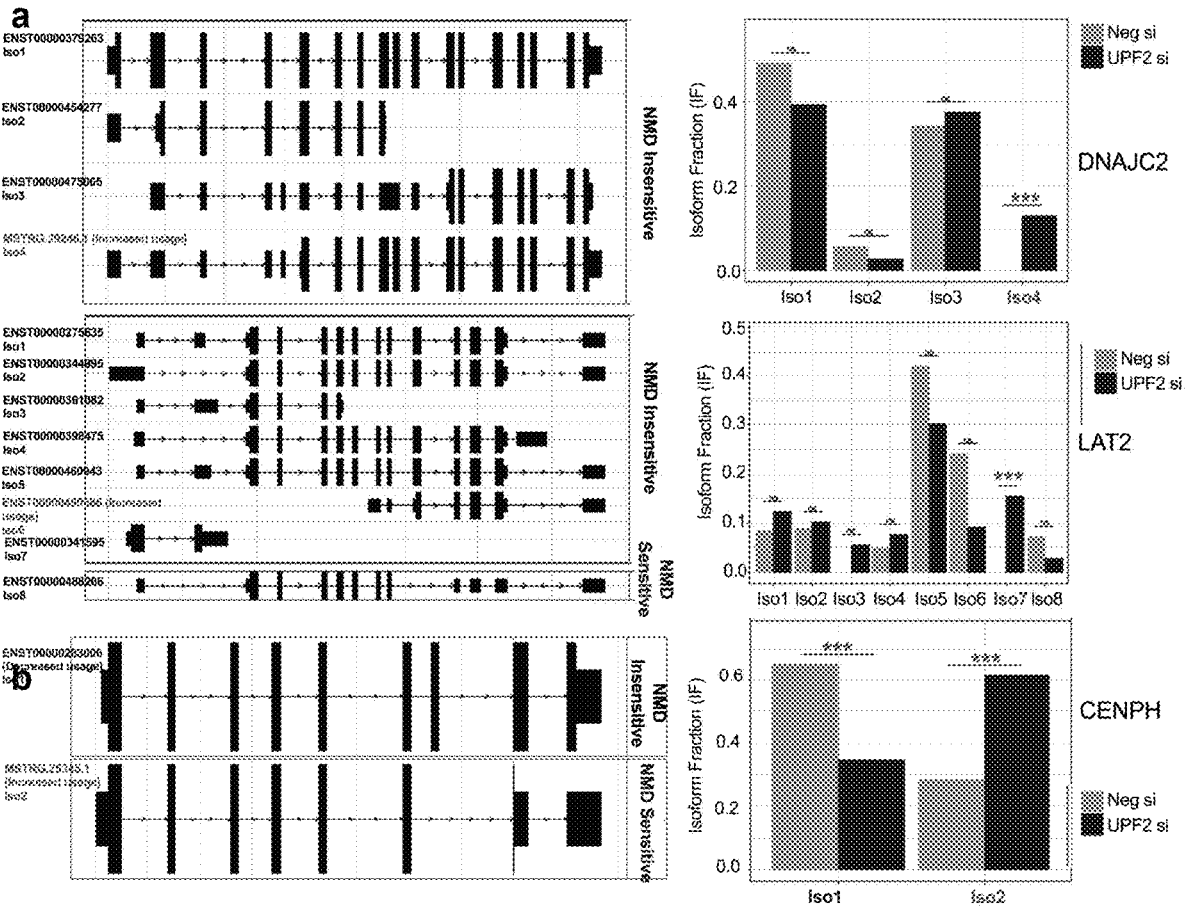
FIGS. 37A-37B demonstrate that UPF2 knockdown in EpCAMhi MDA-MB-231 BC cells generates novel mRNA isoforms and increased the usage of NMD sensitive isoforms.

Because TNBC are heterogeneous cancers defined by exclusion, genome-wide siRNA screens to identify shared dependencies of human basal-A TNBC cell lines identified few shared dependency genes[26,35]. One of the strongest hits was the anti-apoptotic BCL-2 family gene, MCL1 which is commonly amplified in TNBC and whose overexpression correlates with poor prognosis[36]. The inventors hypothesized that tumor cell death induced by Mcl1 knockdown (FIG. 32B) might promote cross-presentation of tumor antigens to CD8+ T cells, thereby improving antitumor immunity. The inventors first verified that MCL1 EpCAM-AsiC reduced 4T1E viability in vitro (FIG. 37A). MCL1 EpCAM-AsiC, injected s.q. every 3 days after orthotopic 4T1E tumors became palpable, slowed down tumor growth significantly (FIG. 37B). MCL1 EpCAM-AsiC also significantly improved the CD8+/CD4+ $T_{reg}$ ratio and antitumor CD4+ and CD8+ T cell functions in the tumor. The inventors also observed a similar improvement in antitumor T cell immunity using another cytotoxic EpCAM-AsiC targeting the essential gene Plk1, encoding a kinase required for mitosis (data not shown). Thus, some EpCAM-AsiCs that are cytotoxic also promote effective antitumor immune responses.

Enhanced Antitumor Activity of Combinations of EpCAM-AsiCs

Figures 28A, 28B, 28C, 28D, 28E, 28F, 28G:
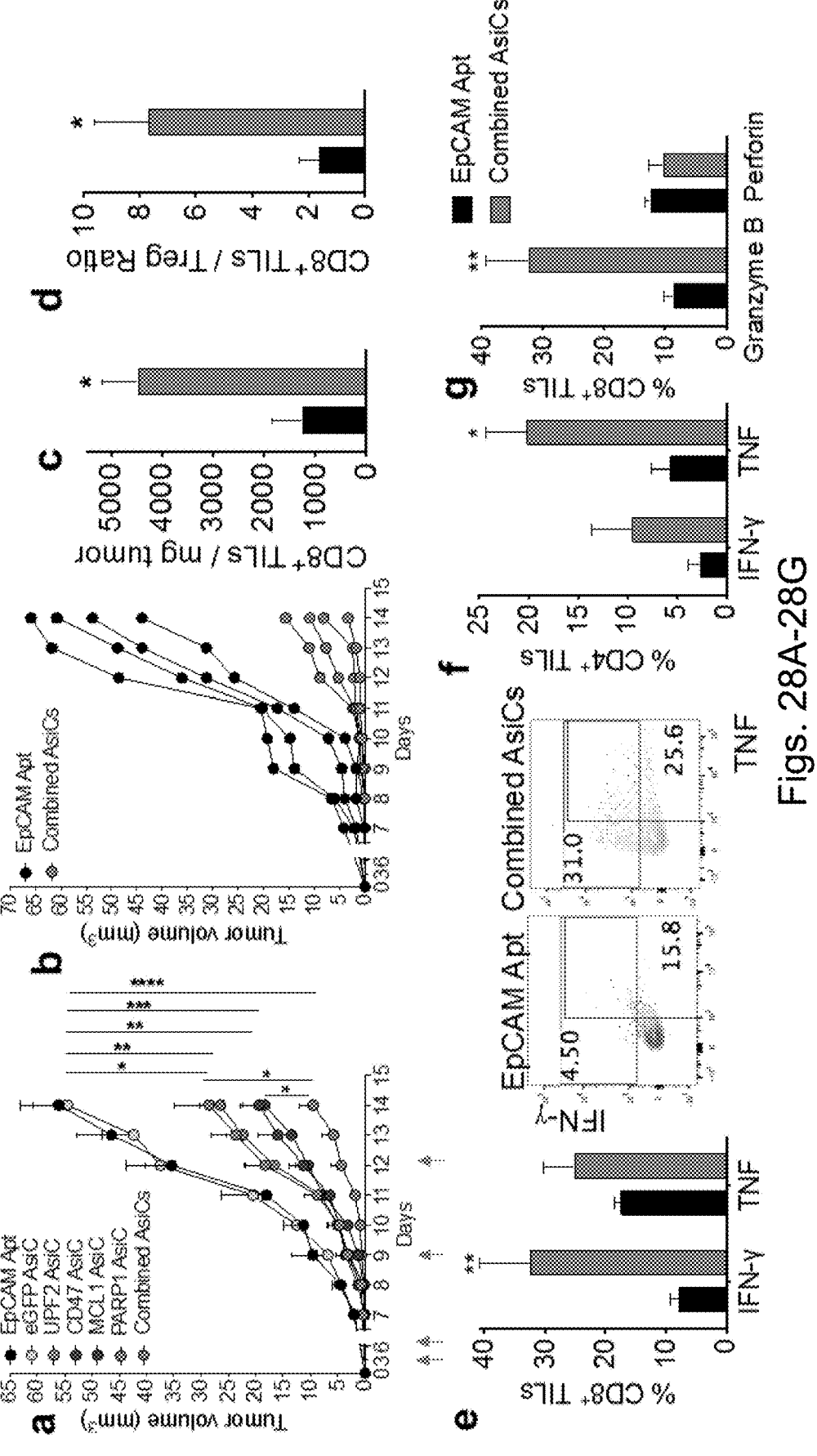
Figure 29A:
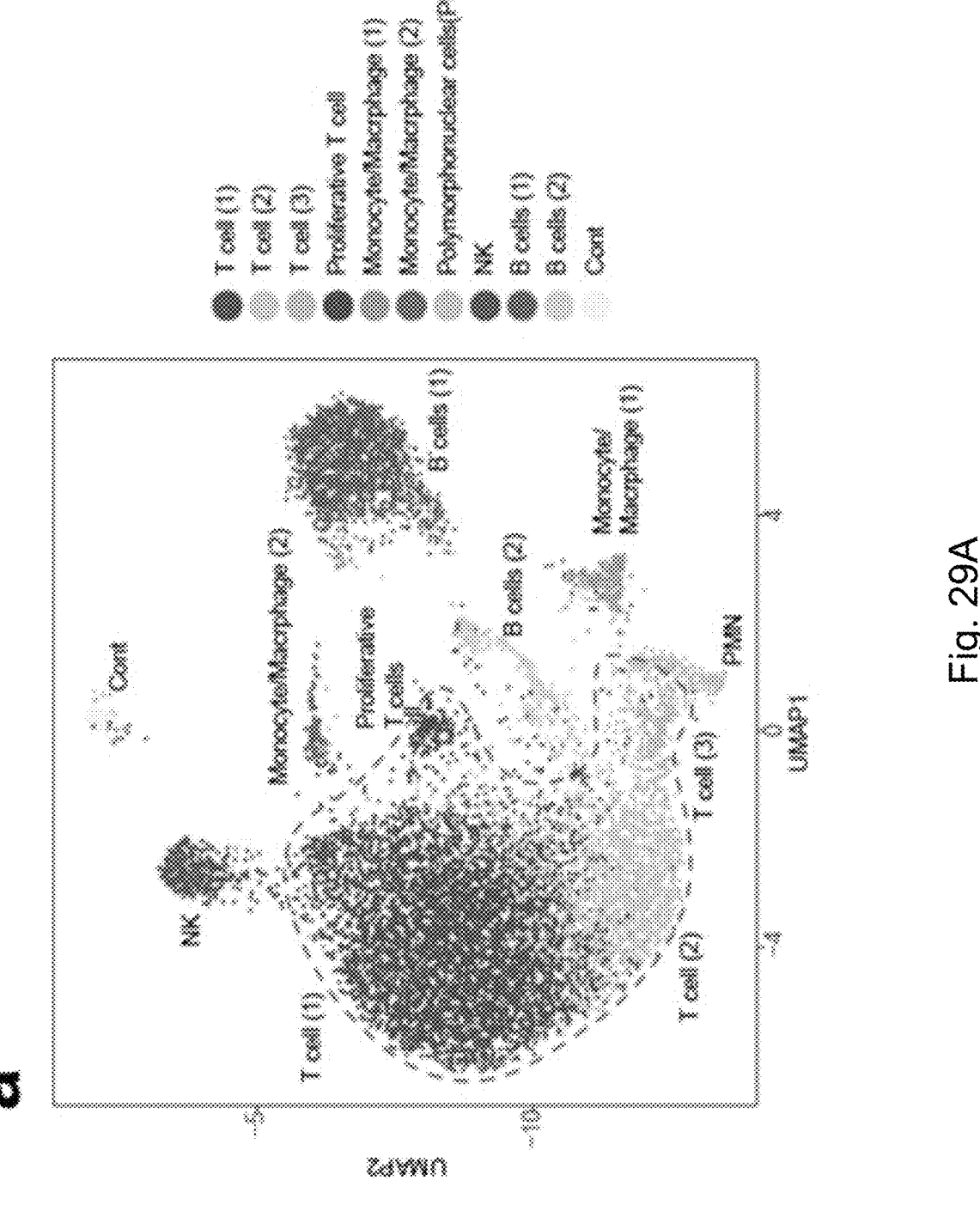
Figure 29B:
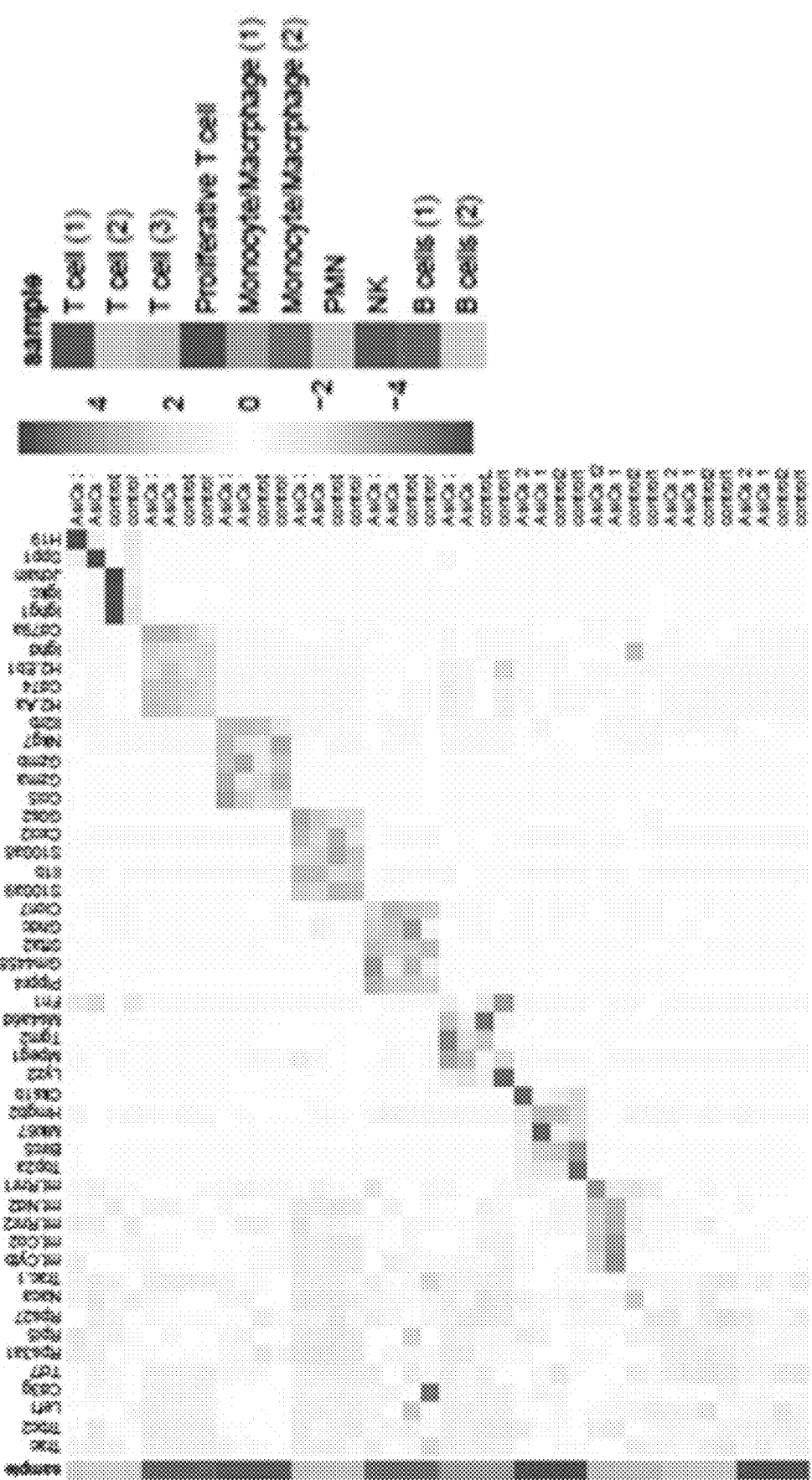
Figures 29E, 29F:
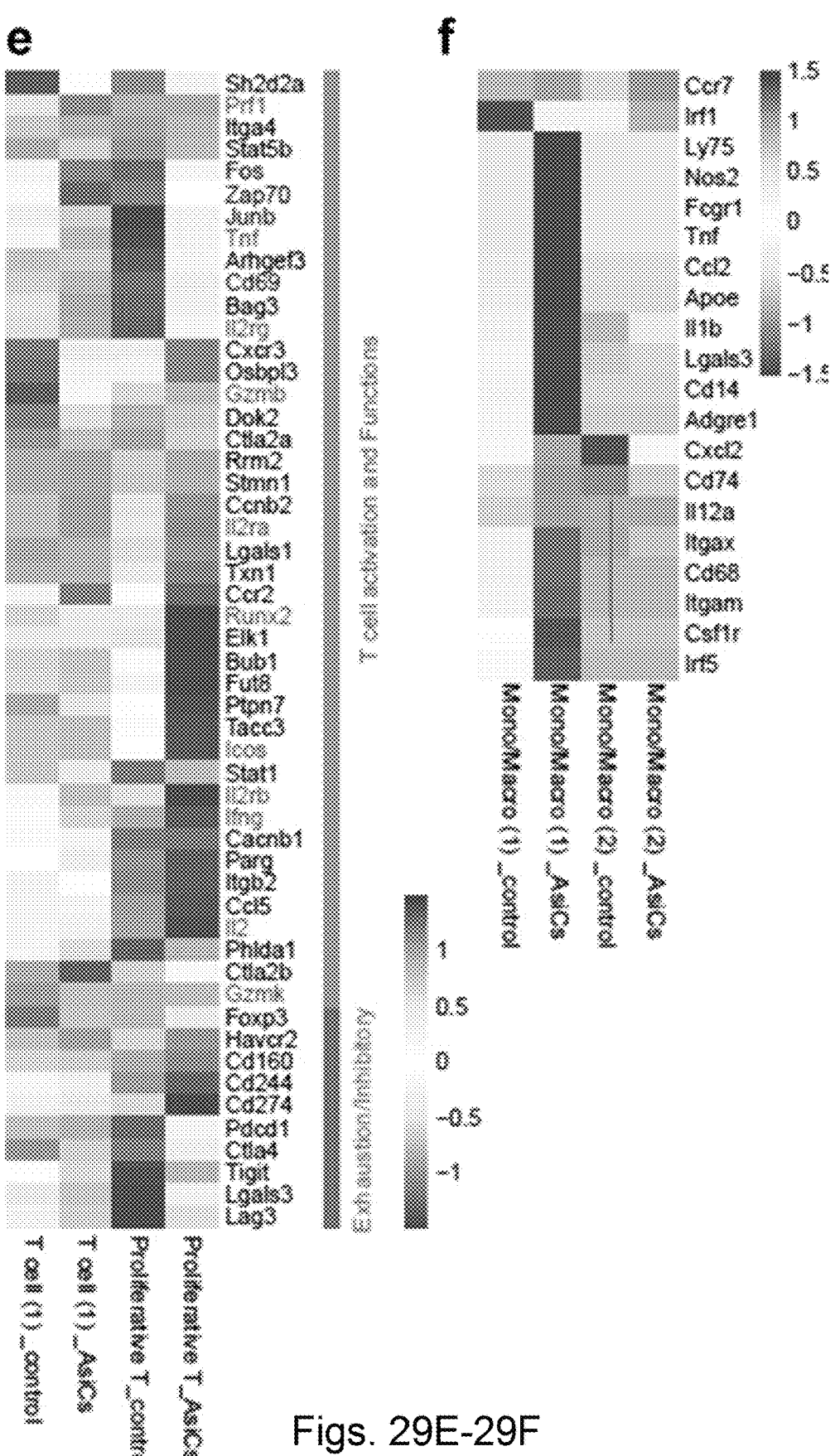
Figures 30A, 30B, 30C, 30D, 30E, 30F:
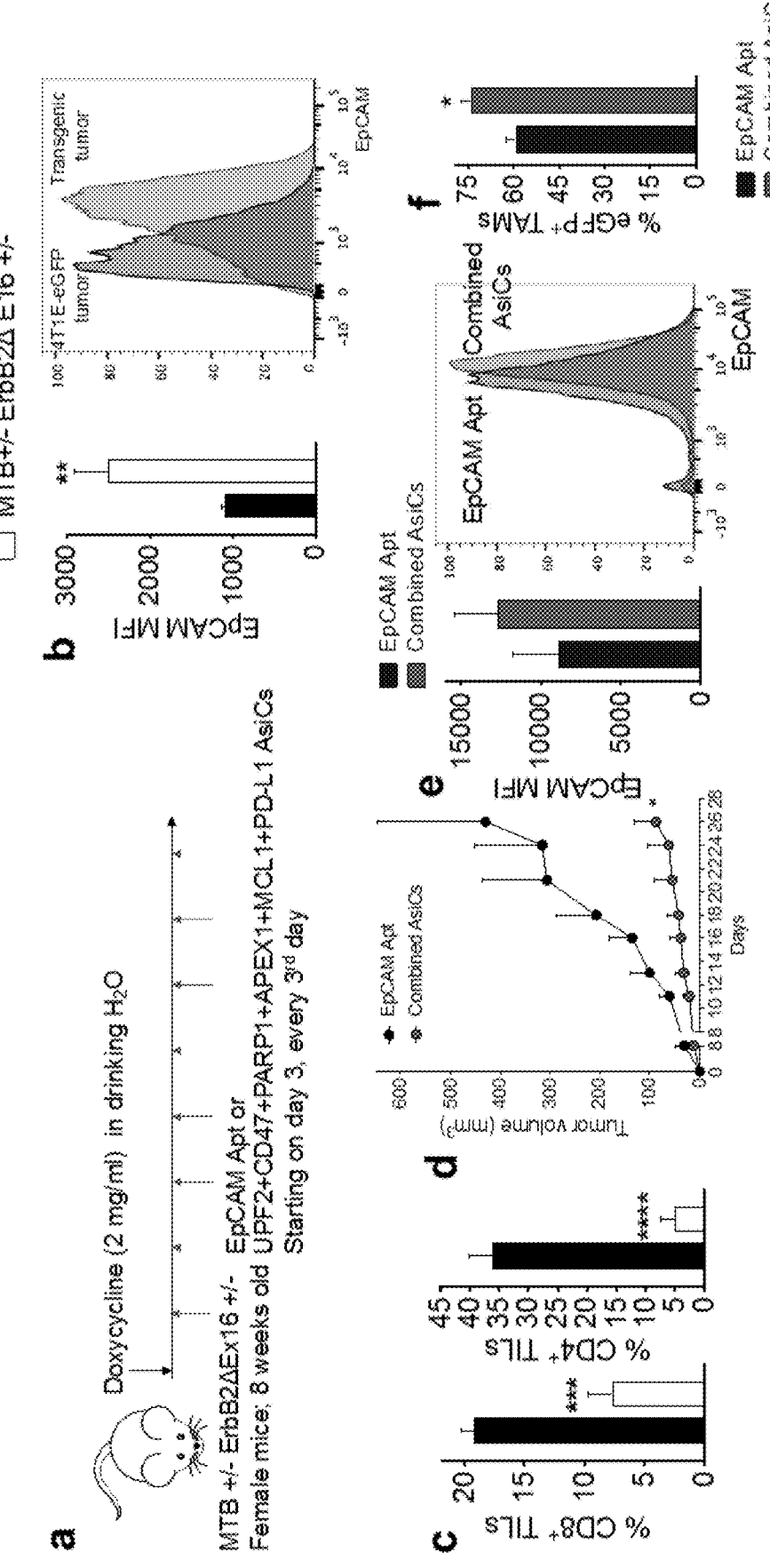
Figure 31A:
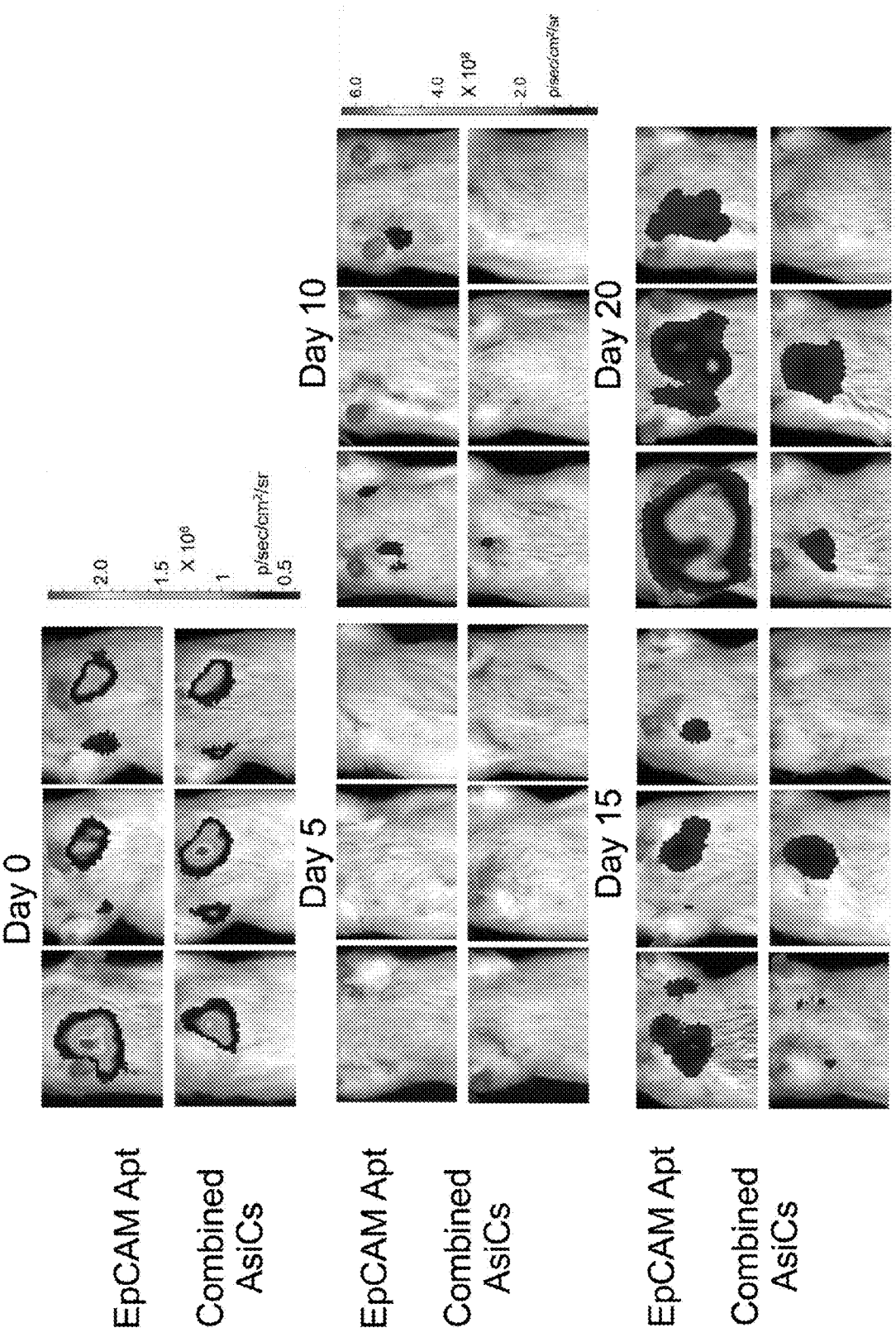
FIGS. 31A-31D demonstrate the antitumor efficacy of combined immune-modulating EpCAM-AsiCs in lung metastatic 4T1E-Luc tumor model.
Figures 31B, 31C, 31D:
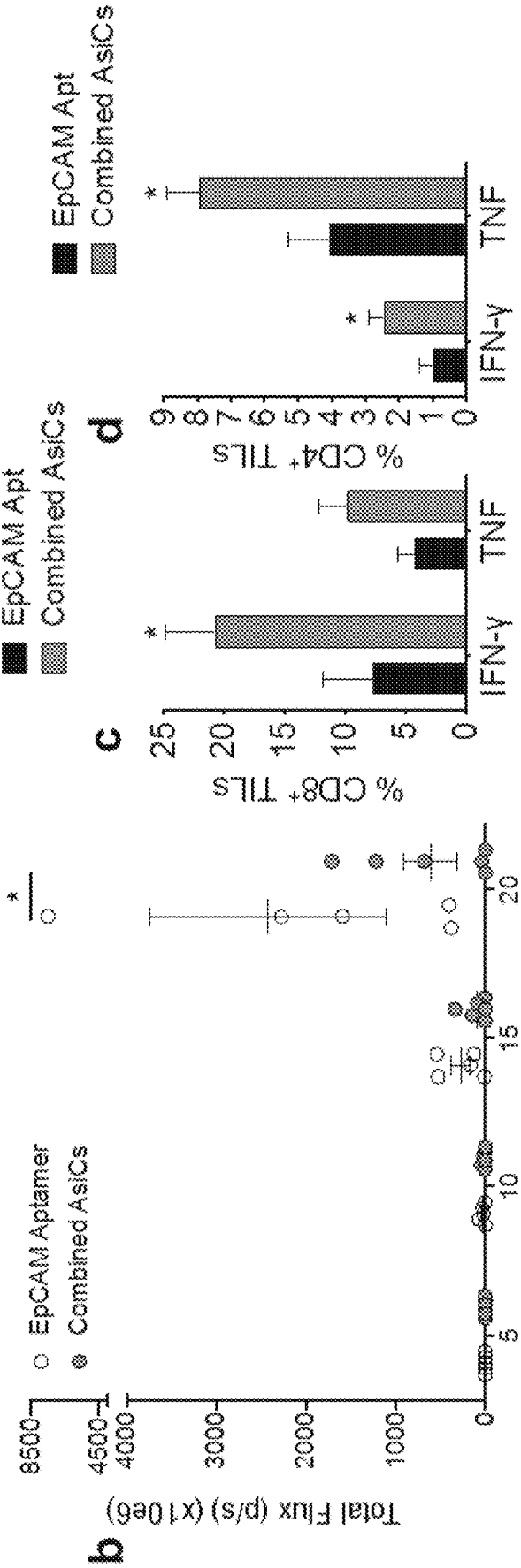

One of the advantages of AsiCs for cancer is that it is relatively easy to combine AsiCs targeting multiple genes to produce drug cocktails that could have additive or synergistic effects to inhibit tumor growth by knocking down genes that promote tumor immunity by different mechanisms. To investigate the effectiveness of EpCAM-AsiC combinations, 4T1E orthotopic tumor-bearing mice were treated with 4 of the most effective EpCAM-AsiCs, targeting Upf2, Parp1, Cd47, or Mcl1, individually or in combination, using EpCAM aptamer or eGFP EpCAM-AsiCs as controls (FIGS. 28A-28B). Each EpCAM-AsiC on its own markedly delayed tumor progression, but the cocktail was significantly better. The cocktail increased the number of CD8+ TIL by ~4-fold (FIG. 28C), improved the CD8+/CD4+ $T_{reg}$ TIL ratio by ~5-fold (FIG. 28C), and increased stimulated production of cytokines and cytotoxic molecules by CD8+ and CD4+ TIL (FIGS. 28E-28G). The combined EpCAM-AsiCs were also evaluated in mice bearing orthotopic 4T1E-eGFP tumors, whose expression of the immunogenic foreign protein causes tumor regression beginning about two weeks after tumor implantation (FIG. 28H). Tumors in mice treated with the AsiC cocktail grew much more slowly and started to regress earlier. The combination therapy also potently boosted T cell immunity in 4T1E-eGFP tumors (FIG. 28I). Importantly, after 5 injections of EpCAM-AsiC combinations, EpCAM expression on 4T1E-eGFP tumors was unchanged, indicating that tumors did not become resistant to the EpCAM-AsiCs by downregulating EpCAM.

Figures 38A, 38B, 38C:
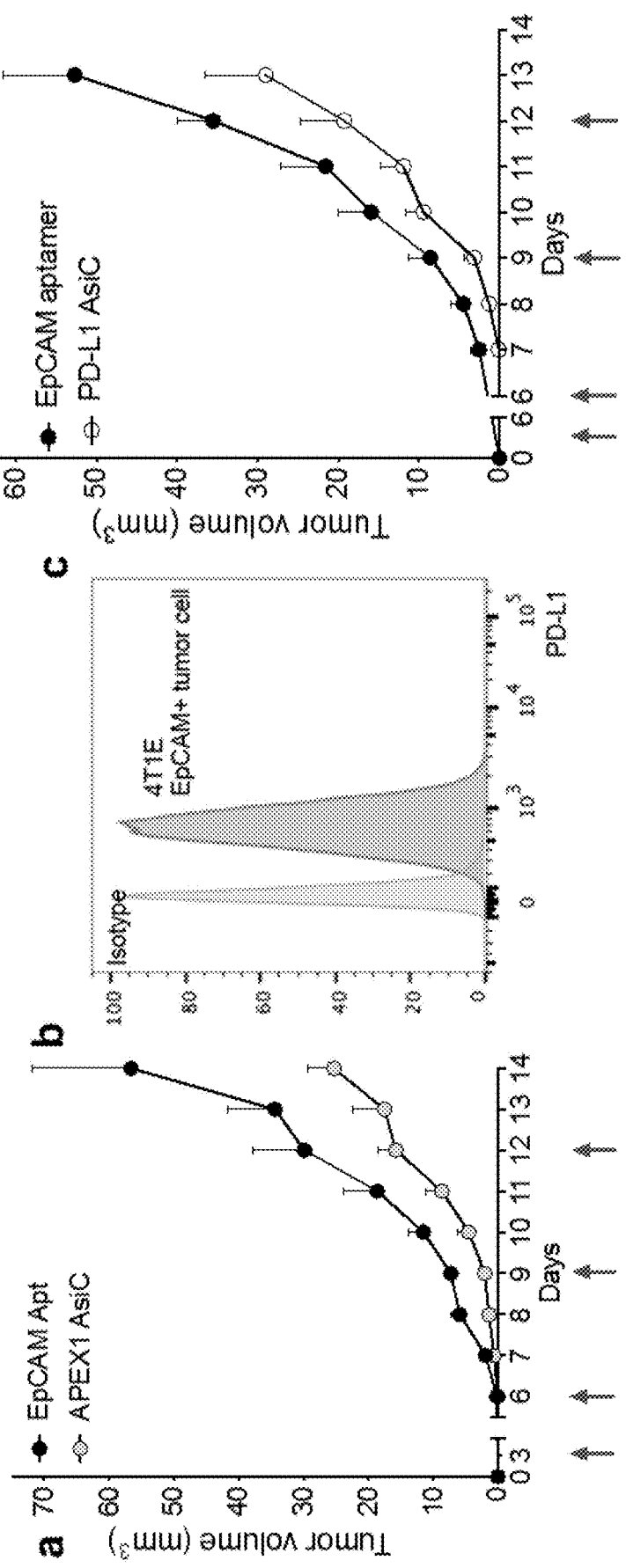
FIGS. 38A-38C demonstrate the tumor inhibition and immune modulation capacity of other EpCAM AsiC.
Figures 39A, 39B, 39C:
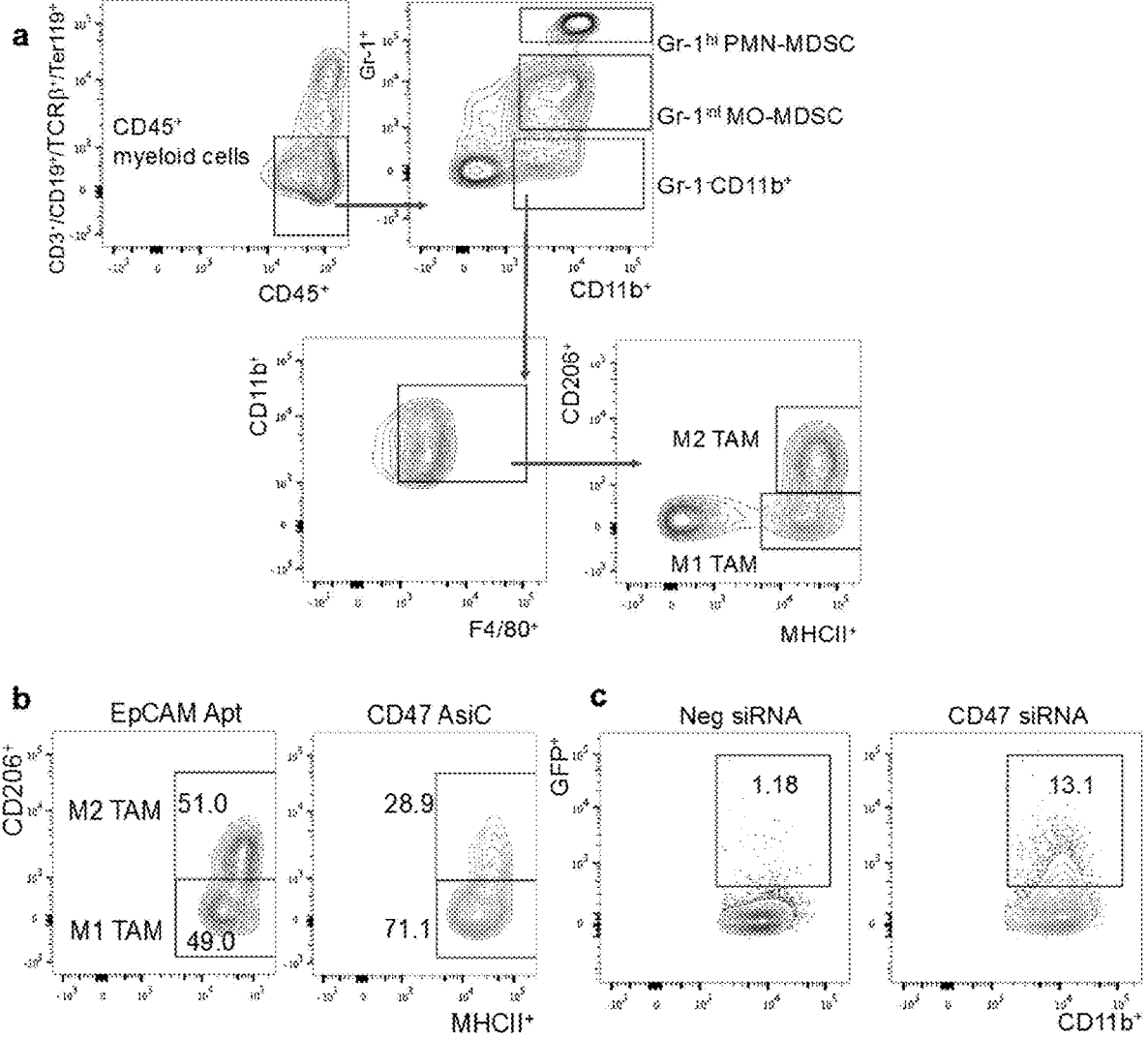
FIGS. 39A-39C depict the gating strategy for MDSC subsets and M1- and M2-like TAMs in 4T1E mouse breast tumors.
Figures 40A, 40B, 40C:
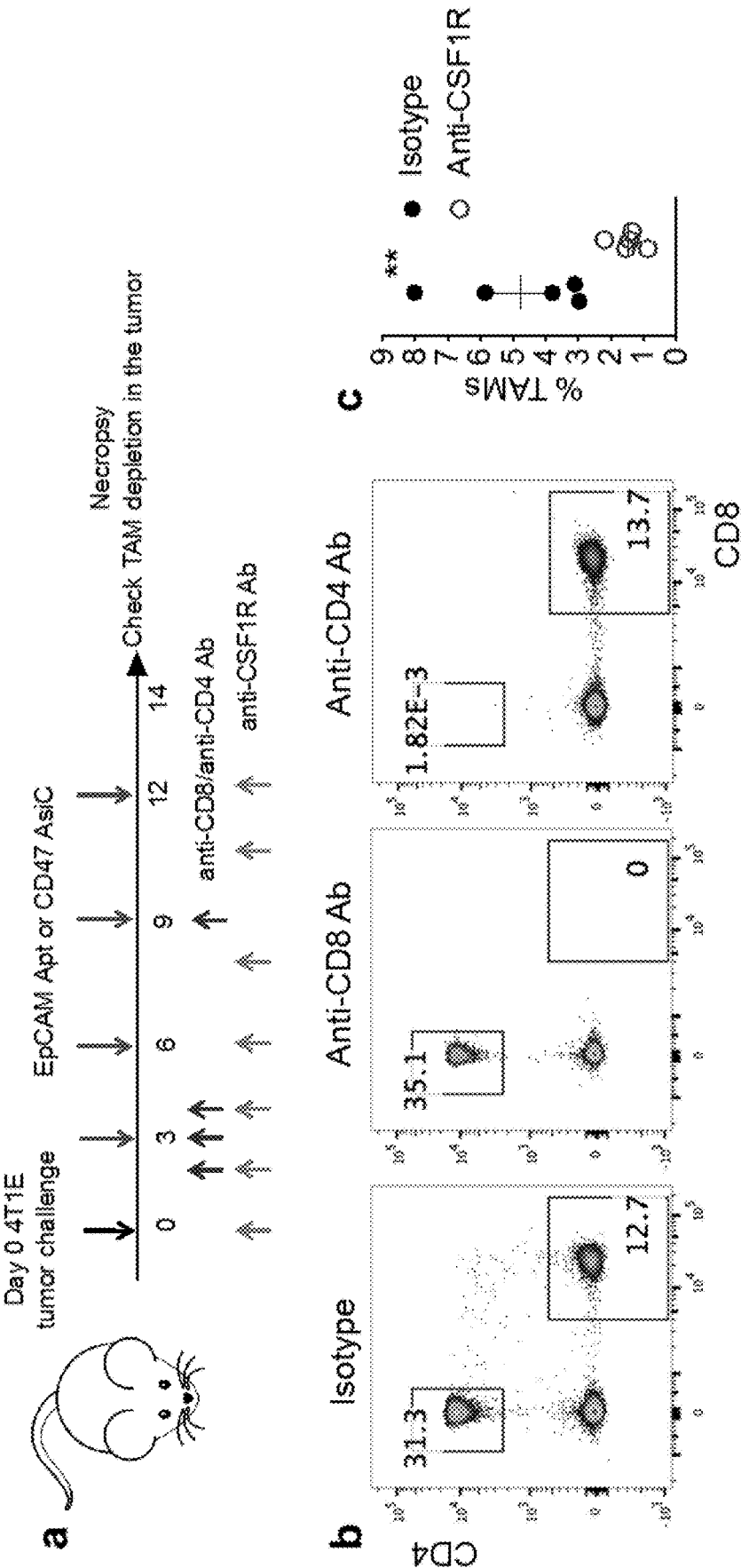
FIGS. 40A-40C depict the depletion of CD8+T, CD4+T and macrophages in mice bearing 4T1E tumors FIG. 40A, Experimental scheme of CD47 AsiC treatment and immune cell depletion in mice bearing 4T1E tumors.
Figures 41A, 41B, 41C:
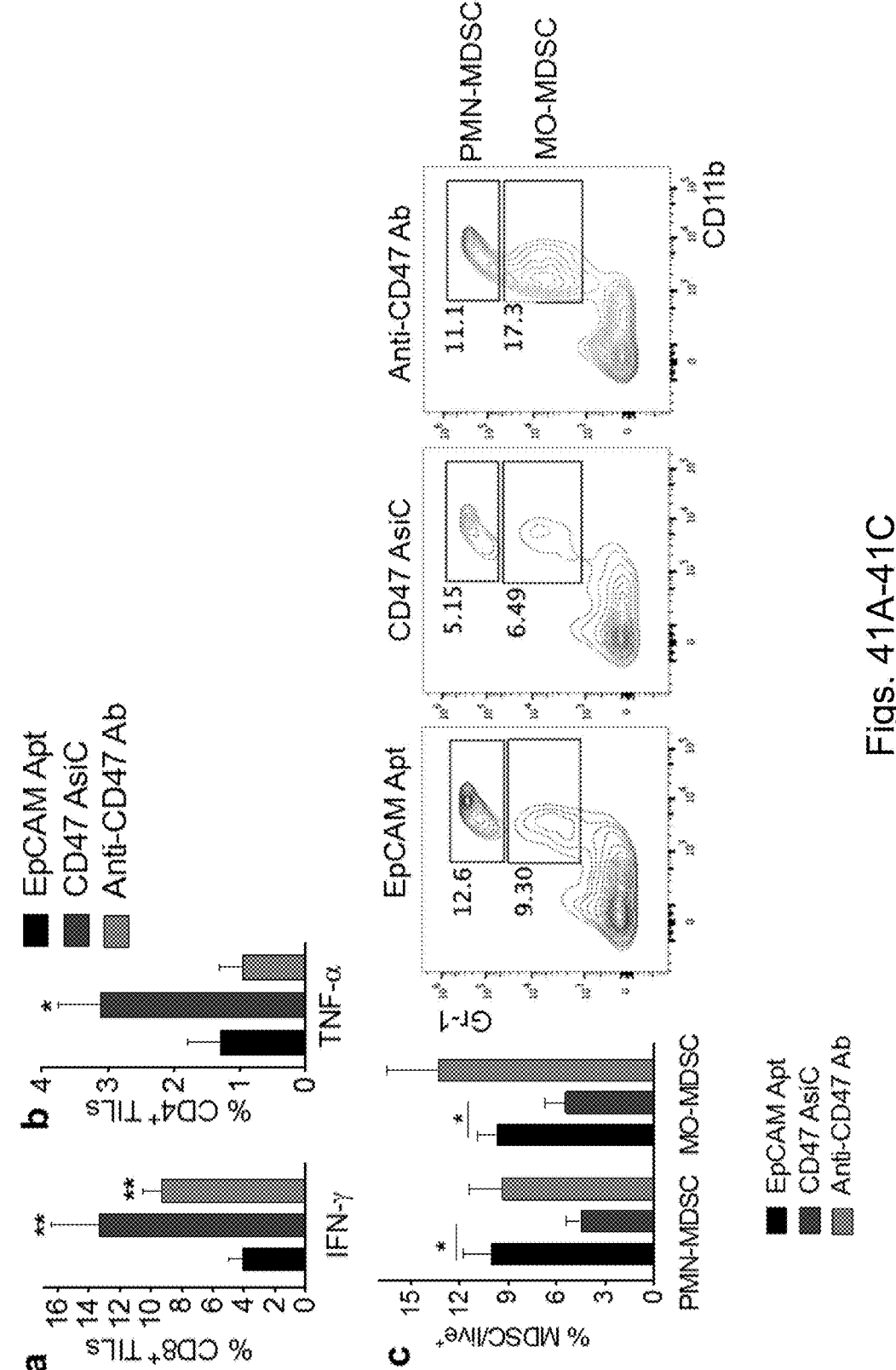
FIGS. 41A-41C depict a comparison of the antitumor efficacy between CD47 AsiC and anti-CD47 Ab.
Figures 42A, 42B, 42C, 42D, 42E, 42F:
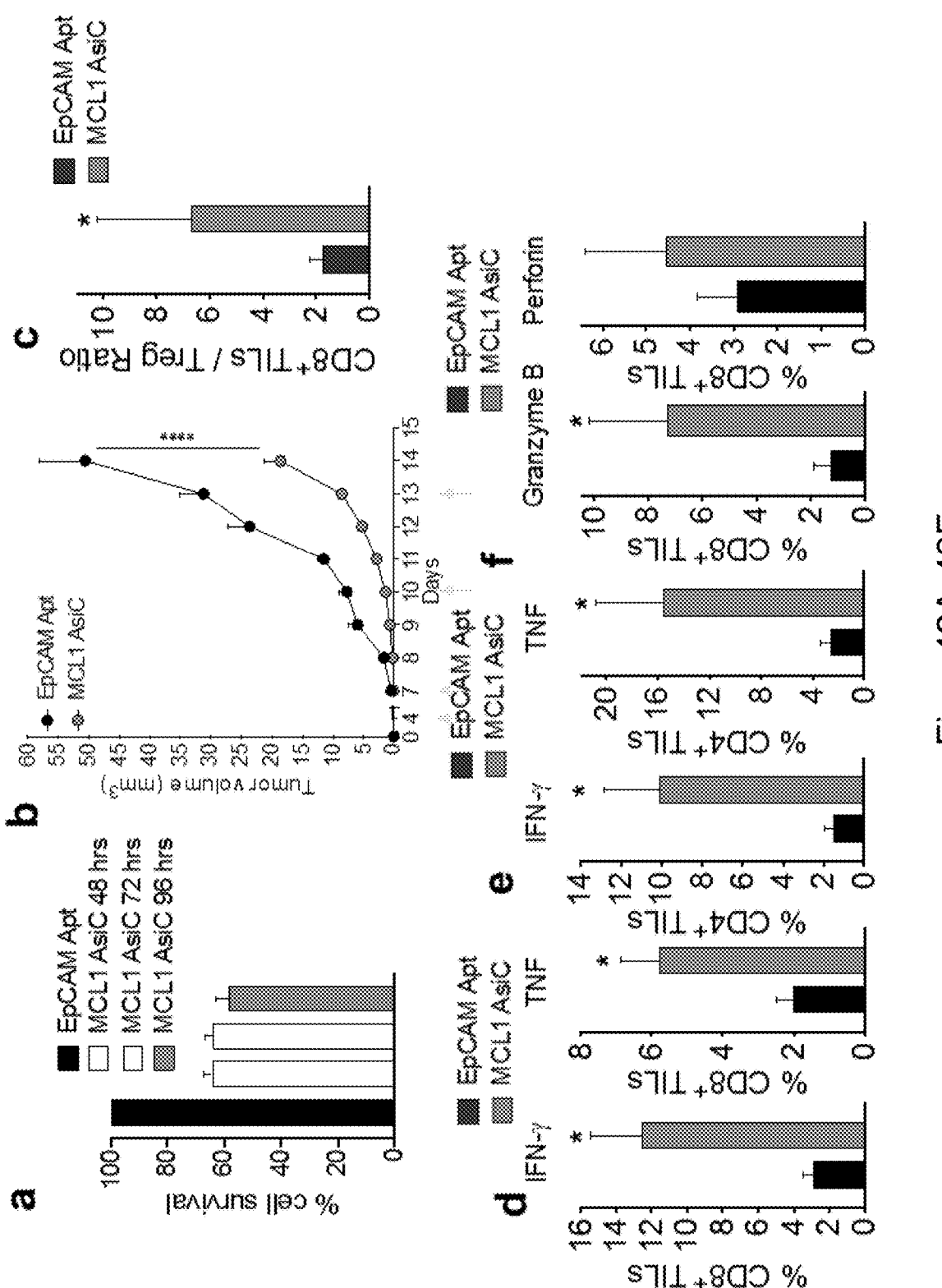
FIGS. 42A-42F depict the tumor inhibition and immune modulation capacity of MCL1 AsiC.
Figures 43A, 43B, 43C, 43D, 43E, 43F, 43G:
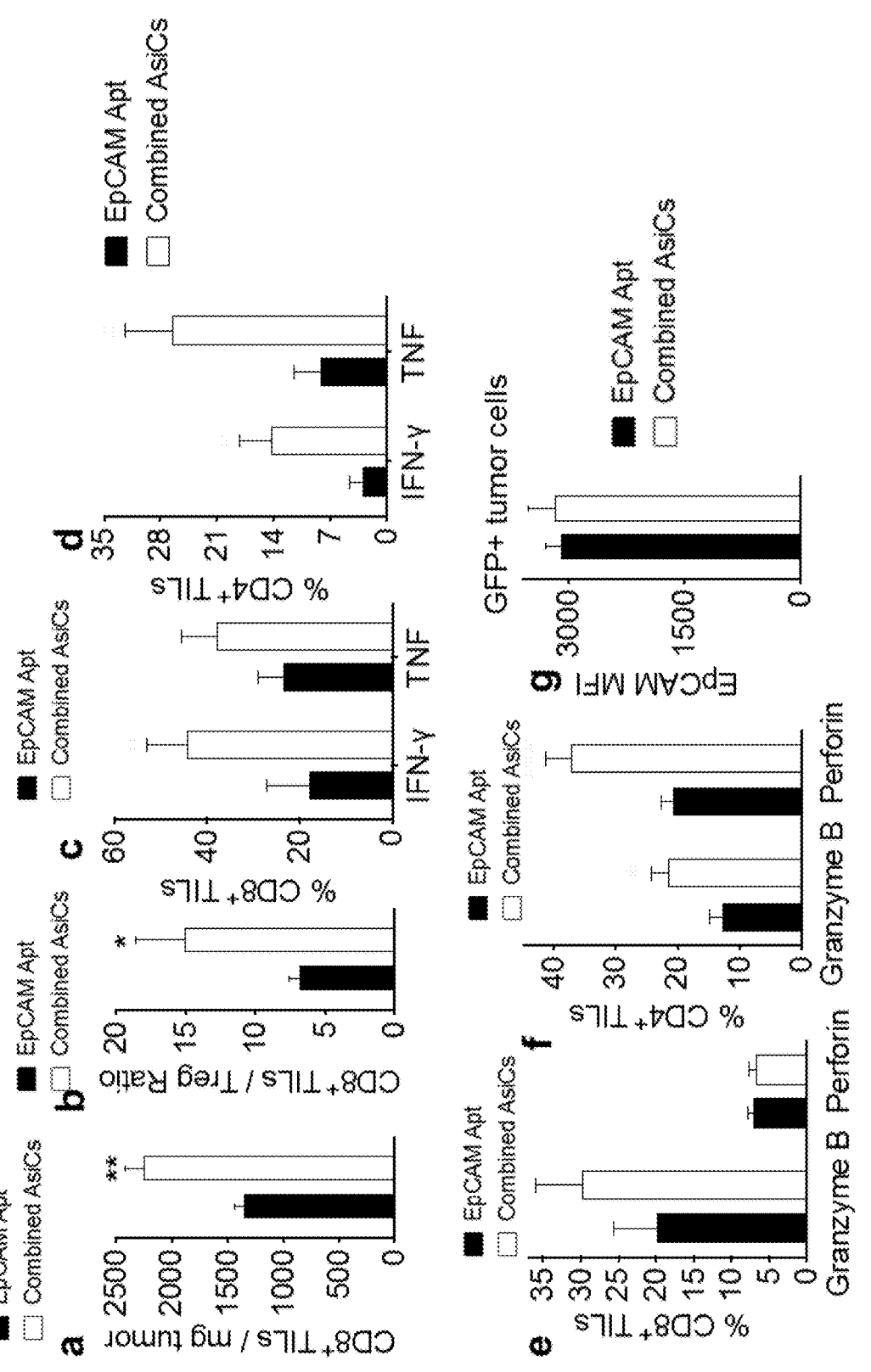
FIGS. 43A-43G depict the synergistic effect of immune-modulating EpCAM-AsiCs in 4T1E-eGFP tumor model.
Figures 44A, 44B, 44C, 44D, 44E:
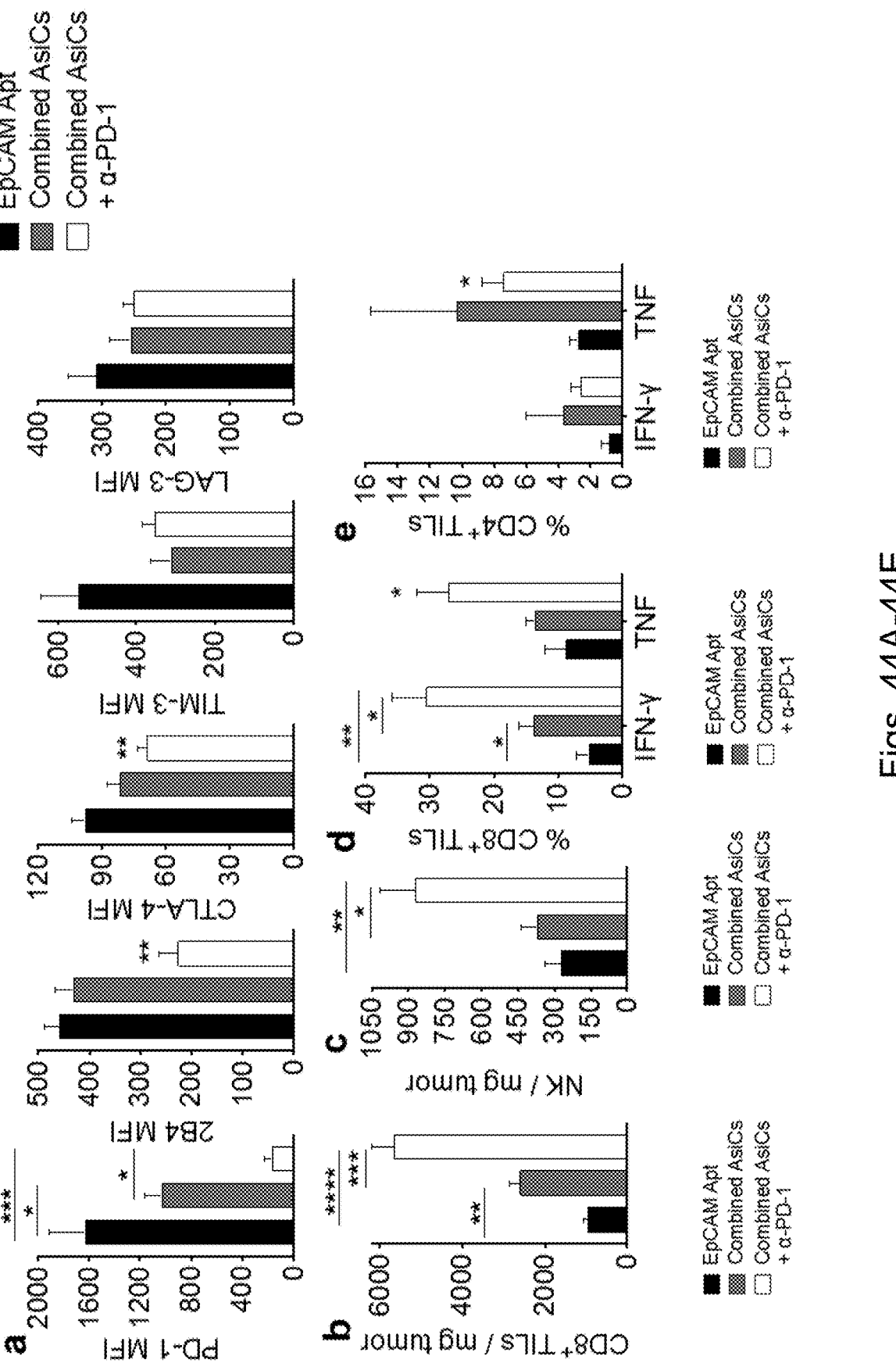
FIGS. 44A-44E depict the synergistic effect of immune-modulating EpCAM-AsiCs with anti-PD-1.

The inventors next investigated whether tumor inhibition by the cocktail of EpCAM-AsiCs directed against the tumor could be improved by adding the checkpoint inhibitor, anti-PD-1 to target exhausted T cells. Treating control mice receiving EpCAM aptamer with anti-PD-1 only slightly, but not significantly slowed 4T1E tumor growth. However, the combination of anti-PD-1 and the EpCAM-AsiC cocktail significantly reduced tumor growth more than the AsiC cocktail on its own. Although the EpCAM-AsiC cocktail significantly reduced PD-1 levels on CD44+CD8+ TILs, the addition of □-PD-1 further reduced PD-1 staining when the same antibody clone (29F.1A12) was used for detection, presumably because the bound therapeutic antibody blocked staining (FIG. 38A). As for the CD47 EpCAM-AsiCs on its own, the combined AsiCs also significantly reduced expression of other inhibitory coreceptors (CTLA-4, TIM-3 and LAG-3) on CD44 CD8+ TIL (FIG. 38B). Adding anti-PD1 had no significant additional effect on these inhibitory receptors. Moreover, addition of anti-PD1 led to reduced expression of the costimulatory receptor 2B4 (CD244) in CD44+CD8+ TIL, compared to T cells from mice treated with just the cocktail, which could reduce T cell responses. However, addition of anti-PD-1 to the AsiCs cocktail strongly increased the number of CD8$^+$ (FIG. 38C) and NK TIL and stimulated cytokine production by CD8+ TIL compared to mice treated with just the AsiCs cocktail. Thus an AsiCs cocktail targeting tumor cell strategies of immune evasion can be synergistic with a checkpoint inhibitor directed against a T cell inhibitory receptor.

An EpCAM-AsiC Cocktail Broadly Augments Antitumor Functionality of Tumor-Infiltrating T Cells and Macrophages To assess without bias the changes in tumor-infiltrating immune cells induced by treatment with the 4 EpCAM-AsiCs cocktail, scRNA-seq analysis was performed on sorted CD45$^+$ tumor-infiltrating cells from mice bearing 4T1E orthotopic tumors treated with EpCAM aptamer or the cocktail (FIGS. 29A-29F). This analysis focused on tumor-infiltrating proliferative T cells and macrophages (FIGS. 29A-29F), which showed the greatest changes with EpCAM-AsiC therapy. A gene ontology analysis of differentially expressed genes (DEG) in proliferative T cells revealed significantly increased expression of gene signatures associated with migration/chemotaxis, immunological synapse formation, T cell activation, proliferation and metabolism in EpCAM-AsiCs-treated tumors compared to control tumors (FIGS. 29A-29F).

The expression of genes related to monocyte/macrophage migration, activation endocytosis were markedly upregulated in the EpCAM-AsiC-treated "M1" macrophage subpopulation, while genes involved in inflammation and Type I IFN and chemokine production, including genes that regulate the immune response to tumors, were upregulated in the "M2" subpopulation (FIGS. 29A-29F). T cells in the AsiCs-treated group expressed higher levels of genes involved in T cell activation and effector functions compared to those of the control group (FIGS. 29A-29F). Cluster 1 T cells expressed higher levels of genes involved in the early signaling events of T cell activation, e.g. Cd69, Zap70, Fos, and Junb, which were further upregulated by EpCAM-AsiCs treatment (FIGS. 29A-29F). Proliferative T cells in AsiCs-treated tumors up-regulated effector and memory and functional T cell genes, e.g. transcripts for effector molecules Ifng, Tnf, Il2, Gzmb, Gzmk; costimulatory gene Icos; IL-2 receptor complex genes IL2ra, IL2rb, and IL2rg; and Runx2, which promotes the long-term persistence of CD8$^+$ memory T cells. A number of T cell functional genes, e.g. Gzmb, Gzmk, Prf1, and Tnf, were also increased in cluster 1 T cells after EpCAM-AsiCs treatment. In contrast, genes encoding co-inhibitory molecules, e.g. Pdcd1, Ctla4, Tigit, Lag3, and Havcr2, and the T$_{reg}$ signature gene Foxp3 were mostly downregulated in T cells from AsiCs-treated tumors, especially for the proliferative T cell cluster (FIGS. 29A-29F), indicating EpCAM-AsiCs ameliorate T cell exhaustion. Furthermore, macrophages in the AsiCs-treated tumors upregulated expression of genes associated with myeloid cell maturation, e.g. Cd74; M1 functionality, e.g. Nos2, Fcgr1, Cd68, Il12a and Ccr7; phagocytosis and antigen processing, e.g. Lgals3, Il1b, Apoe, Cd14 and Ly75; and inflammatory cytokine/chemokine production, e.g. Tnf Ccl2, Cxcl2, and Il12a (FIGS. 29A-29F), indicating improved antitumor functionality.

EpCAM-AsiCs Reduce Growth of Metastatic Tumors

All the experiments reported so far treated orthotopic tumors just after they became palpable. However, BC patients often present with more advanced local or metastatic disease, which is more difficult to treat. Many BC patients also have evidence of microscopic metastases before metastatic disease becomes clinically apparent. Moreover, metastatic disease is usually what kills patients. Therefore the ability to target metastatic tumor cells is critical for effective BC therapy. To determine whether EpCAM-AsiCs are active against metastatic TNBC, the inventors generated a 4T1E cell line stably expressing firefly luciferase (4T1E-Luc) that can be detected by bioluminescence imaging of live animals. Intravenous injection of 4T1E-Luc caused tumor cells to lodge in the lungs and tumors in the lung could be detected 7-10 days later. Mice bearing seven-day old metastatic 4T1E-Luc lung tumors were treated with EpCAM aptamer or the cocktail of EpCAM-AsiCs targeting Upf2, Cd47, Parp1 and Mcl1. EpCAM-AsiCs significantly inhibited breast tumor growth in the lung (FIGS. 30A-30K). Twenty days after tumor challenge CD8$^+$ and CD4$^+$ T cells were isolated from the lungs and analyzed for PMA and ionomycin-stimulated production of IFN-γ and TNF-α. Significantly more CD4+ and CD8+ T cells from mice treated with EpCAM-AsiCs produced these cytokines. Thus EpCAM-AsiCs inhibited the growth of metastatic tumors and augmented anti-tumor immunity at the site of metastases in the lung.

EpCAM-AsiCs Inhibit Aggressive Breast Cancers in Erb2ΔEx16 Transgenic Mice

To evaluate the effectiveness of an EpCAM-AsiCs in a challenging GEMM of aggressive Her2+ breast cancer, the inventors employed a doxycycline inducible mouse model that expresses eGFP and a truncated Her2 gene (ErbB2ΔEx16 with a deletion of exon 16 that causes a juxtamembrane 16 aa deletion and a constitutively active HER2 receptor), under the control of the MMTV promoter[61]. At least 80% of these mice develop multifocal rapidly growing and metastatic HER2+ breast tumors that are uniformly EpCAM+(FIGS. 31A-31D) within ~10-28 days of adding doxycycline. Without any treatment these tumors had few infiltrating CD4 or CD8 T cells (FIGS. 31A-31D). The inventors treated these mice beginning three days after starting doxycycline and every third day thereafter with either EpCAM aptamer as a control or a combination of 6 EpCAM-AsiCs targeting Upf2, Parp1, Apex1, Cd47, Mcl1 and Cd274 (FIGS. 31A-31D). Although treatment with the EpCAM-AsiCs cocktail did not alter the number of mice who developed detectable tumors (four of six mice in each group developed tumors in 10 days), it greatly inhibited tumor growth over 4 weeks of treatment (FIGS. 31A-31D). After 8 treatments, EpCAM expression by the GFP+ tumor did not change (FIGS. 31A-31D). Moreover, anti-tumor immune function was significantly enhanced in mice receiving the EpCAM-AsiC cocktail. More TAM were GFP+, indicating increased tumor cell phagocytosis (FIGS. 31A-31D). Although the EpCAM-AsiCs cocktail did not change the numbers of TILs within spontaneously arising ErbB2ΔEx16 tumors (not shown), stimulated production of IFN-γ and TNF-α by CD4+ and CD8+ TIL (FIGS. 31A-31D) and expression of GzmB and PFN increased in CD8+, CD4+, and NK TIL (FIGS. 31A-31D). Thus, an EpCAM-AsiC cocktail suppressed tumor growth and mobilized anti-tumor immunity in an immunologically "cold" highly aggressive spontaneous GEMM breast tumor.

Discussion

The highly invasive TNBC, with the worst survival rates of all BC subtypes and a lack of potent treatment strategies, represents a critical hurdle for BC therapy[66]. Fortunately, TNBC as well as HER2+ BC, another aggressive subtype of BC that is susceptible to drug resistance and relapse, are more immunogenic with higher levels of tumor mutational burden and TILs compared to other BC subtypes, making them better targets for cancer immunotherapy[67-69]. In this study, the inventors show that tumor cell-targeted gene knockdown with immune-modulating EpCAM-AsiCs can effectively improve tumor immunogenicity and potently inhibit tumor growth in both mouse TNBC and HER2+ BC models, illustrating the antitumor activity of the EpCAM-AsiCs as a powerful approach for BC immunotherapy. To our knowledge, this is the first study illustrating the immune activation potency of EpCAM-AsiCs for aggressive BCs. No evidence of toxicity or weight loss have been detected in treated mice. Moreover, the combined AsiCs synergized with PD-1 checkpoint inhibitor to further restrain tumor progression, highlighting its potential clinical benefits for the majority of BC patients that show limited responses to immune checkpoint inhibitor monotherapy.

The EpCAM aptamer-mediated siRNA delivery system took advantage of the tumor-specific surface overexpression of EpCAM to selective target epithelial tumor cells and stem-like tumor-initiating cells[34]. Normal epithelial cells express much lower levels of EpCAM on the lateral interfaces as apart of the tight junction complex[73], therefore are spared from EpCAM-AsiC targeting. The inventors have demonstrated the selective internalization of EpCAM aptamer by human EpCAM+ tumor in vitro and at distant site in vivo[26]; here it is demonstrated that the EpCAM-AsiCs could bind to and be internalized into mouse EpCAM+ BC cells with high affinity and specificity to knockdown target genes. As an oncogenic signaling protein, the tumor-associated antigen EpCAM is essential for BC cell proliferation and migration[74]. It is demonstrated herein that BC cells treated with EpCAM-AsiCs for multiple times do not downregulate EpCAM levels, presumably due to its oncogenic property.

The EpCAM-AsiCs also do not activate their receptor presumably because they do not crosslink it[28].

Despite their promises, AsiCs could be further modified to promote their therapeutic potential. Various biochemical modifications of the AsiCs have been developed to optimize their performance, such as to decrease systemic clearance and prolong their in vivo half-life, attenuate nuclease degradation, enhance their delivery and cellular uptake, and to avoid the activation of immune sensors[70,78,79]. The EpCAM-AsiCs described herein have been chemically modified with 2'-fluoropymidine substitutions in the RNA aptamer and siRNA sense strand and with a 3'-dTdT overhang, which contribute to their RNase resistance, stability, and help reduce immune activation. In addition, the AsiCs were administered through s.c. injection, which shows a slower release rate into the circulation and could provide more time for the recycling of cellular receptors that mediate uptake in order to improve the efficiency of siRNA delivery[80,81]. Additional modifications of the EpCAM-AsiCs, such as 2' sugar modifications of the siRNA guide strand, phosphorothioate (PS) backbone modification, as well as 5' unlocked nucleic acid modifications of canonical siRNAs, have great potential to further improve gene knockdown efficiency, decrease the dose of AsiCs needed, and reduce off-target RNAi activity[70,82]. Indeed, such changes have led to two orders of magnitude of decrease in the administered dose of N-acetylgalactosamine (GalNac)-conjugated siRNAs while promoting RNAi activity and keeping the low toxicity profile of the reagent[83]. Endosomal escape is a major roadblock to improve the efficacy of RNAi beyond the liver[84]. At a dose of 5 mg/kg, the EpCAM-AsiCs demonstrated good gene silencing profile in tumor cells in vivo, indicating a certain number of the AsiCs could leave endosome for target knockdown. Moreover, conjugating the EpCAM-AsiCs to bulky chemicals, i.e. cholesterol, liposomes or PEG, can further extend their circulation half-life and reduce systemic clearance to achieve superior therapeutic efficacy for cancer patients[88-88].

Tumor neoantigens that are often generated due to the genetic instability of tumor cells are highly immunogenic as they are not expressed by normal tissues. They could prime both CD4+ and CD8+ antitumor T cell responses and are ideal targets for cancer immunotherapy[89,90]. Lack of tumor neoantigen expression due to low non-synonymous mutation rates in BC cells represents a major challenge for BC immunotherapy. Using UPF2 AsiC, we can introduce tumor neoantigen expression by reducing the NMD machinery in BC cells. NMD is conventionally viewed as a key mechanism for mRNA quality control and NMD-targeted transcripts could arise from various mRNA variations that give rise to a PTC. The core NMD machinery contains three trans-acting factors, UPF1-3, in addition to SMG1-7[91].

UPF2 is a key NMD factor that bridges the interaction between UPF3/exon junction complex (EJC) and the UPF1-containing complex that subsequently phosphorylates UPF1 to induce mRNA decay activity[92,93] Cells deficient in NMD activity have been shown to upregulate aberrant mRNA splicing variants[94-96]. In one study, NMD inhibition by UPF1 knockdown in N2A neuroblastoma cells led to altered expression of more than 200 exons[97]. Similarly, it is demonstrated herein that knocking down UPF2 reduced NMD activity in BC cells grown in vitro and in vivo, induced DEU events in 281 genes and generated a number of novel mRNA isoforms and NMD-sensitive transcripts that may encode tumor neoantigens. This was associated with enhanced numbers of CD8+ TILs and their improved functions as well as strong inhibition of breast tumor growth. These findings were supported by a study that knocked down UPF2 or SMG1 with PSMA-targeting aptamer, which suppressed PSMA-CT26/B16F10 tumor growth in a T cell dependent manner[98]. Although many neoantigens induced by NMD inhibition would be generated due to random mutations and therefore are tumor cell-specific, there are also a series of bona fide NMD targets that would be stabilized to express novel antigens upon NMD inhibition[39,42,99]. In particular, NMD has been reported to regulate many nonmutated transcripts that are involved in cellular stress response and nutrient homeostasis pathways[42,100,101]. Amino acid starvation and ER stress in the tumor inhibit NMD activity, which is likely a strategy tumor cells use to upregulate stress responsive transcripts to adapt to these environmental challenges[42,95,101]. Interestingly, this study identified both DEU and DIU events in PFKFB4, UCN2, CDKAL1, and TRIM4 genes with UPF2 knockdown, all of which are involved in the oxidative stress and ER stress regulation pathways[102-105]. These alterations were also observed in all three samples studied, suggesting that NMD inhibition could induce expression of antigens that are shared among all or at least a portion of tumor cells in which UPF2 was downregulated.

TNBC presents around 80% mutations in TP53, which lead to its high genomic instability[106,107]. In addition, a large proportion of TNBC features defective homologous recombination (HR), a high-fidelity DNA repair mechanism that is critical for efficient repair of double-strand DNA breaks (DSB)[108]. As such, TNBC represents a good therapeutic target for PARP1 inhibitors (PARP1). PARP1 is well known for participating in distinct DNA repair processes, such as BER, single-strand DNA break (SSB) repair, and DSB repair. Olaparib mainly works in the HR-defective BRCA mutated BCs, as endogenously generated SSB are no longer repaired in the presence of PARP1 and are converted to DSB during cell duplication, which are unable to get repaired with BRCA deficiency and result in cell death[109].

A similar working mechanism may exist for PARP1 AsiC, which by knocking down PARP1 expression in BC cells promotes cancer cell death in vivo. The dead cells may release more TAs and attract T cell tumor infiltration. Notably, both PARP1 AsiC and Olaparib could also exert antitumor effects in a large portion of TNBC that are BRCA+ but contain other HR-related defects[110]. By reducing the expression of a key DNA repair enzyme, PARP1 AsiC may also introduce more DNA damage, increase the DNA mutation burden and promote tumor neoantigen generation. It is demonstrated herein that PARP1 AsiC strongly enhanced the CD8$^+$ TIL to CD4$^+$ Treg ratio and cytokine production by both CD8$^+$ and CD4$^+$ TILs, which might be attributed to its ability to trigger both tumor cell death and tumor neoantigen expression. Surprisingly, Olaparib did not achieve significant tumor inhibition in the 4T1E TNBC model and fail to boost antitumor T cell immunity, which is in contrast to its therapeutic efficacy in BRCA1-deficient tumor models[111-113] The immunomodulatory effect of Olaparib depends on STING-mediated IFN-I production[112,113], which might be insufficient in 4T1E tumors. The better stability and tumor-penetrating ability of PARP1 AsiC may also contribute to its improved efficacy. In addition, PARP1 is a known coactivator of NF-κB that can induce tumor inflammation[114]. PARP1 knockout could strongly diminish inflammation-driven tumor formation[115]. PARP1 AsiC-mediated gene knockdown may led to similar effects, which might not be achieved by Olaparib-mediated inhibition of PARylation.

APC (macrophage and dendritic cell)-mediated phagocytosis of dying cancer cells and TA cross-presentation are critical for initiating effective antitumor T cell immunity. Tumor cells universally upregulate CD47 expression, presumably to evade the endogenous "eat me" signals that were induced during programmed cell death and cell removal and to avoid being recognized by the immune system[49,50]. Neutralizing CD47's anti-phagocytic signaling via anti-CD47 antibody could restore cancer cell phagocytosis by either macrophages or DCs. Although DC subsets were viewed as the main player to present exogenous antigens to CD8$^+$ T cells, in the context of blocking the CD47-SIRP axis both macrophages and DCs have demonstrated their antigen cross-priming capacity to stimulate effective CD8$^+$ T cell response[50,116,117]. The present data indicate that the antitumor efficacy of CD47 AsiC depends on TAMs, as anti-CSF1R-mediated TAM depletion, although only reduced the number of TAMs by 70%, potently dampened the antitumor function of CD47 AsiC. CD8$^+$ TILs from TAM-depleted tumors almost completely abolished their effector functions, suggesting that TAMs play a key role in cross-priming CD8$^+$ TIL immunity. Though anti-CSF1R is mainly used for macrophage depletion in vivo, CSF1R is also expressed by plasmacytoid and conventional DC subsets, and CSF-1 signaling is required for optimal DC differentiation[118]. Therefore, it is possible that anti-CSF1R antibody also depleted a number of DCs, which contributed to the impaired tumor-inhibitory and immunostimulatory capacity of CD47 AsiC. Indeed, CD47 AsiC increased the percentage of CD11c$^+$DEC205$^+$ DCs in the tumor that are specialized in taking up extracellular antigens and promoted DC maturation. The antigen cross-presentation capacity of these DCs are also likely to be improved by CD47 AsiC treatment.

Furthermore, studies reported that the therapeutic potential of CD47 blockade requires STING-mediated tumor DNA sensing by host DC[116]. Both tumor-infiltrating DC (TIDC) and TAM produced more IFN-I upon antibody-mediated CD47 blockade, which may promote their antigen cross-presentation functions. It is likely that the improved DC maturation upon CD47 AsiC treatment also depends on increased IFN-I signaling. Additionally, CD47 AsiC treatment through promoting DC maturation might also modify the cytokine milieu of tumor, which helped enhance the ratio of M1 to M2 TAM and reduce the presence of MDSCs, creating a TME that is tumor-suppressive and immunostimulatory. Intriguingly, CD47 AsiC outperformed anti-CD47 antibody in suppressing 4T1E tumor growth. Although both therapies increased the function of CD8$^+$ TILs, only CD47 AsiC promoted the function of CD4$^+$ TILs and reduced the number of MDSCs in the tumor, suggesting its superior therapeutic potential in the 4T1E tumor model. Anti-CD47 antibody therapy did not improve CD4$^+$ T cell function, which has been reported before[50]. On the other hand, CD4$^+$ T cell depletion markedly impaired the therapeutic efficacy of CD47 AsiC, clearly indicating its importance for CD47 AsiC treatment. It is possible that directly reducing CD47 signaling by gene knockdown rather than antibody-mediated signal blockade, and the smaller size of CD47 AsiCs with better tumor-penetrating ability make them more efficient at tumor inhibition.

A biomarker consistently identified by targeting each of the factors in the cancer-immunity cycle with EpCAM-AsiCs is the upregulated ratio of CD8$^+$ TILs to CD4$^+$ Tregs, which has been reported as a good prognostic marker associated with improved clinical outcome in patients with different types of cancers including aggressive BC[44,119-121], indicating the potential clinical benefits that could be provided by the therapeutic approach described herein. EpCAM-AsiC targeting PD-L1, however, did not significantly inhibit overall tumor growth, despite the clinical efficacy displayed by anti-PDL1 antibody for patients with TNBC. PD-L1 is actually expressed at higher levels on TICs than on tumor cells, and only high PD-L1 expression on TICs is a favorable prognostic factor for cancer patients[122, 123]. Thus, targeting PD-L1$^+$ tumor cells alone by EpCAM-AsiC may not achieve efficient antitumor effects. When simultaneously inducing tumor neoantigen expression, triggering cancer cell death to increase TA release, and promoting antigen uptake and cross-presentation, the AsiC cocktail therapy exhibited the most potent efficacy to boost antitumor immunity and suppress tumor growth. Immune-modulating AsiC cocktails targeting more than one gene would be ideal for cancer immunotherapeutics to lessen the chances of developing drug resistance.

The scRNA-seq data further revealed the improved activation status and functional profiles of both CD8$^+$ TILs and monocytes/macrophages in tumors treated with the AsiC cocktail, which corroborated the immunological studies that identified the enhanced cytokine production and cytotoxic functions of CD8$^+$ TILs and the increased endocytosis of tumor cells by TAMs. It is highly likely that the proliferating TIL cluster, which exhibited the most pronounced functional improvements with AsiC cocktail therapy, were composed of TILs that mainly recognize TAs. AsiC cocktail treatment also reduced the expression of mRNA transcripts encoding different co-inhibitory molecules in proliferating TILs, suggesting they are protected from hyperactivation/exhaustion. Reduced PD-1 protein expression was also detected on antigen-experienced CD44⁺CD8⁺ TILs from AsiC cocktail-treated tumors. Further diminished co-inhibitors expression, together with enhanced numbers and functions of CD8⁺ and NK TILs were observed when AsiC cocktail was given together with PD-1 checkpoint inhibitor, indicating the combinational approach provides additional therapeutic benefits. Finally, the inducible genetically engineered mouse (GEM) tumors are relatively resistant to immune therapeutic interventions, in part because they do not generally carry many genetic mutations and hence are not well recognized[124,125]. The AsiC cocktail approach displayed promising antitumor potency in both the GEM model of highly aggressive HER2+BC and lung metastatic TNBC, demonstrating the great immunotherapeutic potential offered by immune-modulating EpCAM-AsiCs for patients with aggressive BC.

Materials and Methods

Cell Lines

Human MDA-MB-468, MCF7, T47D, SKBR3 and mouse L929 and P815 cell lines were obtained from ATCC. 4T1E was generated by sorting 4T1 cells for high E-cadherin expression. 4T1E-eGFP cells were generated with pCAG-eGFP lentiviral vector. 4T1E cells stably expressing firefly luciferase (4T1E-Luc) were selected after infection with EF1a-Luciferase(firefly)-2A-RFP-Puro lentiviral vector (amsbio) using puromycin. Cell lines were cultured in DMEM (4T1, 4TO7, 4T1E, 4T1E-eGFP, 4T1E-Luc, L929, P815, MCF10CA1a, EpCAMʰⁱMDA-MB-231 cells), RPMI 1640 (MDA-MB-468, T47D), MEM (MCF7), McCoy's 5A (SKBR3) medium (Gibco, Thermo Fisher Scientific) supplemented with 10% heat-inactivated FBS (Gemini Bioproducts), 6 mM HEPES, 1.6 mM L-glutamine, 50 µM 2-mercapoethanol, 100 U ml₋₁ penicillin G, and 100 µg ml⁻¹ streptomycin sulfate (Sigma-Aldrich). All cell lines were verified to be free of *mycoplasma* by PCR and were authenticated by morphology.

Mouse Studies

All animal experiments were conducted in compliance with all the relevant ethical regulations and were approved by the Harvard Medical School Institutional Animal Care and Use Committee. All mice were housed in the Harvard Medical School Animal Facility. Female BALB/c mice (6-8 weeks old) were purchased from The Jackson Laboratories. Transgene expression was determined by tail clipping and genotyping for ErbB2ΔEx16 (forward primer: 5'-GTGACCTGTTTTGGACCGGA-3' (SEQ ID NO: 145), reverse primer: 5'-TCTCCGCATCGTGTACTTCC-3' (SEQ ID NO: 146)) and MTB (forward primer: 5'-ACCGTACTCGTCAATTCCAAGGG-3' (SEQ ID NO: 147), reverse primer: 5'-TGCCGCCATTAT-TACGACAAGC-3' (SEQ ID NO: 148)). 8-week-old female ErbB2ΔEx16+/–MTB+/– mice were given 2 mg/ml doxycycline (Sigma-Aldrich) in the drinking water for tumor induction throughout the study. Mice with tumor induction for three days were randomly assigned to either control or treatment group and were treated with the EpCAM-AsiCs cocktail (each at 5 mg/kg in PBS and a total of 30 mg/kg) or EpCAM aptamer (30 mg/kg) every third day. Tumor onsite was monitored by palpation and tumor growth was assessed by measuring the perpendicular diameters of tumors every other day. The mice were euthanized on day 28.

For orthotopic tumor challenge, 4T1E (approximately 10⁵ cells per mouse) cells or 4T1E-eGFP (approximately 3×10⁵ cells per mouse) cells were injected into the four mammary fat pad of BALB/c mice. When tumors became palpable (approximately 3-4 days post tumor challenge), mice were injected subcutaneously with medium alone (mock), 5 mg/kg of EpCAM aptamer or eGFP EpCAM-AsiC as control treatment, or each of the immune-modulating EpCAM-AsiCs every third day. Tumor growth was monitored by measuring the perpendicular diameters of tumors daily. When the average diameter of control group tumors reached roughly 4-5 mm (around two weeks), all mice in an experiment were euthanized and tumors were collected for analysis. To determine the longer-term antitumor efficacy of UPF2 EpCAM-AsiC, mice were challenged with 5×10⁴ 4T1E cells and the treatment was initiated on day 8 post tumor challenge. Tumor growth was monitored for 25 days. For cell depletion assay, CD8 antibody (clone 2.43), CD4 antibody (clone GK1.5), CSF1R antibody (clone AFS98) or the isotype control antibody (all from BioXCell) were injected intraperitoneally (i.p., 300 µg/mouse) into mice challenged with 4T1E tumor cells. CD8 or CD4 antibody was given starting on day 2 after tumour challenge for three consecutive days, and every five days thereafter. For TAM depletion, anti-CSF1R antibody was injected starting on day 0 of tumor challenge and every other day afterwards. Immune cell depletion was verified by staining for CD4, CD8, CD11b, F4/80 and MHCII, and by flow cytometry using peripheral blood mononuclear cells obtained on day 7 after tumour challenge and/or tumour-infiltrating immune cells obtained at the time of necropsy. For anti-CD47 antibody (clone MIAP410, BioXcell) treatment, the antibody was injected i.p. (400 g/mouse) starting on day 3 of tumor challenge and every third day thereafter. For PARP1 inhibitor treatment, olaparib (LC Laboratories) was dissolved in DMSO to 50 mg/ml. It was further diluted with 10% 2-hydroxyl-propyl-cyclodextrine/PBS (Sigma-Aldrich), and was given to mice daily at 50 mg/kg by i.p. injection starting on day 3 after tumor challenge for a total of 12 injections. For immunotherapy with PD-1 inhibitor, anti-PD-1 antibody (clone 29F.1A12, BioXCell) was given (200 µg/mouse) starting on day 10 after tumor challenge and every third day thereafter.

To assess the antitumor efficacy of EpCAM-AsiCs against lung metastatic breast tumors, 4T1E-Luc cells were first mixed with 150 g/ml of D-luciferin (PerkinElmer) and their luciferase activity was checked by luminescent imaging using the IVIS Lumina II system (Caliper Life Sciences). BALB/c mice were injected intravenously with 4T1E-Luc cells (approximately 3×10⁵ cells per mouse) and treated with either EpCAM aptamer or the EpCAM-AsiCs cocktail starting on day 7 post tumor challenge. After i.p. injection of 150 mg/kg of D-luciferin, luminescent images of the whole body were taken immediately after tumor challenge and every 5 days thereafter for 20 days. The lungs were isolated upon necropsy for analysis.

RNAs

The 19 nt EpCAM aptamer with 2'-fluoropyrimidines and EpCAM aptamer with fluorescent Cy3 conjugated to its 5' end (EpCAM-Cy3) (Trilink Biotechnologies or Dharmacon) were used as control RNA oligos. The candidate mouse or human gene-specific, or mouse and human gene cross-reactive siRNAs were either predesigned ON-TARGETplus siRNAs and/or designed using siDESIGN tool (both from Dharmacon). The siRNAs used for EpCAM-AsiCs constructions were selected by comparing their gene knockdown efficiency in vitro in mouse and/or human BC cell lines using qRT-PCR. ON-TARGETplus non-targeting pool siRNAs were used as negative control (Dharmacon). siRNA sequences with the best gene knockdown capacity and lowest Tm values were selected. For EpCAM aptamer-siRNA conjugation, the long strand of the AsiC with EpCAM aptamer, the U-U-U linker, and the sense strand of the siRNA were synthesized with 2'-fluoropyrimidines and a dTdT overhang at its 3' end. It was annealed to the antisense strand of the siRNA using a 2-fold molar excess of the short strand (both from Trilink Biotechnologies). The long strand RNA oligo was initially heated to 95° C. for 10 minutes. Then the short strand RNA was added to anneal with the long strand at 65° C. for 7 minutes. The mixture was allowed to cool at room temperature for 20 minutes. The annealed EpCAM-AsiC duplexes were purified further using Illustra MicroSpin G-25 columns (GE Healthcare Life Sciences). The siRNA and EpCAM-AsiC sequences are provided in Tables 5 and 6.

RNA Uptake by Mouse and Human BC Cell Lines

Mouse and human BC cell lines were plated at 30,000 cells per well in 96-well plates. Cells were incubated with a series of concentrations of EpCAM-Cy3 (0-1000 nmol/L) in Opti-MEM medium supplemented with 5 mM $MgCl_2$, 0.1 mg/ml tRNA, and 0.1 mg/ml salmon sperm DNA for 6 hours (all from ThermoFisher). Complete culture medium supplemented with 20% FBS was then added and cells were cultured for 72 hours. Surface bound EpCAM-Cy3 was washed off at 4° C. by incubating and washing with washing buffer of DPBS supplemented with 5 mM $MgCl_2$, 0.5 M NaCl, and 0.2N Acetic acid. The resulting cell suspension was stained for live cells by live/dead fixable aqua dead cell stain (ThermoFisher) and the amount of EpCAM-Cy3 internalization was analyzed by flow cytometry. The kinetic parameter Kd for EpCAM-Cy3 uptake capabilities of each BC cell line were calculated from nonlinear regression analysis of one binding site hyperbola using GraphPad Prism 8.

Gene Knockdown and qRT-PCR

For in vitro siRNA-mediated gene silencing, cells were used immediately following seeding at 10,000 cells per well in 96-well plates. Cells were transfected with siRNAs ranging from 6.25 nmol/L to 100 nmol/L using Dharmafect I according to the manufacturer's protocol (Dharmacon). Cells were transfected in serum- and antibiotics-free medium for 6 to 8 hours before adding culture medium supplemented with 20% FBS. RNA was extracted 24 to 48 hours later and gene knockdown was assessed by qRT-PCR. For in vitro EpCAM=AsiCs mediated gene silencing, cells were incubated with 4 □mol/L of EpCAM aptamer or EpCAM-AsiCs in WIT-T medium. Gene knockdown was assessed by measuring mRNA and protein levels 72 to 96 hours after treatment by qRT-PCR and flow cytometry, respectively. Cell viability was measured by CellTiter-Glo (Promega) 24 to 96 hours after treatment as indicated in the figures. Cell proliferation was measured by CellTiter 96 Aqueous One Solution Cell Proliferation assay (MTS assay, Promega). For in vivo gene silencing experiments, tumors were collected from mice treated with EpCAM aptamer or EpCAM-AsiCs. Single cell suspension was prepared by tumor digestion and homogenization. Dead cells were removed and CD45-EpCAM$^+$ tumor cells were enriched by negative selection using CD45 microbeads and positive selection using CD326 (EpCAM) microbeads according to the manufacturer's protocol (Miltenyi Biotec). CD45-EpCAM$^-$ cells from the same tumors were collected as control. Gene knockdown in both cell subsets was measured at mRNA and protein levels by qRT-PCR and flow cytometry, respectively. For qRT-PCR, total RNA was extracted with TRIzol (ThermoFisher) and Direct-zol RNA miniprep kit (ZYMO Research) and RNA concentrations were quantified with NanoDrop 2000 Spectrophotometer (Thermo Scientific). cDNA synthesis was performed using the High Capacity cDNA Reverse Transcription kit (ThermoFisher). qRT- PCR of cDNAs was performed with primers corresponding to the target genes or housekeeping gene GAPDH (IDT), SsoFast EvaGreen Supermix and Bio-rad C1000 Thermal Cycler (Bio-Rad).

Histology, IHC and Fluorescence Microscopy

Tumors were fixed with 10% formalin, stored in 70% ethanol, and embedded in paraffin. Sections (5 m) were cut, air-dried, fixed for hematoxylin and eosin (H&E) staining and IHC staining by the Dana-Farbar Cancer Institute Rodent Histopathology Core and Dana-Farber/Harvard Cancer Center Specialized Histopathology Core as previously described[113,126] Anti-CD8 antibody (clone 4SM15, ThermoFisher) was used at 5. g/ml. The slides were scanned into the Aperio image analysis platform. The numbers of CD8+ T cells were then visualized and digitally annotated in regions of interest (ROIs, 6 fields/slide) using ImageScope software (Aperio Technology) and the ROIs were analyzed using image analysis algorithms (Aperio Technology).

For confocal microscopy, 10,000 cells were seeded in each well of 16-well chamber slide (ThermoFisher) and cocultured with 1000 nmol/L of EpCAM-Cy3 diluted in Opti-MEM medium supplemented with 5 mM $MgCl_2$, 0.1 mg/ml tRNA, and 0.1 mg/ml salmon sperm DNA. Complete culture medium supplemented with 20% FBS was added 6 hours later. Cells were cultured for 72 hours and washed with ice-cold high-salt wash buffer of DPBS supplemented with 5 mM $MgCl_2$, 0.5 M NaCl, and 0.2N Acetic acid to remove surface bound EpCAM-Cy3. Cells were then counter stained with CellMask Deep Red Plasma Membrane Stain (ThermoFisher), fixed with 3% paraformaldehyde and 0.5% glutaraldehyde, counterstained with Hoechst 33342 and mounted. Fluorescence was detected using Zeiss LSM 800 confocal laser scanning microscope and the images were acquired using ZEN 2.3 imaging software (Carl Zeiss).

Isolation of Immune Cells from Mice

Peripheral blood mononuclear cells and TICs were collected as described[127]. Briefly, blood was collected by submandibular puncture and PBMCs were isolated by Histopaque gradient centrifugation (Sigma Aldrich). Red blood cells were lysed by 1×RBC lysis buffer. To isolate TICs, tumors were cut into small pieces and treated with digestion buffer of RPMI supplemented with 2 mg/ml collagenase D, 100 □g/ml DNase I (both from Sigma Aldrich) and 2% FBS with agitation for 30 mins at 37° C. Samples were then homogenized and filtered through 40 Om strainers, and immune cells were purified by Percoll gradient centrifugation (GE Healthcare) and washed with Leibovitz's L-15 medium (Gibco, ThermoFisher).

Antibody Staining and Flow Cytometry

Immune cells isolated from mice were stained with anti-CD45-PerCPCy5.5 or -PacBlue, CD3-PE-Cy7, -FITC or -APC, CD8-PacBlue, -PerCPCy5.5, -Alexa700, -FITC or -APC, CD4-PE-Cy7, -APC or -PerCPCy5.5, CD19-FITC, CD25-PE, CD44-PerCPCy5.5 or PacBlue, Gr-1-FITC or -PE, CD11b-Alexa700, CD11c-APC or -PE-Cy7, DEC205-PE, CD49b-PerCPCy5.5, -PacBlue, or FITC, NKp46-APC, F4/80-PE-Cy7, MHCII-PacBlue, CD206-APC, TCR-Q-FITC, TER-119-FITC, EpCAM-PE-Cy7, CD47-FITC, CD40-APC, CD86-FITC, CD107a-APC, CD107b-APC, PD-1-PE-Cy7, 2B4-FITC, CTLA-4-PE, LAG-3-APC, TIM-3-PerCPCy5.5 (all from Biolegend). Dead cells were excluded using the live/dead fixable aqua dead cell stain (ThennoFisher) added with cell-surface antibodies.

Mouse TAMs were defined as: live$^+$CD45$^+$CD3$^-$CD19$^-$Ter119TCRβ$^-$CD11b$^+$F4/80$^{+128}$. M1 TAMs were defined as: live$^+$CD45$^+$CD3$^-$CD19$^-$Ter119$^-$TCRβ$^-$CD11b$^+$F4/80$^+$CD206$^-$MHC$^+$, and M2 TAMs were defined as: live$^+$CD45$^+$ CD3⁻CD19⁻Ter119~TCRβ⁻CD11b⁺F4/80⁺CD206⁺MHC⁺.

$CD3^-CD19^-Ter119\sim TCR\beta^-CD11b^+F4/80^+CD206^+MHC^+$.
Note: TAMs that did not adhere to either of these expression panels were not classified as M1 or M2 TAMs. This is consistent with previous study that showed that TAMs in mouse mammary tumors are mainly characterized as $CD45^+$ $CD11b^+F4/80^+MHCII^+$ cells[129]. For intracellular staining of UPF2, granzyme B or perforin, cells were first stained with antibodies to cell-surface markers for 30 mins at 4, then fixed and permeabalized with fixation/permeabilization buffer (BD Pharmingen) and stained with primary antibody against UPF2 (clone D3B10, Cell Signaling Technology) or rabbit monoclonal IgG Isotype antibody (Abcam), anti-granzyme B-PacBlue or -APC (ThennoFisher), and Perforin-PE (Biolegend). UPF2 was further detected with goat anti-rabbit IgG H&L-APC secondary antibody (Abcam). For staining of Foxp3, cells were first stained for surface markers, then fixed and permeabilized with Foxp3/Transcription factor staining buffer and stained with Foxp3-PercpCy5.5 or -PE (ThermoFisher). For intracellular cytokine staining of ex vivo stimulated lymphocytes, approximately $10^6$ cells per sample were cultured in RPMI medium containing 2% FBS and were stimulated with PMA (50 ng/ml, Sigma), ionomycin (2 □g/mil, Sigma) and Golgiplug (1.5 □g/ml, ThermoFisher) for four hours. Cells cultured with medium and Golgiplug alone were served as negative control. Cells were then stained with antibodies to IFN-γ-PacBlue or -APC and TNF-PE-Cy7 after fixation/permeabilization. Cells were analyzed by BD FACSCanto II (BD Biosciences) and data were analyzed with FlowJo V.10 (TreeStrar).

CD8⁺ TIL Degranulation and Cytotoxicity Assay

Single-cell suspensions of tumor-infiltrating immune cells were enriched for $CD45^+$ or $CD8^+$ cells using the CD45 or CD8 microbeads (Miltenyi Biotec). For degranulation assay, the numbers of $CD8^+$ TILs in freshly isolated CD45+ cells were first determined by flow cytometry. $CD8^+$ TILs were co-incubated with autologous target tumor cells plated one day earlier in 48-well plates at a ratio of 1:3 in RPMI medium containing 10% FBS. Antibodies to CD107a-APC and CD107b-APC (each at 1 mg/ml, Biolegend) and IL-2 (100 IU/ml) were added at the start of the coculture. Positive control cells were treated with PMA (50 ng/ml) and ionomycin (2 □g/ml) while negative control samples were treated with medium and IL-2. The coculture was incubated for 1 hour at 37° C. in a 5% CO2 incubator, followed by the addition of the secretion inhibitors monensin (1:1000, Biolegend) and Golgi Plug (1.5 □g/ml) for an additional 5 hours. TILs were washed out of the co-culture and re-plated in 96-well plates after the stimulation and were stained for live cells and then were stained with antibodies to CD8, IFN-L, and TNF after fixation/permeabilization. For $CD8^+$ TIL cytotoxicity assay, autologous target tumor cells were labeled with chromium-51 ($^{51}Cr$) and plated one day earlier in 96-well plates. Freshly isolated $CD8^+$ TILs were co-cultured with target tumor cells at a ratio of 5:1 in RMPI medium containing 10% FBS and supplemented with IL-2 (100 IU/ml) for 30 hours. The time of co-culture $CD8^+$ TILs needed to achieve efficient target tumor cell killing has been determined by previous studies[130]. Maximal $^{51}Cr$ release was set up using $CD8^+$ TILs cultured with 1% SDS and spontaneous $^{51}Cr$ release was set up using $CD8^+$ TILs cultured in medium and IL-2 alone. The percentage of target cell lysis was calculated using the following formula: % specific lysis=((test $^{51}Cr$ release)–(spontaneous $^{51}Cr$ release))/((maximal $^{51}Cr$ release)–(spontaneous $^{51}Cr$ release))×100.

Ex Vivo Phagocytosis Assay

Dead cells were removed by a dead cell removal kit (Miltenyi Biotec) and TAMs were enriched from tumor-infiltrating immune cells using F4/80 microbeads (Miltenyi Biotec). The numbers of live⁺CD11b⁺F4/80⁺ TAMs in freshly isolated F4/80⁺ cells were first determined by flow cytometry. 4T1E-eGFP tumors were either treated with negative control or CD47 siRNA 72 hours earlier to knock-down CD47 expression. 50,000 TAMs were co-cultured with 200,000 4T1E-eGFP cells in RPMI serum-free medium for 3 hours at 37° C. The cells were then washed three times with DPBS supplemented with 0.5% BSA and 2 mM EDTA, stained with anti-CD45, CD11b, and F4/80 and analyzed by flow cytometry. TAMs that were GFP high were considered to be phagocytosing.

Single-Cell RNA Sequencing

Sample Preparation

BALB/c mice were orthotopically challenged with approximately $10^5$ cells per mouse. Three days post tumor challenge mice were treated with either EpCAM aptamer or EpCAM-AsiCs cocktail targeting UPF2, PARP1, CD47 and MCL1 by s.c. injection every third day. On day 14, tumors were harvested, incubated at 37° C. for 15 mins with 100 g/ml Liberase TL (Roche) diluted in $Ca^{2+}$ and $Mg^{2+}$-free RPMI medium (ThermoFisher) followed by shaking at 37° C. for 10 mins. Samples were then filtered twice with 40 μM strainers. Dead cells were removed and $CD45^+$ cells were enriched with CD45 microbeads at 4° C. More than 95% of cells were $CD45^+$ as verified by flow cytometry. The enriched cells were diluted at 200,000 cells/ml in $Ca^{2+}$ and $Mg^{2+}$-free RPMI medium containing 1% FBS and kept on ice until the cells were flowed into the microfluidic device. 6,000 cells per sample were encapsulated using the inDrop technology, with half of the samples used for library preparation and the other half was stored for backup purpose. Two biological replicates per condition were processed independently and sequencing data from both samples were combined for data analysis. Single-cell encapsulation and RNA capture on the InDrop platform as well as libraries preparation were performed at the Harvard Medical School Single Cell Core as published previously[131]. Single-cell transcriptomes were barcoded within the microfluidic droplets. After within droplet reverse transcription, emulsions of approximately 3,000 cells were broken and used for libraries preparation. Libraries were indexed with V3 sequencing adaptors, pooled from different samples at equimolar ratios, and sequenced on an Illumina NextSeq 500 system using the NextSeq 75 High Output Kits using standard Illumina sequencing primers and 61 cycles for read 1 and 14 cycles for read 2, 8 cycles each for index read 1 and index read 2.

Data Processing

Raw data was processed using previously a published pipeline in Python (github.com/indrops/indrops) using default parameters. Briefly, reads were filtered and sorted by the corresponding library index. Valid reads were then demultiplexed and sorted by cell barcodes. Cell barcodes containing fewer than 250 total reads were discarded, and remaining reads were aligned to a reference mouse transcriptome (Ensembl GRCm38 release 87). Aligned reads were then quantified as an imputed count matrix that was used for all downstream analysis.

Pre-Clustering Filtering, Normalization and Batch Correction

Analysis of the processed data was performed in R version 3.5.2 using the Seurat package version 2.3[133]. All samples were merged together. The percentage of mitochondrial transcripts for each cell (percent.mito) and average UMI of each gene (nUMI.nGene.ratio) were calculated.

Low-quality cells were filtered using the following cutoffs: nGene—min. 50, max. 2000; percent.mito—min. –Inf, max. 0.25; nUMI.nGene.ratio—min. 1, max 5. The Normalize-Data function was performed using default parameters to remove the differences in sequencing depth across cells. The ScaleData function was used to eliminate cell-cell variation in gene expression driven by batch and mitochondrial gene expression.

Dimension Reduction and Unsupervised Clustering

Dimension reduction was performed at three stages of the analysis: the selection of variable genes, PCA, and uniform manifold approximation and projection (UMAP). The Find-VariableGenes function was applied to select highly 2274 variable genes covering most biological information contained in the whole transcriptome. Then, the variable genes were used for PCA implemented with the RunPCA function. Next, PCs 1-20 were selected as input to perform the RunUMAP function to obtain bidimensional coordinates for each cell. We performed the FindClusters function (resolution 0.4) to cluster cells using the Louvain algorithm based on the same PCs as RunUMAP function.

Identification of DEGs and GO Analysis

The inventors used the FindMarkers or FindAllMarkers function (test.use="t", logfc.threshold=log(1.6)) based on normalized data to identify differentially expressed genes (DEGs). P-value adjustment was performed using Bonferroni correction based on the total number of genes in the dataset. DEGs with adjusted p-values>0.05 were filtered out. Gene ontology (GO) analysis was performed by using the R package clusterProfiler[14].

Bulk RNA Sequencing

EpCAM$^{hi}$MDA-MB-231 cells were transfected with 100 nM of either negative control siRNA or ON-TARGETplus human UPF2 siRNA-SMARTpool (both from Dharmacon) for 72 hours. The transfection achieved more than 80% UPF2 mRNA knockdown. Total RNA was extracted from each sample using TRIzol and Direct-zol RNA miniprep kit. Three biological replicates per condition were used for RNA-sequencing library preparations. The RNA integrity number (RIN) of all samples were determined by an Agilent 2100 Bioanalyzer in the Harvard Medical School Biopolymers Facility. All RNA samples have RINs greater than 9. Standard mRNA libraries were prepared with NEBNext® Ultra™ II Directional RNA Library Prep Kit after polyA- mRNA isolation (New England BioLabs). Libraries for negative control and UPF2 siRNA transfected samples were pooled separately and each pool was ran on one lane of an Illumina Hiseq X10 PE100 system, yielding around 240 million mapped 150 bp paired-end reads per sample. Sequences were aligned against reference genome GRCh38 (Ensembl release 98) using HISAT2[135]. We used a pipeline incorporating DEXSeq and HTSeq counts to identify differential exon usage (DEU) events using the reference GRCh38_98[136,137] The DEU analysis was limited to exons with at least 10 reads in at least 3 samples. DEU events were significant if they reached a multiple-hypothesis adjusted p-value<0.05. StringTie was used to assemble reads into novel and annotated transcripts using the guided-assembly approach on the GRCh38_98 reference[138]. Per-sample assemblies were then integrated into a unified transcript reference using StringTie's merge functionality. Kallisto was used to quantify transcript abundance from the StringTie-generated reference[139]. Differential isoform usage events (DIU) were identified with IsoformSwitchAnalyzeR[136,140]. IsoformSwitchAnalyzer also provided predictions of premature termination codons (PTC), for readout of potential NMD sensitivity. Changes in isoform usage were significant if they reached a q-value<0.05.

Statistical Analysis

A Student's t-test (two-tailed) or Mann-Whitney test was used to determine differences between two groups. One- or two-way ANOVA was used to calculate differences among multiple populations. Differences between tumour growth curves were compared by first calculating the area-under-curve values for each sample and then comparing different groups using the Student's t-test or one-way ANOVA. Comparisons of tumor volumes at different time points along tumor growth were determined by multiple t-test with type I error correction. Type I errors were corrected by Holm-Sidak method. Significance was set at p values of or below 0.05. For all figures, *p≤0.05,  p≤0.01, * p≤0.001, **** p≤0.0001. All statistical analyses were conducted using GraphPad Prism 8.

REFERENCE

1. Kumar, P. & Aggarwal, R. An overview of triple-negative breast cancer. *Arch. Gynecol. Obstet.* 293, 247-269 (2016).
2. Padmanabhan, R., Kheraldine, H. S., Meskin, N., Vranic, S. & Moustafa, Al, A.-E. Crosstalk between HER2 and PD-1/PD-L1 in Breast Cancer: From Clinical Applications to Mathematical Models. *Cancers* 12, 636 (2020).
3. Al-Mahmood, S., Sapiezynski, J., Garbuzenko, O. B. & Minko, T. Metastatic and triple-negative breast cancer: challenges and treatment options. *Drug Deliv Transl Res* 8, 1483-1507 (2018).
4. Wang, J. & Xu, B. Targeted therapeutic options and future perspectives for HER2-positive breast cancer. *Signal Transduct Target Ther* 4, 34 (2019).
5. Cameron, D. et al. 11 years' follow-up of trastuzumab after adjuvant chemotherapy in HER2-positive early breast cancer: final analysis of the HERceptin Adjuvant (HERA) trial. *Lancet* 389, 1195-1205 (2017).
6. Yang, Y. Cancer immunotherapy: harnessing the immune system to battle cancer. *J. Clin. Invest.* 125, 3335-3337 (2015).
7. Lawrence, M. S. et al. Mutational heterogeneity in cancer and the search for new cancer-associated genes. *Nature* 499, 214-218 (2013).
8. Banerji, S. et al. Sequence analysis of mutations and translocations across breast cancer subtypes. *Nature* 486, 405-409 (2012).
9. Stephens, P. J. et al. The landscape of cancer genes and mutational processes in breast cancer. *Nature* 486, 400-404 (2012).
10. van de Vijver, M. J. et al. A Gene-Expression Signature as a Predictor of Survival in Breast Cancer. *N Engl J Med* 347, 1999-2009 (2002).
11. Kroemer, G., Senovilla, L., Galluzzi, L., André, F. & Zitvogel, L. Natural and therapy-induced immunosurveillance in breast cancer. *Nat. Med.* 21, 1128-1138 (2015).
12. Kwa, M. J. & Adams, S. Checkpoint inhibitors in triple-negative breast cancer (TNBC): Where to go from here. *Cancer* 9, 457 (2018).
13. Adams, S. et al. Current Landscape of Immunotherapy in Breast Cancer: A Review. *JAMA Oncology* 5, 1205-1214 (2019).
14. Disis, M. L. & Stanton, S. E. Triple-negative breast cancer: immune modulation as the new treatment paradigm. Am Soc *Clin Oncol* Educ Book 35, e25-30 (2015).

15. Dieci, M. V. et al. Prognostic and predictive value of tumor-infiltrating lymphocytes in two phase III randomized adjuvant breast cancer trials. *Ann. Oncol.* 26, 1698-1704 (2015).

16. Gao, G., Wang, Z., Qu, X. & Zhang, Z. Prognostic value of tumor-infiltrating lymphocytes in patients with triple-negative breast cancer: a systematic review and meta-analysis. *BMC Cancer* 20, 179-15 (2020).

17. Gubin, M. M. et al. Checkpoint blockade cancer immunotherapy targets tumour-specific mutant antigens. *Nature* 515, 577-581 (2014).

18. Van Allen, E. M. et al. Genomic correlates of response to CTLA-4 blockade in metastatic melanoma. *Science* 350, 207-211 (2015).

19. Asaoka, Y., Ijichi, H. & Koike, K. PD-1 Blockade in Tumors with Mismatch-Repair Deficiency. *N Engl J Med* 373, 1979 (2015).

20. Llosa, N. J. et al. The vigorous immune microenvironment of microsatellite instable colon cancer is balanced by multiple counter-inhibitory checkpoints. *Cancer Discovery* 5, 43-51 (2015).

21. Rizvi, N. A. et al. Cancer immunology. Mutational landscape determines sensitivity to PD-1 blockade in non-small cell lung cancer. *Science* 348, 124-128 (2015).

22. Xiao, Y. & Freeman, G. J. The Microsatellite Instable Subset of Colorectal Cancer Is a Particularly Good Candidate for Checkpoint Blockade Immunotherapy. *Cancer Discovery* 5, 16-18 (2015).

23. Weinmann, S. C. & Pisetsky, D. S. Mechanisms of immune-related adverse events during the treatment of cancer with immune checkpoint inhibitors. *Rheumatology (Oxford)* 58, vii59-vii67 (2019).

24. Chen, D. S. & Mellman, I. Elements of cancer immunity and the cancer-immune set point. *Nature* 541, 321-330 (2017).

25. Chen, D. S. & Mellman, I. Oncology meets immunology: the cancer-immunity cycle. *Immunity* 39, 1-10 (2013).

26. Gilboa-Geffen, A. et al. Gene Knockdown by EpCAM Aptamer-siRNA Chimeras Suppresses Epithelial Breast Cancers and Their Tumor-Initiating Cells. *Mol. Cancer Ther.* 14, 2279-2291 (2015).

27. Wheeler, L. A. et al. Durable knockdown and protection from HIV transmission in humanized mice treated with gel-formulated CD4 aptamer-siRNA chimeras. *Mol. Ther.* 21, 1378-1389 (2013).

28. Wheeler, L. A. et al. Inhibition of HIV transmission in human cervicovaginal explants and humanized mice using CD4 aptamer-siRNA chimeras. *J. Clin. Invest.* 121, 2401-2412 (2011).

29. Berezhnoy, A., Castro, I., Levay, A., Malek, T. R. & Gilboa, E. Aptamer-targeted inhibition of mTOR in T cells enhances antitumor immunity. *J. Clin. Invest.* 124, 188-197 (2014).

30. McNamara, J. O. et al. Cell type-specific delivery of siRNAs with aptamer-siRNA chimeras. *Nat. Biotechnol.* 24, 1005-1015 (2006).

31. Spizzo, G. et al. EpCAM expression in primary tumour tissues and metastases: an immunohistochemical analysis. *Journal of Clinical Pathology* 64, 415-420 (2011).

32. Huang, L. et al. Functions of EpCAM in physiological processes and diseases (Review). *Int. J. Mol. Med.* 42, 1771-1785 (2018).

33. Osta, W. A. et al. EpCAM is overexpressed in breast cancer and is a potential target for breast cancer gene therapy. *Cancer Res.* 64, 5818-5824 (2004).

34. Imrich, S., Hachmeister, M. & Gires, O. EpCAM and its potential role in tumor-initiating cells. *Cell Adh Migr* 6, 30-38 (2012).

35. Goodwin, C. M., Rossanese, O. W., Olejniczak, E. T. & Fesik, S. W. Myeloid cell leukemia-1 is an important apoptotic survival factor in triple-negative breast cancer. *Cell Death and Differentiation* 2015 22:12 22, 2098-2106 (2015).

36. Campbell, K. J. et al. MCL-1 is a prognostic indicator and drug target in breast cancer. *Cell Death Dis* 9, 19-14 (2018).

37. Yang, L. et al. Wnt modulates MCL1 to control cell survival in triple negative breast cancer. *BMC Cancer* 14, 124-13 (2014).

38. Berezhnoy, A., Brenneman, R., Bajgelman, M., Seales, D. & Gilboa, E. Thermal Stability of siRNA Modulates Aptamer-conjugated siRNA Inhibition. *Molecular Therapy—Nucleic Acids* 1, e51 (2012).

39. Popp, M. W. & Maquat, L. E. Attenuation of nonsense-mediated mRNA decay facilitates the response to chemotherapeutics. *Nature Communications* 6, 1-17 (2015).

40. Lou, C. H. et al. Posttranscriptional control of the stem cell and neurogenic programs by the nonsense-mediated RNA decay pathway. *Cell Reports* 6, 748-764 (2014).

41. Maquat, L. E. Nonsense-mediated mRNA decay: splicing, translation and mRNP dynamics. *Nat Rev Mol Cell Biol* 5, 89-99 (2004).

42. Gardner, L. B. Nonsense-mediated RNA decay regulation by cellular stress: implications for tumorigenesis. *Mol. Cancer Res.* 8, 295-308 (2010).

43. Takada, K. et al. Use of the tumor-infiltrating CD8 to FOXP3 lymphocyte ratio in predicting treatment responses to combination therapy with pertuzumab, trastuzumab, and docetaxel for advanced HER2-positive breast cancer. *J Transl Med* 16, 86-11 (2018).

44. Peng, G.-L. et al. CD8+ cytotoxic and FoxP3+ regulatory T lymphocytes serve as prognostic factors in breast cancer. *Am J Transl Res* 11, 5039-5053 (2019).

45. Bouchard, V. J., Rouleau, M. & Poirier, G. G. PARP-1, a determinant of cell survival in response to DNA damage. *Exp. Hematol.* 31, 446-454 (2003).

46. Malyuchenko, N. V., Kotova, E. Y., Kulaeva, O. I., Kirpichnikov, M. P. & Studitskiy, V. M. PARP1 Inhibitors: antitumor drug design. *Acta Naturae* 7, 27-37 (2015).

47. Li, M.-X. et al. Human apurinic/apyrimidinic endonuclease 1 translocalizes to mitochondria after photodynamic therapy and protects cells from apoptosis. *Cancer Sci.* 103, 882-888 (2012).

48. Shah, F. et al. Exploiting the Ref-1-APE1 node in cancer signaling and other diseases: from bench to clinic. *npj Precision Oncology* 2017 1:1 1, 19 (2017).

49. Willingham, S. B. et al. The CD47-signal regulatory protein alpha (SIRPa) interaction is a therapeutic target for human solid tumors. *Proc. Natl. Acad. Sci. U.S.A.* 109, 6662-6667 (2012).

50. Tseng, D. et al. Anti-CD47 antibody-mediated phagocytosis of cancer by macrophages primes an effective antitumor T-cell response. *Proc. Natl. Acad. Sci. U.S.A.* 110, 11103-11108 (2013).

51. Liu, X. et al. CD47 blockade triggers T cell-mediated destruction of immunogenic tumors. *Nat. Med.* 21, 1209-1215 (2015).

52. Genard, G., Lucas, S. & Michiels, C. Reprogramming of Tumor-Associated Macrophages with Anticancer Therapies: Radiotherapy versus Chemo- and Immunotherapies. *Front Immunol* 8, 828 (2017).

53. van Dalen, F. J., van Stevendaal, M. H. M. E., Fennemann, F. L., Verdoes, M. & Ilina, O. Molecular Repolarisation of Tumour-Associated Macrophages. *Molecules* 24, 9 (2018).

54. Lee, C. et al. Targeting of M2-like tumor-associated macrophages with a melittin-based pro-apoptotic peptide. *J Immunother Cancer* 7, 147 (2019).

55. Willis, S. N. et al. Proapoptotic Bak is sequestered by Mcl-1 and Bcl-xL, but not Bel-2, until displaced by BH3-only proteins. *Genes Dev.* 19, 1294-1305 (2005).

56. Marra, A., Viale, G. & Curigliano, G. Recent advances in triple negative breast cancer: the immunotherapy era. *BMC Med* 17, 90-9 (2019).

57. Mittendorf, E. A. et al. PD-L1 expression in triple-negative breast cancer. *Cancer Immunol Res* 2, 361-370 (2014).

58. Zitvogel, L. & Kroemer, G. Targeting PD-1/PD-L1 interactions for cancer immunotherapy. *OncoImmunology* 1, 1223-1225 (2012).

59. Emens, L. A. et al. Long-term Clinical Outcomes and Biomarker Analyses of Atezolizumab Therapy for Patients With Metastatic Triple-Negative Breast Cancer: A Phase 1 Study. *JAMA Oncology* 5, 74-82 (2019).

60. Keenan, T. E. & Tolaney, S. M. Role of Immunotherapy in Triple-Negative Breast Cancer. *Journal of the National Comprehensive Cancer Network* 18, 479-489 (2020).

61. Turpin, J. et al. The ErbB2ΔEx16 splice variant is a major oncogenic driver in breast cancer that promotes a pro-metastatic tumor microenvironment. *Oncogene* 35, 6053-6064 (2016).

62. Tseng, L. M. et al. Distant metastasis in triple-negative breast cancer. *Neoplasma* 60, 290-294 (2013).

63. Jin, L. et al. Breast cancer lung metastasis: Molecular biology and therapeutic implications. *Cancer Biol. Ther.* 19, 858-868 (2018).

64. Gennari, A., Conte, P., Rosso, R., Orlandini, C. & Bruzzi, P. Survival of metastatic breast carcinoma patients over a 20-year period. *Cancer* 104, 1742-1750 (2005).

65. Dan, Z. et al. A pH-Responsive Host-guest Nanosystem Loading Succinobucol Suppresses Lung Metastasis of Breast Cancer. *Theranostics* 6, 435-445 (2016).

66. Anders, C. & Carey, L. A. Understanding and treating triple-negative breast cancer. *Oncology (Williston Park, N.Y.)* 22, 1233-9—discussion 1239-40-1243 (2008).

67. Tarantino, P. & Curigliano, G. Defining the immunogram of breast cancer: a focus on clinical trials. *Expert Opin Biol Ther* 19, 383-385 (2019).

68. Holgado, E., Perez-Garcia, J., Gion, M. & Cortes, J. Is there a role for immunotherapy in HER2-positive breast cancer? *NPJ Breast Cancer* 4, 21-3 (2018).

69. Krasniqi, E. et al. Immunotherapy in HER2-positive breast cancer: state of the art and future perspectives. *J Hematol Oncol* 12, 111-26 (2019).

70. Setten, R. L., Rossi, J. J. & Han, S.-P. The current state and future directions of RNAi-based therapeutics. *Nat Rev Drug Discov* 18, 421-446 (2019).

71. Scott, L. J. Givosiran: First Approval. *Drugs* 80, 335-339 (2020).

72. Lorenzer, C., Dirin, M., Winkler, A.-M., Baumann, V. & Winkler, J. Going beyond the liver: progress and challenges of targeted delivery of siRNA therapeutics. *J Control Release* 203, 1-15 (2015).

73. Wu, C.-J., Mannan, P., Lu, M. & Udey, M. C. Epithelial cell adhesion molecule (EpCAM) regulates claudin dynamics and tight junctions. *J. Biol. Chem.* 288, 12253-12268 (2013).

74. Baeuerle, P. A. & Gires, O. EpCAM (CD326) finding its role in cancer. *Br J Cancer* 96, 417-423 (2007).

75. Wu, S. Y., Lopez-Berestein, G., Calin, G. A. & Sood, A. K. RNAi therapies: drugging the undruggable. *Sci Transl Med* 6, 240ps7-240ps7 (2014).

76. Zhou, J. & Rossi, J. Aptamers as targeted therapeutics: current potential and challenges. *Nat Rev Drug Discov* 16, 440-440 (2017).

77. Zhou, G. et al. Aptamers: A promising chemical antibody for cancer therapy. *Oncotarget* 7, 13446-13463 (2016).

78. Robbins, M. et al. 2'-O-methyl-modified RNAs act as TLR7 antagonists. *Mol. Ther.* 15, 1663-1669 (2007).

79. Bramsen, J. B. et al. A large-scale chemical modification screen identifies design rules to generate siRNAs with high activity, high stability and low toxicity. *Nucleic Acids Research* 37, 2867-2881 (2009).

80. McLennan, D. N., Porter, C. J. H. & Charman, S. A. Subcutaneous drug delivery and the role of the lymphatics. *Drug Discov Today Technol* 2, 89-96 (2005).

81. Nair, J. K. et al. Impact of enhanced metabolic stability on pharmacokinetics and pharmacodynamics of GalNAc-siRNA conjugates. *Nucleic Acids Research* 45, 10969-10977 (2017).

82. Snead, N. M., Escamilla-Powers, J. R., Rossi, J. J. & McCaffrey, A. P. 5' Unlocked Nucleic Acid Modification Improves siRNA Targeting. *Molecular Therapy—Nucleic Acids* 2, e103 (2013).

83. Janas, M. M. et al. Selection of GalNAc-conjugated siRNAs with limited off-target-driven rat hepatotoxicity. *Nature Communications* 9, 723-10 (2018).

84. Dowdy, S. F. Overcoming cellular barriers for RNA therapeutics. *Nat. Biotechnol.* 35, 222-229 (2017).

85. Farokhzad, O. C. et al. Targeted nanoparticle-aptamer bioconjugates for cancer chemotherapy in vivo. *Proceedings of the National Academy of Sciences* 103, 6315-6320 (2006).

86. Xing, H. et al. Selective Delivery of an Anticancer Drug with Aptamer-Functionalized Liposomes to Breast Cancer Cells in Vitro and in Vivo. *J Mater Chem B* 1, 5288-5297 (2013).

87. Tan, L., Neoh, K. G., Kang, E.-T., Choe, W. S. & Su, X. PEGylated anti-MUC1 aptamer-doxorubicin complex for targeted drug delivery to MCF7 breast cancer cells. *Macromol Biosci* 11, 1331-1335 (2011).

88. Zhou, W. et al. Aptamer-nanoparticle bioconjugates enhance intracellular delivery of vinorelbine to breast cancer cells. *J Drug Target* 22, 57-66 (2014).

89. Jiang, T. et al. Tumor neoantigens: from basic research to clinical applications. *J Hematol Oncol* 12, 1-13 (2019).

90. Peng, M. et al. Neoantigen vaccine: an emerging tumor immunotherapy. *Mol. Cancer* 18, 128-14 (2019).

91. Kervestin, S. & Jacobson, A. NMD: a multifaceted response to premature translational termination. *Nat Rev Mol Cell Biol* 13, 700-712 (2012).

92. Chamieh, H., Ballut, L., Bonneau, F. & Le Hir, H. NMD factors UPF2 and UPF3 bridge UPF1 to the exon junction complex and stimulate its RNA helicase activity. *Nat. Struct. Mol. Biol.* 15, 85-93 (2008).

93. Bao, J. et al. UPF2-Dependent Nonsense-Mediated mRNA Decay Pathway Is Essential for Spermatogenesis by Selectively Eliminating Longer 3'UTR Transcripts. *PLoS Genet* 12, e1005863 (2016).

94. Wittmann, J., Hol, E. M. & Jick, H.-M. hUPF2 silencing identifies physiologic substrates of mammalian nonsense-mediated mRNA decay. *Mol. Cell. Biol.* 26, 1272-1287 (2006).

95. Mendell, J. T., Sharifi, N. A., Meyers, J. L., Martinez-Murillo, F. & Dietz, H. C. Nonsense surveillance regulates expression of diverse classes of mammalian transcripts and mutes genomic noise. *Nat. Genet.* 36, 1073-1078 (2004).

96. Weischenfeldt, J. et al. Mammalian tissues defective in nonsense-mediated mRNA decay display highly aberrant splicing patterns. *Genome Biol.* 13, R35-19 (2012).

97. Ni, J. Z. et al. Ultraconserved elements are associated with homeostatic control of splicing regulators by alternative splicing and nonsense-mediated decay. *Genes Dev.* 21, 708-718 (2007).

98. Pastor, F., Kolonias, D., Giangrande, P. H. & Gilboa, E. Induction of tumour immunity by targeted inhibition of nonsense-mediated mRNA decay. *Nature* 465, 227-230 (2010).

99. Tani, H. et al. Identification of hundreds of novel UPF1 target transcripts by direct determination of whole transcriptome stability. *RNA Biol* 9, 1370-1379 (2012).

100. Weischenfeldt, J. et al. NMD is essential for hematopoietic stem and progenitor cells and for eliminating by-products of programmed DNA rearrangements. *Genes Dev.* 22, 1381-1396 (2008).

101. Gardner, L. B. Hypoxic inhibition of nonsense-mediated RNA decay regulates gene expression and the integrated stress response. *Mol. Cell. Biol.* 28, 3729-3741 (2008).

102. Yi, M. et al. 6-Phosphofructo-2-kinase/fructose-2,6-biphosphatase 3 and 4: A pair of valves for fine-tuning of glucose metabolism in human cancer. *Mol Metab* 20, 1-13 (2019).

103. Tillinger, A., Nostramo, R., Kvetnansky, R., Serova, L. & Sabban, E. L. Stress-induced changes in gene expression of urocortin 2 and other CRH peptides in rat adrenal medulla: involvement of glucocorticoids. *J. Neurochem.* 125, 185-192 (2013).

104. Brambillasca, S. et al. CDK5 regulatory subunit-associated protein 1-like 1 (CDKAL1) is a tail-anchored protein in the endoplasmic reticulum (ER) of insulinoma cells. *J. Biol. Chem.* 287, 41808-41819 (2012).

105. Tomar, D. et al. TRIM4; a novel mitochondrial interacting RING E3 ligase, sensitizes the cells to hydrogen peroxide ($H_2O_2$) induced cell death. *Free Radic. Biol. Med.* 89, 1036-1048 (2015).

106. Cancer Genome Atlas Network. Comprehensive molecular portraits of human breast tumours. *Nature* 490, 61-70 (2012).

107. Saravia, C. H. et-al. Patterns of Mutation Enrichment in Metastatic Triple-Negative Breast Cancer. *Clin Med Insights Oncol* 13, 1179554919868482 (2019).

108. Telli, M. L. et al. Homologous recombination deficiency (HRD) status predicts response to standard neoadjuvant chemotherapy in patients with triple-negative or BRCA1/2 mutation-associated breast cancer. *Breast Cancer Res. Treat.* 168, 625-630 (2018).

109. Dziadkowiec, K. N., Gąsiorowska, E., Nowak-Markwitz, E. & Jankowska, A. PARP inhibitors: review of mechanisms of action and BRCA1/2 mutation targeting. *Prz Menopauzalny* 15, 215-219 (2016).

110. Faraoni, I. & Graziani, G. Role of BRCA Mutations in Cancer Treatment with Poly(ADP-ribose) Polymerase (PARP) Inhibitors. *Cancers* 10, 487 (2018).

111. Jiao, S. et al. PARP Inhibitor Upregulates PD-L1 Expression and Enhances Cancer-Associated Immunosuppression. *Clinical Cancer Research* 23, 3711-3720 (2017).

112. Ding, L. et al. PARP Inhibition Elicits STING-Dependent Antitumor Immunity in Breal-Deficient Ovarian Cancer. *Cell Reports* 25, 2972-2980.e5 (2018).

113. Pantelidou, C. et al. PARP Inhibitor Efficacy Depends on CD8+ T-cell Recruitment via Intratumoral STING Pathway Activation in BRCA-Deficient Models of Triple-Negative Breast Cancer. *Cancer Discovery* 9, 722-737 (2019).

114. Mishra, M. & Kowluru, R. A. Role of PARP-1 as a novel transcriptional regulator of MMP-9 in diabetic retinopathy. *Biochimica et Biophysica Acta (BBA)—Molecular Basis of Disease* 1863, 1761-1769 (2017).

115. Dörsam, B. et al. PARP-1 protects against colorectal tumor induction, but promotes inflammation-driven colorectal tumor progression. *Proceedings of the National Academy of Sciences* 115, E4061-E4070 (2018).

116. Liu, X. et al. CD47 blockade triggers T cell-mediated destruction of immunogenic tumors. *Nat. Med.* 21, 1209-1215 (2015).

117. Carbone, F. R., Kurts, C., Bennett, S. R., Miller, J. F. & Heath, W. R. Cross-presentation: a general mechanism for CTL immunity and tolerance. *Immunol. Today* 19, 368-373 (1998).

118. MacDonald, K. P. A. et al. The colony-stimulating factor 1 receptor is expressed on dendritic cells during differentiation and regulates their expansion. *The Journal of Immunology* 175, 1399-1405 (2005).

119. Sideras, K. et al. Prognostic value of intra-tumoral CD8+/FoxP3+ lymphocyte ratio in patients with resected colorectal cancer liver metastasis. *J Surg Oncol* 118, 68-76 (2018).

120. Sato, E. et al. Intraepithelial CD8+ tumor-infiltrating lymphocytes and a high CD8+/regulatory T cell ratio are associated with favorable prognosis in ovarian cancer. *Proceedings of the National Academy of Sciences* 102, 18538-18543 (2005).

121. Sinicrope, F. A. et al. Intraepithelial effector (CD3+)/regulatory (FoxP3+) T-cell ratio predicts a clinical outcome of human colon carcinoma. *Gastroenterology* 137, 1270-1279 (2009).

122. Lin, H. et al. Host expression of PD-L1 determines efficacy of PD-L1 pathway blockade-mediated tumor regression. *J. Clin. Invest.* 128, 1708-1708 (2018).

123. Kim, H. R. et al. PD-L1 expression on immune cells, but not on tumor cells, is a favorable prognostic factor for head and neck cancer patients. *Sci. Rep.* 6, 36956-12 (2016).

124. Pfirschke, C. et al. Immunogenic Chemotherapy Sensitizes Tumors to Checkpoint Blockade Therapy. *Immunity* 44, 343-354 (2016).

125. DuPage, M. & Jacks, T. Genetically engineered mouse models of cancer reveal new insights about the antitumor immune response. *Curr. Opin. Immunol.* 25, 192-199 (2013).

126. Akbay, E. A., Koyama, S., Carretero, J. & Altabef, A. Activation of the PD-1 pathway contributes to immune escape in EGFR-driven lung tumors. *Cancer Discov* 2013; 3 (12): 1355-63; PMID: 24078774.

127. Zhang, Y. et al. Enhancing CD8+ T Cell Fatty Acid Catabolism within a Metabolically Challenging Tumor Microenvironment Increases the Efficacy of Melanoma Immunotherapy. *Cancer Cell* 32, 377-391.e9 (2017).

128. Gordon, S. R. et al. PD-1 expression by tumour-associated macrophages inhibits phagocytosis and tumour immunity. *Nature* 545, 495-499 (2017).

129. Franklin, R. A. et al. The cellular and molecular origin of tumor-associated macrophages. *Science* 344, 921-925 (2014).

130. Committing Cytomegalovirus-Specific CD8 T Cells to Eliminate Tumor Cells by Bifunctional Major Histocompatibility Class I Antibody Fusion Molecules. *Cancer Immunol* Res 3, 764-776 (2015).

131. Single-cell barcoding and sequencing using droplet microfluidics. *Nat Protoc* 12, 44-73 (2017).

132. Klein, A. M. et al. Droplet barcoding for single-cell transcriptomics applied to embryonic stem cells. *Cell* 161, 1187-1201 (2015).

133. Butler, A., Hoffman, P., Smibert, P., Papalexi, E. & Satija, R. Integrating single-cell transcriptomic data across different conditions, technologies, and species. *Nat. Biotechnol.* 36, 411-420 (2018).

134. Yu, G., Wang, L.-G., Han, Y. & He, Q.-Y. clusterProfiler: an R package for comparing biological themes among gene clusters. *OMICS* 16, 284-287 (2012).

135. Kim, D., Paggi, J. M., Park, C., Bennett, C. & Salzberg, S. L. Graph-based genome alignment and genotyping with HISAT2 and HISAT-genotype. *Nat. Biotechnol.* 37, 907-915 (2019).

136. Reyes, A. et al. Drift and conservation of differential exon usage across tissues in primate species. *Proc. Natl. Acad. Sci. U.S.A.* 110, 15377-15382 (2013).

137. Anders, S., Pyl, P. T. & Huber, W. HTSeq—a Python framework to work with high-throughput sequencing data. *Bioinformatics* 31, 166-169 (2015).

138. Pertea, M. et al. StringTie enables improved reconstruction of a transcriptome from RNA-seq reads. *Nat. Biotechnol.* 33, 290-295 (2015).

139. Bray, N. L., Pimentel, H., Melsted, P. & Pachter, L. Near-optimal probabilistic RNA-seq quantification. *Nat. Biotechnol.* 34, 525-527 (2016).

140. Vitting-Seerup, K. & Sandelin, A. The Landscape of Isoform Switches in Human Cancers. *Mol. Cancer Res.* 15, 1206-1220 (2017).

| siRNA sequences | | | SEQ ID NO: |
|---|---|---|---|
| UPF2 | hUPF2 siRNA1 | GGUCUAGAGAGUUGCGAAU | 1 |
|  | hUPF2 siRNA2 | GCAUGUACCUUGUGUAGAA | 2 |
|  | hUPF2 siRNA3 | CGUUAUGUUUGGUGGAAGA | 3 |
|  | hUPF2 siRNA4 | CAUCAGAGUCAGUGCUAUA | 4 |
| CD47 | mCD47 siRNA1 | GAUCAUAGCUCUAGCAGAA | 149 |
|  | mCD47 siRNA2 | GAGAAAAGCCCGUGAAGAA | 150 |
|  | mCD47 siRNA3 | GCGCAAAGCACCGAAGAAA | 151 |
| Parp1 | mParp1 siRNA1 | UAUCCUACCUCAAGAAGUU | 152 |
|  | Parp1 siRNA CR1 | CCAAAGGAAUUCCGAGAAA | 153 |
|  | Parp1 siRNA CR2 | GGGCAAGCACAGUGUCAAA | 154 |
| APEX1 | mApex1 siRNA1 | CCAACACUGCUUACGCUUA | 155 |
|  | Apex1 siRNA CR1 | GGUGAUUGUGGCUGAAUUU | 156 |
|  | Apex1 siRNA CR2 | CUGCAUUGUGUGACAGCAA | 157 |
| MCL1 | mMCL1 siRNA 1 | AAACGAAGGCGAUGUUAAA | 158 |
|  | mMCL1 siRNA 2 | CCGAAAGGCGGCUGCAUAA | 159 |
|  | mMCL1 siRNA 3 | AGGAAGAGGACGACCUAUA | 160 |
| CD274 | mPD-L1 SIRNA 1 | AGACGUAAGCAGUGUUGAA | 161 |
|  | mPD-L1 SIRNA 2 | GGAAAAGGAAGAUGAGCAA | 162 |

TABLE 6

Bolded sequence depicts EpCAM aptamer

| EpCAM AsiC sequences | | SEQ ID NO |
|---|---|---|
| EpCAM-UPF2 sense | GCGACUGGUUACCCGGUCG UUU GCGUUAUGUUUGGUGGAAG dTdT | 163 |
| UPF2 antisense | CUUCCACCAAACAUAACGC dTdT | 72 |
| EpCAM-CD47 sense | GCGACUGGUUACCCGGUCG UUU GAUCAUAGCUCUAGCAGAA dTdT | 164 |
| CD47 antisense | UUCUGCUAGAGCUAUGAUC dTdT | 78 |
| EpCAM-PARP1 sense | GCGACUGGUUACCCGGUCG UUU CCAAAGGAAUUCCGAGAAA dTdT | 165 |
| PARP1 antisense | UUUCUCGGAAUUCCUUUGG dTdT | 84 |
| EpCAM-MCL1 sense | GCGACUGGUUACCCGGUCG UUU AAACGAAGGCGAUGUUAAA dTdT | 166 |
| MCL1 antisense | UUUAACAUCGCCUUCGUUU dTdT | 101 |
| EpCAM-APEX1 sense | GCGACUGGUUACCCGGUCG UUU GGUGAUUGUGGCUGAAUUU dTdT | 167 |
| APEX1 antisense | AAAUUCAGCCACAAUCACC dTdT | 90 |
| EpCAM-CD274 sense | GCGACUGGUUACCCGGUCG UUU AGACGUAAGCAGUGUUGAA dTdT | 168 |
| CD274 antisense | UUCAACACUGCUUACGUCU dTdT | 96 |

TABLE 7

| qRT-PCR primer sequences | | SEQ ID NO: |
|---|---|---|
| mUpf2 Fw | TGTTGCAGTCTCTTGCACAGC | 169 |
| mUpf2 Rev | GGATCAACGTCTCCTCCCACC | 170 |
| mParp1 Fw | CCATCGACGTCAACTACGAG | 171 |
| mParp1 Rev | GTGCGTGGTAGCATGAGTGT | 172 |
| mCd47 Fw | AGGAGAAAAGCCCGTGAAG | 173 |
| mCd47 Rev | TGGCAATGGTGAAAGAGGTC | 174 |
| mMcl1 Fw | TTGTAAGGACGAAACGGGAC | 175 |
| mMcl1 Rev | TCTAGGTCCTGTACGTGGAAG | 176 |
| mApex1 Fw | GGGTGATTGTGGCTGAATTTG | 177 |
| mApex1 Rev | GCTGTGGGTATTCCAGTCTTAC | 178 |
| mPD-L1 Fw | CTCATTGTAGTGTCCACGGTC | 179 |
| mPD-L1 Rev | ACGATCAGAGGGTTCAACAC | 180 |

TABLE 7-continued

| qRT-PCR primer sequences | | SEQ ID NO: |
|---|---|---|
| mGapdh Fw | CCACTCACGGCAAATTCAAC | 181 |
| mGapdh Rev | CTCCACGACATACTCAGCAC | 182 |
| hUPF2 Fw | CAAGAACAGGGATCTAGGTGAG | 183 |
| hUPF2 Rev | AGAGGCTGTAAACCCATGAAG | 184 |
| hGAPDH Fw | AATCCCATCACCATCTTCCAG | 185 |
| hGAPDH Rev | AAATGAGCCCCAGCCTTC | 186 |
| mGadd45a Fw | AGACCCCGGACCTGCACTG | 187 |
| mGadd45a Rev | TTCGGATGCCATCACCGTTC | 188 |
| mGadd45a pre-mRNA Fw | AGACCCCGGACCTGCACTG | 189 |
| mGadd45a pre-mRNA Rev | ACCCACGAGCTTAGACACGC | 190 |
| mGadd45b Fw | GCCAAACTGATGAATGTGGACC | 191 |
| mGadd45b Rev | AGCAGAACGACTGGATCAGG | 192 |

TABLE 7-continued

| qRT-PCR primer sequences | | SEQ ID NO: |
|---|---|---|

| mGadd45b pre-mRNA Fw | TCTGACGACCCCCTGACACTC | 193 |
|---|---|---|
| mGadd45b pre-mRNA Rev | ATGCCTGATACCCGGACGATG | 194 |
| mCDNK1a Fw | CAGATCCACAGCGATATCCAG | 195 |
| mCDNK1a Rev | AGAGACAACGGCACACTTTG | 196 |
| mCDNK1a pre-mRNA Fw | TGGCCTTGTCGCTGTCTTGC | 197 |
| mCDNK1a pre-mRNA Rev | TTTCTCCTTCTCTGCTCCTGTCC | 198 |
| mNat9 Fw | GGAGTATGAGATGCAGTGTAGC | 199 |
| mNat9 Rev | CAAGGTCTGTGAGGAAGAGG | 200 |
| mNat9 pre-mRNA Fw | AGATCGAGGTCATGATTGCAG | 201 |
| mNat9 pre-mRNA Rev | ACAATCAGCCACCATCCAG | 202 |

What is claimed herein is:

1. A pharmaceutical composition, kit, or combination comprising at least two different chimeric molecules,
    wherein each chimeric molecule comprises an EpCAM-binding aptamer domain and an inhibitory nucleic acid domain comprising an siRNA which inhibits the expression of a gene selected from the group consisting of:
        CD47; UPF2; PD-L1; and MCL1;
    wherein the at least two different chimeric molecules collectively comprise inhibitory nucleic acid domains that inhibit the expression of each of CD47; UPF2; PD-L1; and MCL1.

2. The pharmaceutical composition, kit, or combination of claim 1, wherein the at least two different chimeric molecules collectively comprise inhibitory nucleic acid domains that inhibit the expression of each of:
    CD47; UPF2; PARP1; APE1; PD-L1; and MCL1.

3. The pharmaceutical composition, kit, or combination of claim 1, wherein the inhibitory nucleic acid specifically binds to a gene product of the selected gene.

4. The pharmaceutical composition, kit, or combination of claim 1, wherein the EpCam-binding aptamer domain comprises the sequence of any of SEQ ID NOs: 63-68.

5. The pharmaceutical composition, kit, or combination of claim 1, wherein at least one of the inhibitory nucleic acid domains comprises a sequence selected from SEQ ID NOs: 1-11, 26-37, 69-80, 93-102, 149-151, and 158-162, or the reverse complement thereof.

6. The pharmaceutical composition, kit, or combination of claim 1, wherein at least one of the chimeric molecules comprises a first and at least one further inhibitory nucleic acid domain.

7. The pharmaceutical composition, kit, or combination of claim 6, wherein the first and at least one further inhibitory nucleic acid domains comprise different sequences but each inhibit the expression of the same gene.

8. The pharmaceutical composition, kit, or combination of claim 6, wherein the first and at least one further inhibitory nucleic acid domains each inhibit the expression of a different gene.

9. The pharmaceutical composition, kit, or combination of claim 8, wherein the at least a second inhibitory nucleic acid domain inhibits the expression of a gene selected from the group consisting of:
    PLK1 and MCL1.

10. The pharmaceutical composition, kit, or combination of claim 1, comprising the sequence of one of SEQ ID NOs: 127-137 or 163-168.

11. The pharmaceutical composition, kit, or combination of claim 1, wherein at least one of the chimeric molecules is conjugated or bound to a cholesterol, a PEG, or a liposome.

12. The pharmaceutical composition, kit, or combination of claim 1, wherein at least one of the chimeric molecules further comprises a chemotherapeutic agent.

13. The pharmaceutical composition, kit, or combination of claim 1, wherein at least two of the chimeric molecules have different aptamer domains.

14. The pharmaceutical composition, kit, or combination of claim 1, further in combination with an immune checkpoint inhibitor.

15. A method of treating cancer in a subject in need thereof, the method comprising administering a pharmaceutical composition, kit, or combination of claim 1 to the subject.

16. The method of claim 15, wherein the cancer is an epithelial cancer, breast cancer, or colon cancer.

17. The method of claim 16, wherein the breast cancer is a HER2+ or triple-negative breast cancer (TNBC).

18. The pharmaceutical composition, kit, or combination of claim 1, wherein at least one of the at least two different chimeric molecules comprises dTdT.

19. The pharmaceutical composition, kit, or combination of claim 1, wherein at least one of the at least two different chimeric molecules comprises one or more of a 2'-F pyrimidine, 2' sugar modification, a phosphothiorate backbone modification, and a 5' unlocked nucleic acid modification.

20. The pharmaceutical composition, kit, or combination of claim 1, wherein at least one of the at least two different chimeric molecules is conjugated or bound to a cholesterol, a PEG, or a liposome.

* * * * *